United States Patent
Haines et al.

(10) Patent No.: US 11,891,618 B2
(45) Date of Patent: Feb. 6, 2024

(54) MOUSE COMPRISING A HUMANIZED TTR LOCUS WITH A BETA-SLIP MUTATION AND METHODS OF USE

(71) Applicant: Regeneron Pharmaceuticals, Inc., Tarrytown, NY (US)

(72) Inventors: Jeffery Haines, New York, NY (US); Keith Crosby, Pleasantville, NY (US); Meghan Drummond Samuelson, Katonah, NY (US); David Frendewey, New York, NY (US); Brian Zambrowicz, Sleepy Hollow, NY (US); Andrew J. Murphy, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 626 days.

(21) Appl. No.: 16/891,571

(22) Filed: Jun. 3, 2020

(65) Prior Publication Data

US 2020/0385760 A1 Dec. 10, 2020

Related U.S. Application Data

(60) Provisional application No. 62/856,999, filed on Jun. 4, 2019.

(51) Int. Cl.
*C12N 15/87* (2006.01)
*A01K 67/027* (2006.01)

(52) U.S. Cl.
CPC .......... *C12N 15/87* (2013.01); *A01K 67/0275* (2013.01); *A01K 2227/105* (2013.01)

(58) Field of Classification Search
CPC ............... C12N 15/87; A01K 67/0275; A01K 2227/105
See application file for complete search history.

(56) References Cited

U.S. PATENT DOCUMENTS

| | | | |
|---|---|---|---|
| 5,942,435 A | 8/1999 | Wheeler | |
| 6,340,783 B1 | 1/2002 | Snow | |
| 6,586,251 B2 | 7/2003 | Economides et al. | |
| 7,294,754 B2 | 11/2007 | Poueymirou et al. | |
| 7,309,812 B2 | 12/2007 | Snow | |
| 7,576,259 B2 | 8/2009 | Poueymirou et al. | |
| 7,659,442 B2 | 2/2010 | Poueymirou et al. | |
| 10,329,582 B2 | 6/2019 | Lee et al. | |
| 10,385,359 B2 | 8/2019 | Lee et al. | |
| 10,577,630 B2 | 3/2020 | Zhang et al. | |
| 2002/0160394 A1 | 10/2002 | Wu | |
| 2008/0038227 A1 | 2/2008 | Torres Aleman et al. | |
| 2008/0078000 A1 | 3/2008 | Poueymirou et al. | |
| 2011/0200982 A1 | 8/2011 | Stevens et al. | |
| 2013/0042330 A1 | 2/2013 | Murphy et al. | |
| 2013/0111617 A1 | 5/2013 | Macdonald et al. | |
| 2013/0117873 A1 | 5/2013 | Wang et al. | |
| 2013/0340104 A1 | 12/2013 | Murphy | |
| 2014/0134662 A1 | 5/2014 | Flavell et al. | |
| 2014/0178879 A1 | 6/2014 | Economides et al. | |
| 2014/0235933 A1 | 8/2014 | Lee et al. | |
| 2014/0245467 A1 | 8/2014 | Macdonald et al. | |
| 2014/0310828 A1 | 10/2014 | Lee et al. | |
| 2015/0106961 A1 | 4/2015 | Rojas et al. | |
| 2015/0176007 A1 | 6/2015 | Prakash et al. | |
| 2015/0313194 A1 | 11/2015 | Hu et al. | |
| 2015/0320021 A1 | 11/2015 | Wang et al. | |
| 2015/0327524 A1 | 11/2015 | Murphy et al. | |
| 2015/0342163 A1 | 12/2015 | Voronina et al. | |
| 2015/0376628 A1 | 12/2015 | Schoenherr et al. | |
| 2015/0376651 A1 | 12/2015 | Frendewey et al. | |
| 2016/0090593 A1 | 3/2016 | Sah | |
| 2016/0145646 A1 | 5/2016 | Frendewey et al. | |
| 2016/0175462 A1 | 6/2016 | Zhang et al. | |
| 2016/0257736 A1 | 9/2016 | Nijjar et al. | |
| 2017/0080107 A1 | 3/2017 | Chivukula et al. | |
| 2017/0142943 A1 | 5/2017 | Mujica et al. | |
| 2017/0245481 A1 | 8/2017 | Gusarova et al. | |
| 2018/0064827 A1 | 3/2018 | Conway et al. | |
| 2018/0110877 A1 | 4/2018 | Wilson et al. | |

(Continued)

FOREIGN PATENT DOCUMENTS

| | | | |
|---|---|---|---|
| EP | | 3620524 A1 | 11/2020 |
| WO | WO 2006/105602 A1 | | 10/2006 |

(Continued)

OTHER PUBLICATIONS

Aigner et al. (J Mol Med (2010) 88:653-664). (Year: 2010).*
Loi et al. (Trends in Biotechnology, (2016) vol. 34, No. 10). (Year: 2016).*
Wilmut et al. (Phil. Trans. R. Soc. (2015) B 370: 20140366, 9 pages). (Year: 2015).*
Ackermann, et al., "Clinical development of an antisense therapy for the treatment of transthyretin-associated polyneuropathy," Amyloid, 19(51):43-44 (2012).
Almeida, et al., "Clearance of extracellular misfolded proteins in systemic amyloidosis: Experience with transthyretin," FEBS Letters, 586:2891-2896, (2012).
Amdo, et al., "Guideline of transthyretin-related hereditary amyloidosis for clinicians," Orphanet Journal of Rare Diseases, 8:31, (2013).

(Continued)

*Primary Examiner* — J. E. Angell
(74) *Attorney, Agent, or Firm* — Yongkin Choi; Alston & Bird LLP

(57) ABSTRACT

Non-human animal cells and non-human animals comprising a humanized TTR locus comprising a beta-slip mutation and methods of using such non-human animal cells and non-human animals are provided. Non-human animal cells or non-human animals comprising a humanized TTR locus comprising a beta-slip mutation express a human transthyretin protein or a chimeric transthyretin protein, fragments of which are from human transthyretin. Methods are provided for using such non-human animals comprising a humanized TTR locus to assess in vivo efficacy of human-TTR-targeting reagents such as nuclease agents designed to target human TTR.

28 Claims, 12 Drawing Sheets

Specification includes a Sequence Listing.

(56) References Cited

U.S. PATENT DOCUMENTS

| | | |
|---|---|---|
| 2018/0139940 A1 | 5/2018 | Macdonald et al. |
| 2018/0243450 A1 | 8/2018 | Devalaraja-Narashimha et al. |
| 2019/0002869 A1 | 1/2019 | Yin et al. |
| 2019/0098879 A1 | 4/2019 | Drummond-Samuelson et al. |
| 2019/0100772 A1 | 4/2019 | Prasad et al. |
| 2019/0290783 A1 | 9/2019 | Voronina et al. |
| 2019/0365924 A1 | 12/2019 | Conway et al. |
| 2019/0390195 A1 | 12/2019 | Tondera et al. |
| 2020/0015462 A1 | 1/2020 | Murphy et al. |
| 2020/0248180 A1 | 8/2020 | Kanjolia et al. |
| 2020/0315149 A1 | 10/2020 | Tang et al. |
| 2020/0383304 A1 | 12/2020 | Fang et al. |
| 2020/0392541 A1 | 12/2020 | Zhang et al. |
| 2023/0078551 A1 | 3/2023 | Drummond Samuelson et al. |
| 2023/0102342 A1 | 3/2023 | Drummond Samuelson et al. |

FOREIGN PATENT DOCUMENTS

| | | |
|---|---|---|
| WO | WO 2010/017509 A1 | 2/2010 |
| WO | WO 2010/030203 A1 | 3/2010 |
| WO | WO 2010/048228 A2 | 4/2010 |
| WO | WO 2014/130706 A1 | 8/2014 |
| WO | WO 2014/172489 A2 | 10/2014 |
| WO | WO 2015/006498 A2 | 1/2015 |
| WO | WO 2015/010118 A2 | 1/2015 |
| WO | WO 2015/042557 A1 | 3/2015 |
| WO | WO 2015/051159 A1 | 4/2015 |
| WO | WO 2015/088643 A1 | 6/2015 |
| WO | WO 2015/092077 A1 | 6/2015 |
| WO | WO 2015/115331 A1 | 8/2015 |
| WO | WO 2015/148582 A1 | 10/2015 |
| WO | WO 2015/200334 A1 | 12/2015 |
| WO | WO 2015/200805 A2 | 12/2015 |
| WO | WO 2016/044745 A1 | 3/2016 |
| WO | WO 2016/081923 A2 | 5/2016 |
| WO | WO 2016/176191 A1 | 11/2016 |
| WO | WO 2017/053431 A1 | 3/2017 |
| WO | WO 2017/087780 A1 | 5/2017 |
| WO | WO 2017/173054 A1 | 10/2017 |
| WO | WO 2018/007871 A1 | 1/2018 |
| WO | WO 2018/049009 A2 | 3/2019 |
| WO | WO 2019/067872 A1 | 4/2019 |
| WO | WO 2019/067875 A1 | 4/2019 |
| WO | WO 2019/183123 A1 | 9/2019 |
| WO | WO 2019/237069 A1 | 12/2019 |
| WO | WO 2019/246203 A1 | 12/2019 |
| WO | WO 2020/240876 A1 | 12/2020 |
| WO | WO 2020/247452 A1 | 12/2020 |
| WO | WO 2021/108363 A1 | 6/2021 |

OTHER PUBLICATIONS

Andersson, "Prefibrillar oligomeric Transthyretin mutants—amyloid conformation, toxicity and association with Serum amyloid P component," UMEA University Medical Dissertations, New Series No. 958, ISSN 0346-6612, ISBN 91-7305-862-9, (2005).

Andersson, et al., "Inhibition of TTR Aggregation-Induced Cell Death—A New Role for Serum Amyloid P Component," PLOS One, 8(2):e55766, (Feb. 2013).

Azevedo, et al., "Transthyretin-Related Amyloidoses: A Structural and Thermodynamic Approach," Published by Intech, open sciences, open minds, Retrieved <http://dx.doi.org/10.5772/53148> (2013).

Barthold, "Genetically altered mice: phenotypes, no phenotypes, and Faux phenotypes," Genetica, 122(1):75-88, (2004).

Benson, et al., "Targeted Suppression of an Amyloidogenic Transthyretin with Antisense Oligonucleotides," Muscle Nerve, 33:609-618, (2006).

Birling, et al., "Modeling human disease in rodents by CRISPR/Cas9 genome editing," Mamm. Genome, 28(7-8):291-301, (2017).

Brett, et al., "Transthyretin Leu12Pro is associated with systemic, neuropathic and leptomeningeal amyloidosis," Brain, 122:182-190, (1999).

Brevini, et al., "No shortcuts to pig embryonic stem cells," Theriogenology, 74(4):544-550, (2010).

Brevini, et al., "Porcine embryonic stem cells: Facts, challenges and hopes," Theriogenology, 68 Suppl. 1:S206-S213, (2007).

Burova, et al., "Characterization of the Anti-PD-1 Antibody REGN2810 and Its Antitumor Activity in Human PD-1 Knock-In Mice," Mol. Cancer Ther., 16(5):861-870, (2017).

Buxbaum, "Animal models of human amyloidoses: Are transgenic mice worth the time and trouble," FEBS Lett., 583(16):2663-2673, (2009).

Buxbaum, et al., "Transthyretin protects Alzheimer's mice from behavioral and biochemical effects of Aβ toxicity," PNAS, 105(7):2681-2686, (Feb. 19, 2008).

Cao, et al., "Isolation and Culture of Primary Bovine Embryonic Stem Cell Colonies by a Novel Method," J. Exp. Zool. A. Ecol. Genet. Physiol., 311(5):368-376, (2009).

Cardoso, et al., "Doxycycline disrupts transthyretin amyloid: evidence from studies in a FAP transgenic mice model," The FASEB Journal, 20(2):234-239, (Sep. 2017).

Choi, et al., "Accelerated AB Deposition in APPswe/PSIΔE9 Mice with Hemizygous Deletions of TTR (Transthyretin)," The Journal of Neurosciences, 27(26):7006-7010, (Jun. 27, 2007).

Chow et al., "AAV-mediated direct in vivo CRISPR screen identifies functional suppressors in glioblastoma," Nat. Neurosci. 20(10):1329-1341 plus supplementary materials, (Aug. 14, 2017).

Clark, et al., "A future for transgenic livestock," Nat. Rev. Genet., 4(10):825-833, (2003).

Coelho et al., "Compound heterozygotes of transthyretin Met30 and transthyretin Met119 are protected from the devastating effects of familial amyloid polyneuropathy," Neuromuscular Disorders 6(1):S20, (1996).

Coelho, et al., "Safety and Efficacy of RNAi Therapy for Transthyretin Amyloidosis," N. Engl. J. Med, 369:819-829, (2013).

Conceicao, et al., ""Red-flag" symptom clusters in transthyretin familial amyloid polyneuropathy," Journal of the Peripheral Nervous System, 21:5-9, (2016).

Connelly, et al., "Structure-based design of kinetic stabilizers that ameliorate the transthyretin amyloidoses," Curr Opin Struct Biol., 20(1):54-62, (Feb. 2010), Abstract only.

Cornwell, et al., "Evidence that the amyloid fibril protein in senile systemic amyloidosis is derived from normal prealbumin," Biochem Biophys Res Commun., 154(2):648-652 (Jul. 29, 1988), Abstract only.

Dechiara, T.M., et al., "VelociMouse: Fully ES Cell-Derived FO-Generation Mice Obtained from the Injection of ES Cells into Eight-Cell-Stage Embryos," Jan. 1, 2009, Methods in Molecular Biology, 530(16): 311-324.

Dennis, "Welfare Issues of Genetically Modified Animals," ILAR J., 43(2):100-109, (2002).

Ellie, et al., "Recurrent subarachnoid hemorrhage associated with a new transthyretin variant (Gly53Glu)," Neurology, 57:135-137, (2001).

Eneqvist, et al., "The β-Slip: A Novel Concept in Transthyretin Amyloidosis," Mol. Cell, 6(5):1207-1218, (2000).

Ferreira, et al., "Molecular Tweezers Targeting Transthyretin Amyloidosis," Neurotherapeutics, 11:451-461, (2014).

Finn, et al., "A Single Administration of CRISPR/Cas9 Lipid Nanoparticles Achieves Robust and Persistent In Vivo Genome Editing," Cell Reports, 22:1-9 plus Supplemental Information, (Feb. 27, 2018).

Fleming, et al., "Transthyretin enhances nerve regeneration," Journal of Neurochemistry, 103:831-839, (2007).

Frendewey, et al., "The Loss-of-Allele Assay for ES Cell Screening and Mouse Genotyping," Methods Enzymol., 476:295-307, (2010).

Genoway, "Humanized Mouse Model," retrieved from https://www.genoway.com/services/customized-mouse/knockin-models/humanisation.htm on May 12, 2018.

Gertz, et al., "Diagnosis, Prognosis, and Therapy of Transthyretin Amyloidosis," J. Am. Coll. Cardiol., 66(21):2451-2466, (2015).

Goldsteins, et al., "Exposure of cryptic epitopes on transthyretin only in amyloid and in amyloidogenic mutants," Proc. Natl. Acad. Sci. USA, 96:3108-3113, (Mar. 1999).

(56) References Cited

OTHER PUBLICATIONS

Gomez, et al., "Derivation of cat embryonic stem-like cells from in vitro-produced blastocysts on homologous and heterologous feeder cells," Theriogenology, 74(4): 498-515, (2010).
Graham, et al., "Resources for the design of CRISPR gene editing experiments," Genome Biol., 16:260, (2015).
Groenning, et al., "Considerably Unfolded Transthyretin Monomers Preceed and Exchange with Dynamically Structured Amyloid Protofibrils," Sci. Rep., 5, 11443; doi: 10.1038/srep11443, (2015).
Hammarström, et al., "Prevention of Transthyretin Amyloid Disease by Changing Protein Misfoldings Energetics," Science, 299:713-716, (Jan. 31, 2003).
Hammarström, et al., "Trans-Suppression of Misfolding in an Amyloid Disease," Science, 293:2459-2462, {Sep. 28, 2001).
Harari et al., "Bridging the species divide: transgenic mice humanized for type-I interferon response," PLOS One 9(1):e84259, (2014).
Herndler-Brandstetter, et al., "Humanized mouse model supports development, function, and tissue residency of human natural killer cells," Proc. Natl. Acad. Sci. U.S.A., 114(45):E9626-E9634, (2017).
Houdebine, "Methods to Generate Transgenic Animals," pp. 31-48 in "Genetic Engineering in Livestock: New Applications and Interdisciplinary Perspectives," Ed. Engelhard et al., (2009).
Inoue, et al., "Specific pathogen free conditions prevent transthyretin amyloidosis in mouse models," Transgenic Res., 17:817-826, (2008).
Intellia Therapeutics, "Company Overview," presented at Jefferies Healthcare Conference (Jun. 6, 2017).
Jacobson, et al., "Transthyretin Pro55, a variant associated with early-onset, aggressive, diffuse amyloidosis with cardiac and neurologic involvement," Hum Genet, 89:353-356, (1992).
Jacobson, et al., "Variant-Sequence Transthyretin (Isoleucine 122) In Late-Onset Cardiac Amyloidosis in Black Americans," The New England Journal of Medicine, 336(7):466-473, (Feb. 13, 1997).
Jean, et al., "Pluripotent genes in avian stem cells," Dev. Growth Differ., 55(1): 41-51, (2013).
Johnson, et al., "The Transthyretin Amyloidoses: From Delineating the Molecular Mechanism of Aggregation Linked to Pathology to a Regulatory Agency Approved Drug," J Mol Biol., 421(2-3): 185-203, doi:10.1016/j.jmb.2011.12.060 (Aug. 10, 2012).
Karlsson, et al., "Heating of proteins as a means of improving crystallization: a successful case study on a highly amyloidogenic triple mutant of human transthyretin," Acta Cryst., F63:695-700, (2007).
Kawamata, et al., "Generation of genetically modified rats from embryonic stem cells," Proc. Natl. Acad. Sci. U.S.A., 7(32):14223-14228, (2010).
Keetch, et al., "L55P Transthyretin Accelerates Subunit Exchange and Leads to Rapid Formation of Hybrid Tetramers," The Journal of Biological Chemistry, 280(50):41667-41674, (Dec. 16, 2005).
Kohno, et al., "Analysis of Amyloid Deposition in a Transgenic Mouse Model of Homozygous Familial Amyloidotic Polyneuropathy," American Journal of Pathology, 150(4):1497-1508, (Apr. 1997).
Kruse, "Treating TTR Amyloidosis: Introducing CRISPR," Biotechr, published Apr. 30, 2016 at http://www.biotechr.com/2016/04/hunt-to-cure-ttr-amylodiosis-crispr.html.
Kumar, et al., "Transgenic Mouse Technology: Principles and Methods," Methods Mol. Biol., 590:335-362, (2009).
Li, et al., "Amyloid deposition in a mouse model humanized at the transthyretin and retinol-binding protein 4 loci," Lab. Invest., 98(4):512-524, (Jan. 12, 2018).
Lobato, et al., "Transthyretin Amyloidosis and the Kidney," Clin J Am Soc Nephrol, 7:1337-1346, doi: 10.2215/CJN.08720811, (2012).
Lute, et al., "Human CTLA4 knock-in mice unravel the quantitative link between tumor immunity and autoimmunity induced by anti-CTLA-4 antibodies," Blood, 106(9):3127-3133, (2005).
Misumi, et al., "Fibroblasts endocytose and degrade transthyretin aggregates in transthyretin-related amyloidosis," Laboratory Investigation, 93:911-920, (2013).
Mu, et al., "CHF5074 (CSP-1103) stabilizes human transthyretin in mice humanized at the transthyretin and retinol-binding protein loci," FEBS Letters, 589:849-856, (2015).

Mullins, et al., "Transgenesis in the rat and larger mammals," J. Clin. Invest. 97(7):1557-1560, (1996).
Munoz, et al., "Conventional pluripotency markers are unspecific for bovine embryonic-derived cell-lines," Theriogenology, 69(9): 1159-1164, (2008).
Murakami, et al., "Schwann cells contribute to neurodegeneration in transthyretin amyloidosis," Journal of Neurochemistry, 134:66-74, (2015).
Nagata, et al., "A 6-kb Upstream Region of the Human Transthyretin Gene Can Direct Developmental, Tissue-Specific , and Quantitatively Normal Expression in Transgenic Mouse," J. Biochem., 117: 169-175, (1995).
Niemann, "Transgenic farm animals get off the ground. Transgenic Animals in Agriculture, Conference Tahoe City, California, USA. Aug. 24-27, 1997." Transgenic Res., 7(1): 73-75, (1998).
Pankowicz, et al., "CRISPR/Cas9: at the cutting edge of hepatology," Gut, 66(7):1329-1340, (2017).
Paris, et al., "Equine embryos and embryonic stem cells: defining reliable markers of pluripotency, " Theriogenology, 74(4): 516-524, (2010).
Parman, et al., "Sixty years of transthyretin familial amyloid polyneuropathy (TTR-FAB) in Europe: where are we now? A European network approach to defining the epidemiology and management patterns for TTR-FAB," Curr Opin Neurol, 29 (suppl 1): S3-S13, (2016).
PCT/US2018/053389 International Search Report and Written Opinion of the International Searching Authority dated Jan. 14, 2019.
Poueymirou, et al., "F0 generation mice fully derived from gene-targeted embryonic stem cells allowing immediate phenotypic analyses," Nat. Biotechnol., 25(1):91-99, (2007).
Quadro, et al., "Impaired retinal function and vitamin A availability in mice lacking retinol-binding protein," The EMBO Journal, 18(17):4633-4644, (1999).
Reixach, et al., "Cell based screening of inhibitors of transthyretin aggregation," Biochemical and Biophysical Research Communications, 348:889-897, (2006).
Rezza, et al., "Unexpected genomic rearrangements at targeted loci associated with CRISPR/Cas9-mediated knock-in," Sci. Rep., 9(1):3486, (2019).
Ristevski, "Making better transgenic models: conditional, temporal, and spatial approaches," Mol. Biotechnol., 29(2):153-163, (2005).
Rogers, et al., "Disruption of the CFTR Gene Produces a Model of Cystic Fibrosis in Newborn Pigs," Science, 321(5897):1837-1841, (2008).
Ruberg, et al., "Transthyretin (TTR) Cardiac Amyloidosis," Circulation, 126:1286-1300, doi.10.1161/circulationaha.111.078915, (2012).
Santos, et al., "The heat shock response modulates transthyretin deposition in the peripheral and autonomic nervous systems," Neurobiology, 21:280-289, (2010).
Saraiva, et al., "Transthyretin amyloidosis: a tale of weak interactions," FEBS Letters, 498:201-203, (2001).
Sasaki, et al., "Generation of Transgenic Mice Producing A Human Transthyretin Variant: A Possible Mouse Model for Familial Amyloidotic Polyneuropathy," Biochemical and Biophysical Research Communications, 139(2):794-799, (Sep. 17, 1986).
Sekijima, et al., "Energetic Characteristics of the New Transthyretin Variant A25T May Explain Its Atypical Central Nervous System Pathology," Laboratory Investigation, 83(3):409-417, (2003).
Sekijima, et al., "R104H may suppress transthyretin amyloidogenesis by thermodynamic stabilization, but not by the kinetic mechanism characterizing T119 interallelic trans-suppression," Amyloid, 12(2): 57-60, (Jun. 2006).
Sigmund, "Viewpoint: Are Studies in Genetically Altered Mice Out of Control?," Arterioscler. Thromb. Vasc. Biol., 20(6):1425-1429, (2000).
Smith, et al., "The Effects of Disease of the Liver, Thyroid, and Kidneys on the Transport of Vitamin A in Human Plasma," The Journal of Clinical Investigation, 50:2426-2436, (1971).
Sousa, et al., "Deposition and passage of transthyretin through the blood-nerve barrier in recipients of familial amyloid polyneuropathy livers," Laboratory Investigation, 84:865-873, (2004).

(56) References Cited

OTHER PUBLICATIONS

Sousa, et al., "Evidence for Early Cytotoxic Aggregates in Transgenic Mice for Human Transthyretin Leu55Pro," American Journal of Pathology, 161(5):1935-1948, (Nov. 2002).
Sousa, et al., "Familial Amyloidotic Polyneuropathy in Sweden: Geographical Distribution, Age of Onset, and Prevalence," Hum Hered, 43:288-294, (1993).
Sousa, et al., "Transthyretin is involved in depression-like behaviour and exploratory activity," J. Neurochem., 88(5):1052-1058, (2004).
Stangou, et al., "Transmission of Systemic Transthyretin Amyloidosis by Means of Domino Liver Transplantation," The New England Journal of Medicine, 352(22):2356, (Jun. 2, 2005).
Steward, et al., "Different disease-causing mutations in transthyretin trigger the same conformational conversion," Protein Engineering, Design Selection, 21(3):187-195, (2008).
Tagoe, et al., "Amyloidogenesis is neither accelerated nor enhanced by injections of preformed fibrils in mice transgenic for wild-type human transthyretin: the question of infectivity," Amyloid: J. Protein Folding Disord., 11:21-26, (2004).
Tagoe, et al., "In vivo stabilization of mutant human transthyretin in transgenic mice," Amyloid, 14(3):227-236, (2007).
Takaoka, et al., "Comparison of amyloid deposition in two lines of transgenic mouse that model familial amyloidotic polyneuropathy, type I," Transgenic Research, 6:261-269, (1997).
Takaoka, et al., "Cysteine 10 Is a Key Residue in Amyloidogenesis of Human Transthyretin Val30Met," American Journal of Pathology, 164(1):337-345, (Jan. 2004).
Teng, et al., "Amyloid and Nonfibrillar Deposits in Mice Transgenic for Wild-Type Human Transthyretin: A Possible Model for Senile Systemic Amyloidosis," Lab. Invest., 81(3):385-396, (2001).
Terazaki, et al., "Immunization in familial amyloidotic polyneuropathy: counteracting deposition by immunization with a Y78F TTR mutant,", Laboratory Investigation, 86:23-31, (2006).
Ueda, et al., "A transgenic rat with the human ATTR V30M: A novel tool for analyses of ATTR metabolisms," Biochemical and Biophysical Research Communications, 352:299-304, (2007).
Ueda, et al., "Recent advances in transthyretin amyloidosis therapy," Translational Neurodegeneration, 3:19, pp. 1-10, (2014).
Valenzuela, et al., "High-throughput engineering of the mouse genome coupled with high-resolution expression analysis," Nat. Biotechnol., 21(6):652-659, (2003).
Vidal, et al., "Meningocerebrovascular Amyloidosis Associated with a Novel Transthyretin Mis-Sense Mutation at Codon 18 (TTRD18G)," American Journal of Pathology, 148(2):361-366, (1996).
Vranckx, et al., "Immunological quantitation of rat and mouse thyroxime-binding globulins. Ontogenesis and sex-dependence of the circulating levels of the thyroxine-binding globulins," Acta Endocrinologica (Copenh), 123:649-656, (1990).
Wakchaure, et al., "Transgenic Animals: A Review on its Various Dimensions and Applications in Animal Biotechnology," International Journal of Emerging Technology and Advanced Engineering, 5(11):210-213, (2015).
Wang et al., "Mapping a functional cancer genome atlas of tumor suppressors in mouse liver using AAV-CRISPR-mediated direct in vivo screening," Sci. Adv. 4(2):eaao5508, (Feb. 28, 2018).
Wati, et al., "Transthyretin Accelerates Vascular Aβ Deposition in a Mouse Model of Alzheimer's Disease," Brain Pathology, 19(1):48-57, (Jan. 2009) Abstract only.
Westermark, et al., "Prion-like aggregates: infectious agents in human disease," Trends in Molecular Medicine, 16(1):501-507, (Nov. 2010).
White, et al., "Support for the multigenic hypothesis of amyloidosis: The binding stoichiometry of retinol-binding protein, vitamin A, and thyroid hormone influences transthyretin amyloidogenicity in vitro," PNAS, 98(23):12019-13024, (Nov. 6, 2001).
Yamamura, et al., "Expression of tissue-specific genes in transgenic mice," Regulatory Mechanisms in Developmental Processes, eds. G. Eguchi, T.S. Okada, L. Saxén, pp. 47-52, (1998).
Yang, et al., "Initial Conformational Changes of Human Transthyretin under Partially Denaturing Conditions," Biophysical Journal, 89:433-443, (Jul. 2005).
Yi, et al., "Systemic Amyloidosis in Transgenic Mice Carrying the Human Mutant Transthyretin (Met30) Gene," American Journal of Pathology, 138(2):403-412, (1991).
Zhao, et al., "Inconsistency between hepatic expression and serum concentration of transthyretin in mice humanized at the transthyretin locus," Genes to Cells, 13:1257-1268, (2008).
Zhou, et al., "Developing tTA transgenic rats for inducible and reversible gene expression," Int. J. Biol. Sci., 5(2):171-181, (2009).
Ibrahim, et al., "Contributions of Animal Models to the Mechanisms and Terapies of Transthyretin Amyloidosis," Front. Physiol., vol. 10, Article 338, (2019).
Kan, et al., "Sensory nerve degeneration in a mouse model mimicking early manifestations of familial amyloid polyneuropathy due to transthyretin Ala97Ser," Neuropathol. Appl. Neurobiol. 44(7):673-686, (2018).
PCT International Search Report and Written Opinion of the International Searching Authority for application PCT/US2020/035859 dated Sep. 17, 2020.
Aigner, et al., "Transgenic pigs as models for translational biomedical research," J. Mol. Med. (Berl). 88(7):653-664, (2010).
Kohno et al., "Analysis of amyloid deposition in a transgenic mouse model of homozygous familial amyloidotic polyneuropathy," Am. J. Pathol. 150(4):1497-1508, (Apr. 1997).
Loi, et al., "A New, Dynamic Era for Somatic Cell Nuclear Transfer?" Trends Biotechnol. 34(10:791-797, (2016).
Noborn, et al., "Heparan sulfate/heparin promotes transthyretin fibrillization through selective binding to a basic motif in the protein," Proc. Natl. Acad. Sci. U.S.A., 108(4):5584-5589, (Apr. 2011).
Olsson, et al., "A possible role for miRNA silencing in disease phenotype variation in Swedish transthyretin V30M carriers," BMC Med. Genet. 11:130, (2010).
Reixach, et al., "Tissue damage in the amyloidoses: Transthyretin monomers and nonnative oligomers are the major *cytotoxic* species in tissue culture," Proc. Natl. Acad. Sci. U.S.A., 101(9):2817-2822, (Mar. 2004).
Saelices, et al., "Amyloid seeding of transthyretin by ex vivo cardiac fibrils and its inhibition," Proc. Natl. Acad. Sci. U.S.A., 115(29):e6741-e6750, (Jun. 2018).
Sosa, et al., "Animal transgenesis: an overview," Brain Struct. Funct. 214(2-3):91-109, (2010).
Vasconcelos, et al., "Heterotypic seeding of Tau fibrillization by pre-aggregated Abeta provides potent seeds for prion-like seeding and propagation of Tau-pathology in vivo," Acta Neuropathol, 131(4):549-569, (Apr. 2016).
Wei, et al., "Deposition of transthyretin amyloid is not accelerated by the sam amyloid in vivo," Amyloid, 11(2):113-120, (Jun. 2004).
Wilmut, et al., "Somatic cell nuclear transfer: origins, the present position and future opportunities," Philos. Trans. R. Soc. Lond. B. Biol. Sci. 370(1680):20140366, (2015).
Zeng et al., "Viral transduction of male germline stem cells results in transgene transmission after germ cell transplantation in pigs," Biol. Reprod. 88(1):27, (2013).
Zhu et al., "Humanising the mouse genome piece by piece," Nat. Commun. 10(1):1845, (Apr. 23, 2019).

* cited by examiner

```
           10         20         30         40         50         60         70         80         90        100
mTTR       ATGGCTTCCCTTCGACTCTTCCTCCTTTGCCTCGCTGGACTGGTATTTGTGTCTCTGAAGCTGGGGGTGCTGGAGAATCCAAATGTCCTCTGATGG
hTTR       ATGGCTTCTCATCGTCTGCTCCTCCTCTGCCTTGCTGGACTGGTATTTGTGTCTGAGGCTGGCCACGGGTGGCTGGGAATCCAAGTGTCCTCTGATGG
hTTR 8-slip ATGGCTTCTCATCGTCTGCTCCTCCTCTGCCTTGCTGGACTGGTATTTGTGTCTCTGAGGCTGGCCACGGGTGGCTGGGAATCCAAGTGTCCTCTGATGG 110        120        130        140        150        160        170        180        190        200
mTTR       TCAAAGTTCCTGATGCTGTCCGAGGCAGCCTGCTGTAGACGTTGGCTGTAAAAAGACCTCTGAGGATCCTGGAGCCCTTTGCCTCTGG
hTTR       TCAAAGTTCTAGATGCTGTCCGAGGCAGCAGTCCTGCCATCAATGTGGCCGTGCATGTGTTCAGAAAGGCTGCTGATGACACCTGGGAGCCATTTGCCTCTGG
hTTR 8-slip TCAAAGTTCTAGATGCTGTCCGAGGCAGCAGTCCTGCCATCAATGTGGCCGTGCATGTGTTCAGAAAGGCTGCTGATGACACCTGGGAGCCATTTGCCTCTGG 210        220        230        240        250        260        270        280        290        300
mTTR       GAAGACCGCGGAGTCTGGAGAGCTGCACGGGCTCACCACAGAGAAGTTTGTAGAAGGAGTGTACAGAGTAGAACTGGACACCAAATCGTACTGGAAG
hTTR       GAAAACCAGTGAGTCTGGAGAGCTGCATGGGCTCACAACTGAGGAGGAATTTGTAGAAGGGATATACAAAGTGGAAATAGACACCAAATCTTACTGGAAG
hTTR 8-slip GAAAACCAGTGAGTCTGGAGAGCTGCATGGGCTCACAACTGAGGAGGAATTTGTAGAAGGGATATACAAAGTGGAAATAGACACCAAATCTTACTGGAAG 310        320        330        340        350        360        370        380        390        400
mTTR       ACACTTGGCATTCCCGTCTCCATGAATTCGCGGATGTGGTTTCACAGCCAACGACTCTGGCCACTACACCATCGCAGCCCTGCTCAGCCCAT
hTTR       GCACTTGGCATCTCCCCATTCCATGAGCATGCAGAGGTGGTATTCACAGACAGCAGCAGCACCAGCAGCACCAGCAAGCCGGGCCGCTGAGCCCCT
hTTR 8-slip GCACTTGGCATCTCCCCATTCCCATGAGCATGCAGAGGTGGTATTCACAGACAGCAGCAGCACCAGCAGCACCAGCAAGCCGGGCCGCTGAGCCCCT 410        420        430        440
mTTR       ACTCCTACAGCACCACGGCTGTCGTCAGCAACCCCCAGAATTGA        (SEQ ID NO: 8)
hTTR       ACTCCTATTCCACCACGGCTGTCGTCACCAATCCCAAGGAATGA        (SEQ ID NO: 4)
hTTR 8-slip ACTCCTATTCCACCACGGCTGTCGTCACCAATCCCAAGGAATGA       (SEQ ID NO: 10)
```

*FIG. 1B*

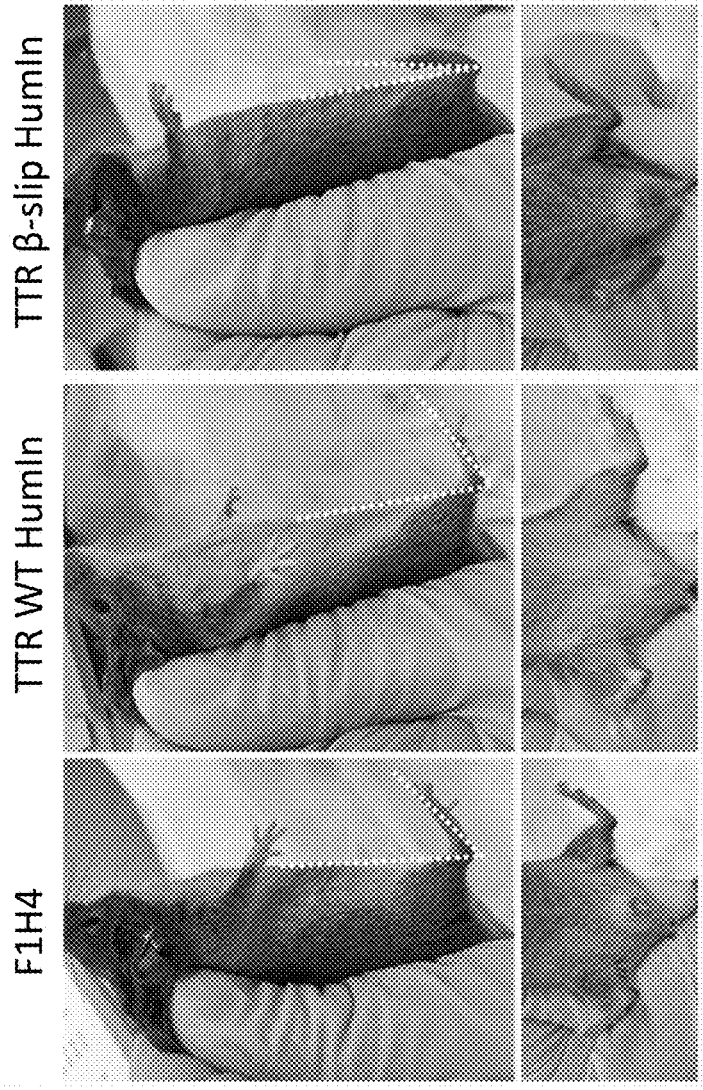
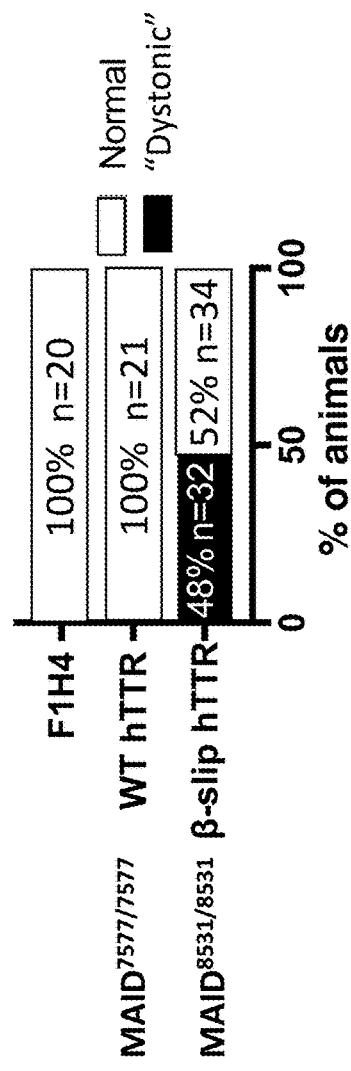
FIG. 7A
FIG. 7B

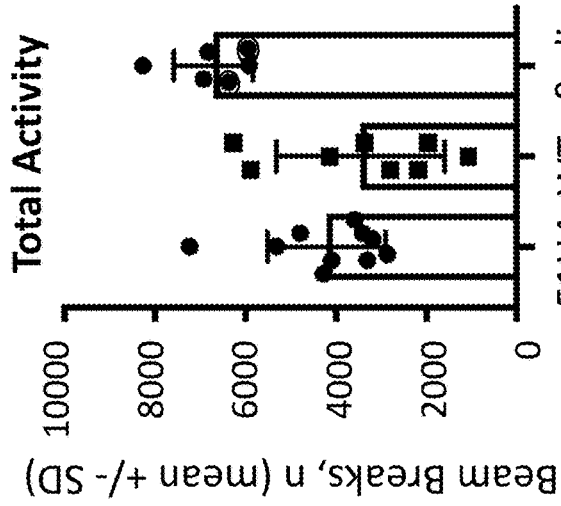
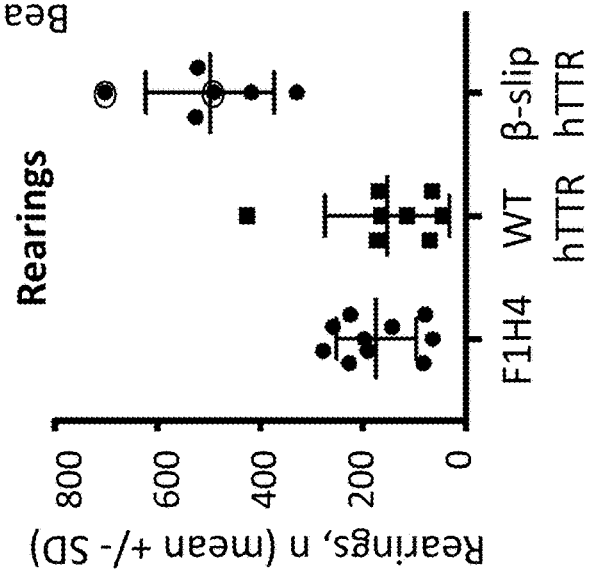
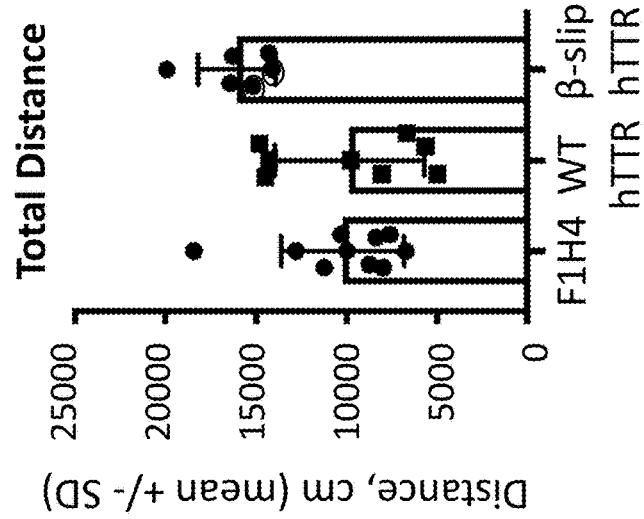
FIG. 8A
FIG. 8B
FIG. 8C

MOUSE COMPRISING A HUMANIZED TTR LOCUS WITH A BETA-SLIP MUTATION AND METHODS OF USE

CROSS-REFERENCE TO RELATED APPLICATIONS

This application claims the benefit of U.S. Application No. 62/856,999, filed Jun. 4, 2019, which is herein incorporated by reference in its entirety for all purposes.

REFERENCE TO A SEQUENCE LISTING SUBMITTED AS A TEXT FILE VIA EFS WEB

The Sequence Listing written in file 547048SEQLIST.txt is 124 kilobytes, was created on Jun. 2, 2020, and is hereby incorporated by reference.

BACKGROUND

Transthyretin (TTR) is a protein found in the serum and cerebrospinal fluid that carries thyroid hormone and retinol-binding protein to retinol. The liver secretes TTR into the blood, while the choroid plexus secretes it into the cerebrospinal fluid. TTR is also produced in the retinal pigmented epithelium and secreted into the vitreous. Misfolded and aggregated TTR accumulates in multiple tissues and organs in the amyloid diseases senile systemic amyloidosis (SSA), familial amyloid polyneuropathy (FAP), and familial amyloid cardiomyopathy (FAC).

There remains a need for suitable non-human animals providing the true human target or a close approximation of the true human target of human-TTR-targeting reagents at the endogenous Ttr locus, thereby enabling testing of the efficacy and mode of action of such agents in live animals as well as pharmacokinetic and pharmacodynamics studies in a setting where the humanized protein and humanized gene are the only version of TTR present.

SUMMARY

Non-human animals comprising a humanized TTR locus comprising a beta-slip mutation are provided, as well as methods of using such non-human animals. Also provided are non-human animals, non-human animal cells, and non-human animal genomes comprising a humanized TTR locus comprising a beta-slip mutation are provided, as well as methods of making and using such non-human animals, non-human animal cells, and non-human animal genomes. Also provided are humanized non-human animal TTR genes comprising a beta-slip mutation, nuclease agents and/or targeting vectors for use in humanizing a non-human animal TTR gene, and methods of making and using such humanized TTR genes.

In one aspect, provided are non-human animals comprising a humanized TTR locus comprising a beta-slip mutation. Also provided are non-human animals, non-human animal cells, and non-human animal genomes comprising in their genome a humanized TTR locus comprising a beta-slip mutation. Such non-human animals can comprise a genetically modified endogenous Ttr locus, wherein a region of the endogenous Ttr locus comprising both Ttr coding sequence and non-coding sequence has been deleted and replaced with an orthologous human TTR sequence comprising both TTR coding sequence and non-coding sequence, and wherein the genetically modified endogenous Ttr locus comprises a mutation that causes a shift in beta-strand D of the encoded transthyretin protein. Some such non-human animals, non-human animal cells, and non-human animal genomes can comprise a genetically modified endogenous Ttr locus, wherein a region of the endogenous Ttr locus comprising both Ttr coding sequence and non-coding sequence has been deleted and replaced with a corresponding human TTR sequence comprising both TTR coding sequence and non-coding sequence, and wherein the genetically modified endogenous Ttr locus comprises a mutation that causes a shift in beta-strand D of the encoded transthyretin protein. Optionally, the mutation causes a three-residue shift in beta strand D that places a residue corresponding to residue L58 in a human transthyretin protein at a position normally occupied by a residue corresponding to residue L55 in the human transthyretin protein when the encoded transthyretin protein is optimally aligned with the human transthyretin protein. Optionally, the mutation is a triple mutation corresponding to G53S/E54D/L55S in the human transthyretin protein when the encoded transthyretin protein is optimally aligned with the human transthyretin protein. Optionally, the triple mutation is in the orthologous human TTR sequence. Optionally, the triple mutation is in the corresponding human TTR sequence.

In some such non-human animals, the genetically modified endogenous Ttr locus comprises the endogenous Ttr promoter. In some such non-human animals, non-human animal cells, and non-human animal genomes the genetically modified endogenous Ttr locus comprises the endogenous Ttr promoter, wherein the human TTR sequence is operably linked to the endogenous Ttr promoter. Optionally, at least one intron and at least one exon of the endogenous Ttr locus have been deleted and replaced with the orthologous human TTR sequence. Optionally, at least one intron and at least one exon of the endogenous Ttr locus have been deleted and replaced with the corresponding human TTR sequence.

In some such non-human animals, the entire Ttr coding sequence of the endogenous Ttr locus has been deleted and replaced with the orthologous human TTR sequence. Optionally, the region of the endogenous Ttr locus from the Ttr start codon to the Ttr stop codon has been deleted and replaced with the orthologous human TTR sequence. In some such non-human animals, non-human animal cells, and non-human animal genomes the entire Ttr coding sequence of the endogenous Ttr locus has been deleted and replaced with the corresponding human TTR sequence. Optionally, the region of the endogenous Ttr locus from the Ttr start codon to the Ttr stop codon has been deleted and replaced with the corresponding human TTR sequence.

In some such non-human animals, the genetically modified endogenous Ttr locus comprises a human TTR 3' untranslated region. In some such non-human animals, the endogenous Ttr 5' untranslated region has not been deleted and replaced with the orthologous human TTR sequence. In some such non-human animals, non-human animal cells, and non-human animal genomes the genetically modified endogenous Ttr locus comprises a human TTR 3' untranslated region. In some such non-human animals, non-human animal cells, and non-human animal genomes the endogenous Ttr 5' untranslated region has not been deleted and replaced with the corresponding human TTR sequence.

In some such non-human animals, the region of the endogenous Ttr locus from the Ttr start codon to the Ttr stop codon has been deleted and replaced with a human TTR sequence comprising the orthologous human TTR sequence and a human TTR 3' untranslated region, and the endogenous Ttr 5' untranslated region has not been deleted and replaced with the orthologous human TTR sequence, and the endogenous Ttr promoter has not been deleted and replaced with the orthologous human TTR sequence. In some such non-human animals, non-human animal cells, and non-human animal genomes the region of the endogenous Ttr locus from the Ttr start codon to the Ttr stop codon has been deleted and replaced with a human TTR sequence comprising the corresponding human TTR sequence and a human TTR 3' untranslated region, and the endogenous Ttr 5' untranslated region has not been deleted and replaced with the corresponding human TTR sequence, and the endogenous Ttr promoter has not been deleted and replaced with the corresponding human TTR sequence. Optionally, the human TTR sequence at the genetically modified endogenous Ttr locus comprises, consists essentially of, or consists of a sequence at least 90%, 95%, 96%, 97%, 98%, 99%, or 100% identical to the sequence set forth in SEQ ID NO: 14. Optionally, the human TTR sequence at the genetically modified endogenous Ttr locus comprises, consists essentially of, or consists of a sequence at least about 90%, at least about 95%, at least about 96%, at least about 97%, at least about 98%, at least about 99%, or about 100% identical to the sequence set forth in SEQ ID NO: 14. Optionally, the genetically modified endogenous Ttr locus encodes a protein comprising, consisting essentially of, or consisting of a sequence at least 90%, 95%, 96%, 97%, 98%, 99%, or 100% identical to the sequence set forth in SEQ ID NO: 9. Optionally, the genetically modified endogenous Ttr locus encodes a protein comprising, consisting essentially of, or consisting of a sequence at least about 90%, at least about 95%, at least about 96%, at least about 97%, at least about 98%, at least about 99%, or about 100% identical to the sequence set forth in SEQ ID NO: 9. Optionally, the genetically modified endogenous Ttr locus comprises a coding sequence comprising, consisting essentially of, or consisting of a sequence at least 90%, 95%, 96%, 97%, 98%, 99%, or 100% identical to the sequence set forth in SEQ ID NO: 10. Optionally, the genetically modified endogenous Ttr locus comprises a coding sequence comprising, consisting essentially of, or consisting of a sequence at least about 90%, at least about 95%, at least about 96%, at least about 97%, at least about 98%, at least about 99%, or about 100% identical to the sequence set forth in SEQ ID NO: 10. Optionally, the genetically modified endogenous Ttr locus comprises, consists essentially of, or consists of a sequence at least 90%, 95%, 96%, 97%, 98%, 99%, or 100% identical to the sequence set forth in SEQ ID NO: 12 or 13. Optionally, the genetically modified endogenous Ttr locus comprises, consists essentially of, or consists of a sequence at least about 90%, at least about 95%, at least about 96%, at least about 97%, at least about 98%, at least about 99%, or about 100% identical to the sequence set forth in SEQ ID NO: 12 or 13.

In some such non-human animals, the genetically modified endogenous Ttr locus encodes a transthyretin precursor protein comprising a signal peptide, and the region of the endogenous Ttr locus encoding the signal peptide has not been deleted and replaced with the orthologous human TTR sequence. Optionally, the first exon of the endogenous Ttr locus has not been deleted and replaced with the orthologous human TTR sequence. Optionally, the first exon and first intron of the endogenous Ttr locus have not been deleted and replaced with the orthologous human TTR sequence. Optionally, the region of the endogenous Ttr locus from the start of the second Ttr exon to the Ttr stop codon has been deleted and replaced with the orthologous human TTR sequence. Optionally, the genetically modified endogenous Ttr locus comprises a human TTR 3' untranslated region. In some such non-human animals, non-human animal cells, and non-human animal genomes the genetically modified endogenous Ttr locus encodes a transthyretin precursor protein comprising a signal peptide, and the region of the endogenous Ttr locus encoding the signal peptide has not been deleted and replaced with the corresponding human TTR sequence. Optionally, the first exon of the endogenous Ttr locus has not been deleted and replaced with the corresponding human TTR sequence. Optionally, the first exon and first intron of the endogenous Ttr locus have not been deleted and replaced with the corresponding human TTR sequence. Optionally, the region of the endogenous Ttr locus from the start of the second Ttr exon to the Ttr stop codon has been deleted and replaced with the corresponding human TTR sequence. Optionally, the genetically modified endogenous Ttr locus comprises a human TTR 3' untranslated region.

In some such non-human animals, the region of the endogenous Ttr locus from the second Ttr exon to the Ttr stop codon has been deleted and replaced with a human TTR sequence comprising the orthologous human TTR sequence and a human TTR 3' untranslated region, and the endogenous Ttr 5' untranslated region has not been deleted and replaced with the orthologous human TTR sequence, and the endogenous Ttr promoter has not been deleted and replaced with the orthologous human TTR sequence. In some such non-human animals, non-human animal cells, and non-human animal genomes the region of the endogenous Ttr locus from the second Ttr exon to the Ttr stop codon has been deleted and replaced with a human TTR sequence comprising the corresponding human TTR sequence and a human TTR 3' untranslated region, and the endogenous Ttr 5' untranslated region has not been deleted and replaced with the corresponding human TTR sequence, and the endogenous Ttr promoter has not been deleted and replaced with the corresponding human TTR sequence.

In some such non-human animals, the genetically modified endogenous Ttr locus does not comprise a selection cassette or a reporter gene. In some such non-human animals, the genetically modified endogenous Ttr locus does comprise a selection cassette or a reporter gene. In some such non-human animals, the non-human animal is homozygous for the genetically modified endogenous Ttr locus. In some such non-human animals, the non-human animal is heterozygous for the genetically modified endogenous Ttr locus. In some such non-human animals, non-human animal cells, and non-human animal genomes the genetically modified endogenous Ttr locus does not comprise a selection cassette or a reporter gene. In some such non-human animals, non-human animal cells, and non-human animal genomes the genetically modified endogenous Ttr locus does comprise a selection cassette or a reporter gene. In some such non-human animals, non-human animal cells, and non-human animal genomes the non-human animal is homozygous for the genetically modified endogenous Ttr locus. In some such non-human animals, non-human animal cells, and non-human animal genomes the non-human animal is heterozygous for the genetically modified endogenous Ttr locus. In some such non-human animals, the non-human animal comprises the genetically modified endogenous Ttr locus in its germline.

In some such non-human animals, the non-human animal is a mammal. In some such non-human animals, non-human animal cells, and non-human animal genomes the non-human animal is a mammal. Optionally, the mammal is a rodent. Optionally, the rodent is a rat or mouse. Optionally, the non-human animal is a mouse.

In some such non-human animals, the non-human animal is hyperactive relative to a control wild type non-human animal or a non-human animal comprising the genetically modified endogenous Ttr locus without the mutation. In some such non-human animals, non-human animal cells, and non-human animal genomes the non-human animal is hyperactive relative to a control wild type non-human animal or a non-human animal comprising the genetically modified endogenous Ttr locus without the mutation. Optionally, the hyperactivity is as measured by one or more or all of total distance, total activity, or total rearings in an open field test. In some such non-human animals, the non-human animal displays hindlimb dystonia. In some such non-human animals, non-human animal cells, and non-human animal genomes the non-human animal displays hindlimb dystonia. In some such non-human animals, wherein the non-human animal comprises amyloid deposits. In some such non-human animals, non-human animal cells, and non-human animal genomes wherein the non-human animal comprises amyloid deposits. Optionally, the non-human animal comprises amyloid deposits in the sciatic nerve. Optionally, the non-human animal develops amyloidosis by about two months of age.

In another aspect, provided are targeting vectors for generating a genetically modified endogenous Ttr locus in which a region of the endogenous Ttr locus comprising both Ttr coding sequence and non-coding sequence has been deleted and replaced with a corresponding human TTR sequence comprising both TTR coding sequence and non-coding sequence, and wherein the genetically modified endogenous Ttr locus comprises a mutation that causes a shift in beta-strand D of the encoded transthyretin protein, wherein the targeting vector comprises an insert nucleic acid comprising the corresponding human TTR sequence flanked by a 5' homology arm targeting a 5' target sequence at the endogenous Ttr locus and a 3' homology arm targeting a 3' target sequence at the endogenous Ttr locus.

In another aspect, provided are genetically modified non-human animal Ttr genes in which a region of the endogenous Ttr gene comprising both Ttr coding sequence and non-coding sequence has been deleted and replaced with a corresponding human TTR sequence comprising both TTR coding sequence and non-coding sequence, and wherein the genetically modified non-human animal Ttr gene comprises a mutation that causes a shift in beta-strand D of the encoded transthyretin protein.

In another aspect, provided are methods of using the non-human animals comprising a humanized TTR locus to assess the activity of human-TTR-targeting reagents in vivo. Such methods can comprise: (a) administering the human-TTR-targeting reagent to any of the above non-human animals; and (b) assessing the activity of the human-TTR-targeting reagent in the non-human animal.

In some such methods, the introducing comprises adeno-associated virus (AAV)-mediated delivery, lipid nanoparticle (LNP)-mediated delivery, or hydrodynamic delivery (HDD). Optionally, the introducing comprises LNP-mediated delivery. Optionally, the introducing comprises AAV8-mediated delivery.

In some such methods, step (b) comprises isolating a liver from the non-human animal and assessing activity of the human-TTR-targeting reagent in the liver. Optionally, step (b) further comprises assessing activity of the human-TTR-targeting reagent in an organ or tissue other than the liver.

In some such methods, the assessing comprises assessing modification of the genetically modified Ttr locus. In some such methods, the assessing comprises assessing expression of a Ttr messenger RNA encoded by the genetically modified Ttr locus. In some such methods, the assessing comprises assessing expression of a TTR protein encoded by the genetically modified Ttr locus. Optionally, assessing expression of the TTR protein comprises measuring serum levels of the TTR protein in the non-human animal. Optionally, the activity is assessed in the liver of the non-human animal.

In some such methods, the assessing comprises assessing hyperactivity. In some such methods, the assessing comprises assessing hindlimb dystonia. In some such methods, the assessing comprises assessing amyloid deposition. Optionally, the assessing comprises assessing amyloid deposition in the sciatic nerve. In some such methods, the assessing is in comparison to an untreated control non-human animal.

In some such methods, the human-TTR-targeting reagent comprises a nuclease agent designed to target a region of a human TTR gene. Optionally, the nuclease agent comprises a Cas protein and a guide RNA designed to target a guide RNA target sequence in the human TTR gene. Optionally, the Cas protein is a Cas9 protein. In some such methods, the human-TTR-targeting reagent comprises an exogenous donor nucleic acid, wherein the exogenous donor nucleic acid is designed to recombine with the human TTR gene. Optionally, the exogenous donor nucleic acid is a single-stranded oligodeoxynucleotide (ssODN). In some such methods, the human-TTR-targeting reagent comprises an antigen-binding protein. In some such methods, the human-TTR-targeting reagent comprises an RNAi agent or an antisense oligonucleotide.

In some such methods, assessing the activity of the human-TTR-targeting reagent in the non-human animal comprises assessing transthyretin activity. In some such methods, the assessing is in comparison to an untreated control non-human animal.

In another aspect, provided are methods of optimizing the activity of a human-TTR-targeting reagent in vivo. Such methods can comprise: (I) performing any of the above methods of assessing the activity of human-TTR-targeting reagents in vivo a first time in a first non-human animal; (II) changing a variable and performing the method of step (I) a second time with the changed variable in a second non-human animal; and (III) comparing the activity of the human-TTR-targeting reagent in step (I) with the activity of the human-TTR-targeting reagent in step (II), and selecting the method resulting in the higher efficacy, higher precision, higher consistency, or higher specificity. Such methods can comprise: (I) performing any of the above methods of assessing the activity of human-TTR-targeting reagents in vivo a first time in a first non-human animal comprising in its genome the genetically modified endogenous Ttr locus; (II) changing a variable and performing the method of step (I) a second time with the changed variable in a second non-human animal comprising in its genome the genetically modified endogenous Ttr locus; and (III) comparing the activity of the human-TTR-targeting reagent in step (I) with the activity of the human-TTR-targeting reagent in step (II), and selecting the method resulting in the higher efficacy, higher precision, higher consistency, or higher specificity.

Optionally, the changed variable in step (II) is the delivery method of introducing the human-TTR-targeting reagent into the non-human animal. Optionally, the changed variable in step (II) is the route of administration of introducing the human-TTR-targeting reagent into the non-human animal. Optionally, the changed variable in step (II) is the concentration or amount of the human-TTR-targeting reagent introduced into the non-human animal. Optionally, the changed variable in step (II) is the form of the human-TTR-targeting reagent introduced into the non-human animal. Optionally, the changed variable in step (II) is the human-TTR-targeting reagent introduced into the non-human animal.

In another aspect, provided are methods of making the non-human animals comprising a humanized TTR locus. Such methods can comprise: (a) modifying the genome of a pluripotent non-human animal cell to comprise the genetically modified endogenous Ttr locus; (b) identifying or selecting the genetically modified pluripotent non-human animal cell comprising the genetically modified endogenous Ttr locus; (c) introducing the genetically modified pluripotent non-human animal cell into a non-human animal host embryo; and (d) gestating the non-human animal host embryo in a surrogate mother. Such methods can alternatively comprise: (a) modifying the genome of a non-human animal one-cell stage embryo to comprise the genetically modified endogenous Ttr locus; (b) selecting the genetically modified non-human animal one-cell stage embryo comprising the genetically modified endogenous Ttr locus; and (c) gestating the genetically modified non-human animal one-cell stage embryo in a surrogate mother.

BRIEF DESCRIPTION OF THE FIGURES

FIG. 1B shows an alignment of mouse, human wild type, and human beta-slip transthyretin (TTR) coding sequences (SEQ ID NOS: 8, 4, and 10, respectively). The signal peptide, T4 binding domain, phase 0 exon/intron boundaries, and phase 1/2 exon/intron boundaries are denoted, along with the beta-slip mutations.

FIGS. 7A-7B show the dystonic phenotype in humanized TTR beta-slip mice.

FIG. 7A show pictures of two-month old humanized TTR beta-slip mice, humanized TTR wild type mice, and control F1H4 mice after scruffing to assess the angle of their hindlimbs relative to the axis of their bodies. FIG. 7B shows a quantification of the number of normal mice and the number of mice with a dystonic phenotype. Dystonic mice are marked by the encircled red dots.

FIGS. 8A-8C show various readouts from two-month old humanized TTR beta-slip mice, humanized TTR wild type mice, and control F1H4 mice in an open field behavioral test, including total distance (FIG. 8A), total activity (FIG. 8B), and rearings (FIG. 8C).

DEFINITIONS

Figure 1A:
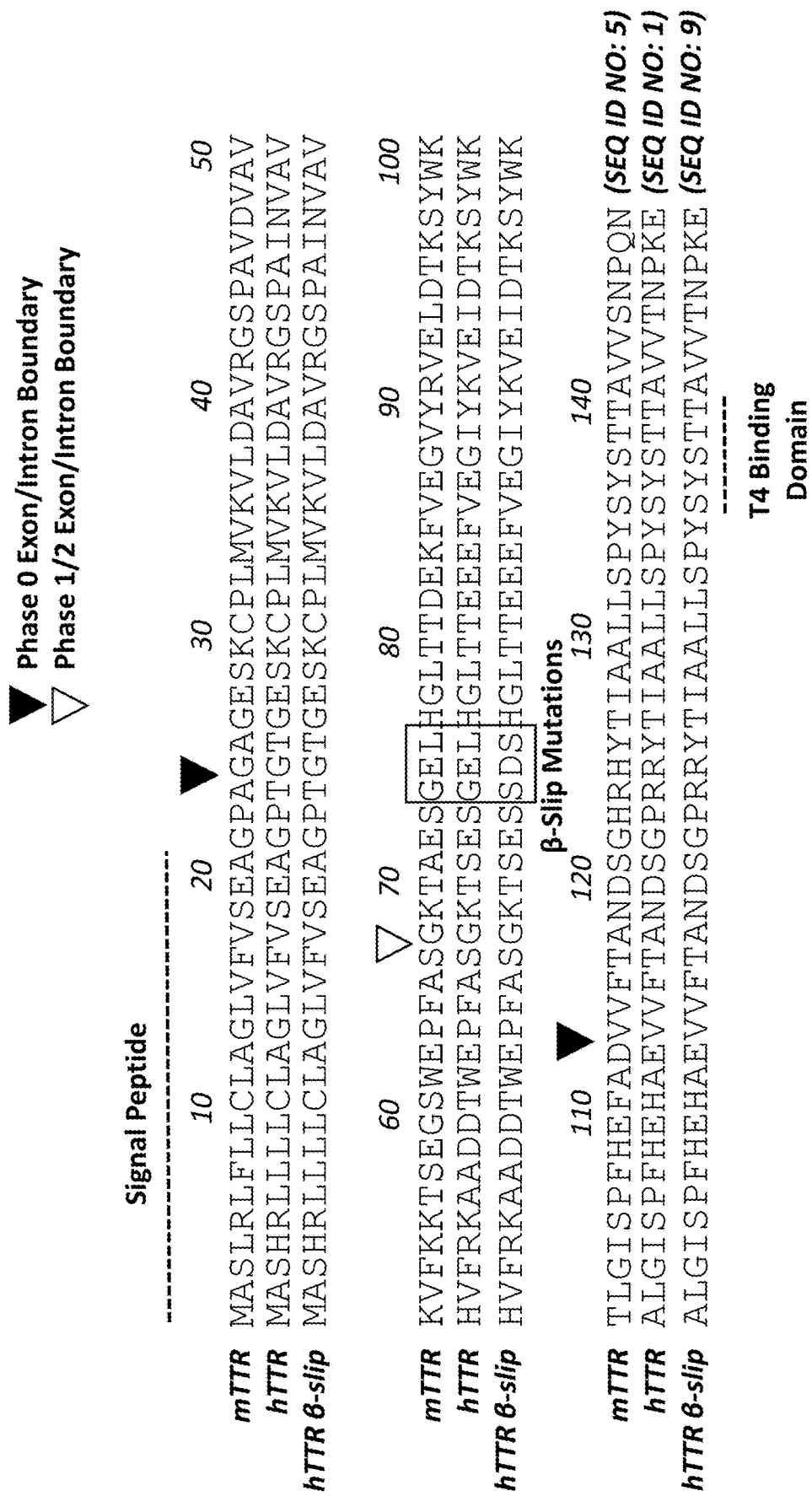
FIG. 1A shows an alignment of mouse, human wild type, and human beta-slip transthyretin (TTR) precursor proteins (SEQ ID NOS: 5, 1, and 9, respectively). The signal peptide, T4 binding domain, phase 0 exon/intron boundaries, and phase 1/2 exon/intron boundaries are denoted, along with the beta-slip mutations.

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones. The term "domain" refers to any part of a protein or polypeptide having a particular function or structure.

Proteins are said to have an "N-terminus" and a "C-terminus." The term "N-terminus" relates to the start of a protein or polypeptide, terminated by an amino acid with a free amine group (—NH2). The term "C-terminus" relates to the end of an amino acid chain (protein or polypeptide), terminated by a free carboxyl group (—COOH).

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

Nucleic acids are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. An end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. A nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements.

The term "genomically integrated" refers to a nucleic acid that has been introduced into a cell such that the nucleotide sequence integrates into the genome of the cell. Any protocol may be used for the stable incorporation of a nucleic acid into the genome of a cell.

The term "expression vector" or "expression construct" or "expression cassette" refers to a recombinant nucleic acid containing a desired coding sequence operably linked to appropriate nucleic acid sequences necessary for the expression of the operably linked coding sequence in a particular host cell or organism. Nucleic acid sequences necessary for expression in prokaryotes usually include a promoter, an operator (optional), and a ribosome binding site, as well as other sequences. Eukaryotic cells are generally known to utilize promoters, enhancers, and termination and polyadenylation signals, although some elements may be deleted and other elements added without sacrificing the necessary expression.

The term "targeting vector" refers to a recombinant nucleic acid that can be introduced by homologous recombination, non-homologous-end-joining-mediated ligation, or any other means of recombination to a target position in the genome of a cell.

The term "viral vector" refers to a recombinant nucleic acid that includes at least one element of viral origin and includes elements sufficient for or permissive of packaging into a viral vector particle. The vector and/or particle can be utilized for the purpose of transferring DNA, RNA, or other nucleic acids into cells in vitro, ex vivo, or in vivo. Numerous forms of viral vectors are known.

The term "isolated" with respect to proteins, nucleic acids, and cells includes proteins, nucleic acids, and cells that are relatively purified with respect to other cellular or organism components that may normally be present in situ, up to and including a substantially pure preparation of the protein, nucleic acid, or cell. The term "isolated" also includes cells, proteins, and nucleic acids that have no naturally occurring counterpart or proteins or nucleic acids that have been chemically synthesized and are thus substantially uncontaminated by other proteins or nucleic acids. The term "isolated" also includes proteins, nucleic acids, or cells that have been separated or purified from most other cellular components or organism components with which they are naturally accompanied (e.g., other cellular proteins, nucleic acids, or cellular or extracellular components).

The term "wild type" includes entities having a structure and/or activity as found in a normal (as contrasted with mutant, diseased, altered, or so forth) state or context. Wild type genes and polypeptides often exist in multiple different forms (e.g., alleles).

The term "endogenous sequence" refers to a nucleic acid sequence that occurs naturally within a cell or non-human animal. For example, an endogenous Ttr sequence of a non-human animal refers to a native Ttr sequence that naturally occurs at the Ttr locus in the non-human animal.

"Exogenous" molecules or sequences include molecules or sequences that are not normally present in a cell in that form. Normal presence includes presence with respect to the particular developmental stage and environmental conditions of the cell. An exogenous molecule or sequence, for example, can include a mutated version of a corresponding endogenous sequence within the cell, such as a humanized version of the endogenous sequence, or can include a sequence corresponding to an endogenous sequence within the cell but in a different form (i.e., not within a chromosome). In contrast, endogenous molecules or sequences include molecules or sequences that are normally present in that form in a particular cell at a particular developmental stage under particular environmental conditions.

The term "heterologous" when used in the context of a nucleic acid or a protein indicates that the nucleic acid or protein comprises at least two segments that do not naturally occur together in the same molecule. For example, the term "heterologous," when used with reference to segments of a nucleic acid or segments of a protein, indicates that the nucleic acid or protein comprises two or more sub-sequences that are not found in the same relationship to each other (e.g., joined together) in nature. As one example, a "heterologous" region of a nucleic acid vector is a segment of nucleic acid within or attached to another nucleic acid molecule that is not found in association with the other molecule in nature. For example, a heterologous region of a nucleic acid vector could include a coding sequence flanked by sequences not found in association with the coding sequence in nature. Likewise, a "heterologous" region of a protein is a segment of amino acids within or attached to another peptide molecule that is not found in association with the other peptide molecule in nature (e.g., a fusion protein, or a protein with a tag). Similarly, a nucleic acid or protein can comprise a heterologous label or a heterologous secretion or localization sequence.

"Codon optimization" takes advantage of the degeneracy of codons, as exhibited by the multiplicity of three-base pair codon combinations that specify an amino acid, and generally includes a process of modifying a nucleic acid sequence for enhanced expression in particular host cells by replacing at least one codon of the native sequence with a codon that is more frequently or most frequently used in the genes of the host cell while maintaining the native amino acid sequence. For example, a nucleic acid encoding a Cas9 protein can be modified to substitute codons having a higher frequency of usage in a given prokaryotic or eukaryotic cell, including a bacterial cell, a yeast cell, a human cell, a non-human cell, a mammalian cell, a rodent cell, a mouse cell, a rat cell, a hamster cell, or any other host cell, as compared to the naturally occurring nucleic acid sequence. Codon usage tables are readily available, for example, at the "Codon Usage Database." These tables can be adapted in a number of ways. See Nakamura et al. (2000) *Nucleic Acids Research* 28:292, herein incorporated by reference in its entirety for all purposes. Computer algorithms for codon optimization of a particular sequence for expression in a particular host are also available (see, e.g., Gene Forge).

The term "locus" refers to a specific location of a gene (or significant sequence), DNA sequence, polypeptide-encoding sequence, or position on a chromosome of the genome of an organism. For example, a "Ttr locus" may refer to the specific location of a Ttr gene, Ttr DNA sequence, transthyretin-encoding sequence, or Ttr position on a chromosome of the genome of an organism that has been identified as to where such a sequence resides. A "Ttr locus" may comprise a regulatory element of a Ttr gene, including, for example, an enhancer, a promoter, 5' and/or 3' untranslated region (UTR), or a combination thereof.

The term "gene" refers to a DNA sequence in a chromosome that codes for a product (e.g., an RNA product and/or a polypeptide product) and includes the coding region interrupted with non-coding introns and sequence located adjacent to the coding region on both the 5' and 3' ends such that the gene corresponds to the full-length mRNA (including the 5' and 3' untranslated sequences). The term "gene" also includes other non-coding sequences including regulatory sequences (e.g., promoters, enhancers, and transcription factor binding sites), polyadenylation signals, internal ribosome entry sites, silencers, insulating sequence, and matrix attachment regions may be present in a gene. These sequences may be close to the coding region of the gene (e.g., within 10 kb) or at distant sites, and they influence the level or rate of transcription and translation of the gene.

The term "allele" refers to a variant form of a gene. Some genes have a variety of different forms, which are located at the same position, or genetic locus, on a chromosome. A diploid organism has two alleles at each genetic locus. Each pair of alleles represents the genotype of a specific genetic locus. Genotypes are described as homozygous if there are two identical alleles at a particular locus and as heterozygous if the two alleles differ.

The "coding region" or "coding sequence" of a gene consists of the portion of a gene's DNA or RNA, composed of exons, that codes for a protein. The region begins at the start codon on the 5' end and ends at the stop codon on the 3' end.

A "promoter" is a regulatory region of DNA usually comprising a TATA box capable of directing RNA polymerase II to initiate RNA synthesis at the appropriate transcription initiation site for a particular polynucleotide sequence. A promoter may additionally comprise other regions which influence the transcription initiation rate. The promoter sequences disclosed herein modulate transcription of an operably linked polynucleotide. A promoter can be active in one or more of the cell types disclosed herein (e.g., a eukaryotic cell, a non-human mammalian cell, a human cell, a rodent cell, a pluripotent cell, a one-cell stage embryo, a differentiated cell, or a combination thereof). A promoter can be, for example, a constitutively active promoter, a conditional promoter, an inducible promoter, a temporally restricted promoter (e.g., a developmentally regulated promoter), or a spatially restricted promoter (e.g., a cell-specific or tissue-specific promoter). Examples of promoters can be found, for example, in WO 2013/176772, herein incorporated by reference in its entirety for all purposes.

"Operable linkage" or being "operably linked" includes juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors. Operable linkage can include such sequences being contiguous with each other or acting in trans (e.g., a regulatory sequence can act at a distance to control transcription of the coding sequence).

"Complementarity" of nucleic acids means that a nucleotide sequence in one strand of nucleic acid, due to orientation of its nucleobase groups, forms hydrogen bonds with another sequence on an opposing nucleic acid strand. The complementary bases in DNA are typically A with T and C with G. In RNA, they are typically C with G and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm (melting temperature) of hybridized strands, or by empirical determination of Tm by using routine methods. Tm includes the temperature at which a population of hybridization complexes formed between two nucleic acid strands are 50% denatured (i.e., a population of double-stranded nucleic acid molecules becomes half dissociated into single strands). At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+ 0.41(% G+C), although other known Tm computations consider nucleic acid structural characteristics.

"Hybridization condition" includes the cumulative environment in which one nucleic acid strand bonds to a second nucleic acid strand by complementary strand interactions and hydrogen bonding to produce a hybridization complex. Such conditions include the chemical components and their concentrations (e.g., salts, chelating agents, formamide) of an aqueous or organic solution containing the nucleic acids, and the temperature of the mixture. Other factors, such as the length of incubation time or reaction chamber dimensions may contribute to the environment. See, e.g., Sambrook et al., Molecular Cloning, A Laboratory Manual, 2.sup.nd ed., pp. 1.90-1.91, 9.47-9.51, 1 1.47-11.57 (Cold Spring Harbor Laboratory Press, Cold Spring Harbor, N.Y., 1989), herein incorporated by reference in its entirety for all purposes.

Hybridization requires that the two nucleic acids contain complementary sequences, although mismatches between bases are possible. The conditions appropriate for hybridization between two nucleic acids depend on the length of the nucleic acids and the degree of complementation, variables which are well known. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or fewer, 30 or fewer, 25 or fewer, 22 or fewer, 20 or fewer, or 18 or fewer nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid include at least about 15 nucleotides, at least about 20 nucleotides, at least about 22 nucleotides, at least about 25 nucleotides, and at least about 30 nucleotides. Furthermore, the temperature and wash solution salt concentration may be adjusted as necessary according to factors such as length of the region of complementation and the degree of complementation.

The sequence of polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure). A polynucleotide (e.g., gRNA) can comprise at least 70%, at least 80%, at least 90%, at least 95%, at least 99%, or 100% sequence complementarity to a target region within the target nucleic acid sequence to which they are targeted. For example, a gRNA in which 18 of 20 nucleotides are complementary to a target region, and would therefore specifically hybridize, would represent 90% complementarity. In this example, the remaining noncomplementary nucleotides may be clustered or interspersed with complementary nucleotides and need not be contiguous to each other or to complementary nucleotides.

Percent complementarity between particular stretches of nucleic acid sequences within nucleic acids can be determined routinely using BLAST programs (basic local alignment search tools) and PowerBLAST programs (Altschul et al. (1990) *J. Mol. Biol.* 215:403-410; Zhang and Madden (1997) *Genome Res.* 7:649-656, each of which is herein incorporated by reference in its entirety for all purposes) or by using the Gap program (Wisconsin Sequence Analysis Package, Version 8 for Unix, Genetics Computer Group, University Research Park, Madison Wis.), using default settings, which uses the algorithm of Smith and Waterman (1981) *Adv. Appl. Math.* 2:482-489, herein incorporated by reference in its entirety for all purposes.

The methods and compositions provided herein employ a variety of different components. Some components throughout the description can have active variants and fragments. Such components include, for example, Cas proteins, CRISPR RNAs, tracrRNAs, and guide RNAs. Biological activity for each of these components is described elsewhere herein. The term "functional" refers to the innate ability of a protein or nucleic acid (or a fragment or variant thereof) to exhibit a biological activity or function. Such biological activities or functions can include, for example, the ability of a Cas protein to bind to a guide RNA and to a target DNA sequence. The biological functions of functional fragments or variants may be the same or may in fact be changed (e.g., with respect to their specificity or selectivity or efficacy) in comparison to the original molecule, but with retention of the molecule's basic biological function.

The term "variant" refers to a nucleotide sequence differing from the sequence most prevalent in a population (e.g., by one nucleotide) or a protein sequence different from the sequence most prevalent in a population (e.g., by one amino acid).

The term "fragment" when referring to a protein means a protein that is shorter or has fewer amino acids than the full-length protein. The term "fragment" when referring to a nucleic acid means a nucleic acid that is shorter or has fewer nucleotides than the full-length nucleic acid. A fragment can be, for example, when referring to a protein fragment, an N-terminal fragment (i.e., removal of a portion of the C-terminal end of the protein), a C-terminal fragment (i.e., removal of a portion of the N-terminal end of the protein), or an internal fragment (i.e., removal of a portion of each of the N-terminal and C-terminal ends of the protein). A fragment can be, for example, when referring to a nucleic acid fragment, a 5' fragment (i.e., removal of a portion of the 3' end of the nucleic acid), a 3' fragment (i.e., removal of a portion of the 5' end of the nucleic acid), or an internal fragment (i.e., removal of a portion each of the 5' and 3' ends of the nucleic acid).

"Sequence identity" or "identity" in the context of two polynucleotides or polypeptide sequences refers to the residues in the two sequences that are the same when aligned for maximum correspondence over a specified comparison window. When percentage of sequence identity is used in reference to proteins, residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

"Percentage of sequence identity" includes the value determined by comparing two optimally aligned sequences (greatest number of perfectly matched residues) over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. Unless otherwise specified (e.g., the shorter sequence includes a linked heterologous sequence), the comparison window is the full length of the shorter of the two sequences being compared.

Unless otherwise stated, sequence identity/similarity values include the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof "Equivalent program" includes any sequence comparison program that, for any two sequences in question, generates an alignment having identical nucleotide or amino acid residue matches and an identical percent sequence identity when compared to the corresponding alignment generated by GAP Version 10.

The term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine, or leucine for another non-polar residue. Likewise, examples of conservative substitutions include the substitution of one polar (hydrophilic) residue for another such as between arginine and lysine, between glutamine and asparagine, or between glycine and serine. Additionally, the substitution of a basic residue such as lysine, arginine, or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, or methionine for a polar (hydrophilic) residue such as cysteine, glutamine, glutamic acid or lysine and/or a polar residue for a non-polar residue. Typical amino acid categorizations are summarized in Table 1 below.

TABLE 1

Amino Acid Categorizations.

| Alanine | Ala | A | Nonpolar | Neutral | 1.8 |
|---|---|---|---|---|---|
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

A "homologous" sequence (e.g., nucleic acid sequence) includes a sequence that is either identical or substantially similar to a known reference sequence, such that it is, for example, at least 50%, at least 55%, at least 60%, at least 65%, at least 70%, at least 75%, at least 80%, at least 85%, at least 90%, at least 95%, at least 96%, at least 97%, at least 98%, at least 99%, or 100% identical to the known reference sequence. Homologous sequences can include, for example, orthologous sequence and paralogous sequences. Homologous genes, for example, typically descend from a common ancestral DNA sequence, either through a speciation event (orthologous genes) or a genetic duplication event (paralogous genes). "Orthologous" genes include genes in different species that evolved from a common ancestral gene by speciation. Orthologs typically retain the same function in the course of evolution. "Paralogous" genes include genes related by duplication within a genome. Paralogs can evolve new functions in the course of evolution.

The term "in vitro" includes artificial environments and to processes or reactions that occur within an artificial environment (e.g., a test tube or an isolated cell or cell line). The term "in vivo" includes natural environments (e.g., a cell or organism or body) and to processes or reactions that occur within a natural environment. The term "ex vivo" includes cells that have been removed from the body of an individual and processes or reactions that occur within such cells.

The term "reporter gene" refers to a nucleic acid having a sequence encoding a gene product (typically an enzyme) that is easily and quantifiably assayed when a construct comprising the reporter gene sequence operably linked to an endogenous or heterologous promoter and/or enhancer element is introduced into cells containing (or which can be made to contain) the factors necessary for the activation of the promoter and/or enhancer elements. Examples of reporter genes include, but are not limited, to genes encoding beta-galactosidase (lacZ), the bacterial chloramphenicol acetyltransferase (cat) genes, firefly luciferase genes, genes encoding beta-glucuronidase (GUS), and genes encoding fluorescent proteins. A "reporter protein" refers to a protein encoded by a reporter gene.

The term "fluorescent reporter protein" as used herein means a reporter protein that is detectable based on fluorescence wherein the fluorescence may be either from the reporter protein directly, activity of the reporter protein on a fluorogenic substrate, or a protein with affinity for binding to a fluorescent tagged compound. Examples of fluorescent proteins include green fluorescent proteins (e.g., GFP, GFP-2, tagGFP, turboGFP, eGFP, Emerald, Azami Green, Monomeric Azami Green, CopGFP, AceGFP, and ZsGreen1), yellow fluorescent proteins (e.g., YFP, eYFP, Citrine, Venus, YPet, PhiYFP, and ZsYellow1), blue fluorescent proteins (e.g., BFP, eBFP, eBFP2, Azurite, mKalama1, GFPuv, Sapphire, and T-sapphire), cyan fluorescent proteins (e.g., CFP, eCFP, Cerulean, CyPet, AmCyan1, and Midoriishi-Cyan), red fluorescent proteins (e.g., RFP, mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, and Jred), orange fluorescent proteins (e.g., mOrange, mKO, Kusabira-Orange, Monomeric Kusabira-Orange, mTangerine, and tdTomato), and any other suitable fluorescent protein whose presence in cells can be detected by flow cytometry methods.

Repair in response to double-strand breaks (DSBs) occurs principally through two conserved DNA repair pathways: homologous recombination (HR) and non-homologous end joining (NHEJ). See Kasparek & Humphrey (2011) *Seminars in Cell & Dev. Biol.* 22:886-897, herein incorporated by reference in its entirety for all purposes. Likewise, repair of a target nucleic acid mediated by an exogenous donor nucleic acid can include any process of exchange of genetic information between the two polynucleotides.

The term "recombination" includes any process of exchange of genetic information between two polynucleotides and can occur by any mechanism. Recombination can occur via homology directed repair (HDR) or homologous recombination (HR). HDR or HR includes a form of nucleic acid repair that can require nucleotide sequence homology, uses a "donor" molecule as a template for repair of a "target" molecule (i.e., the one that experienced the double-strand break), and leads to transfer of genetic information from the donor to target. Without wishing to be bound by any particular theory, such transfer can involve mismatch correction of heteroduplex DNA that forms between the broken target and the donor, and/or synthesis-dependent strand annealing, in which the donor is used to resynthesize genetic information that will become part of the target, and/or related processes. In some cases, the donor polynucleotide, a portion of the donor polynucleotide, a copy of the donor polynucleotide, or a portion of a copy of the donor polynucleotide integrates into the target DNA. See Wang et al. (2013) *Cell* 153:910-918; Mandalos et al. (2012) *PLOS ONE* 7:e45768:1-9; and Wang et al. (2013) *Nat Biotechnol.* 31:530-532, each of which is herein incorporated by reference in its entirety for all purposes.

Non-homologous end joining (NHEJ) includes the repair of double-strand breaks in a nucleic acid by direct ligation of the break ends to one another or to an exogenous sequence without the need for a homologous template. Ligation of non-contiguous sequences by NHEJ can often result in deletions, insertions, or translocations near the site of the double-strand break. For example, NHEJ can also result in the targeted integration of an exogenous donor nucleic acid through direct ligation of the break ends with the ends of the exogenous donor nucleic acid (i.e., NHEJ-based capture). Such NHEJ-mediated targeted integration can be preferred for insertion of an exogenous donor nucleic acid when homology directed repair (HDR) pathways are not readily usable (e.g., in non-dividing cells, primary cells, and cells which perform homology-based DNA repair poorly). In addition, in contrast to homology-directed repair, knowledge concerning large regions of sequence identity flanking the cleavage site is not needed, which can be beneficial when attempting targeted insertion into organisms that have genomes for which there is limited knowledge of the genomic sequence. The integration can proceed via ligation of blunt ends between the exogenous donor nucleic acid and the cleaved genomic sequence, or via ligation of sticky ends (i.e., having 5' or 3' overhangs) using an exogenous donor nucleic acid that is flanked by overhangs that are compatible with those generated by a nuclease agent in the cleaved genomic sequence. See, e.g., US 2011/020722, WO 2014/033644, WO 2014/089290, and Maresca et al. (2013) *Genome Res.* 23(3):539-546, each of which is herein incorporated by reference in its entirety for all purposes. If blunt ends are ligated, target and/or donor resection may be needed to generation regions of microhomology needed for fragment joining, which may create unwanted alterations in the target sequence.

The term "antigen-binding protein" includes any protein that binds to an antigen. Examples of antigen-binding proteins include an antibody, an antigen-binding fragment of an antibody, a multispecific antibody (e.g., a bi-specific antibody), an scFV, a bis-scFV, a diabody, a triabody, a tetrabody, a V-NAR, a VHH, a VL, a F(ab), a F(ab)$_2$, a DVD (dual variable domain antigen-binding protein), an SVD (single variable domain antigen-binding protein), a bispecific T-cell engager (BiTE), or a Davisbody (U.S. Pat. No. 8,586,713, herein incorporated by reference herein in its entirety for all purposes).

The term "antigen" refers to a substance, whether an entire molecule or a domain within a molecule, which is capable of eliciting production of antibodies with binding specificity to that substance. The term antigen also includes substances, which in wild type host organisms would not elicit antibody production by virtue of self-recognition, but can elicit such a response in a host animal with appropriate genetic engineering to break immunological tolerance.

The term "epitope" refers to a site on an antigen to which an antigen-binding protein (e.g., antibody) binds. An epitope can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996), herein incorporated by reference in its entirety for all purposes.

An antibody paratope as described herein generally comprises at a minimum a complementarity determining region (CDR) that specifically recognizes the heterologous epitope (e.g., a CDR3 region of a heavy and/or light chain variable domain).

The term "antibody" includes immunoglobulin molecules comprising four polypeptide chains, two heavy (H) chains and two light (L) chains inter-connected by disulfide bonds. Each heavy chain comprises a heavy chain variable domain and a heavy chain constant region ($C_H$). The heavy chain constant region comprises three domains: $C_H1$, $C_H2$ and $C_H3$. Each light chain comprises a light chain variable domain and a light chain constant region (CO. The heavy chain and light chain variable domains can be further subdivided into regions of hypervariability, termed complementarity determining regions (CDR), interspersed with regions that are more conserved, termed framework regions (FR). Each heavy and light chain variable domain comprises three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3). The term "high affinity" antibody refers to an antibody that has a $K_D$ with respect to its target epitope about of $10^{-9}$ M or lower (e.g., about $1\times10^{-9}$M, $1\times10^{-10}$ m, $1\times10^{-11}$ M, or about $1\times10^{-12}$M). In one embodiment, $K_D$ is measured by surface plasmon resonance, e.g., BIACORE™; in another embodiment, $K_D$ is measured by ELISA.

Specific binding of an antigen-binding protein to its target antigen includes binding with an affinity of at least $10^6$, $10^7$, $10^8$, $10^9$, or $10^{10}$ M$^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas non-specific binding is usually the result of van der Waals forces. Specific binding does not however necessarily imply that an antigen-binding protein binds one and only one target.

The term "antisense RNA" refers to a single-stranded RNA that is complementary to a messenger RNA strand transcribed in a cell.

The term "small interfering RNA (siRNA)" refers to a typically double-stranded RNA molecule that induces the RNA interference (RNAi) pathway. These molecules can vary in length (generally between 18-30 base pairs) and contain varying degrees of complementarity to their target mRNA in the antisense strand. Some, but not all, siRNAs have unpaired overhanging bases on the 5' or 3' end of the sense strand and/or the antisense strand. The term "siRNA" includes duplexes of two separate strands, as well as single strands that can form hairpin structures comprising a duplex region. The double-stranded structure can be, for example, less than 20, 25, 30, 35, 40, 45, or 50 nucleotides in length. For example, the double-stranded structure can be from about 21-23 nucleotides in length, from about 19-25 nucleotides in length, or from about 19-23 nucleotides in length.

The term "short hairpin RNA (shRNA)" refers to a single strand of RNA bases that self-hybridizes in a hairpin structure and can induce the RNA interference (RNAi) pathway upon processing. These molecules can vary in length (generally about 50-90 nucleotides in length, or in some cases up to greater than 250 nucleotides in length, e.g., for microRNA-adapted shRNA). shRNA molecules are processed within the cell to form siRNAs, which in turn can knock down gene expression. shRNAs can be incorporated into vectors. The term "shRNA" also refers to a DNA molecule from which a short, hairpin RNA molecule may be transcribed.

Compositions or methods "comprising" or "including" one or more recited elements may include other elements not specifically recited. For example, a composition that "comprises" or "includes" a protein may contain the protein alone or in combination with other ingredients. The transitional phrase "consisting essentially of" means that the scope of a claim is to be interpreted to encompass the specified elements recited in the claim and those that do not materially affect the basic and novel characteristic(s) of the claimed invention. Thus, the term "consisting essentially of" when used in a claim of this invention is not intended to be interpreted to be equivalent to "comprising."

"Optional" or "optionally" means that the subsequently described event or circumstance may or may not occur and that the description includes instances in which the event or circumstance occurs and instances in which the event or circumstance does not.

Designation of a range of values includes all integers within or defining the range, and all subranges defined by integers within the range.

Unless otherwise apparent from the context, the term "about" encompasses values within a standard margin of error of measurement (e.g., SEM) of a stated value.

The term "and/or" refers to and encompasses any and all possible combinations of one or more of the associated listed items, as well as the lack of combinations when interpreted in the alternative ("or").

The term "or" refers to any one member of a particular list and also includes any combination of members of that list.

The singular forms of the articles "a," "an," and "the" include plural references unless the context clearly dictates otherwise. For example, the term "a protein" or "at least one protein" can include a plurality of proteins, including mixtures thereof.

Statistically significant means p≤0.05.

DETAILED DESCRIPTION

I. Overview

Disclosed herein are non-human animal cells and non-human animals comprising a humanized TTR locus comprising a beta-slip mutation and methods of using such non-human animal cells and non-human animals. Also disclosed herein are methods of making such non-human animal cells and non-human animals. Also disclosed herein are non-human animal genomes comprising a humanized TTR locus comprising a beta-slip mutation and methods of using such non-human animal genomes. Also disclosed herein are humanized non-human animal TTR genes comprising a beta-slip mutation and nuclease agents and targeting vectors for use in humanizing a non-human animal TTR gene. Non-human animal cells or non-human animals comprising a humanized TTR locus comprising a beta-slip mutation express a human transthyretin protein or a chimeric transthyretin protein comprising one or more fragments of a human transthyretin protein. Non-human animals comprising a humanized TTR locus comprising a beta-slip mutation develop amyloidosis very early. For example, mice comprising a humanized TTR locus comprising a beta-slip mutation develop amyloidosis as early as about two months of age. This is the first reported in vivo model of TTR amyloidosis to develop amyloidosis so rapidly. Such non-human animal cells and non-human animals can be used to assess delivery or efficacy of human-TTR-targeting agents (e.g., CRISPR/Cas9 genome editing agents) ex vivo or in vivo and can be used in methods of optimizing the delivery of efficacy of such agents ex vivo or in vivo.

In some of the non-human animal cells and non-human animals disclosed herein, most or all of the non-human animal genomic DNA is replaced one-for-one with orthologous human genomic DNA. Compared to non-human animals with cDNA insertions, expression levels should be higher when the intron-exon structure and splicing machinery are maintained because conserved regulator elements are more likely to be left intact, and spliced transcripts that undergo RNA processing are more stable than cDNAs. In contrast, insertion of human TTR cDNA (e.g., along with insertion of an artificial beta-globin intron in the 5' UTR) into a non-human animal Ttr locus would abolish conserved regulatory elements such as those contained within the first exon and intron of the non-human animal Ttr. Replacing the non-human animal genomic sequence with the orthologous human genomic sequence is more likely to result in faithful expression of the transgene from the endogenous Ttr locus. Similarly, transgenic non-human animals with transgenic insertion of human-TTR-coding sequences at a random genomic locus rather than the endogenous non-human-animal Ttr locus will not as accurately reflect the endogenous regulation of Ttr expression. A humanized TTR allele resulting from replacing most or all of the non-human animal genomic DNA one-for-one with orthologous human genomic DNA will provide the true human target or a close approximation of the true human target of human-TTR-targeting reagents (e.g., CRISPR/Cas9 reagents designed to target human TTR), thereby enabling testing of the efficacy and mode of action of such agents in live animals as well as pharmacokinetic and pharmacodynamics studies in a setting where the humanized protein and humanized gene are the only version of TTR present.

II. Non-Human Animals Comprising a Humanized TTR Locus Comprising a Beta-Slip Mutation The cells and non-human animals disclosed herein comprise a humanized TTR locus comprising a beta-slip mutation. Cells or non-human animals comprising a humanized TTR locus comprising a beta-slip mutation express a human transthyretin protein or a partially humanized, chimeric transthyretin protein in which one or more fragments of the native transthyretin protein have been replaced with corresponding fragments from human transthyretin.

A. Transthyretin (TTR)

The cells and non-human animals described herein comprise a humanized transthyretin (Ttr) locus comprising a beta-slip mutation. Transthyretin (TTR) is a 127-amino acid, 55 kDa serum and cerebrospinal fluid transport protein primarily synthesized by the liver but also produced by the choroid plexus. It has also been referred to as prealbumin, thyroxine binding prealbumin, ATTR, TBPA, CTS, CTS1, HEL111, HsT2651, and PALB. In its native state, TTR exists as a tetramer. In homozygotes, homo-tetramers comprise identical 127-amino-acid beta-sheet-rich subunits. In heterozygotes, TTR tetramers can be made up of variant and/or wild-type subunits, typically combined in a statistical fashion. TTR is responsible for carrying thyroxine (T4) and retinol-bound RBP (retinol-binding protein) in both the serum and the cerebrospinal fluid.

Unless otherwise apparent from context, reference to human transthyretin (TTR) or its fragments or domains includes the natural, wild type human amino acid sequences including isoforms and allelic variants thereof. Transthyretin precursor protein includes a signal sequence (typically 20 amino acids), whereas the mature transthyretin protein does not. Exemplary TTR polypeptide sequences are designated by Accession Numbers NP_000362.1 (NCBI) and P02766.1 (UniProt) (identical, each set forth SEQ ID NO: 1). Residues may be numbered according to UniProt Accession Number P02766.1, with the first amino acid of the mature protein (i.e., not including the 20 amino acid signal sequence) designated residue 1. In any other TTR protein, residues are numbered according to the corresponding residues in UniProt Accession Number P02766.1 on maximum alignment.

The human TTR gene is located on chromosome 18 and includes four exons and three introns. An exemplary human TTR gene is from residues 5001-12258 in the sequence designated by GenBank Accession Number NG_009490.1 (SEQ ID NO: 3). The four exons in SEQ ID NO: 3 include residues 1-205, 1130-1260, 3354-3489, and 6802-7258, respectively. The TTR coding sequence in SEQ ID NO: 3 includes residues 137-205, 1130-1260, 3354-3489, and 6802-6909. An exemplary human TTR mRNA is designated by NCBI Accession Number NM_000371.3 (SEQ ID NO: 2). An exemplary human TTR coding sequence encoding a TTR protein comprising the G53S/E54D/L55S beta-slip mutation is set forth in SEQ ID NO: 10. An transthyretin precursor protein comprising the G53S/E54D/L55S beta-slip mutation is set forth in SEQ ID NO: 9.

The mouse Ttr gene is located and chromosome 18 and also includes four exons and three introns. An exemplary mouse Ttr gene is from residues 20665250 to 20674326 the sequence designated by GenBank Accession Number NC_000084.6 (SEQ ID NO: 7). The four exons in SEQ ID NO: 7 include residues 1-258, 1207-1337, 4730-4865, and 8382-9077, respectively. The Ttr coding sequence in SEQ ID NO: 7 includes residues 190-258, 1207-1337, 4730-4865, and 8382-8489. An exemplary mouse TTR protein is designated by UniProt Accession Number P07309.1 or NCBI Accession Number NP_038725.1 (identical, each set forth SEQ ID NO: 5). An exemplary mouse Ttr mRNA is designated by NCBI Accession Number NM_013697.5 (SEQ ID NO: 6).

An exemplary rat TTR protein is designated by UniProt Accession Number P02767. An exemplary pig TTR protein is designated by UniProt Accession Number P50390. An exemplary chicken TTR protein is designated by UniProt Accession Number P27731. An exemplary cow TTR protein is designated by UniProt Accession Number O46375. An exemplary sheep TTR protein is designated by UniProt Accession Number P12303. An exemplary chimpanzee TTR protein designated by UniProt Accession Number Q5U715. An exemplary orangutan TTR protein is designated by UniProt Accession Number Q5NVS2. An exemplary rabbit TTR protein is designated by UniProt Accession Number P07489. An exemplary cynomolgus monkey (macaque) TTR protein is designated by UniProt Accession Number Q8HW1.

Transthyretin (TTR) amyloidosis is a systemic disorder characterized by pathogenic, misfolded TTR and the extracellular deposition of amyloid fibrils composed of TTR. TTR amyloidosis is generally caused by destabilization of the native TTR tetramer form (due to environmental or genetic conditions), leading to dissociation, misfolding, and aggregation of TTR into amyloid fibrils that accumulate in various organs and tissues, causing progressive dysfunction. The dissociated monomers have a propensity to form misfolded protein aggregates and amyloid fibrils.

In humans, both wild-type TTR tetramers and mixed tetramers made up of mutant and wild-type subunits can dissociate, misfold, and aggregate, with the process of amyloidogenesis leading to the degeneration of post-mitotic tissue. Thus, TTR amyloidoses encompass diseases caused by pathogenic misfolded TTR resulting from mutations in TTR or resulting from non-mutated, misfolded TTR.

Senile systemic amyloidosis (SSA) and senile cardiac amyloidosis (SCA) are age-related types of amyloidosis that result from the deposition of wild-type TTR amyloid outside and within the cardiomyocytes of the heart. TTR amyloidosis is also the most common form of hereditary (familial) amyloidosis, which is caused by mutations that destabilize the TTR protein. TTR amyloidoses associated with point mutations in the TTR gene include familial amyloid polyneuropathy (FAP), familial amyloid cardiomyopathy (FAC), and central nervous system selective amyloidosis (CNSA).

B. Humanized TTR Loci Comprising a Beta-Slip Mutation

The humanized TTR loci described herein comprise a beta-slip mutation. An example of a beta-slip mutation is one that describes a conformational change caused by the human transthyretin triple mutant G53S/E54D/L55S. The numbering of the residues here and below refers to numbering in the mature human transthyretin protein without the signal peptide (e.g., beginning at residue 21 of the transthyretin precursor protein, so these residues in the transthyretin precursor protein would be residues 73, 74, and 75, respectively). A three-residue shift in the beta strand D places L58 at the position normally occupied by L55. This results in structural consequences on the neighboring residues in the CD loop, beta strand D, and DE loop area comprising residues S50-G63, but leaves the position of the beta strand C intact. See Eneqvist et al. (2000) *Mol. Cell* 6:1207-1218, herein incorporated by reference in its entirety for all purposes. The G53S/E54D/L55S variant polymerizes spontaneously at physiological conditions and gives rise to high molecular weight aggregates showing all the characteristics of amyloid, except they are still soluble. The G53S/E54D/L55S variant binds thioflavin T and Congo red, has an elevated sensitivity to trypsin, and forms fibrillar structures, which produce a fiber diffraction pattern consistent with cross-beta structure. See Eneqvist et al. (2000) *Mol. Cell* 6:1207-1218, herein incorporated by reference in its entirety for all purposes.

Generally, a beta-slip mutation as referred to herein comprises a mutation that causes a shift in beta-strand D of a TTR protein. By beta-strand D is meant beta-strand D in the human TTR protein or a corresponding region of a non-human TTR protein when optimally aligned with the human TTR protein. For example, the mutation can cause a three-residue shift in beta strand D that places a residue corresponding to residue L58 in human TTR at a position normally occupied by a residue corresponding to residue L55 in human TTR when the mutated TTR protein is optimally aligned with the human TTR protein. More specifically, the beta-slip mutation can be a triple mutation corresponding to G53S/E54D/L55S in the human TTR protein when the mutated TTR protein is optimally aligned with the human TTR protein. A residue (e.g., nucleotide or amino acid) in an endogenous Ttr gene (or TTR protein) can be determined to correspond with a residue in the human TTR gene (or TTR protein) by optimally aligning the two sequences for maximum correspondence over a specified comparison window (e.g., the TTR coding sequence), wherein the portion of the polynucleotide (or amino acid) sequence in the comparison window may comprise additions or deletions (i.e., gaps) as compared to the reference sequence (which does not comprise additions or deletions)

for optimal alignment of the two sequences (see, e.g., discussion elsewhere herein with regard to sequence identity and complementarity). Two residues correspond if they are located at the same position when optimally aligned.

A humanized beta-slip TTR locus disclosed herein can be a Ttr locus in which the entire Ttr gene is replaced with the corresponding orthologous human TTR sequence comprising a beta-slip mutation, or it can be a Ttr locus in which only a portion of the Ttr gene is replaced with the corresponding orthologous human TTR sequence (i.e., humanized). Alternatively, it can be a Ttr locus in which a portion of the Ttr gene is deleted and a portion of the corresponding orthologous human TTR sequence is inserted. If only a portion of the Ttr locus is humanized, the beta-slip mutation can be in the remaining endogenous Ttr sequence or in the inserted orthologous human TTR sequence. In some examples, the portion of the orthologous human TTR locus that is inserted comprises more of the human TTR locus than is deleted from the endogenous Ttr locus. A human TTR sequence corresponding to a particular segment of endogenous Ttr sequence refers to the region of human TTR that aligns with the particular segment of endogenous Ttr sequence when human TTR and the endogenous Ttr are optimally aligned (greatest number of perfectly matched residues). The corresponding orthologous human sequence can comprise, for example, complementary DNA (cDNA) or genomic DNA. Optionally, the corresponding orthologous human TTR sequence is modified to be codon-optimized based on codon usage in the non-human animal. Replaced or inserted (i.e., humanized) regions can include coding regions such as an exon, non-coding regions such as an intron, untranslated regions, or regulatory regions (e.g., a promoter, an enhancer, or a transcriptional repressor-binding element), or any combination thereof. A humanized TTR locus can also comprise human TTR sequence inserted into an endogenous Ttr locus without replacing the corresponding orthologous endogenous sequence. As one example, exons corresponding to 1, 2, 3, or all 4 exons (or all or portions of 1, 2, 3, or all 4 exons) of the human TTR gene can be humanized. In a specific example, exons corresponding to exons 2 and 3 and the coding regions of exons 1 and 4 (i.e., not including the 5' UTR and the 3' UTR) can be deleted from the endogenous TTR locus, and a region of the human TTR gene including exons 2-4 and the coding region of exon 1 (i.e., not including the 5' UTR) of the human TTR gene can be inserted. In a specific example, exons corresponding to exons 2 and 3 and the coding regions of exons 1 and 4 (i.e., not including the 5' UTR and the 3' UTR) can be deleted from the endogenous TTR locus, and a region of the human TTR gene including exons 2 and 3 and the coding regions of exons 1 and 4 as well as all or part of the 3' UTR (i.e., not including the 5' UTR) of the human TTR gene can be inserted. Alternatively, a region of TTR encoding an epitope recognized by an anti-human-TTR antigen-binding protein or a region targeted by human-TTR-targeting reagent (e.g., a small molecule) can be humanized. Likewise, introns corresponding to 1, 2, or all 3 introns of the human TTR gene can be humanized or can remain endogenous. In one example, introns corresponding to all 3 introns of the human TTR gene can be humanized (e.g., deleted from the endogenous locus and replaced with the corresponding human introns).

A humanized TTR locus can be one in which a region of the endogenous Ttr locus has been deleted and replaced with an orthologous human TTR sequence (e.g., orthologous wild type human TTR sequence). As one example, the replaced region of the endogenous Ttr locus can comprise both a coding sequence (i.e., all or part of an exon) and a non-coding sequence (i.e., all or part of intron), such as at least one exon and at least one intron. For example, the replaced region can comprise at least one exon and at least one intron. The replaced region comprising both coding sequence and non-coding sequence can be a contiguous region of the endogenous Ttr locus, meaning there is no intervening sequence between the replaced coding sequence and the replaced non-coding sequence. For example, the replaced region can comprise at least one exon and at least one adjacent intron. The replaced region can comprise one exon, two exons, three exons, four exons, or all exons of the endogenous Ttr locus. The inserted human TTR sequence can comprise one exon, two exons, three exons, four exons, or all exons of a human TTR gene. Likewise, the replaced region can comprise one intron, two introns, three introns, or all introns of the endogenous Ttr locus. The inserted human TTR sequence can comprise one intron, two introns, three introns, or all introns of a human TTR gene. Optionally, one or more introns and/or one or more exons of the endogenous Ttr locus remain unmodified (i.e., not deleted and replaced). For example, the first exon of the endogenous Ttr locus can remain unmodified. Similarly, the first exon and the first intron of the endogenous Ttr locus can remain unmodified.

The transthyretin precursor protein encoded by the humanized TTR locus can retain the activity of the native transthyretin precursor protein and/or the human transthyretin precursor protein. For example, the transthyretin precursor protein encoded by the humanized TTR locus can retain the activity of a native transthyretin precursor protein comprising a beta-slip mutation and/or a human transthyretin precursor protein comprising the beta-slip mutation.

In one specific example, the entire coding sequence for the transthyretin precursor protein can be deleted and replaced with the orthologous human TTR sequence. For example, the region of the endogenous Ttr locus beginning at the start codon and ending at the stop codon can be deleted and replaced with the orthologous human TTR sequence.

Flanking untranslated regions including regulatory sequences can also be humanized. Alternatively, flanking untranslated regions including regulatory sequences can remain endogenous. The first exon of a Ttr locus typically include a 5' untranslated region upstream of the start codon. Likewise, the last exon of a Ttr locus typically includes a 3' untranslated region downstream of the stop codon. Regions upstream of the Ttr start codon and downstream of the Ttr stop codon can either be unmodified or can be deleted and replaced with the orthologous human TTR sequence. For example, the 5' untranslated region (UTR), the 3'UTR, or both the 5' UTR and the 3' UTR can be humanized, or the 5' UTR, the 3'UTR, or both the 5' UTR and the 3' UTR can remain endogenous. One or both of the human 5' and 3' UTRs can be inserted, and/or one or both of the endogenous 5' and 3' UTRs can be deleted. In one specific example, the 5' UTR remains endogenous. In another specific example, the 3' UTR is humanized, but the 5' UTR remains endogenous. In another specific example, the 5' UTR remains endogenous, and a human TTR 3' UTR is inserted into the endogenous Ttr locus. For example, the human TTR 3' UTR can replace the endogenous 3' UTR or can be inserted without replacing the endogenous 3' UTR (e.g., it can be inserted upstream of the endogenous 3' UTR). For example, the endogenous 5' UTR (or a portion thereof) and the endogenous 3' UTR (or a portion thereof) can remain at the humanized TTR locus, and the human 3' UTR (or a portion thereof) can be inserted upstream of the endogenous 3' UTR.

One or more regions of the endogenous Ttr locus encoding one or more domains of the transthyretin precursor protein can be humanized. Likewise, one or more regions of the endogenous Ttr locus encoding one or more domains of the transthyretin precursor protein can remain unmodified (i.e., not deleted and replaced). For example, transthyretin precursor proteins typically have a signal peptide at the N-terminus. The signal peptide can be, for example, about 20 amino acids in length. The region of the endogenous Ttr locus encoding the signal peptide can remain unmodified (i.e., not deleted and replaced), or can be deleted and replaced with the orthologous human TTR sequence. Similarly, a region of the endogenous Ttr locus encoding an epitope recognized by an anti-human-TTR antigen-binding protein can be humanized.

Depending on the extent of replacement by orthologous sequences, regulatory sequences, such as a promoter, can be endogenous or supplied by the replacing human orthologous sequence. For example, the humanized TTR locus can include the endogenous non-human animal Ttr promoter. The coding sequence for the transthyretin precursor protein at the genetically modified endogenous Ttr locus can be operably linked to the endogenous Ttr promoter.

As a specific example, the humanized TTR locus comprising the beta-slip mutation can be one in which the region of the endogenous Ttr locus being deleted and replaced with the orthologous human TTR sequence comprises, consists essentially of, or consists of the region from the Ttr start codon to the stop codon. The human TTR sequence being inserted can further comprise a human TTR 3' UTR. For example, the human TTR sequence at the humanized TTR locus comprising the beta-slip mutation can comprise, consist essentially of, or consist of the region from the TTR start codon to the end of the 3' UTR. Optionally, the Ttr coding sequence in the modified endogenous Ttr locus is operably linked to the endogenous Ttr promoter. The human TTR sequence at the humanized TTR locus comprising the beta-slip mutation can comprise, consist essentially of, or consist of a sequence that is at least 85%, 90%, 95%, 96%, 97%, 98%, 99%, or 100% identical to SEQ ID NO: 14. The human TTR sequence at the humanized TTR locus comprising the beta-slip mutation can comprise, consist essentially of, or consist of a sequence that is at least about 85%, at least about 90%, at least about 95%, at least about 96%, at least about 97%, at least about 98%, at least about 99%, or about 100% identical to SEQ ID NO: 14. The humanized TTR locus comprising the beta-slip mutation can comprise, consist essentially of, or consist of a sequence that is at least 85%, 90%, 95%, 96%, 97%, 98%, 99%, or 100% identical to SEQ ID NO: 12 or 13. The humanized TTR locus comprising the beta-slip mutation can comprise, consist essentially of, or consist of a sequence that is at least about 85%, at least about 90%, at least about 95%, at least about 96%, at least about 97%, at least about 98%, at least about 99%, or about 100% identical to SEQ ID NO: 12 or 13. The coding sequence (CDS) at the humanized TTR locus comprising the beta-slip mutation can comprise, consist essentially of, or consist of a sequence that is at least 85%, 90%, 95%, 96%, 97%, 98%, 99%, or 100% identical to SEQ ID NO: 10 (or degenerates thereof that encode the same protein). The coding sequence (CDS) at the humanized TTR locus comprising the beta-slip mutation can comprise, consist essentially of, or consist of a sequence that is at least about 85%, at least about 90%, at least about 95%, at least about 96%, at least about 97%, at least about 98%, at least about 99%, or about 100% identical to SEQ ID NO: 10 (or degenerates thereof that encode the same protein). The resulting human transthyretin precursor protein encoded by the humanized TTR locus comprising the beta-slip mutation can comprise, consist essentially of, or consist of a sequence that is at least 85%, 90%, 95%, 96%, 97%, 98%, 99%, or 100% identical to SEQ ID NO: 9. The resulting human transthyretin precursor protein encoded by the humanized TTR locus comprising the beta-slip mutation can comprise, consist essentially of, or consist of a sequence that is at least about 85%, at least about 90%, at least about 95%, at least about 96%, at least about 97%, at least about 98%, at least about 99%, or about 100% identical to SEQ ID NO: 9.

A control non-human animal comprising a humanized TTR wild type locus can also be generated. The wild type human TTR sequence at the humanized TTR locus can comprise, consist essentially of, or consist of a sequence that is at least 85%, 90%, 95%, 96%, 97%, 98%, 99%, or 100% identical to SEQ ID NO: 17. The wild type human TTR sequence at the humanized TTR locus can comprise, consist essentially of, or consist of a sequence that is at least about 85%, at least about 90%, at least about 95%, at least about 96%, at least about 97%, at least about 98%, at least about 99%, or about 100% identical to SEQ ID NO: 17. The humanized TTR wild type locus can comprise, consist essentially of, or consist of a sequence that is at least 85%, 90%, 95%, 96%, 97%, 98%, 99%, or 100% identical to SEQ ID NO: 15 or 16. The humanized TTR wild type locus can comprise, consist essentially of, or consist of a sequence that is at least about 85%, at least about 90%, at least about 95%, at least about 96%, at least about 97%, at least about 98%, at least about 99%, or about 100% identical to SEQ ID NO: 15 or 16. The coding sequence (CDS) at the humanized TTR wild type locus can comprise, consist essentially of, or consist of a sequence that is at least 85%, 90%, 95%, 96%, 97%, 98%, 99%, or 100% identical to SEQ ID NO: 4 (or degenerates thereof that encode the same protein). The coding sequence (CDS) at the humanized TTR wild type locus can comprise, consist essentially of, or consist of a sequence that is at least about 85%, at least about 90%, at least about 95%, at least about 96%, at least about 97%, at least about 98%, at least about 99%, or about 100% identical to SEQ ID NO: 4 (or degenerates thereof that encode the same protein). The resulting human transthyretin precursor protein encoded by the humanized TTR wild type locus can comprise, consist essentially of, or consist of a sequence that is at least 85%, 90%, 95%, 96%, 97%, 98%, 99%, or 100% identical to SEQ ID NO: 1. The resulting human transthyretin precursor protein encoded by the humanized TTR wild type locus can comprise, consist essentially of, or consist of a sequence that is at least about 85%, at least about 90%, at least about 95%, at least about 96%, at least about 97%, at least about 98%, at least about 99%, or about 100% identical to SEQ ID NO: 1.

As another specific example, the humanized TTR locus can be one in which the region of the endogenous Ttr locus being deleted and replaced with the orthologous human TTR sequence comprises, consists essentially of, or consists of the region from the start of the second Ttr exon to the stop codon. The human TTR sequence being inserted can further comprise a human TTR 3' UTR. For example, the human TTR sequence at the humanized TTR locus can comprise, consist essentially of, or consist of the region from the start of the second human TTR exon to the end of the 3' UTR. Optionally, the Ttr coding sequence in the modified endogenous Ttr locus is operably linked to the endogenous Ttr promoter.

TTR protein expressed from a humanized TTR locus can be an entirely human TTR protein or a chimeric endogenous/ human TTR protein (e.g., if the non-human animal is a mouse, a chimeric mouse/human TTR protein). For example, the signal peptide of the transthyretin precursor protein can be endogenous, and the remainder of the protein can be human. Alternatively, the N-terminus of the transthyretin precursor protein can be endogenous, and the remainder of the protein can be human. For example, the N-terminal 5, 6, 7, 8, 9, 10, 11, 12, 13, 14, 15, 16, 17, 18, 19, 20, 21, 22, 23, 24, or 25 amino acids can be endogenous, and the remainder can be human. In a specific example, the 23 amino acids at the N-terminus are endogenous, and the remainder of the protein is human.

Optionally, a humanized TTR locus can comprise other elements. Examples of such elements can include selection cassettes, reporter genes, recombinase recognition sites, or other elements. As one example, a humanized TTR locus can comprise a removable selection cassette (e.g., a self-deleting selection cassette) flanked by recombinase recognition sequences (e.g., loxP sites). Alternatively, the humanized TTR locus can lack other elements (e.g., can lack a selection cassette and/or can lack a reporter gene). Examples of suitable reporter genes and reporter proteins are disclosed elsewhere herein. Examples of suitable selection markers include neomycin phosphotransferase (neon), hygromycin B phosphotransferase ($hyg_r$), puromycin-N-acetyltransferase ($puro_r$), blasticidin S deaminase ($bsr_r$), xanthine/guanine phosphoribosyl transferase (gpt), and herpes simplex virus thymidine kinase (HSV-k). Examples of recombinases include Cre, Flp, and Dre recombinases. One example of a Cre recombinase gene is Crei, in which two exons encoding the Cre recombinase are separated by an intron to prevent its expression in a prokaryotic cell. Such recombinases can further comprise a nuclear localization signal to facilitate localization to the nucleus (e.g., NLS-Crei). Recombinase recognition sites include nucleotide sequences that are recognized by a site-specific recombinase and can serve as a substrate for a recombination event. Examples of recombinase recognition sites include FRT, FRT11, FRT71, attp, att, rox, and lox sites such as loxP, lox511, lox2272, lox66, lox71, loxM2, and lox5171.

Other elements such as reporter genes or selection cassettes can be self-deleting cassettes flanked by recombinase recognition sites. See, e.g., U.S. Pat. No. 8,697,851 and US 2013/0312129, each of which is herein incorporated by reference in its entirety for all purposes. As an example, the self-deleting cassette can comprise a Crei gene (comprises two exons encoding a Cre recombinase, which are separated by an intron) operably linked to a mouse Prm1 promoter and a neomycin resistance gene operably linked to a human ubiquitin promoter. By employing the Prm1 promoter, the self-deleting cassette can be deleted specifically in male germ cells of F0 animals. The polynucleotide encoding the selection marker can be operably linked to a promoter active in a cell being targeted. Examples of promoters are described elsewhere herein. As another specific example, a self-deleting selection cassette can comprise a hygromycin resistance gene coding sequence operably linked to one or more promoters (e.g., both human ubiquitin and EM7 promoters) followed by a polyadenylation signal, followed by a Crei coding sequence operably linked to one or more promoters (e.g., an mPrm1 promoter), followed by another polyadenylation signal, wherein the entire cassette is flanked by loxP sites.

The humanized TTR locus can also be a conditional allele. For example, the conditional allele can be a multifunctional allele, as described in US 2011/0104799, herein incorporated by reference in its entirety for all purposes. For example, the conditional allele can comprise: (a) an actuating sequence in sense orientation with respect to transcription of a target gene; (b) a drug selection cassette (DSC) in sense or antisense orientation; (c) a nucleotide sequence of interest (NSI) in antisense orientation; and (d) a conditional by inversion module (COIN, which utilizes an exon-splitting intron and an invertible gene-trap-like module) in reverse orientation. See, e.g., US 2011/0104799. The conditional allele can further comprise recombinable units that recombine upon exposure to a first recombinase to form a conditional allele that (i) lacks the actuating sequence and the DSC; and (ii) contains the NSI in sense orientation and the COIN in antisense orientation. See, e.g., US 2011/0104799.

C. Non-Human Cells and Non-Human Animals Comprising a Humanized TTR Locus Comprising a Beta-Slip Mutation Non-human animal cells and non-human animals comprising a humanized TTR locus comprising a beta-slip mutation as described elsewhere herein are provided. Non-human animal genomes comprising a humanized TTR locus comprising a beta-slip mutation as described elsewhere herein are also provided. The genomes, cells, or non-human animals can be male or female. The cells or non-human animals can be heterozygous or homozygous for the humanized TTR locus comprising the beta-slip mutation. Likewise, the genomes can be heterozygous or homozygous for the humanized TTR locus comprising the beta-slip mutation. A diploid organism has two alleles at each genetic locus. Each pair of alleles represents the genotype of a specific genetic locus. Genotypes are described as homozygous if there are two identical alleles at a particular locus and as heterozygous if the two alleles differ. A non-human animal comprising a humanized TTR locus comprising a beta-slip mutation can comprise the humanized TTR locus in its germline.

The non-human animal cells provided herein can be, for example, any non-human cell comprising a Ttr locus or a genomic locus homologous or orthologous to the human TTR locus. Likewise, the non-human animal genomes provided herein can be, for example, any non-human animal genome comprising a Ttr locus or a genomic locus homologous or orthologous to the human TTR locus. The cells can be eukaryotic cells, which include, for example, animal cells, mammalian cells, non-human mammalian cells, and human cells. The term "animal" includes mammals, fishes, and birds. Likewise, the genomes can be from eukaryotic cells. A mammalian cell can be, for example, a non-human mammalian cell, a rodent cell, a rat cell, a mouse cell, or a hamster cell. Other non-human mammals include, for example, non-human primates, monkeys, apes, orangutans, cats, dogs, rabbits, horses, livestock (e.g., bovine species such as cows, steer, and so forth; ovine species such as sheep, goats, and so forth; and porcine species such as pigs and boars). Domesticated animals and agricultural animals are also included. The term "non-human" excludes humans.

The cells can also be any type of undifferentiated or differentiated state. For example, a cell can be a totipotent cell, a pluripotent cell (e.g., a human pluripotent cell or a non-human pluripotent cell such as a mouse embryonic stem (ES) cell or a rat ES cell), or a non-pluripotent cell. Totipotent cells include undifferentiated cells that can give rise to any cell type, and pluripotent cells include undifferentiated cells that possess the ability to develop into more than one differentiated cell types. Such pluripotent and/or totipotent cells can be, for example, ES cells or ES-like cells, such as an induced pluripotent stem (iPS) cells. ES cells include embryo-derived totipotent or pluripotent cells that are capable of contributing to any tissue of the developing embryo upon introduction into an embryo. ES cells can be derived from the inner cell mass of a blastocyst and are capable of differentiating into cells of any of the three vertebrate germ layers (endoderm, ectoderm, and mesoderm).

The cells provided herein can also be germ cells (e.g., sperm or oocytes). The cells can be mitotically competent cells or mitotically-inactive cells, meiotically competent cells or meiotically-inactive cells. Similarly, the cells can also be primary somatic cells or cells that are not a primary somatic cell. Somatic cells include any cell that is not a gamete, germ cell, gametocyte, or undifferentiated stem cell. For example, the cells can be liver cells, such as hepatoblasts or hepatocytes.

Suitable cells provided herein also include primary cells. Primary cells include cells or cultures of cells that have been isolated directly from an organism, organ, or tissue. Primary cells include cells that are neither transformed nor immortal. They include any cell obtained from an organism, organ, or tissue which was not previously passed in tissue culture or has been previously passed in tissue culture but is incapable of being indefinitely passed in tissue culture. Such cells can be isolated by conventional techniques and include, for example, hepatocytes.

Other suitable cells provided herein include immortalized cells. Immortalized cells include cells from a multicellular organism that would normally not proliferate indefinitely but, due to mutation or alteration, have evaded normal cellular senescence and instead can keep undergoing division. Such mutations or alterations can occur naturally or be intentionally induced. A specific example of an immortalized cell line is the HepG2 human liver cancer cell line. Numerous types of immortalized cells are well known. Immortalized or primary cells include cells that are typically used for culturing or for expressing recombinant genes or proteins.

The cells provided herein also include one-cell stage embryos (i.e., fertilized oocytes or zygotes). Such one-cell stage embryos can be from any genetic background (e.g., BALB/c, C57BL/6, 129, or a combination thereof for mice), can be fresh or frozen, and can be derived from natural breeding or in vitro fertilization.

The cells provided herein can be normal, healthy cells, or can be diseased or mutant-bearing cells.

In a specific example, the non-human animal cells are embryonic stem (ES) cells or liver cells, such as mouse or rat ES cells or liver cells.

Non-human animals comprising a humanized TTR locus comprising a beta-slip mutation as described herein can be made by the methods described elsewhere herein. The term "animal" includes mammals, fishes, and birds. Non-human mammals include, for example, non-human primates, monkeys, apes, orangutans, cats, dogs, horses, rabbits, rodents (e.g., mice, rats, hamsters, and guinea pigs), and livestock (e.g., bovine species such as cows and steer; ovine species such as sheep and goats; and porcine species such as pigs and boars). Domesticated animals and agricultural animals are also included. The term "non-human animal" excludes humans. Preferred non-human animals include, for example, rodents, such as mice and rats.

The non-human animals can be from any genetic background. For example, suitable mice can be from a 129 strain, a C57BL/6 strain, a mix of 129 and C57BL/6, a BALB/c strain, or a Swiss Webster strain. Examples of 129 strains include 129P1, 129P2, 129P3, 129X1, 129S1 (e.g., 129S1/SV, 129S1/Svlm), 129S2, 129S4, 129S5, 12959/SvEvH, 129S6 (129/SvEvTac), 129S7, 129S8, 129T1, and 129T2. See, e.g., Festing et al. (1999) *Mammalian Genome* 10:836, herein incorporated by reference in its entirety for all purposes. Examples of C57BL strains include C57BL/A, C57BL/An, C57BL/GrFa, C57BL/Kal_wN, C57BL/6, C57BL/6J, C57BL/6ByJ, C57BL/6NJ, C57BL/10, C57BL/10ScSn, C57BL/10Cr, and C57BL/01a. Suitable mice can also be from a mix of an aforementioned 129 strain and an aforementioned C57BL/6 strain (e.g., 50% 129 and 50% C57BL/6). Likewise, suitable mice can be from a mix of aforementioned 129 strains or a mix of aforementioned BL/6 strains (e.g., the 129S6 (129/SvEvTac) strain).

Similarly, rats can be from any rat strain, including, for example, an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. Rats can also be obtained from a strain derived from a mix of two or more strains recited above. For example, a suitable rat can be from a DA strain or an ACI strain. The ACI rat strain is characterized as having black agouti, with white belly and feet and an $RT^{av1}$ haplotype. Such strains are available from a variety of sources including Harlan Laboratories. The Dark Agouti (DA) rat strain is characterized as having an agouti coat and an $RT1^{av1}$ haplotype. Such rats are available from a variety of sources including Charles River and Harlan Laboratories. Some suitable rats can be from an inbred rat strain. See, e.g., US 2014/0235933, herein incorporated by reference in its entirety for all purposes.

Non-human animals comprising a humanized TTR locus comprising a beta-slip mutation can have several phenotypes. As one example, such non-human animals can be hyperactive relative to control wild type non-human animals or control animals comprising a humanized TTR locus without the beta-slip mutation. Hyperactivity can be assessed by measuring one or more or all of total distance, total activity, and total rearings in an open field test as described in more detail in the working examples.

The non-human animals can also display dystonia or of a dystopic muscle phenotype. For example, the non-human animal can display hindlimb dystonia or a hindlimb dystonic phenotype (e.g., dystonic hindlimb retraction) as described in more detail in the working examples.

The non-human animals can also comprise aggregated forms of TTR and/or amyloid deposits (e.g., specifically TTR amyloid deposits). For example, the amyloid deposits can be in the sciatic nerve as shown in more detail in the working examples. However, the amyloid deposits can be in other organs and tissues as well.

In some non-human animals, any of these phenotypes (e.g., amyloid deposits) are apparent as early as about 1, 2, 3, 4, 5, 6, 7, 8, 9, 10, 11, or 12 months of age. For example, the phenotypes (e.g., amyloid deposits) can be apparent by about 2 months of age.

Non-human animals comprising a humanized TTR locus comprising a beta-slip mutation can express the humanized TTR protein at any level. For example, non-human animals comprising a humanized TTR locus comprising a beta-slip mutation can express humanized TTR proteins at levels of at least about 0.1, at least about 0.2, or at least about 0.3 µg/mL in the serum. Alternatively, non-human animals comprising a humanized TTR locus comprising a beta-slip mutation can express humanized TTR protein at levels of at least about 0.5, at least about 1, at least about 2, at least about 3, at least about 4, at least about 5, at least about 6, at least about 7, at least about 8, at least about 9, at least about 10, at least about 12, at least about 14, at least about 15, at least about 16, at least about 18, at least about 20, at least about 22, at least about 24, at least about 25, at least about 26, at least about 28, or at least about 30 µg/mL in the serum.

III. Methods of Using Non-Human Animals Comprising a Humanized TTR Locus Comprising a Beta-Slip Mutation for Assessing Efficacy of Human-TTR-Targeting Reagents In Vivo or Ex Vivo Various methods are provided for using the non-human animals comprising a humanized TTR locus comprising a beta-slip mutation as described elsewhere herein for assessing or optimizing delivery or efficacy of human-TTR-targeting reagents (e.g., therapeutic molecules or complexes) in vivo or ex vivo. The non-human animals produce a humanized TTR protein comprising a beta-slip mutation that results in amyloid deposition and phenotypes reflecting the phenotypes of TTR amyloidosis in humans. These phenotypes and the amyloid deposition occur at a very early age. Because this is the first reported in vivo model of TTR amyloidosis to develop amyloidosis so rapidly, the non-human animals are a useful tool to study TTR amyloidosis. In addition, because the non-human animals comprise a humanized TTR locus, the non-human animals will more accurately reflect the efficacy of a human TTR-targeting reagent. Such non-human animals are particularly useful for testing genome-editing reagents designed to target the human TTR gene because the non-human animals disclosed herein comprise humanized endogenous Ttr loci rather than transgenic insertions of human TTR sequence at random genomic loci, and the humanized endogenous Ttr loci comprise orthologous human genomic TTR sequence from both coding and non-coding regions rather than an artificial cDNA sequence.

A. Methods of Testing Efficacy of Human-TTR-Targeting Reagents In Vivo or Ex Vivo Various methods are provided for assessing delivery or efficacy of human-TTR-targeting reagents in vivo using non-human animals comprising a humanized TTR locus comprising a beta-slip mutation as described elsewhere herein. Such methods can comprise: (a) introducing into the non-human animal a human-TTR-targeting reagent; and (b) assessing the activity of the human-TTR-targeting reagent.

The human-TTR-targeting reagent can be any biological or chemical agent that targets the human TTR locus (the human TTR gene), the human TTR mRNA, or the human transthyretin protein. Examples of human-TTR-targeting reagents are disclosed elsewhere herein. For example, the human-TTR-targeting reagent can be a TTR-targeting nucleic acid (e.g., CRISPR/Cas guide RNAs, short hairpin RNAs (shRNAs), or small interfering RNAs (siRNAs)) or nucleic acid encoding a TTR-targeting protein (e.g., a Cas proteins such as Cas9, a ZFN, or a TALEN). Alternatively, the human-TTR-targeting reagent can be a TTR-targeting antibody or antigen-binding protein, or any other large molecule or small molecule that targets human TTR.

Such human-TTR-targeting reagents can be administered by any delivery method (e.g., AAV, LNP, or HDD) as disclosed in more detail elsewhere herein and by any route of administration. Means of delivering therapeutic complexes and molecules and routes of administration are disclosed in more detail elsewhere herein. In particular methods, the reagents delivered via AAV-mediated delivery. For example, AAV8 can be used to target the liver. In other particular methods, the reagents are delivered by LNP-mediated delivery. In other particular methods, the reagents are delivered by hydrodynamic delivery (HDD). The dose can be any suitable dose. For example, in some methods in which the reagents (e.g., Cas9 mRNA and gRNA) are delivered by LNP-mediated delivery, the dose can be between about 0.01 and about 10 mg/kg, about 0.01 and about 5 mg/kg, between about 0.01 and about 4 mg/kg, between about 0.01 and about 3 mg/kg, between about 0.01 and about 2 mg/kg, between about 0.01 and about 1 mg/kg, between about 0.1 and about 10 mg/kg, between about 0.1 and about 6 mg/kg; between about 0.1 and about 5 mg/kg, between about 0.1 and about 4 mg/kg, between about 0.1 and about 3 mg/kg, between about 0.1 and about 2 mg/kg, between about 0.1 and about 1 mg/kg, between about 0.3 and about 10 mg/kg, between about 0.3 and about 6 mg/kg; between about 0.3 and about 5 mg/kg, between about 0.3 and about 4 mg/kg, between about 0.3 and about 3 mg/kg, between about 0.3 and about 2 mg/kg, between about 0.3 and about 1 mg/kg, about 0.1 mg/kg, about 0.3 mg/kg, about 1 mg/kg, about 2 mg/kg, or about 3 mg/kg. In a specific example, the dose is between about 0.1 and about 6 mg/kg; between about 0.1 and about 3 mg/kg, or between about 0.1 and about 2 mg/kg. In a specific example, the human-TTR-targeting reagent is a genome editing reagent, the LNP dose is about 1 mg/kg, and the percent genome editing at the humanized TTR locus is between about 70% and about 80%. In another specific example, the human-TTR-targeting reagent is a genome editing reagent, the LNP dose is about 0.3 mg/kg, and the percent editing is between about 50% and about 80%. In another specific example, the human-TTR-targeting reagent is a genome editing reagent, the LNP dose is about 0.1 mg/kg, and the percent editing is between about 20% and about 80%. In another specific example, the LNP dose is about 1 mg/kg, and the serum TTR levels are reduced to between about 0% and about 10% or between about 0% and about 35% of control levels. In another specific example, the LNP dose is about 0.3 mg/kg, and the serum TTR levels are reduced to between about 0% and about 20% or about 0% and about 95% of control levels. In another specific example, the LNP dose is about 0.1 mg/kg, and the serum TTR levels are reduced to between about 0% and about 60% or about 0% and about 99% of control levels.

Methods for assessing activity of the human-TTR-targeting reagent are well-known and are provided elsewhere herein. Assessment of activity can be in any cell type, any tissue type, or any organ type as disclosed elsewhere herein. In some methods, assessment of activity is in liver cells. As one example, the assessing can comprise measuring non-homologous end joining (NHEJ) activity at the humanized TTR locus. This can comprise, for example, measuring the frequency of insertions or deletions within the humanized TTR locus. If the TTR-targeting reagent is a genome editing reagent (e.g., a nuclease agent), such methods can comprise assessing modification of the humanized TTR locus comprising the beta-slip mutation. For example, the assessing can comprise sequencing the humanized TTR locus in one or more cells isolated from the non-human animal (e.g., next-generation sequencing). Assessment can comprise isolating a target organ (e.g., liver) or tissue from the non-human animal and assessing modification of humanized TTR locus in the target organ or tissue. Assessment can also comprise assessing modification of humanized TTR locus in two or more different cell types within the target organ or tissue. Similarly, assessment can comprise isolating a non-target organ or tissue (e.g., two or more non-target organs or tissues) from the non-human animal and assessing modification of humanized TTR locus in the non-target organ or tissue.

Such methods can also comprise measuring expression levels of the mRNA produced by the humanized TTR locus comprising the beta-slip mutation, or by measuring expression levels of the protein encoded by the humanized TTR locus comprising the beta-slip mutation. For example, protein levels can be measured in a particular cell, tissue, or organ type (e.g., liver), or secreted levels can be measured in the serum. Methods for assessing expression of Ttr mRNA or protein expressed from the humanized TTR locus are provided elsewhere herein and are well-known.

As one specific example, if the human-TTR-targeting reagent is a genome editing reagent (e.g., a nuclease agent), percent editing (e.g., total number of insertions or deletions observed over the total number of sequences read in the PCR reaction from a pool of lysed cells) at the humanized TTR locus can be assessed (e.g., in liver cells).

As one example, if the human-TTR-targeting reagent is a genome editing reagent (e.g., a nuclease agent), percent editing at the humanized TTR locus can be assessed (e.g., in liver cells). For example, the percent editing (e.g., total number of insertions or deletions observed over the total number of sequences read in the PCR reaction from a pool of lysed cells) can be at least about 10%, at least about 20%, at least about 30%, at least about 40%, at least about 50%, at least about 60%, at least about 70%, at least about 80%, at least about 90%, at least about 95%, at least about 99%, or, for example, between about 1% and about 99%, between about 10% and about 99%, between about 20% and about 99%, between about 30% and about 99%, between about 40% and about 99%, between about 50% and about 99%, between about 60% and about 99%, between about 1% and about 90%, between about 10% and about 90%, between about 20% and about 90%, between about 30% and about 90%, between about 40% and about 90%, between about 50% and about 90%, between about 60% and about 90%, between about 1% and about 80%, between about 10% and about 80%, between about 20% and about 80%, between about 30% and about 80%, between about 40% and about 80%, between about 50% and about 80%, or between about 60% and about 80%.

As another example, serum TTR levels can be assessed. For example, serum TTR levels can be reduced by at least about 10%, at least about 20%, at least about 30%, at least about 40%, at least about 50%, at least about 60%, at least about 65%, at least about 70%, at least about 80%, at least about 90%, at least about 95%, at least about 99%, or, for example, between about 1% and about 99%, between about 10% and about 99%, between about 20% and about 99%, between about 30% and about 99%, between about 40% and about 99%, between about 50% and about 99%, between about 60% and about 99%, between about 70% and about 99%, between about 80% and about 99%, between about 1% and about 90%, between about 10% and about 90%, between about 20% and about 90%, between about 30% and about 90%, between about 40% and about 90%, between about 50% and about 90%, between about 60% and about 90%, between about 70% and about 90%, or between about 80% and about 90%.

Such methods can also comprise assessing activity/hyperactivity of the non-human animals, such as in an open field test as described in more detail elsewhere herein. Such methods can also comprise assessing the presence of aggregated forms of TTR (e.g., by native PAGE and western blots) or assessing the presence of amyloid deposits as described in more detail elsewhere herein. Such methods can also comprise assessing whether the non-human animals display dystonia or dystonic phenotypes as described in more detail elsewhere herein.

The various methods provided above for assessing activity in vivo can also be used to assess the activity of human-TTR-targeting reagents ex vivo as described elsewhere herein.

In some methods, the human-TTR-targeting reagent is a nuclease agent, such as a CRISPR/Cas nuclease agent, that targets the human TTR gene. Such methods can comprise, for example: (a) introducing into the non-human animal a nuclease agent designed to cleave the human TTR gene (e.g., Cas protein such as Cas9 and a guide RNA designed to target a guide RNA target sequence in the human TTR gene); and (b) assessing modification of the humanized TTR locus comprising the beta-slip mutation.

In the case of a CRISPR/Cas nuclease, for example, modification of the humanized TTR locus comprising the beta-slip mutation will be induced when the guide RNA forms a complex with the Cas protein and directs the Cas protein to the humanized TTR locus, and the Cas/guide RNA complex cleaves the guide RNA target sequence, triggering repair by the cell (e.g., via non-homologous end joining (NHEJ) if no donor sequence is present).

Optionally, two or more guide RNAs can be introduced, each designed to target a different guide RNA target sequence within the human TTR gene. For example, two guide RNAs can be designed to excise a genomic sequence between the two guide RNA target sequences. Modification of the humanized TTR locus will be induced when the first guide RNA forms a complex with the Cas protein and directs the Cas protein to the humanized TTR locus, the second guide RNA forms a complex with the Cas protein and directs the Cas protein to the humanized TTR locus, the first Cas/guide RNA complex cleaves the first guide RNA target sequence, and the second Cas/guide RNA complex cleaves the second guide RNA target sequence, resulting in excision of the intervening sequence.

Optionally, an exogenous donor nucleic acid capable of recombining with and modifying a human TTR gene is also introduced into the non-human animal. Optionally, the nuclease agent or Cas protein can be tethered to the exogenous donor nucleic acid as described elsewhere herein. Modification of the humanized TTR locus will be induced, for example, when the guide RNA forms a complex with the Cas protein and directs the Cas protein to the humanized TTR locus, the Cas/guide RNA complex cleaves the guide RNA target sequence, and the humanized TTR locus recombines with the exogenous donor nucleic acid to modify the humanized TTR locus. The humanized TTR locus can then be repaired with the exogenous donor nucleic acid, for example, via homology-directed repair (HDR) or via NHEJ-mediated insertion. Any type of exogenous donor nucleic acid can be used, examples of which are provided elsewhere herein.

B. Methods of Optimizing Delivery or Efficacy of Human-TTR-Targeting Reagent In Vivo or Ex Vivo Various methods are provided for optimizing delivery of human-TTR-targeting reagents to a cell or non-human animal or optimizing the activity or efficacy of human-TTR-targeting reagents in vivo. Such methods can comprise, for example: (a) performing the method of testing the efficacy of a human-TTR-targeting reagent as described above a first time in a first non-human animal or first cell; (b) changing a variable and performing the method a second time in a second non-human animal (i.e., of the same species) or a second cell with the changed variable; and (c) comparing the activity of the human-TTR-targeting reagent in step (a) with the activity of the human-TTR-targeting reagent in step (b), and selecting the method resulting in the higher activity.

Methods of measuring delivery, efficacy, or activity of human-TTR-targeting reagents are disclosed elsewhere herein. For example, such methods can comprise measuring modification of the humanized TTR locus comprising the beta-slip mutation. More effective modification of the humanized TTR locus can mean different things depending on the desired effect within the non-human animal or cell. For example, more effective modification of the humanized TTR locus can mean one or more or all of higher levels of modification, higher precision, higher consistency, or higher specificity. Higher levels of modification (i.e., higher efficacy) of the humanized TTR locus refers to a higher percentage of cells is targeted within a particular target cell type, within a particular target tissue, or within a particular target organ (e.g., liver). Higher precision refers to more precise modification of the humanized TTR locus (e.g., a higher percentage of targeted cells having the same modification or having the desired modification without extra unintended insertions and deletions (e.g., NHEJ indels)). Higher consistency refers to more consistent modification of the humanized TTR locus among different types of targeted cells, tissues, or organs if more than one type of cell, tissue, or organ is being targeted (e.g., modification of a greater number of cell types within the liver). If a particular organ is being targeted, higher consistency can also refer to more consistent modification throughout all locations within the organ (e.g., the liver). Higher specificity can refer to higher specificity with respect to the genomic locus or loci targeted, higher specificity with respect to the cell type targeted, higher specificity with respect to the tissue type targeted, or higher specificity with respect to the organ targeted. For example, increased genomic locus specificity refers to less modification of off-target genomic loci (e.g., a lower percentage of targeted cells having modifications at unintended, off-target genomic loci instead of or in addition to modification of the target genomic locus). Likewise, increased cell type, tissue, or organ type specificity refers to less modification of off-target cell types, tissue types, or organ types if a particular cell type, tissue type, or organ type is being targeted (e.g., when a particular organ is targeted (e.g., the liver), there is less modification of cells in organs or tissues that are not intended targets).

Alternatively, such methods can comprise measuring expression of TTR mRNA or TTR protein. In one example, a more effective human-TTR-targeting agent results in a greater decrease in TTR mRNA or TTR protein expression. Alternatively, such methods can comprise measuring TTR activity. In one example, a more effective human-TTR-targeting agent results in a greater decrease in TTR activity.

The variable that is changed can be any parameter. As one example, the changed variable can be the packaging or the delivery method by which the human-TTR-targeting reagent or reagents are introduced into the cell or non-human animal. Examples of delivery methods, such as LNP, HDD, and AAV, are disclosed elsewhere herein. For example, the changed variable can be the AAV serotype. Similarly, the administering can comprise LNP-mediated delivery, and the changed variable can be the LNP formulation. As another example, the changed variable can be the route of administration for introduction of the human-TTR-targeting reagent or reagents into the cell or non-human animal. Examples of routes of administration, such as intravenous, intravitreal, intraparenchymal, and nasal instillation, are disclosed elsewhere herein.

As another example, the changed variable can be the concentration or amount of the human-TTR-targeting reagent or reagents introduced. As another example, the changed variable can be the concentration or the amount of one human-TTR-targeting reagent introduced (e.g., guide RNA, Cas protein, exogenous donor nucleic acid, RNAi agent, or ASO) relative to the concentration or the amount another human-TTR-targeting reagent introduced (e.g., guide RNA, Cas protein, exogenous donor nucleic acid, RNAi agent, or ASO).

As another example, the changed variable can be the timing of introducing the human-TTR-targeting reagent or reagents relative to the timing of assessing the activity or efficacy of the reagents. As another example, the changed variable can be the number of times or frequency with which the human-TTR-targeting reagent or reagents are introduced. As another example, the changed variable can be the timing of introduction of one human-TTR-targeting reagent introduced (e.g., guide RNA, Cas protein, exogenous donor nucleic acid, RNAi agent, or ASO) relative to the timing of introduction of another human-TTR-targeting reagent introduced (e.g., guide RNA, Cas protein, exogenous donor nucleic acid, RNAi agent, or ASO).

As another example, the changed variable can be the form in which the human-TTR-targeting reagent or reagents are introduced. For example, a guide RNA can be introduced in the form of DNA or in the form of RNA. A Cas protein (e.g., Cas9) can be introduced in the form of DNA, in the form of RNA, or in the form of a protein (e.g., complexed with a guide RNA). An exogenous donor nucleic acid can be DNA, RNA, single-stranded, double-stranded, linear, circular, and so forth. Similarly, each of the components can comprise various combinations of modifications for stability, to reduce off-target effects, to facilitate delivery, and so forth. Likewise, RNAi agents and ASOs, for example, can comprise various combinations of modifications for stability, to reduce off-target effects, to facilitate delivery, and so forth. As another example, the changed variable can be the human-TTR-targeting reagent or reagents that are introduced (e.g., introducing a different guide RNA with a different sequence, introducing a different Cas protein (e.g., introducing a different Cas protein with a different sequence, or a nucleic acid with a different sequence but encoding the same Cas protein amino acid sequence), or introducing a different exogenous donor nucleic acid with a different sequence).

In a specific example, the human-TTR-targeting reagent comprises a Cas protein and a guide RNA designed to target a guide RNA target sequence in a human TTR gene. In such methods, the changed variable can be the guide RNA sequence and/or the guide RNA target sequence. Similarly, if the human-TTR-targeting reagent comprises an RNAi agent or an ASO, the changed variable can be introducing a different RNAi agent or ASO with a different sequence. In some such methods, the Cas protein and the guide RNA can each be administered in the form of RNA, and the changed variable can be the ratio of Cas mRNA to guide RNA (e.g., in an LNP formulation). In some such methods, the changed variable can be guide RNA modifications (e.g., a guide RNA with a modification is compared to a guide RNA without the modification).

C. Human-TTR-Targeting Reagents

A human-TTR-targeting reagent can be any reagent that targets a human TTR gene, a human TTR mRNA, or a human TTR protein. The human-TTR-targeting reagent can target any region of a human TTR gene, a human TTR mRNA, or a human TTR protein (i.e., not only the region comprising the beta-slip mutation but also any other region as well). For example, it can be a genome editing reagent such as a nuclease agent that cleaves a target sequence within the human TTR gene, it can be an antisense oligonucleotide targeting a human TTR mRNA, it can be an antigen-binding protein targeting an epitope of a human TTR protein, or it can be a small molecule targeting human TTR. Human-TTR-targeting reagents in the methods disclosed herein can be known human-TTR-targeting reagents, can be putative-TTR-targeting reagents (e.g., candidate reagents designed to target human TTR), or can be reagents being screened for human-TTR-targeting activity.

(1) Nuclease Agents Targeting Human TTR Gene

A human-TTR-targeting reagent can be a genome editing reagent such as a nuclease agent that cleaves a target sequence within the human TTR gene. A nuclease target sequence includes a DNA sequence at which a nick or double-strand break is induced by a nuclease agent. The target sequence for a nuclease agent can be endogenous (or native) to the cell or the target sequence can be exogenous to the cell. A target sequence that is exogenous to the cell is not naturally occurring in the genome of the cell. The target sequence can also exogenous to the polynucleotides of interest that one desires to be positioned at the target locus. In some cases, the target sequence is present only once in the genome of the host cell.

The length of the target sequence can vary, and includes, for example, target sequences that are about 30-36 bp for a zinc finger nuclease (ZFN) pair (i.e., about 15-18 bp for each ZFN), about 36 bp for a Transcription Activator-Like Effector Nuclease (TALEN), or about 20 bp for a CRISPR/Cas9 guide RNA.

Any nuclease agent that induces a nick or double-strand break at a desired target sequence can be used in the methods and compositions disclosed herein. A naturally occurring or native nuclease agent can be employed so long as the nuclease agent induces a nick or double-strand break in a desired target sequence. Alternatively, a modified or engineered nuclease agent can be employed. An "engineered nuclease agent" includes a nuclease that is engineered (modified or derived) from its native form to specifically recognize and induce a nick or double-strand break in the desired target sequence. Thus, an engineered nuclease agent can be derived from a native, naturally occurring nuclease agent or it can be artificially created or synthesized. The engineered nuclease can induce a nick or double-strand break in a target sequence, for example, wherein the target sequence is not a sequence that would have been recognized by a native (non-engineered or non-modified) nuclease agent. The modification of the nuclease agent can be as little as one amino acid in a protein cleavage agent or one nucleotide in a nucleic acid cleavage agent. Producing a nick or double-strand break in a target sequence or other DNA can be referred to herein as "cutting" or "cleaving" the target sequence or other DNA.

Active variants and fragments of the exemplified target sequences are also provided. Such active variants can comprise at least 65%, 70%, 75%, 80%, 85%, 90%, 91%, 92%, 93%, 94%, 95%, 96%, 97%, 98%, 99% or more sequence identity to the given target sequence, wherein the active variants retain biological activity and hence are capable of being recognized and cleaved by a nuclease agent in a sequence-specific manner. Assays to measure the double-strand break of a target sequence by a nuclease agent are well-known. See, e.g., Frendewey et al. (2010) *Methods in Enzymology* 476:295-307, which is incorporated by reference herein in its entirety for all purposes.

The target sequence of the nuclease agent can be positioned anywhere in or near the Ttr locus. The target sequence can be located within a coding region of the Ttr gene, or within regulatory regions that influence the expression of the gene. A target sequence of the nuclease agent can be located in an intron, an exon, a promoter, an enhancer, a regulatory region, or any non-protein coding region.

One type of nuclease agent is a Transcription Activator-Like Effector Nuclease (TALEN). TAL effector nucleases are a class of sequence-specific nucleases that can be used to make double-strand breaks at specific target sequences in the genome of a prokaryotic or eukaryotic organism. TAL effector nucleases are created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See WO 2010/079430; Morbitzer et al. (2010) *PNAS* 10.1073/pnas.1013133107; Scholze & Boch (2010) *Virulence* 1:428-432; Christian et al. *Genetics* (2010) 186:757-761; Li et al. (2010) *Nuc. Acids Res*. (2010) doi:10.1093/nar/gkq704; and Miller et al. (2011) *Nature Biotechnology* 29:143-148, each of which is herein incorporated by reference in its entirety.

Examples of suitable TAL nucleases, and methods for preparing suitable TAL nucleases, are disclosed, e.g., in US 2011/0239315 A1, US 2011/0269234 A1, US 2011/0145940 A1, US 2003/0232410 A1, US 2005/0208489 A1, US 2005/0026157 A1, US 2005/0064474 A1, US 2006/0188987 A1, and US 2006/0063231 A1, each of which is herein incorporated by reference in its entirety. In various embodiments, TAL effector nucleases are engineered that cut in or near a target nucleic acid sequence in, e.g., a locus of interest or a genomic locus of interest, wherein the target nucleic acid sequence is at or near a sequence to be modified by a targeting vector. The TAL nucleases suitable for use with the various methods and compositions provided herein include those that are specifically designed to bind at or near target nucleic acid sequences to be modified by targeting vectors as described herein.

In some TALENs, each monomer of the TALEN comprises 33-35 TAL repeats that recognize a single base pair via two hypervariable residues. In some TALENs, the nuclease agent is a chimeric protein comprising a TAL-repeat-based DNA binding domain operably linked to an independent nuclease such as a FokI endonuclease. For example, the nuclease agent can comprise a first TAL-repeat-based DNA binding domain and a second TAL-repeat-based DNA binding domain, wherein each of the first and the second TAL-repeat-based DNA binding domains is operably linked to a FokI nuclease, wherein the first and the second TAL-repeat-based DNA binding domain recognize two contiguous target DNA sequences in each strand of the target DNA sequence separated by a spacer sequence of varying length (12-20 bp), and wherein the FokI nuclease subunits dimerize to create an active nuclease that makes a double strand break at a target sequence.

The nuclease agent employed in the various methods and compositions disclosed herein can further comprise a zinc-finger nuclease (ZFN). In some ZFNs, each monomer of the ZFN comprises 3 or more zinc finger-based DNA binding domains, wherein each zinc finger-based DNA binding domain binds to a 3 bp subsite. In other ZFNs, the ZFN is a chimeric protein comprising a zinc finger-based DNA binding domain operably linked to an independent nuclease such as a FokI endonuclease. For example, the nuclease agent can comprise a first ZFN and a second ZFN, wherein each of the first ZFN and the second ZFN is operably linked to a FokI nuclease subunit, wherein the first and the second ZFN recognize two contiguous target DNA sequences in each strand of the target DNA sequence separated by about 5-7 bp spacer, and wherein the FokI nuclease subunits dimerize to create an active nuclease that makes a double strand break. See, e.g., US20060246567; US20080182332; US20020081614; US20030021776; WO/2002/057308A2; US20130123484; US20100291048; WO/2011/017293A2; and Gaj et al. (2013) Trends in Biotechnology, 31(7):397-405, each of which is herein incorporated by reference.

Another type of nuclease agent is a meganuclease. Meganucleases have been classified into four families based on conserved sequence motifs, the families are the LAGLIDADG, GIY-YIG, H-N-H, and His-Cys box families. These motifs participate in the coordination of metal ions and hydrolysis of phosphodiester bonds. Meganucleases are notable for their long target sequences, and for tolerating some sequence polymorphisms in their DNA substrates. Meganuclease domains, structure and function are known, see for example, Guhan and Muniyappa (2003) Crit Rev Biochem Mol Biol 38:199-248; Lucas et al., (2001) Nucleic Acids Res 29:960-9; Jurica and Stoddard, (1999) Cell Mol Life Sci 55:1304-26; Stoddard, (2006) Q Rev Biophys 38:49-95; and Moure et al., (2002) Nat Struct Biol 9:764. In some examples, a naturally occurring variant and/or engineered derivative meganuclease is used. Methods for modifying the kinetics, cofactor interactions, expression, optimal conditions, and/or target sequence specificity, and screening for activity are known. See, e.g., Epinat et al., (2003) Nucleic Acids Res 31:2952-62; Chevalier et al., (2002) Mol Cell 10:895-905; Gimble et al., (2003) Mol Biol 334:993-1008; Seligman et al., (2002) Nucleic Acids Res 30:3870-9; Sussman et al., (2004) J Mol Blot 342:31-41; Rosen et al., (2006) Nucleic Acids Res 34:4791-800; Chames et al., (2005) Nucleic Acids Res 33:e178; Smith et al., (2006) Nucleic Acids Res 34:e149; Gruen et al., (2002) Nucleic Acids Res 30:e29; Chen and Zhao, (2005) Nucleic Acids Res 33:e154; WO2005105989; WO2003078619; WO2006097854; WO2006097853; WO2006097784; and WO2004031346, each of which is herein incorporated by reference in its entirety.

Any meganuclease can be used, including, for example, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, PI-PspI, F-SceI, F-SceII, F-SuvI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NcIIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp6803I, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, PI-TliII, or any active variants or fragments thereof.

Meganucleases can recognize, for example, double-stranded DNA sequences of 12 to 40 base pairs. In some cases, the meganuclease recognizes one perfectly matched target sequence in the genome.

Some meganucleases are homing nucleases. One type of homing nuclease is a LAGLIDADG family of homing nucleases including, for example, I-SceI, I-CreI, and I-DmoI.

Nuclease agents can further comprise CRISPR/Cas systems as described in more detail below.

Active variants and fragments of nuclease agents (i.e., an engineered nuclease agent) are also provided. Such active variants can comprise at least 65%, 70%, 75%, 80%, 85%, 90%, 91%, 92%, 93%, 94%, 95%, 96%, 97%, 98%, 99% or more sequence identity to the native nuclease agent, wherein the active variants retain the ability to cut at a desired target sequence and hence retain nick or double-strand-break-inducing activity. For example, any of the nuclease agents described herein can be modified from a native endonuclease sequence and designed to recognize and induce a nick or double-strand break at a target sequence that was not recognized by the native nuclease agent. Thus, some engineered nucleases have a specificity to induce a nick or double-strand break at a target sequence that is different from the corresponding native nuclease agent target sequence. Assays for nick or double-strand-break-inducing activity are known and generally measure the overall activity and specificity of the endonuclease on DNA substrates containing the target sequence.

The nuclease agent may be introduced into a cell or non-human animal by any known means. A polypeptide encoding the nuclease agent may be directly introduced into the cell or non-human animal. Alternatively, a polynucleotide encoding the nuclease agent can be introduced into the cell or non-human animal. When a polynucleotide encoding the nuclease agent is introduced, the nuclease agent can be transiently, conditionally, or constitutively expressed within the cell. The polynucleotide encoding the nuclease agent can be contained in an expression cassette and be operably linked to a conditional promoter, an inducible promoter, a constitutive promoter, or a tissue-specific promoter. Examples of promoters are discussed in further detail elsewhere herein. Alternatively, the nuclease agent can be introduced into the cell as an mRNA encoding the nuclease agent.

A polynucleotide encoding a nuclease agent can be stably integrated in the genome of a cell and operably linked to a promoter active in the cell. Alternatively, a polynucleotide encoding a nuclease agent can be in a targeting vector.

When the nuclease agent is provided to the cell through the introduction of a polynucleotide encoding the nuclease agent, such a polynucleotide encoding a nuclease agent can be modified to substitute codons having a higher frequency of usage in the cell of interest, as compared to the naturally occurring polynucleotide sequence encoding the nuclease agent. For example, the polynucleotide encoding the nuclease agent can be modified to substitute codons having a higher frequency of usage in a given eukaryotic cell of interest, including a human cell, a non-human cell, a mammalian cell, a rodent cell, a mouse cell, a rat cell or any other host cell of interest, as compared to the naturally occurring polynucleotide sequence.

(2) CRISPR/Cas Systems Targeting Human TTR Gene

A particular type of human-TTR-targeting reagent can be a CRISPR/Cas system that targets the human TTR gene. CRISPR/Cas systems include transcripts and other elements involved in the expression of, or directing the activity of, Cas genes. A CRISPR/Cas system can be, for example, a type I, a type II, a type III, or a type V system (e.g., subtype V-A or subtype V-B). CRISPR/Cas systems used in the compositions and methods disclosed herein can be non-naturally occurring. A "non-naturally occurring" system includes anything indicating the involvement of the hand of man, such as one or more components of the system being altered or mutated from their naturally occurring state, being at least substantially free from at least one other component with which they are naturally associated in nature, or being associated with at least one other component with which they are not naturally associated. For example, some CRISPR/Cas systems employ non-naturally occurring CRISPR complexes comprising a gRNA and a Cas protein that do not naturally occur together, employ a Cas protein that does not occur naturally, or employ a gRNA that does not occur naturally.

Cas Proteins and Polynucleotides Encoding Cas Proteins.

Cas proteins generally comprise at least one RNA recognition or binding domain that can interact with guide RNAs (gRNAs, described in more detail below). Cas proteins can also comprise nuclease domains (e.g., DNase domains or RNase domains), DNA-binding domains, helicase domains, protein-protein interaction domains, dimerization domains, and other domains. Some such domains (e.g., DNase domains) can be from a native Cas protein. Other such domains can be added to make a modified Cas protein. A nuclease domain possesses catalytic activity for nucleic acid cleavage, which includes the breakage of the covalent bonds of a nucleic acid molecule. Cleavage can produce blunt ends or staggered ends, and it can be single-stranded or double-stranded. For example, a wild type Cas9 protein will typically create a blunt cleavage product. Alternatively, a wild type Cpf1 protein (e.g., FnCpf1) can result in a cleavage product with a 5-nucleotide 5' overhang, with the cleavage occurring after the 18th base pair from the PAM sequence on the non-targeted strand and after the 23rd base on the targeted strand. A Cas protein can have full cleavage activity to create a double-strand break at a target genomic locus (e.g., a double-strand break with blunt ends), or it can be a nickase that creates a single-strand break at a target genomic locus.

Examples of Cas proteins include Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof.

An exemplary Cas protein is a Cas9 protein or a protein derived from a Cas9 protein. Cas9 proteins are from a type II CRISPR/Cas system and typically share four key motifs with a conserved architecture. Motifs 1, 2, and 4 are RuvC-like motifs, and motif 3 is an HNH motif. Exemplary Cas9 proteins are from *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp. *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp *Arthrospira maxima, Arthrospira platensis, Arthrospira* sp., *Lyngbya* sp., *Microcoleus chthonoplastes, Oscillatoria* sp., *Petrotoga mobilis, Thermosipho africanus, Acaryochloris marina, Neisseria meningitidis,* or *Campylobacter jejuni.* Additional examples of the Cas9 family members are described in WO 2014/131833, herein incorporated by reference in its entirety for all purposes. Cas9 from *S. pyogenes* (SpCas9) (assigned SwissProt accession number Q99ZW2) is an exemplary Cas9 protein. Cas9 from *S. aureus* (SaCas9) (assigned UniProt accession number J7RUA5) is another exemplary Cas9 protein. Cas9 from *Campylobacter jejuni* (CjCas9) (assigned UniProt accession number Q0P897) is another exemplary Cas9 protein. See, e.g., Kim et al. (2017) *Nat. Comm.* 8:14500, herein incorporated by reference in its entirety for all purposes. SaCas9 is smaller than SpCas9, and CjCas9 is smaller than both SaCas9 and SpCas9.

Another example of a Cas protein is a Cpf1 (CRISPR from *Prevotella* and *Francisella* 1) protein. Cpf1 is a large protein (about 1300 amino acids) that contains a RuvC-like nuclease domain homologous to the corresponding domain of Cas9 along with a counterpart to the characteristic arginine-rich cluster of Cas9. However, Cpf1 lacks the HNH nuclease domain that is present in Cas9 proteins, and the RuvC-like domain is contiguous in the Cpf1 sequence, in contrast to Cas9 where it contains long inserts including the HNH domain. See, e.g., Zetsche et al. (2015) *Cell* 163(3): 759-771, herein incorporated by reference in its entirety for all purposes. Exemplary Cpf1 proteins are from *Francisella tularensis* 1, *Francisella tularensis* subsp. *novicida, Prevotella albensis,* Lachnospiraceae bacterium MC2017 1, *Butyrivibrio proteoclasticus,* Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus* Methanoplasma termitum, Eubacterium eligens, *Moraxella bovoculi* 237, *Leptospira inadai,* Lachnospiraceae bacterium ND2006, *Porphyromonas crevioricanis* 3, *Prevotella disiens,* and *Porphyromonas macacae.* Cpf1 from *Francisella novicida* U112 (FnCpf1; assigned UniProt accession number A0Q7Q2) is an exemplary Cpf1 protein.

Cas proteins can be wild type proteins (i.e., those that occur in nature), modified Cas proteins (i.e., Cas protein variants), or fragments of wild type or modified Cas proteins. Cas proteins can also be active variants or fragments with respect to catalytic activity of wild type or modified Cas proteins. Active variants or fragments with respect to catalytic activity can comprise at least 80%, 85%, 90%, 91%, 92%, 93%, 94%, 95%, 96%, 97%, 98%, 99% or more sequence identity to the wild type or modified Cas protein or a portion thereof, wherein the active variants retain the ability to cut at a desired cleavage site and hence retain nick-inducing or double-strand-break-inducing activity. Assays for nick-inducing or double-strand-break-inducing activity are known and generally measure the overall activity and specificity of the Cas protein on DNA substrates containing the cleavage site.

Cas proteins can be modified to increase or decrease one or more of nucleic acid binding affinity, nucleic acid binding specificity, and enzymatic activity. Cas proteins can also be modified to change any other activity or property of the protein, such as stability. For example, one or more nuclease domains of the Cas protein can be modified, deleted, or inactivated, or a Cas protein can be truncated to remove domains that are not essential for the function of the protein or to optimize (e.g., enhance or reduce) the activity or a property of the Cas protein.

One example of a modified Cas protein is the modified SpCas9-HF1 protein, which is a high-fidelity variant of Streptococcus pyogenes Cas9 harboring alterations (N497A/R661A/Q695A/Q926A) designed to reduce non-specific DNA contacts. See, e.g., Kleinstiver et al. (2016) Nature 529(7587):490-495, herein incorporated by reference in its entirety for all purposes. Another example of a modified Cas protein is the modified eSpCas9 variant (K848A/K1003A/R1060A) designed to reduce off-target effects. See, e.g., Slaymaker et al. (2016) Science 351(6268):84-88, herein incorporated by reference in its entirety for all purposes. Other SpCas9 variants include K855A and K810A/K1003A/R1060A.

Cas proteins can comprise at least one nuclease domain, such as a DNase domain. For example, a wild type Cpf1 protein generally comprises a RuvC-like domain that cleaves both strands of target DNA, perhaps in a dimeric configuration. Cas proteins can also comprise at least two nuclease domains, such as DNase domains. For example, a wild type Cas9 protein generally comprises a RuvC-like nuclease domain and an HNH-like nuclease domain. The RuvC and HNH domains can each cut a different strand of double-stranded DNA to make a double-stranded break in the DNA. See, e.g., Jinek et al. (2012) Science 337:816-821, herein incorporated by reference in its entirety for all purposes.

One or more or all of the nuclease domains can be deleted or mutated so that they are no longer functional or have reduced nuclease activity. For example, if one of the nuclease domains is deleted or mutated in a Cas9 protein, the resulting Cas9 protein can be referred to as a nickase and can generate a single-strand break within a double-stranded target DNA but not a double-strand break (i.e., it can cleave the complementary strand or the non-complementary strand, but not both). If both of the nuclease domains are deleted or mutated, the resulting Cas protein (e.g., Cas9) will have a reduced ability to cleave both strands of a double-stranded DNA (e.g., a nuclease-null or nuclease-inactive Cas protein, or a catalytically dead Cas protein (dCas)). An example of a mutation that converts Cas9 into a nickase is a D10A (aspartate to alanine at position 10 of Cas9) mutation in the RuvC domain of Cas9 from S. pyogenes. Likewise, H939A (histidine to alanine at amino acid position 839), H840A (histidine to alanine at amino acid position 840), or N863A (asparagine to alanine at amino acid position N863) in the HNH domain of Cas9 from S. pyogenes can convert the Cas9 into a nickase. Other examples of mutations that convert Cas9 into a nickase include the corresponding mutations to Cas9 from S. thermophilus. See, e.g., Sapranauskas et al. (2011) Nucleic Acids Research 39:9275-9282 and WO 2013/141680, each of which is herein incorporated by reference in its entirety for all purposes. Such mutations can be generated using methods such as site-directed mutagenesis, PCR-mediated mutagenesis, or total gene synthesis. Examples of other mutations creating nickases can be found, for example, in WO 2013/176772 and WO 2013/142578, each of which is herein incorporated by reference in its entirety for all purposes. If all of the nuclease domains are deleted or mutated in a Cas protein (e.g., both of the nuclease domains are deleted or mutated in a Cas9 protein), the resulting Cas protein (e.g., Cas9) will have a reduced ability to cleave both strands of a double-stranded DNA (e.g., a nuclease-null or nuclease-inactive Cas protein). One specific example is a D10A/H840A S. pyogenes Cas9 double mutant or a corresponding double mutant in a Cas9 from another species when optimally aligned with S. pyogenes Cas9. Another specific example is a D10A/N863A S. pyogenes Cas9 double mutant or a corresponding double mutant in a Cas9 from another species when optimally aligned with S. pyogenes Cas9.

Examples of inactivating mutations in the catalytic domains of Staphylococcus aureus Cas9 proteins are also known. For example, the Staphylococcus aureus Cas9 enzyme (SaCas9) may comprise a substitution at position N580 (e.g., N580A substitution) and a substitution at position D10 (e.g., D10A substitution) to generate a nuclease-inactive Cas protein. See, e.g., WO 2016/106236, herein incorporated by reference in its entirety for all purposes.

Examples of inactivating mutations in the catalytic domains of Cpf1 proteins are also known. With reference to Cpf1 proteins from Francisella novicida U112 (FnCpf1), Acidaminococcus sp. BV3L6 (AsCpf1), Lachnospiraceae bacterium ND2006 (LbCpf1), and Moraxella bovoculi 237 (MbCpf1 Cpf1), such mutations can include mutations at positions 908, 993, or 1263 of AsCpf1 or corresponding positions in Cpf1 orthologs, or positions 832, 925, 947, or 1180 of LbCpf1 or corresponding positions in Cpf1 orthologs. Such mutations can include, for example one or more of mutations D908A, E993A, and D1263A of AsCpf1 or corresponding mutations in Cpf1 orthologs, or D832A, E925A, D947A, and D1180A of LbCpf1 or corresponding mutations in Cpf1 orthologs. See, e.g., US 2016/0208243, herein incorporated by reference in its entirety for all purposes.

Cas proteins can also be operably linked to heterologous polypeptides as fusion proteins. For example, a Cas protein can be fused to a cleavage domain or an epigenetic modification domain. See WO 2014/089290, herein incorporated by reference in its entirety for all purposes. Cas proteins can also be fused to a heterologous polypeptide providing increased or decreased stability. The fused domain or heterologous polypeptide can be located at the N-terminus, the C-terminus, or internally within the Cas protein.

As one example, a Cas protein can be fused to one or more heterologous polypeptides that provide for subcellular localization. Such heterologous polypeptides can include, for example, one or more nuclear localization signals (NLS) such as the monopartite SV40 NLS and/or a bipartite alpha-importin NLS for targeting to the nucleus, a mitochondrial localization signal for targeting to the mitochondria, an ER retention signal, and the like. See, e.g., Lange et al. (2007) J. Biol. Chem. 282:5101-5105, herein incorporated by reference in its entirety for all purposes. Such subcellular localization signals can be located at the N-terminus, the C-terminus, or anywhere within the Cas protein. An NLS can comprise a stretch of basic amino acids, and can be a monopartite sequence or a bipartite sequence. Optionally, a Cas protein can comprise two or more NLSs, including an NLS (e.g., an alpha-importin NLS or a monopartite NLS) at the N-terminus and an NLS (e.g., an SV40 NLS or a bipartite NLS) at the C-terminus. A Cas protein can also comprise two or more NLSs at the N-terminus and/or two or more NLSs at the C-terminus.

Cas proteins can also be operably linked to a cell-penetrating domain or protein transduction domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. See, e.g., WO 2014/089290 and WO 2013/176772, each of which is herein incorporated by reference in its entirety for all purposes. The cell-penetrating domain can be located at the N-terminus, the C-terminus, or anywhere within the Cas protein.

Cas proteins can also be operably linked to a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreen1), yellow fluorescent proteins (e.g., YFP, eYFP, Citrine, Venus, YPet, PhiYFP, ZsYellow1), blue fluorescent proteins (e.g., eBFP, eBFP2, Azurite, mKalama1, GFPuv, Sapphire, T-sapphire), cyan fluorescent proteins (e.g., eCFP, Cerulean, CyPet, AmCyan1, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, Jred), orange fluorescent proteins (e.g., mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly(NANP), tandem affinity purification (TAP) tag, myc, AcV5, AU1, AUS, E, ECS, E2, FLAG, hemagglutinin (HA), nus, Softag 1, Softag 3, Strep, SBP, Glu-Glu, HSV, KT3, S, 51, T7, V5, VSV-G, histidine (His), biotin carboxyl carrier protein (BCCP), and calmodulin.

Cas proteins can also be tethered to exogenous donor nucleic acids or labeled nucleic acids. Such tethering (i.e., physical linking) can be achieved through covalent interactions or noncovalent interactions, and the tethering can be direct (e.g., through direct fusion or chemical conjugation, which can be achieved by modification of cysteine or lysine residues on the protein or intein modification), or can be achieved through one or more intervening linkers or adapter molecules such as streptavidin or aptamers. See, e.g., Pierce et al. (2005) *Mini Rev. Med. Chem.* 5(1):41-55; Duckworth et al. (2007) *Angew. Chem. Int. Ed. Engl.* 46(46):8819-8822; Schaeffer and Dixon (2009) *Australian J. Chem.* 62(10): 1328-1332; Goodman et al. (2009) *Chembiochem.* 10(9): 1551-1557; and Khatwani et al. (2012) *Bioorg. Med. Chem.* 20(14):4532-4539, each of which is herein incorporated by reference in its entirety for all purposes. Noncovalent strategies for synthesizing protein-nucleic acid conjugates include biotin-streptavidin and nickel-histidine methods. Covalent protein-nucleic acid conjugates can be synthesized by connecting appropriately functionalized nucleic acids and proteins using a wide variety of chemistries. Some of these chemistries involve direct attachment of the oligonucleotide to an amino acid residue on the protein surface (e.g., a lysine amine or a cysteine thiol), while other more complex schemes require post-translational modification of the protein or the involvement of a catalytic or reactive protein domain. Methods for covalent attachment of proteins to nucleic acids can include, for example, chemical cross-linking of oligonucleotides to protein lysine or cysteine residues, expressed protein-ligation, chemoenzymatic methods, and the use of photoaptamers. The exogenous donor nucleic acid or labeled nucleic acid can be tethered to the C-terminus, the N-terminus, or to an internal region within the Cas protein. In one example, the exogenous donor nucleic acid or labeled nucleic acid is tethered to the C-terminus or the N-terminus of the Cas protein. Likewise, the Cas protein can be tethered to the 5' end, the 3' end, or to an internal region within the exogenous donor nucleic acid or labeled nucleic acid. That is, the exogenous donor nucleic acid or labeled nucleic acid can be tethered in any orientation and polarity. For example, the Cas protein can be tethered to the 5' end or the 3' end of the exogenous donor nucleic acid or labeled nucleic acid.

Cas proteins can be provided in any form. For example, a Cas protein can be provided in the form of a protein, such as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism. For example, the nucleic acid encoding the Cas protein can be modified to substitute codons having a higher frequency of usage in a bacterial cell, a yeast cell, a human cell, a non-human cell, a mammalian cell, a rodent cell, a mouse cell, a rat cell, or any other host cell of interest, as compared to the naturally occurring polynucleotide sequence. When a nucleic acid encoding the Cas protein is introduced into the cell, the Cas protein can be transiently, conditionally, or constitutively expressed in the cell.

Cas proteins provided as mRNAs can be modified for improved stability and/or immunogenicity properties. The modifications may be made to one or more nucleosides within the mRNA. Examples of chemical modifications to mRNA nucleobases include pseudouridine, 1-methyl-pseudouridine, and 5-methyl-cytidine. For example, capped and polyadenylated Cas mRNA containing N1-methyl pseudouridine can be used. Likewise, Cas mRNAs can be modified by depletion of uridine using synonymous codons.

Nucleic acids encoding Cas proteins can be stably integrated in the genome of a cell and operably linked to a promoter active in the cell. Alternatively, nucleic acids encoding Cas proteins can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. For example, the nucleic acid encoding the Cas protein can be in a vector comprising a DNA encoding a gRNA. Alternatively, it can be in a vector or plasmid that is separate from the vector comprising the DNA encoding the gRNA. Promoters that can be used in an expression construct include promoters active, for example, in one or more of a eukaryotic cell, a human cell, a non-human cell, a mammalian cell, a non-human mammalian cell, a rodent cell, a mouse cell, a rat cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Optionally, the promoter can be a bidirectional promoter driving expression of both a Cas protein in one direction and a guide RNA in the other direction. Such bidirectional promoters can consist of (1) a complete, conventional, unidirectional Pol III promoter that contains 3 external control elements: a distal sequence element (DSE), a proximal sequence element (PSE), and a TATA box; and (2) a second basic Pol III promoter that includes a PSE and a TATA box fused to the 5' terminus of the DSE in reverse orientation. For example, in the H1 promoter, the DSE is adjacent to the PSE and the TATA box, and the promoter can be rendered bidirectional by creating a hybrid promoter in which transcription in the reverse direction is controlled by appending a PSE and TATA box derived from the U6 promoter. See, e.g., US 2016/0074535, herein incorporated by references in its entirety for all purposes. Use of a bidirectional promoter to express genes encoding a Cas protein and a guide RNA simultaneously allow for the generation of compact expression cassettes to facilitate delivery.

Guide RNAs.

A "guide RNA" or "gRNA" is an RNA molecule that binds to a Cas protein (e.g., Cas9 protein) and targets the Cas protein to a specific location within a target DNA. Guide RNAs can comprise two segments: a "DNA-targeting segment" and a "protein-binding segment." "Segment" includes a section or region of a molecule, such as a contiguous stretch of nucleotides in an RNA. Some gRNAs, such as those for Cas9, can comprise two separate RNA molecules: an "activator-RNA" (e.g., tracrRNA) and a "targeter-RNA" (e.g., CRISPR RNA or crRNA). Other gRNAs are a single RNA molecule (single RNA polynucleotide), which can also be called a "single-molecule gRNA," a "single-guide RNA," or an "sgRNA." See, e.g., WO 2013/176772, WO 2014/065596, WO 2014/089290, WO 2014/093622, WO 2014/099750, WO 2013/142578, and WO 2014/131833, each of which is herein incorporated by reference in its entirety for all purposes. For Cas9, for example, a single-guide RNA can comprise a crRNA fused to a tracrRNA (e.g., via a linker). For Cpf1, for example, only a crRNA is needed to achieve binding to a target sequence. The terms "guide RNA" and "gRNA" include both double-molecule (i.e., modular) gRNAs and single-molecule gRNAs.

An exemplary two-molecule gRNA comprises a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA") molecule. A crRNA comprises both the DNA-targeting segment (single-stranded) of the gRNA and a stretch of nucleotides that forms one half of the dsRNA duplex of the protein-binding segment of the gRNA. An example of a crRNA tail, located downstream (3') of the DNA-targeting segment, comprises, consists essentially of, or consists of GUUUUAGAGCUAUGCU (SEQ ID NO: 84). Any of the DNA-targeting segments disclosed herein can be joined to the 5' end of SEQ ID NO: 84 to form a crRNA.

A corresponding tracrRNA (activator-RNA) comprises a stretch of nucleotides that forms the other half of the dsRNA duplex of the protein-binding segment of the gRNA. A stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA. An example of a tracrRNA sequence comprises, consists essentially of, or consists of AGCAUAGCAAGUUAAAAUAAGGCUAGU-CCGUUAUCAACUUGAAAAAGUGGCACC GAGUCG-GUGCUUU (SEQ ID NO: 85).

In systems in which both a crRNA and a tracrRNA are needed, the crRNA and the corresponding tracrRNA hybridize to form a gRNA. In systems in which only a crRNA is needed, the crRNA can be the gRNA. The crRNA additionally provides the single-stranded DNA-targeting segment that hybridizes to the complementary strand of a target DNA. If used for modification within a cell, the exact sequence of a given crRNA or tracrRNA molecule can be designed to be specific to the species in which the RNA molecules will be used. See, e.g., Mali et al. (2013) Science 339:823-826; Jinek et al. (2012) Science 337:816-821; Hwang et al. (2013) Nat. Biotechnol. 31:227-229; Jiang et al. (2013) Nat. Biotechnol. 31:233-239; and Cong et al. (2013) Science 339:819-823, each of which is herein incorporated by reference in its entirety for all purposes.

The DNA-targeting segment (crRNA) of a given gRNA comprises a nucleotide sequence that is complementary to a sequence on the complementary strand of the target DNA, as described in more detail below. The DNA-targeting segment of a gRNA interacts with the target DNA in a sequence-specific manner via hybridization (i.e., base pairing). As such, the nucleotide sequence of the DNA-targeting segment may vary and determines the location within the target DNA with which the gRNA and the target DNA will interact. The DNA-targeting segment of a subject gRNA can be modified to hybridize to any desired sequence within a target DNA. Naturally occurring crRNAs differ depending on the CRISPR/Cas system and organism but often contain a targeting segment of between 21 to 72 nucleotides length, flanked by two direct repeats (DR) of a length of between 21 to 46 nucleotides (see, e.g., WO 2014/131833, herein incorporated by reference in its entirety for all purposes). In the case of S. pyogenes, the DRs are 36 nucleotides long and the targeting segment is 30 nucleotides long. The 3' located DR is complementary to and hybridizes with the corresponding tracrRNA, which in turn binds to the Cas protein.

The DNA-targeting segment can have, for example, a length of at least about 12, 15, 17, 18, 19, 20, 25, 30, 35, or 40 nucleotides. Such DNA-targeting segments can have, for example, a length from about 12 to about 100, from about 12 to about 80, from about 12 to about 50, from about 12 to about 40, from about 12 to about 30, from about 12 to about 25, or from about 12 to about 20 nucleotides. For example, the DNA targeting segment can be from about 15 to about 25 nucleotides (e.g., from about 17 to about 20 nucleotides, or about 17, 18, 19, or 20 nucleotides). See, e.g., US 2016/0024523, herein incorporated by reference in its entirety for all purposes. For Cas9 from S. pyogenes, a typical DNA-targeting segment is between 16 and 20 nucleotides in length or between 17 and 20 nucleotides in length. For Cas9 from S. aureus, a typical DNA-targeting segment is between 21 and 23 nucleotides in length. For Cpf1, a typical DNA-targeting segment is at least 16 nucleotides in length or at least 18 nucleotides in length.

TracrRNAs can be in any form (e.g., full-length tracrRNAs or active partial tracrRNAs) and of varying lengths. They can include primary transcripts or processed forms. For example, tracrRNAs (as part of a single-guide RNA or as a separate molecule as part of a two-molecule gRNA) may comprise, consist essentially of, or consist of all or a portion of a wild type tracrRNA sequence (e.g., about or more than about 20, 26, 32, 45, 48, 54, 63, 67, 85, or more nucleotides of a wild type tracrRNA sequence). Examples of wild type tracrRNA sequences from S. pyogenes include 171-nucleotide, 89-nucleotide, 75-nucleotide, and 65-nucleotide versions. See, e.g., Deltcheva et al. (2011) Nature 471:602-607; WO 2014/093661, each of which is herein incorporated by reference in its entirety for all purposes. Examples of tracrRNAs within single-guide RNAs (sgRNAs) include the tracrRNA segments found within +48, +54, +67, and +85 versions of sgRNAs, where "+n" indicates that up to the +n nucleotide of wild type tracrRNA is included in the sgRNA. See U.S. Pat. No. 8,697,359, herein incorporated by reference in its entirety for all purposes.

The percent complementarity between the DNA-targeting segment of the guide RNA and the complementary strand of the target DNA can be at least 60% (e.g., at least 65%, at least 70%, at least 75%, at least 80%, at least 85%, at least 90%, at least 95%, at least 97%, at least 98%, at least 99%, or 100%). The percent complementarity between the DNA-targeting segment and the complementary strand of the target DNA can be at least 60% over about 20 contiguous nucleotides. As an example, the percent complementarity between the DNA-targeting segment and the complementary strand of the target DNA can be 100% over the 14 contiguous nucleotides at the 5' end of the complementary strand of the target DNA and as low as 0% over the remainder. In such a case, the DNA-targeting segment can be considered to be 14 nucleotides in length. As another example, the percent complementarity between the DNA-targeting segment and the complementary strand of the target DNA can be 100% over the seven contiguous nucleotides at the 5' end of the complementary strand of the target DNA and as low as 0% over the remainder. In such a case, the DNA-targeting segment can be considered to be 7 nucleotides in length. In some guide RNAs, at least 17 nucleotides within the DNA-targeting segment are complementary to the complementary strand of the target DNA. For example, the DNA-targeting segment can be 20 nucleotides in length and can comprise 1, 2, or 3 mismatches with the complementary strand of the target DNA. In one example, the mismatches are not adjacent to the region of the complementary strand corresponding to the protospacer adjacent motif (PAM) sequence (i.e., the reverse complement of the PAM sequence) (e.g., the mismatches are in the 5' end of the DNA-targeting segment of the guide RNA, or the mismatches are at least 2, 3, 4, 5, 6, 7, 8, 9, 10, 11, 12, 13, 14, 15, 16, 17, 18, or 19 base pairs away from the region of the complementary strand corresponding to the PAM sequence).

The protein-binding segment of a gRNA can comprise two stretches of nucleotides that are complementary to one another. The complementary nucleotides of the protein-binding segment hybridize to form a double-stranded RNA duplex (dsRNA). The protein-binding segment of a subject gRNA interacts with a Cas protein, and the gRNA directs the bound Cas protein to a specific nucleotide sequence within target DNA via the DNA-targeting segment.

Single-guide RNAs can comprise a DNA-targeting segment and a scaffold sequence (i.e., the protein-binding or Cas-binding sequence of the guide RNA). For example, such guide RNAs can have a 5' DNA-targeting segment joined to a 3' scaffold sequence. Exemplary scaffold sequences comprise, consist essentially of, or consist of: GUUUUAGAGC-UAGAAAUAGCAAGUUAAAAUAAGGCUAGU-CCGUUAUCAACUUGA AAAAGUGGCACCGAGUCGGUGCU (version 1; SEQ ID NO: 86); GUUGGAACCAUUCAAAACAG-CAUAGCAAGUUAAAAUAAGGCUAGU-CCGUUAUCA ACUUGAAAAAGUGGCACCGAGUCG-GUGC (version 2; SEQ ID NO: 87); GUUUUAGAGCUA-GAAAUAGCAAGUUAAAAUAAGGCUAGU-CCGUUAUCAACUUGA AAAAGUGGCACCGAGUCG-GUGC (version 3; SEQ ID NO: 88); and GUUUAAGAGCUAUGCUGGAAACAG-CAUAGCAAGUUUAAAUAAGGCUAGUCCGUU AUCAACUUGAAAAAGUGGCACCGAGUCGGUGC (version 4; SEQ ID NO: 89). Guide RNAs targeting any of the guide RNA target sequences disclosed herein can include, for example, a DNA-targeting segment on the 5' end of the guide RNA fused to any of the exemplary guide RNA scaffold sequences on the 3' end of the guide RNA. That is, any of the DNA-targeting segments disclosed herein can be joined to the 5' end of any one of the above scaffold sequences to form a single guide RNA (chimeric guide RNA).

Guide RNAs can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); a modification or sequence that provides a binding site for proteins (e.g., proteins that act on DNA, including DNA methyltransferases, DNA demethylases, histone acetyltransferases, histone deacetylases, and the like); and combinations thereof. Other examples of modifications include engineered stem loop duplex structures, engineered bulge regions, engineered hairpins 3' of the stem loop duplex structure, or any combination thereof. See, e.g., US 2015/0376586, herein incorporated by reference in its entirety for all purposes. A bulge can be an unpaired region of nucleotides within the duplex made up of the crRNA-like region and the minimum tracrRNA-like region. A bulge can comprise, on one side of the duplex, an unpaired 5'-XXXY-3' where X is any purine and Y can be a nucleotide that can form a wobble pair with a nucleotide on the opposite strand, and an unpaired nucleotide region on the other side of the duplex.

Unmodified nucleic acids can be prone to degradation. Exogenous nucleic acids can also induce an innate immune response. Modifications can help introduce stability and reduce immunogenicity. Guide RNAs can comprise modified nucleosides and modified nucleotides including, for example, one or more of the following: (1) alteration or replacement of one or both of the non-linking phosphate oxygens and/or of one or more of the linking phosphate oxygens in the phosphodiester backbone linkage; (2) alteration or replacement of a constituent of the ribose sugar such as alteration or replacement of the 2' hydroxyl on the ribose sugar; (3) replacement of the phosphate moiety with dephospho linkers; (4) modification or replacement of a naturally occurring nucleobase; (5) replacement or modification of the ribose-phosphate backbone; (6) modification of the 3' end or 5' end of the oligonucleotide (e.g., removal, modification or replacement of a terminal phosphate group or conjugation of a moiety); and (7) modification of the sugar. Other possible guide RNA modifications include modifications of or replacement of uracils or poly-uracil tracts. See, e.g., WO 2015/048577 and US 2016/0237455, each of which is herein incorporated by reference in its entirety for all purposes. Similar modifications can be made to Cas-encoding nucleic acids, such as Cas mRNAs.

As one example, nucleotides at the 5' or 3' end of a guide RNA can include phosphorothioate linkages (e.g., the bases can have a modified phosphate group that is a phosphorothioate group). For example, a guide RNA can include phosphorothioate linkages between the 2, 3, or 4 terminal nucleotides at the 5' or 3' end of the guide RNA. As another example, nucleotides at the 5' and/or 3' end of a guide RNA can have 2'-O-methyl modifications. For example, a guide RNA can include 2'-O-methyl modifications at the 2, 3, or 4 terminal nucleotides at the 5' and/or 3' end of the guide RNA (e.g., the 5' end). See, e.g., WO 2017/173054 A1 and Finn et al. (2018) *Cell Reports* 22:1-9, each of which is herein incorporated by reference in its entirety for all purposes. In one specific example, the guide RNA comprises 2'-O-methyl analogs and 3' phosphorothioate internucleotide linkages at the first three 5' and 3' terminal RNA residues. In another specific example, the guide RNA is modified such that all 2'OH groups that do not interact with the Cas9 protein are replaced with 2'-O-methyl analogs, and the tail region of the guide RNA, which has minimal interaction with Cas9, is modified with 5' and 3' phosphorothioate internucleotide linkages. See, e.g., Yin et al. (2017) *Nat. Biotech.* 35(12): 1179-1187, herein incorporated by reference in its entirety for all purposes. Other examples of modified guide RNAs are provided, e.g., in WO 2018/107028 A1, herein incorporated by reference in its entirety for all purposes.

Guide RNAs can be provided in any form. For example, the gRNA can be provided in the form of RNA, either as two molecules (separate crRNA and tracrRNA) or as one molecule (sgRNA), and optionally in the form of a complex with a Cas protein. The gRNA can also be provided in the form of DNA encoding the gRNA. The DNA encoding the gRNA can encode a single RNA molecule (sgRNA) or separate RNA molecules (e.g., separate crRNA and tracrRNA). In the latter case, the DNA encoding the gRNA can be provided as one DNA molecule or as separate DNA molecules encoding the crRNA and tracrRNA, respectively.

When a gRNA is provided in the form of DNA, the gRNA can be transiently, conditionally, or constitutively expressed in the cell. DNAs encoding gRNAs can be stably integrated into the genome of the cell and operably linked to a promoter active in the cell. Alternatively, DNAs encoding gRNAs can be operably linked to a promoter in an expression construct. For example, the DNA encoding the gRNA can be in a vector comprising a heterologous nucleic acid, such as a nucleic acid encoding a Cas protein. Alternatively, it can be in a vector or a plasmid that is separate from the vector comprising the nucleic acid encoding the Cas protein. Promoters that can be used in such expression constructs include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Such promoters can also be, for example, bidirectional promoters. Specific examples of suitable promoters include an RNA polymerase III promoter, such as a human U6 promoter, a rat U6 polymerase III promoter, or a mouse U6 polymerase III promoter.

Alternatively, gRNAs can be prepared by various other methods. For example, gRNAs can be prepared by in vitro transcription using, for example, T7 RNA polymerase (see, e.g., WO 2014/089290 and WO 2014/065596, each of which is herein incorporated by reference in its entirety for all purposes). Guide RNAs can also be a synthetically produced molecule prepared by chemical synthesis.

Guide RNA Target Sequences.

Target DNAs for guide RNAs include nucleic acid sequences present in a DNA to which a DNA-targeting segment of a gRNA will bind, provided sufficient conditions for binding exist. Suitable DNA/RNA binding conditions include physiological conditions normally present in a cell. Other suitable DNA/RNA binding conditions (e.g., conditions in a cell-free system) are known in the art (see, e.g., Molecular Cloning: A Laboratory Manual, 3rd Ed. (Sambrook et al., Harbor Laboratory Press 2001), herein incorporated by reference in its entirety for all purposes). The strand of the target DNA that is complementary to and hybridizes with the gRNA can be called the "complementary strand," and the strand of the target DNA that is complementary to the "complementary strand" (and is therefore not complementary to the Cas protein or gRNA) can be called "noncomplementary strand" or "template strand."

The target DNA includes both the sequence on the complementary strand to which the guide RNA hybridizes and the corresponding sequence on the non-complementary strand (e.g., adjacent to the protospacer adjacent motif (PAM)). The term "guide RNA target sequence" as used herein refers specifically to the sequence on the non-complementary strand corresponding to (i.e., the reverse complement of) the sequence to which the guide RNA hybridizes on the complementary strand. That is, the guide RNA target sequence refers to the sequence on the non-complementary strand adjacent to the PAM (e.g., upstream or 5' of the PAM in the case of Cas9). A guide RNA target sequence is equivalent to the DNA-targeting segment of a guide RNA, but with thymines instead of uracils. As one example, a guide RNA target sequence for an SpCas9 enzyme can refer to the sequence upstream of the 5'-NGG-3' PAM on the non-complementary strand. A guide RNA is designed to have complementarity to the complementary strand of a target DNA, where hybridization between the DNA-targeting segment of the guide RNA and the complementary strand of the target DNA promotes the formation of a CRISPR complex. Full complementarity is not necessarily required, provided that there is sufficient complementarity to cause hybridization and promote formation of a CRISPR complex. If a guide RNA is referred to herein as targeting a guide RNA target sequence, what is meant is that the guide RNA hybridizes to the complementary strand sequence of the target DNA that is the reverse complement of the guide RNA target sequence on the non-complementary strand.

A target DNA or guide RNA target sequence can comprise any polynucleotide, and can be located, for example, in the nucleus or cytoplasm of a cell or within an organelle of a cell, such as a mitochondrion or chloroplast. A target DNA or guide RNA target sequence can be any nucleic acid sequence endogenous or exogenous to a cell. The guide RNA target sequence can be a sequence coding a gene product (e.g., a protein) or a non-coding sequence (e.g., a regulatory sequence) or can include both.

Site-specific binding and cleavage of a target DNA by a Cas protein can occur at locations determined by both (i) base-pairing complementarity between the guide RNA and the complementary strand of the target DNA and (ii) a short motif, called the protospacer adjacent motif (PAM), in the non-complementary strand of the target DNA. The PAM can flank the guide RNA target sequence. Optionally, the guide RNA target sequence can be flanked on the 3' end by the PAM (e.g., for Cas9). Alternatively, the guide RNA target sequence can be flanked on the 5' end by the PAM (e.g., for Cpf1). For example, the cleavage site of Cas proteins can be about 1 to about 10 or about 2 to about 5 base pairs (e.g., 3 base pairs) upstream or downstream of the PAM sequence (e.g., within the guide RNA target sequence). In the case of SpCas9, the PAM sequence (i.e., on the non-complementary strand) can be 5'-N$_1$GG-3', where N$_1$ is any DNA nucleotide, and where the PAM is immediately 3' of the guide RNA target sequence on the non-complementary strand of the target DNA. As such, the sequence corresponding to the PAM on the complementary strand (i.e., the reverse complement) would be 5'-CCN$_2$-3', where N$_2$ is any DNA nucleotide and is immediately 5' of the sequence to which the DNA-targeting segment of the guide RNA hybridizes on the complementary strand of the target DNA. In some such cases, N$_1$ and N$_2$ can be complementary and the N$_1$-N$_2$ base pair can be any base pair (e.g., N$_1$=C and N$_2$=G; N$_1$=G and N$_2$=C; N$_1$=A and N$_2$=T; or N$_1$=T, and N$_2$=A). In the case of Cas9 from S. aureus, the PAM can be NNGRRT or NNGRR, where N can A, G, C, or T, and R can be G or A. In the case of Cas9 from C. jejuni, the PAM can be, for example, NNNNACAC or NNNNRYAC, where N can be A, G, C, or T, and R can be G or A. In some cases (e.g., for FnCpf1), the PAM sequence can be upstream of the 5' end and have the sequence 5'-TTN-3'.

An example of a guide RNA target sequence is a 20-nucleotide DNA sequence immediately preceding an NGG motif recognized by an SpCas9 protein. For example, two examples of guide RNA target sequences plus PAMs are GN$_{19}$NGG (SEQ ID NO: 90) or N$_{20}$NGG (SEQ ID NO: 91). See, e.g., WO 2014/165825, herein incorporated by reference in its entirety for all purposes. The guanine at the 5' end can facilitate transcription by RNA polymerase in cells. Other examples of guide RNA target sequences plus PAMs can include two guanine nucleotides at the 5' end (e.g., GGN$_{20}$NGG; SEQ ID NO: 92) to facilitate efficient transcription by T7 polymerase in vitro. See, e.g., WO 2014/065596, herein incorporated by reference in its entirety for all purposes. Other guide RNA target sequences plus PAMs can have between 4-22 nucleotides in length of SEQ ID NOS: 90-92, including the 5' G or GG and the 3' GG or NGG. Yet other guide RNA target sequences plus PAMs can have between 14 and 20 nucleotides in length of SEQ ID NOS: 90-92.

Formation of a CRISPR complex hybridized to a target DNA can result in cleavage of one or both strands of the target DNA within or near the region corresponding to the guide RNA target sequence (i.e., the guide RNA target sequence on the non-complementary strand of the target DNA and the reverse complement on the complementary strand to which the guide RNA hybridizes). For example, the cleavage site can be within the guide RNA target sequence (e.g., at a defined location relative to the PAM sequence). The "cleavage site" includes the position of a target DNA at which a Cas protein produces a single-strand break or a double-strand break. The cleavage site can be on only one strand (e.g., when a nickase is used) or on both strands of a double-stranded DNA. Cleavage sites can be at the same position on both strands (producing blunt ends; e.g. Cas9)) or can be at different sites on each strand (producing staggered ends (i.e., overhangs); e.g., Cpf1). Staggered ends can be produced, for example, by using two Cas proteins, each of which produces a single-strand break at a different cleavage site on a different strand, thereby producing a double-strand break. For example, a first nickase can create a single-strand break on the first strand of double-stranded DNA (dsDNA), and a second nickase can create a single-strand break on the second strand of dsDNA such that overhanging sequences are created. In some cases, the guide RNA target sequence or cleavage site of the nickase on the first strand is separated from the guide RNA target sequence or cleavage site of the nickase on the second strand by at least 2, 3, 4, 5, 6, 7, 8, 9, 10, 15, 20, 25, 30, 40, 50, 75, 100, 250, 500, or 1,000 base pairs.

(3) Exogenous Donor Nucleic Acids Targeting Human TTR Gene

The methods and compositions disclosed herein can utilize exogenous donor nucleic acids to modify the humanized TTR locus comprising the beta-slip mutation following cleavage of the humanized TTR locus with a nuclease agent. In such methods, the nuclease agent protein cleaves the humanized TTR locus to create a single-strand break (nick) or double-strand break, and the exogenous donor nucleic acid recombines the humanized TTR locus via non-homologous end joining (NHEJ)-mediated ligation or through a homology-directed repair event. Optionally, repair with the exogenous donor nucleic acid removes or disrupts the nuclease target sequence so that alleles that have been targeted cannot be re-targeted by the nuclease agent.

Exogenous donor nucleic acids can comprise deoxyribonucleic acid (DNA) or ribonucleic acid (RNA), they can be single-stranded or double-stranded, and they can be in linear or circular form. For example, an exogenous donor nucleic acid can be a single-stranded oligodeoxynucleotide (ssODN). See, e.g., Yoshimi et al. (2016) Nat. Commun. 7:10431, herein incorporated by reference in its entirety for all purposes. An exemplary exogenous donor nucleic acid is between about 50 nucleotides to about 5 kb in length, is between about 50 nucleotides to about 3 kb in length, or is between about 50 to about 1,000 nucleotides in length. Other exemplary exogenous donor nucleic acids are between about 40 to about 200 nucleotides in length. For example, an exogenous donor nucleic acid can be between about 50-60, 60-70, 70-80, 80-90, 90-100, 100-110, 110-120, 120-130, 130-140, 140-150, 150-160, 160-170, 170-180, 180-190, or 190-200 nucleotides in length. Alternatively, an exogenous donor nucleic acid can be between about 50-100, 100-200, 200-300, 300-400, 400-500, 500-600, 600-700, 700-800, 800-900, or 900-1000 nucleotides in length. Alternatively, an exogenous donor nucleic acid can be between about 1-1.5, 1.5-2, 2-2.5, 2.5-3, 3-3.5, 3.5-4, 4-4.5, or 4.5-5 kb in length. Alternatively, an exogenous donor nucleic acid can be, for example, no more than 5 kb, 4.5 kb, 4 kb, 3.5 kb, 3 kb, 2.5 kb, 2 kb, 1.5 kb, 1 kb, 900 nucleotides, 800 nucleotides, 700 nucleotides, 600 nucleotides, 500 nucleotides, 400 nucleotides, 300 nucleotides, 200 nucleotides, 100 nucleotides, or 50 nucleotides in length. Exogenous donor nucleic acids (e.g., targeting vectors) can also be longer.

In one example, an exogenous donor nucleic acid is an ssODN that is between about 80 nucleotides and about 200 nucleotides in length. In another example, an exogenous donor nucleic acids is an ssODN that is between about 80 nucleotides and about 3 kb in length. Such an ssODN can have homology arms, for example, that are each between about 40 nucleotides and about 60 nucleotides in length. Such an ssODN can also have homology arms, for example, that are each between about 30 nucleotides and 100 nucleotides in length. The homology arms can be symmetrical (e.g., each 40 nucleotides or each 60 nucleotides in length), or they can be asymmetrical (e.g., one homology arm that is 36 nucleotides in length, and one homology arm that is 91 nucleotides in length).

Exogenous donor nucleic acids can include modifications or sequences that provide for additional desirable features (e.g., modified or regulated stability; tracking or detecting with a fluorescent label; a binding site for a protein or protein complex; and so forth). Exogenous donor nucleic acids can comprise one or more fluorescent labels, purification tags, epitope tags, or a combination thereof. For example, an exogenous donor nucleic acid can comprise one or more fluorescent labels (e.g., fluorescent proteins or other fluorophores or dyes), such as at least 1, at least 2, at least 3, at least 4, or at least 5 fluorescent labels. Exemplary fluorescent labels include fluorophores such as fluorescein (e.g., 6-carboxyfluorescein (6-FAM)), Texas Red, HEX, Cy3, Cy5, Cy5.5, Pacific Blue, 5-(and-6)-carboxytetramethylrhodamine (TAMRA), and Cy7. A wide range of fluorescent dyes are available commercially for labeling oligonucleotides (e.g., from Integrated DNA Technologies). Such fluorescent labels (e.g., internal fluorescent labels) can be used, for example, to detect an exogenous donor nucleic acid that has been directly integrated into a cleaved target nucleic acid having protruding ends compatible with the ends of the exogenous donor nucleic acid. The label or tag can be at the 5' end, the 3' end, or internally within the exogenous donor nucleic acid. For example, an exogenous donor nucleic acid can be conjugated at 5' end with the IR700 fluorophore from Integrated DNA Technologies (5'IRDYE®700).

Exogenous donor nucleic acids can also comprise nucleic acid inserts including segments of DNA to be integrated at the humanized TTR locus comprising the beta-slip mutation. Integration of a nucleic acid insert at a humanized TTR locus can result in addition of a nucleic acid sequence of interest to the humanized TTR locus, deletion of a nucleic acid sequence of interest at the humanized TTR locus, or replacement of a nucleic acid sequence of interest at the humanized TTR locus (i.e., deletion and insertion). Some exogenous donor nucleic acids are designed for insertion of a nucleic acid insert at the humanized TTR locus without any corresponding deletion at the humanized TTR locus. Other exogenous donor nucleic acids are designed to delete a nucleic acid sequence of interest at the humanized TTR locus without any corresponding insertion of a nucleic acid insert. Yet other exogenous donor nucleic acids are designed to delete a nucleic acid sequence of interest at the humanized TTR locus and replace it with a nucleic acid insert.

The nucleic acid insert or the corresponding nucleic acid at the humanized TTR locus being deleted and/or replaced can be various lengths. An exemplary nucleic acid insert or corresponding nucleic acid at the humanized TTR locus being deleted and/or replaced is between about 1 nucleotide to about 5 kb in length or is between about 1 nucleotide to about 1,000 nucleotides in length. For example, a nucleic acid insert or a corresponding nucleic acid at the humanized TTR locus being deleted and/or replaced can be between about 1-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, or 190-120 nucleotides in length. Likewise, a nucleic acid insert or a corresponding nucleic acid at the humanized TTR locus being deleted and/or replaced can be between 1-100, 100-200, 200-300, 300-400, 400-500, 500-600, 600-700, 700-800, 800-900, or 900-1000 nucleotides in length. Likewise, a nucleic acid insert or a corresponding nucleic acid at the humanized TTR locus being deleted and/or replaced can be between about 1-1.5, 1.5-2, 2-2.5, 2.5-3, 3-3.5, 3.5-4, 4-4.5, or 4.5-5 kb in length or longer.

The nucleic acid insert can comprise a sequence that is homologous or orthologous to all or part of sequence targeted for replacement. For example, the nucleic acid insert can comprise a sequence that comprises one or more point mutations (e.g., 1, 2, 3, 4, 5, or more) compared with a sequence targeted for replacement at the humanized TTR locus. Optionally, such point mutations can result in a conservative amino acid substitution (e.g., substitution of aspartic acid [Asp, D] with glutamic acid [Glu, E]) in the encoded polypeptide.

Donor Nucleic Acids for Non-Homologous-End-Joining-Mediated Insertion.

Some exogenous donor nucleic acids have short single-stranded regions at the 5' end and/or the 3' end that are complementary to one or more overhangs created by nuclease-mediated cleavage at the humanized TTR locus comprising the beta-slip mutation. These overhangs can also be referred to as 5' and 3' homology arms. For example, some exogenous donor nucleic acids have short single-stranded regions at the 5' end and/or the 3' end that are complementary to one or more overhangs created by nuclease-mediated cleavage at 5' and/or 3' target sequences at the humanized TTR locus. Some such exogenous donor nucleic acids have a complementary region only at the 5' end or only at the 3' end. For example, some such exogenous donor nucleic acids have a complementary region only at the 5' end complementary to an overhang created at a 5' target sequence at the humanized TTR locus or only at the 3' end complementary to an overhang created at a 3' target sequence at the humanized TTR locus. Other such exogenous donor nucleic acids have complementary regions at both the 5' and 3' ends. For example, other such exogenous donor nucleic acids have complementary regions at both the 5' and 3' ends e.g., complementary to first and second overhangs, respectively, generated by nuclease-mediated cleavage at the humanized TTR locus. For example, if the exogenous donor nucleic acid is double-stranded, the single-stranded complementary regions can extend from the 5' end of the top strand of the donor nucleic acid and the 5' end of the bottom strand of the donor nucleic acid, creating 5' overhangs on each end. Alternatively, the single-stranded complementary region can extend from the 3' end of the top strand of the donor nucleic acid and from the 3' end of the bottom strand of the template, creating 3' overhangs.

The complementary regions can be of any length sufficient to promote ligation between the exogenous donor nucleic acid and the target nucleic acid. Exemplary complementary regions are between about 1 to about 5 nucleotides in length, between about 1 to about 25 nucleotides in length, or between about 5 to about 150 nucleotides in length. For example, a complementary region can be at least about 1, 2, 3, 4, 5, 6, 7, 8, 9, 10, 11, 12, 13, 14, 15, 16, 17, 18, 19, 20, 21, 22, 23, 24, or 25 nucleotides in length. Alternatively, the complementary region can be about 5-10, 10-20, 20-30, 30-40, 40-50, 50-60, 60-70, 70-80, 80-90, 90-100, 100-110, 110-120, 120-130, 130-140, or 140-150 nucleotides in length, or longer.

Such complementary regions can be complementary to overhangs created by two pairs of nickases. Two double-strand breaks with staggered ends can be created by using first and second nickases that cleave opposite strands of DNA to create a first double-strand break, and third and fourth nickases that cleave opposite strands of DNA to create a second double-strand break. For example, a Cas protein can be used to nick first, second, third, and fourth guide RNA target sequences corresponding with first, second, third, and fourth guide RNAs. The first and second guide RNA target sequences can be positioned to create a first cleavage site such that the nicks created by the first and second nickases on the first and second strands of DNA create a double-strand break (i.e., the first cleavage site comprises the nicks within the first and second guide RNA target sequences). Likewise, the third and fourth guide RNA target sequences can be positioned to create a second cleavage site such that the nicks created by the third and fourth nickases on the first and second strands of DNA create a double-strand break (i.e., the second cleavage site comprises the nicks within the third and fourth guide RNA target sequences). Preferably, the nicks within the first and second guide RNA target sequences and/or the third and fourth guide RNA target sequences can be off-set nicks that create overhangs. The offset window can be, for example, at least about 5 bp, 10 bp, 20 bp, 30 bp, 40 bp, 50 bp, 60 bp, 70 bp, 80 bp, 90 bp, 100 bp or more. See Ran et al. (2013) *Cell* 154:1380-1389; Mali et al. (2013) *Nat. Biotech.* 31:833-838; and Shen et al. (2014) *Nat. Methods* 11:399-404, each of which is herein incorporated by reference in its entirety for all purposes. In such cases, a double-stranded exogenous donor nucleic acid can be designed with single-stranded complementary regions that are complementary to the overhangs created by the nicks within the first and second guide RNA target sequences and by the nicks within the third and fourth guide RNA target sequences. Such an exogenous donor nucleic acid can then be inserted by non-homologous-end-joining-mediated ligation.

Donor Nucleic Acids for Insertion by Homology-Directed Repair.

Some exogenous donor nucleic acids comprise homology arms. If the exogenous donor nucleic acid also comprises a nucleic acid insert, the homology arms can flank the nucleic acid insert. For ease of reference, the homology arms are referred to herein as 5' and 3' (i.e., upstream and downstream) homology arms. This terminology relates to the relative position of the homology arms to the nucleic acid insert within the exogenous donor nucleic acid. The 5' and 3' homology arms correspond to regions within the humanized TTR locus, which are referred to herein as "5' target sequence" and "3' target sequence," respectively.

A homology arm and a target sequence "correspond" or are "corresponding" to one another when the two regions share a sufficient level of sequence identity to one another to act as substrates for a homologous recombination reaction. The term "homology" includes DNA sequences that are either identical or share sequence identity to a corresponding sequence. The sequence identity between a given target sequence and the corresponding homology arm found in the exogenous donor nucleic acid can be any degree of sequence identity that allows for homologous recombination to occur. For example, the amount of sequence identity shared by the homology arm of the exogenous donor nucleic acid (or a fragment thereof) and the target sequence (or a fragment thereof) can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination. Moreover, a corresponding region of homology between the homology arm and the corresponding target sequence can be of any length that is sufficient to promote homologous recombination. Exemplary homology arms are between about 25 nucleotides to about 2.5 kb in length, are between about 25 nucleotides to about 1.5 kb in length, or are between about 25 to about 500 nucleotides in length. For example, a given homology arm (or each of the homology arms) and/or corresponding target sequence can comprise corresponding regions of homology that are between about 25-30, 30-40, 40-50, 50-60, 60-70, 70-80, 80-90, 90-100, 100-150, 150-200, 200-250, 250-300, 300-350, 350-400, 400-450, or 450-500 nucleotides in length, such that the homology arms have sufficient homology to undergo homologous recombination with the corresponding target sequences within the target nucleic acid. Alternatively, a given homology arm (or each homology arm) and/or corresponding target sequence can comprise corresponding regions of homology that are between about 0.5 kb to about 1 kb, about 1 kb to about 1.5 kb, about 1.5 kb to about 2 kb, or about 2 kb to about 2.5 kb in length. For example, the homology arms can each be about 750 nucleotides in length. The homology arms can be symmetrical (each about the same size in length), or they can be asymmetrical (one longer than the other).

When a nuclease agent is used in combination with an exogenous donor nucleic acid, the 5' and 3' target sequences are preferably located in sufficient proximity to the nuclease cleavage site (e.g., within sufficient proximity to a the nuclease target sequence) so as to promote the occurrence of a homologous recombination event between the target sequences and the homology arms upon a single-strand break (nick) or double-strand break at the nuclease cleavage site. The term "nuclease cleavage site" includes a DNA sequence at which a nick or double-strand break is created by a nuclease agent (e.g., a Cas9 protein complexed with a guide RNA). The target sequences within the targeted locus that correspond to the 5' and 3' homology arms of the exogenous donor nucleic acid are "located in sufficient proximity" to a nuclease cleavage site if the distance is such as to promote the occurrence of a homologous recombination event between the 5' and 3' target sequences and the homology arms upon a single-strand break or double-strand break at the nuclease cleavage site. Thus, the target sequences corresponding to the 5' and/or 3' homology arms of the exogenous donor nucleic acid can be, for example, within at least 1 nucleotide of a given nuclease cleavage site or within at least 10 nucleotides to about 1,000 nucleotides of a given nuclease cleavage site. As an example, the nuclease cleavage site can be immediately adjacent to at least one or both of the target sequences.

The spatial relationship of the target sequences that correspond to the homology arms of the exogenous donor nucleic acid and the nuclease cleavage site can vary. For example, target sequences can be located 5' to the nuclease cleavage site, target sequences can be located 3' to the nuclease cleavage site, or the target sequences can flank the nuclease cleavage site.

(4) Other Human-TTR-Targeting Reagents

The activity of any other known or putative human-TTR-targeting reagent can also be assessed using the non-human animals disclosed herein. Similarly, any other molecule can be screened for human-TTR-targeting activity using the non-human animals disclosed herein.

Other human-TTR-targeting reagents can include RNAi agents. An "RNAi agent" is a composition that comprises a small double-stranded RNA or RNA-like (e.g., chemically modified RNA) oligonucleotide molecule capable of facilitating degradation or inhibition of translation of a target RNA, such as messenger RNA (mRNA), in a sequence-specific manner. The oligonucleotide in the RNAi agent is a polymer of linked nucleosides, each of which can be independently modified or unmodified. RNAi agents operate through the RNA interference mechanism (i.e., inducing RNA interference through interaction with the RNA interference pathway machinery (RNA-induced silencing complex or RISC) of mammalian cells). While it is believed that RNAi agents, as that term is used herein, operate primarily through the RNA interference mechanism, the disclosed RNAi agents are not bound by or limited to any particular pathway or mechanism of action. RNAi agents disclosed herein comprise a sense strand and an antisense strand, and include, but are not limited to, short interfering RNAs (siRNAs), double-stranded RNAs (dsRNA), micro RNAs (miRNAs), short hairpin RNAs (shRNA), and dicer substrates. The antisense strand of the RNAi agents described herein is at least partially complementary to a sequence (i.e., a succession or order of nucleobases or nucleotides, described with a succession of letters using standard nomenclature) in the target RNA.

Other human-TTR-targeting reagents can include antisense oligonucleotides (ASOs). Single-stranded ASOs and RNA interference (RNAi) share a fundamental principle in that an oligonucleotide binds a target RNA through Watson-Crick base pairing. Without wishing to be bound by theory, during RNAi, a small RNA duplex (RNAi agent) associates with the RNA-induced silencing complex (RISC), one strand (the passenger strand) is lost, and the remaining strand (the guide strand) cooperates with RISC to bind complementary RNA. Argonaute 2 (Ago2), the catalytic component of the RISC, then cleaves the target RNA. The guide strand is always associated with either the complementary sense strand or a protein (RISC). In contrast, an ASO must survive and function as a single strand. ASOs bind to the target RNA and block ribosomes or other factors, such as splicing factors, from binding the RNA or recruit proteins such as nucleases. Different modifications and target regions are chosen for ASOs based on the desired mechanism of action. A gapmer is an ASO oligonucleotide containing 2-5 chemically modified nucleotides (e.g. LNA or 2'-MOE) on each terminus flanking a central 8-10 base gap of DNA. After binding the target RNA, the DNA-RNA hybrid acts substrate for RNase H.

Other human-TTR-targeting reagents include antibodies or antigen-binding proteins designed to specifically bind a human TTR epitope. The term "antigen-binding protein" includes any protein that binds to an antigen. Examples of antigen-binding proteins include an antibody, an antigen-binding fragment of an antibody, a multispecific antibody (e.g., a bi-specific antibody), an scFV, a bis-scFV, a diabody, a triabody, a tetrabody, a V-NAR, a VHH, a VL, a F(ab), a F(ab)$_2$, a DVD (dual variable domain antigen-binding protein), an SVD (single variable domain antigen-binding protein), a bispecific T-cell engager (BiTE), or a Davisbody (U.S. Pat. No. 8,586,713, herein incorporated by reference herein in its entirety for all purposes).

Other human-TTR-targeting reagents include small-molecule reagents. One example of such a small-molecule reagent is tafamidis, which functions by kinetic stabilization of the correctly folded tetrameric form of the transthyretin (TTR) protein. See, e.g., Hammarstrom et al. (2003) *Science* 299:713-716, herein incorporated by reference in its entirety for all purposes.

D. Administering Human-TTR-Targeting Reagents to Non-Human Animals or Cells

The methods disclosed herein can comprise introducing into a non-human animal or cell various molecules (e.g., human-TTR-targeting reagents such as therapeutic molecules or complexes), including nucleic acids, proteins, nucleic-acid-protein complexes, protein complexes, or small molecules. "Introducing" includes presenting to the cell or non-human animal the molecule (e.g., nucleic acid or protein) in such a manner that it gains access to the interior of the cell or to the interior of cells within the non-human animal. The introducing can be accomplished by any means, and two or more of the components (e.g., two of the components, or all of the components) can be introduced into the cell or non-human animal simultaneously or sequentially in any combination. For example, a Cas protein can be introduced into a cell or non-human animal before introduction of a guide RNA, or it can be introduced following introduction of the guide RNA. As another example, an exogenous donor nucleic acid can be introduced prior to the introduction of a Cas protein and a guide RNA, or it can be introduced following introduction of the Cas protein and the guide RNA (e.g., the exogenous donor nucleic acid can be administered about 1, 2, 3, 4, 8, 12, 24, 36, 48, or 72 hours before or after introduction of the Cas protein and the guide RNA). See, e.g., US 2015/0240263 and US 2015/0110762, each of which is herein incorporated by reference in its entirety for all purposes. In addition, two or more of the components can be introduced into the cell or non-human animal by the same delivery method or different delivery methods. Similarly, two or more of the components can be introduced into a non-human animal by the same route of administration or different routes of administration.

In some methods, components of a CRISPR/Cas system are introduced into a non-human animal or cell. A guide RNA can be introduced into a non-human animal or cell in the form of an RNA (e.g., in vitro transcribed RNA) or in the form of a DNA encoding the guide RNA. When introduced in the form of a DNA, the DNA encoding a guide RNA can be operably linked to a promoter active in a cell in the non-human animal. For example, a guide RNA may be delivered via AAV and expressed in vivo under a U6 promoter. Such DNAs can be in one or more expression constructs. For example, such expression constructs can be components of a single nucleic acid molecule. Alternatively, they can be separated in any combination among two or more nucleic acid molecules (i.e., DNAs encoding one or more CRISPR RNAs and DNAs encoding one or more tracrRNAs can be components of a separate nucleic acid molecules).

Likewise, Cas proteins can be provided in any form. For example, a Cas protein can be provided in the form of a protein, such as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism. For example, the nucleic acid encoding the Cas protein can be modified to substitute codons having a higher frequency of usage in a mammalian cell, a rodent cell, a mouse cell, a rat cell, or any other host cell of interest, as compared to the naturally occurring polynucleotide sequence. When a nucleic acid encoding the Cas protein is introduced into a non-human animal, the Cas protein can be transiently, conditionally, or constitutively expressed in a cell in the non-human animal.

Nucleic acids encoding Cas proteins or guide RNAs can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. For example, the nucleic acid encoding the Cas protein can be in a vector comprising a DNA encoding one or more gRNAs. Alternatively, it can be in a vector or plasmid that is separate from the vector comprising the DNA encoding one or more gRNAs. Suitable promoters that can be used in an expression construct include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Optionally, the promoter can be a bidirectional promoter driving expression of both a Cas protein in one direction and a guide RNA in the other direction. Such bidirectional promoters can consist of (1) a complete, conventional, unidirectional Pol III promoter that contains 3 external control elements: a distal sequence element (DSE), a proximal sequence element (PSE), and a TATA box; and (2) a second basic Pol III promoter that includes a PSE and a TATA box fused to the 5' terminus of the DSE in reverse orientation. For example, in the H1 promoter, the DSE is adjacent to the PSE and the TATA box, and the promoter can be rendered bidirectional by creating a hybrid promoter in which transcription in the reverse direction is controlled by appending a PSE and TATA box derived from the U6 promoter. See, e.g., US 2016/0074535, herein incorporated by references in its entirety for all purposes. Use of a bidirectional promoter to express genes encoding a Cas protein and a guide RNA simultaneously allows for the generation of compact expression cassettes to facilitate delivery.

Molecules (e.g., Cas proteins or guide RNAs or RNAi agents or ASOs) introduced into the non-human animal or cell can be provided in compositions comprising a carrier increasing the stability of the introduced molecules (e.g., prolonging the period under given conditions of storage (e.g., −20° C., 4° C., or ambient temperature) for which degradation products remain below a threshold, such below 0.5% by weight of the starting nucleic acid or protein; or increasing the stability in vivo). Non-limiting examples of such carriers include poly(lactic acid) (PLA) microspheres, poly(D,L-lactic-coglycolic-acid) (PLGA) microspheres, liposomes, micelles, inverse micelles, lipid cochleates, and lipid microtubules.

Various methods and compositions are provided herein to allow for introduction of a molecule (e.g., nucleic acid or protein) into a cell or non-human animal. Methods for introducing molecules into various cell types are known and include, for example, stable transfection methods, transient transfection methods, and virus-mediated methods.

Transfection protocols as well as protocols for introducing nucleic acid sequences into cells may vary. Non-limiting transfection methods include chemical-based transfection methods using liposomes; nanoparticles; calcium phosphate (Graham et al. (1973) *Virology* 52 (2): 456-67, Bacchetti et al. (1977) *Proc. Natl. Acad. Sci. USA* 74 (4): 1590-4, and Kriegler, M (1991). Transfer and Expression: A Laboratory Manual. New York: W. H. Freeman and Company. pp. 96-97); dendrimers; or cationic polymers such as DEAE-dextran or polyethylenimine. Non-chemical methods include electroporation, sonoporation, and optical transfection. Particle-based transfection includes the use of a gene gun, or magnet-assisted transfection (Bertram (2006) *Current Pharmaceutical Biotechnology* 7, 277-28). Viral methods can also be used for transfection.

Introduction of molecules (e.g., nucleic acids or proteins) into a cell can also be mediated by electroporation, by intracytoplasmic injection, by viral infection, by adenovirus, by adeno-associated virus, by lentivirus, by retrovirus, by transfection, by lipid-mediated transfection, or by nucleofection. Nucleofection is an improved electroporation technology that enables nucleic acid substrates to be delivered not only to the cytoplasm but also through the nuclear membrane and into the nucleus. In addition, use of nucleofection in the methods disclosed herein typically requires much fewer cells than regular electroporation (e.g., only about 2 million compared with 7 million by regular electroporation). In one example, nucleofection is performed using the LONZA® NUCLEOFECTOR™ system.

Introduction of molecules (e.g., nucleic acids or proteins) into a cell (e.g., a zygote) can also be accomplished by microinjection. In zygotes (i.e., one-cell stage embryos), microinjection can be into the maternal and/or paternal pronucleus or into the cytoplasm. If the microinjection is into only one pronucleus, the paternal pronucleus is preferable due to its larger size. Microinjection of an mRNA is preferably into the cytoplasm (e.g., to deliver mRNA directly to the translation machinery), while microinjection of a Cas protein or a polynucleotide encoding a Cas protein or encoding an RNA is preferable into the nucleus/pronucleus. Alternatively, microinjection can be carried out by injection into both the nucleus/pronucleus and the cytoplasm: a needle can first be introduced into the nucleus/pronucleus and a first amount can be injected, and while removing the needle from the one-cell stage embryo a second amount can be injected into the cytoplasm. If a Cas protein is injected into the cytoplasm, the Cas protein preferably comprises a nuclear localization signal to ensure delivery to the nucleus/pronucleus. Methods for carrying out microinjection are well known. See, e.g., Nagy et al. (Nagy A, Gertsenstein M, Vintersten K, Behringer R., 2003, Manipulating the Mouse Embryo. Cold Spring Harbor, New York: Cold Spring Harbor Laboratory Press); see also Meyer et al. (2010) *Proc. Natl. Acad. Sci. USA* 107:15022-15026 and Meyer et al. (2012) *Proc. Natl. Acad. Sci. USA* 109: 9354-9359.

Other methods for introducing molecules (e.g., nucleic acid or proteins) into a cell or non-human animal can include, for example, vector delivery, particle-mediated delivery, exosome-mediated delivery, lipid-nanoparticle-mediated delivery, cell-penetrating-peptide-mediated delivery, or implantable-device-mediated delivery. As specific examples, a nucleic acid or protein can be introduced into a cell or non-human animal in a carrier such as a poly(lactic acid) (PLA) microsphere, a poly(D,L-lactic-coglycolic-acid) (PLGA) microsphere, a liposome, a micelle, an inverse micelle, a lipid cochleate, or a lipid microtubule. Some specific examples of delivery to a non-human animal include hydrodynamic delivery, virus-mediated delivery (e.g., adeno-associated virus (AAV)-mediated delivery), and lipid-nanoparticle-mediated delivery.

Introduction of nucleic acids and proteins into cells or non-human animals can be accomplished by hydrodynamic delivery (HDD). For gene delivery to parenchymal cells, only essential DNA sequences need to be injected via a selected blood vessel, eliminating safety concerns associated with current viral and synthetic vectors. When injected into the bloodstream, DNA is capable of reaching cells in the different tissues accessible to the blood. Hydrodynamic delivery employs the force generated by the rapid injection of a large volume of solution into the incompressible blood in the circulation to overcome the physical barriers of endothelium and cell membranes that prevent large and membrane-impermeable compounds from entering parenchymal cells. In addition to the delivery of DNA, this method is useful for the efficient intracellular delivery of RNA, proteins, and other small compounds in vivo. See, e.g., Bonamassa et al. (2011) *Pharm. Res.* 28(4):694-701, herein incorporated by reference in its entirety for all purposes.

Introduction of nucleic acids can also be accomplished by virus-mediated delivery, such as AAV-mediated delivery or lentivirus-mediated delivery. Other exemplary viruses/viral vectors include retroviruses, adenoviruses, vaccinia viruses, poxviruses, and herpes simplex viruses. The viruses can infect dividing cells, non-dividing cells, or both dividing and non-dividing cells. The viruses can integrate into the host genome or alternatively do not integrate into the host genome. Such viruses can also be engineered to have reduced immunity. The viruses can be replication-competent or can be replication-defective (e.g., defective in one or more genes necessary for additional rounds of virion replication and/or packaging). Viruses can cause transient expression, long-lasting expression (e.g., at least 1 week, 2 weeks, 1 month, 2 months, or 3 months), or permanent expression (e.g., of Cas9 and/or gRNA). Exemplary viral titers (e.g., AAV titers) include $10^{12}$, $10^{13}$, $10^{14}$, $10^{15}$, and $10^{16}$ vector genomes/mL.

The ssDNA AAV genome consists of two open reading frames, Rep and Cap, flanked by two inverted terminal repeats that allow for synthesis of the complementary DNA strand. When constructing an AAV transfer plasmid, the transgene is placed between the two ITRs, and Rep and Cap can be supplied in trans. In addition to Rep and Cap, AAV can require a helper plasmid containing genes from adenovirus. These genes (E4, E2a, and VA) mediate AAV replication. For example, the transfer plasmid, Rep/Cap, and the helper plasmid can be transfected into HEK293 cells containing the adenovirus gene E1+ to produce infectious AAV particles. Alternatively, the Rep, Cap, and adenovirus helper genes may be combined into a single plasmid. Similar packaging cells and methods can be used for other viruses, such as retroviruses.

Multiple serotypes of AAV have been identified. These serotypes differ in the types of cells they infect (i.e., their tropism), allowing preferential transduction of specific cell types. Serotypes for CNS tissue include AAV1, AAV2, AAV4, AAV5, AAV8, and AAV9. Serotypes for heart tissue include AAV1, AAV8, and AAV9. Serotypes for kidney tissue include AAV2. Serotypes for lung tissue include AAV4, AAV5, AAV6, and AAV9. Serotypes for pancreas tissue include AAV8. Serotypes for photoreceptor cells include AAV2, AAV5, and AAV8. Serotypes for retinal pigment epithelium tissue include AAV1, AAV2, AAV4, AAV5, and AAV8. Serotypes for skeletal muscle tissue include AAV1, AAV6, AAV7, AAV8, and AAV9. Serotypes for liver tissue include AAV7, AAV8, and AAV9, and particularly AAV8.

Tropism can be further refined through pseudotyping, which is the mixing of a capsid and a genome from different viral serotypes. For example AAV2/5 indicates a virus containing the genome of serotype 2 packaged in the capsid from serotype 5. Use of pseudotyped viruses can improve transduction efficiency, as well as alter tropism. Hybrid capsids derived from different serotypes can also be used to alter viral tropism. For example, AAV-DJ contains a hybrid capsid from eight serotypes and displays high infectivity across a broad range of cell types in vivo. AAV-DJ8 is another example that displays the properties of AAV-DJ but with enhanced brain uptake. AAV serotypes can also be modified through mutations. Examples of mutational modifications of AAV2 include Y444F, Y500F, Y730F, and S662V. Examples of mutational modifications of AAV3 include Y705F, Y731F, and T492V. Examples of mutational modifications of AAV6 include S663V and T492V. Other pseudotyped/modified AAV variants include AAV2/1, AAV2/6, AAV2/7, AAV2/8, AAV2/9, AAV2.5, AAV8.2, and AAV/SASTG.

To accelerate transgene expression, self-complementary AAV (scAAV) variants can be used. Because AAV depends on the cell's DNA replication machinery to synthesize the complementary strand of the AAV's single-stranded DNA genome, transgene expression may be delayed. To address this delay, scAAV containing complementary sequences that are capable of spontaneously annealing upon infection can be used, eliminating the requirement for host cell DNA synthesis. However, single-stranded AAV (ssAAV) vectors can also be used.

To increase packaging capacity, longer transgenes may be split between two AAV transfer plasmids, the first with a 3' splice donor and the second with a 5' splice acceptor. Upon co-infection of a cell, these viruses form concatemers, are spliced together, and the full-length transgene can be expressed. Although this allows for longer transgene expression, expression is less efficient. Similar methods for increasing capacity utilize homologous recombination. For example, a transgene can be divided between two transfer plasmids but with substantial sequence overlap such that co-expression induces homologous recombination and expression of the full-length transgene.

Introduction of nucleic acids and proteins can also be accomplished by lipid nanoparticle (LNP)-mediated delivery. For example, LNP-mediated delivery can be used to deliver a combination of Cas mRNA and guide RNA or a combination of Cas protein and guide RNA. Delivery through such methods results in transient Cas expression, and the biodegradable lipids improve clearance, improve tolerability, and decrease immunogenicity. Lipid formulations can protect biological molecules from degradation while improving their cellular uptake. Lipid nanoparticles are particles comprising a plurality of lipid molecules physically associated with each other by intermolecular forces. These include microspheres (including unilamellar and multilamellar vesicles, e.g., liposomes), a dispersed phase in an emulsion, micelles, or an internal phase in a suspension. Such lipid nanoparticles can be used to encapsulate one or more nucleic acids or proteins for delivery. Formulations which contain cationic lipids are useful for delivering polyanions such as nucleic acids. Other lipids that can be included are neutral lipids (i.e., uncharged or zwitterionic lipids), anionic lipids, helper lipids that enhance transfection, and stealth lipids that increase the length of time for which nanoparticles can exist in vivo. Examples of suitable cationic lipids, neutral lipids, anionic lipids, helper lipids, and stealth lipids can be found in WO 2016/010840 A1 and WO 2017/173054 A1, each of which is herein incorporated by reference in its entirety for all purposes. An exemplary lipid nanoparticle can comprise a cationic lipid and one or more other components. In one example, the other component can comprise a helper lipid such as cholesterol. In another example, the other components can comprise a helper lipid such as cholesterol and a neutral lipid such as DSPC. In another example, the other components can comprise a helper lipid such as cholesterol, an optional neutral lipid such as DSPC, and a stealth lipid such as S010, S024, S027, S031, or S033.

The LNP may contain one or more or all of the following: (i) a lipid for encapsulation and for endosomal escape; (ii) a neutral lipid for stabilization; (iii) a helper lipid for stabilization; and (iv) a stealth lipid. See, e.g., Finn et al. (2018) *Cell Reports* 22:1-9 and WO 2017/173054 A1, each of which is herein incorporated by reference in its entirety for all purposes. In certain LNPs, the cargo can include a guide RNA or a nucleic acid encoding a guide RNA. In certain LNPs, the cargo can include an mRNA encoding a Cas nuclease, such as Cas9, and a guide RNA or a nucleic acid encoding a guide RNA.

The lipid for encapsulation and endosomal escape can be a cationic lipid. The lipid can also be a biodegradable lipid, such as a biodegradable ionizable lipid. One example of a suitable lipid is Lipid A or LP01, which is (9Z,12Z)-3-((4, 4-bis(octyloxy)butanoyl)oxy)-2-((((3-(diethylamino) propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z,12Z)-octadeca-9,12-dienoate. See, e.g., Finn et al. (2018) *Cell Reports* 22:1-9 and WO 2017/173054 A1, each of which is herein incorporated by reference in its entirety for all purposes. Another example of a suitable lipid is Lipid B, which is ((5-((dimethylamino)methyl)-1,3-phenylene)bis (oxy))bis(octane-8,1-diyl)bis(decanoate), also called ((5-((dimethylamino)methyl)-1,3-phenylene)bis(oxy))bis(octane-8,1-diyl)bis(decanoate). Another example of a suitable lipid is Lipid C, which is 2-((4-(((3-(dimethylamino) propoxy)carbonyl)oxy)hexadecanoyl)oxy)propane-1,3-diyl (9Z,9'Z,12Z,12'Z)-bis(octadeca-9,12-dienoate). Another example of a suitable lipid is Lipid D, which is 3-(((3-(dimethylamino)propoxy)carbonyl)oxy)-13-(octanoyloxy) tridecyl 3-octylundecanoate. Other suitable lipids include heptatriaconta-6,9,28,31-tetraen-19-yl 4-(dimethylamino) butanoate (also known as Dlin-MC3-DMA (MC3))).

Some such lipids suitable for use in the LNPs described herein are biodegradable in vivo. For example, LNPs comprising such a lipid include those where at least 75% of the lipid is cleared from the plasma within 8, 10, 12, 24, or 48 hours, or 3, 4, 5, 6, 7, or 10 days. As another example, at least 50% of the LNP is cleared from the plasma within 8, 10, 12, 24, or 48 hours, or 3, 4, 5, 6, 7, or 10 days.

Such lipids may be ionizable depending upon the pH of the medium they are in. For example, in a slightly acidic medium, the lipids may be protonated and thus bear a positive charge. Conversely, in a slightly basic medium, such as, for example, blood where pH is approximately 7.35, the lipids may not be protonated and thus bear no charge. In some embodiments, the lipids may be protonated at a pH of at least about 9, 9.5, or 10. The ability of such a lipid to bear a charge is related to its intrinsic pKa. For example, the lipid may, independently, have a pKa in the range of from about 5.8 to about 6.2.

Neutral lipids function to stabilize and improve processing of the LNPs. Examples of suitable neutral lipids include a variety of neutral, uncharged or zwitterionic lipids. Examples of neutral phospholipids suitable for use in the present disclosure include, but are not limited to, 5-heptadecylbenzene-1,3-diol (resorcinol), dipalmitoylphosphatidylcholine (DPPC), distearoylphosphatidylcholine (DSPC), phosphocholine (DOPC), dimyristoylphosphatidylcholine (DMPC), phosphatidylcholine (PLPC), 1,2-distearoyl-sn-glycero-3-phosphocholine (DAPC), phosphatidylethanolamine (PE), egg phosphatidylcholine (EPC), dilauryloylphosphatidylcholine (DLPC), dimyristoylphosphatidylcholine (DMPC), 1-myristoyl-2-palmitoyl phosphatidylcholine (MPPC), 1-palmitoyl-2-myristoyl phosphatidylcholine (PMPC), 1-palmitoyl-2-stearoyl phosphatidylcholine (PSPC), 1,2-diarachidoyl-sn-glycero-3-phosphocholine (DBPC), 1-stearoyl-2-palmitoyl phosphatidylcholine (SPPC), 1,2-dieicosenoyl-sn-glycero-3-phosphocholine (DEPC), palmitoyloleoyl phosphatidylcholine (POPC), lysophosphatidyl choline, dioleoyl phosphatidylethanolamine (DOPE), dilinoleoylphosphatidylcholine di stearoylphosphatidylethanolamine (DSPE), dimyristoyl phosphatidylethanolamine (DMPE), dipalmitoyl phosphatidylethanolamine (DPPE), palmitoyloleoyl phosphatidylethanolamine (POPE), lyso-phosphatidylethanolamine, and combinations thereof. For example, the neutral phospholipid may be selected from the group consisting of distearoylphosphatidylcholine (DSPC) and dimyristoyl phosphatidyl ethanolamine (DMPE).

Helper lipids include lipids that enhance transfection. The mechanism by which the helper lipid enhances transfection can include enhancing particle stability. In certain cases, the helper lipid can enhance membrane fusogenicity. Helper lipids include steroids, sterols, and alkyl resorcinols. Examples of suitable helper lipids suitable include cholesterol, 5-heptadecylresorcinol, and cholesterol hemisuccinate. In one example, the helper lipid may be cholesterol or cholesterol hemisuccinate.

Stealth lipids include lipids that alter the length of time the nanoparticles can exist in vivo. Stealth lipids may assist in the formulation process by, for example, reducing particle aggregation and controlling particle size. Stealth lipids may modulate pharmacokinetic properties of the LNP. Suitable stealth lipids include lipids having a hydrophilic head group linked to a lipid moiety.

The hydrophilic head group of stealth lipid can comprise, for example, a polymer moiety selected from polymers based on PEG (sometimes referred to as poly(ethylene oxide)), poly(oxazoline), poly(vinyl alcohol), poly(glycerol), poly(N-vinylpyrrolidone), polyaminoacids, and poly N-(2-hydroxypropyl)methacrylamide. The term PEG means any polyethylene glycol or other polyalkylene ether polymer. In certain LNP formulations, the PEG, is a PEG-2K, also termed PEG 2000, which has an average molecular weight of about 2,000 daltons. See, e.g., WO 2017/173054 A1, herein incorporated by reference in its entirety for all purposes.

The lipid moiety of the stealth lipid may be derived, for example, from diacylglycerol or diacylglycamide, including those comprising a dialkylglycerol or dialkylglycamide group having alkyl chain length independently comprising from about C4 to about C40 saturated or unsaturated carbon atoms, wherein the chain may comprise one or more functional groups such as, for example, an amide or ester. The dialkylglycerol or dialkylglycamide group can further comprise one or more substituted alkyl groups.

As one example, the stealth lipid may be selected from PEG-dilauroylglycerol, PEG-dimyristoylglycerol (PEG-DMG), PEG-dipalmitoylglycerol, PEG-di stearoylglycerol (PEG-DSPE), PEG-dilaurylglycamide, PEG-dimyristylglycamide, PEG-dipalmitoylglycamide, and PEG-di stearoylglycamide, PEG-cholesterol (1-[8'-(Cholest-5-en-3 [beta]-oxy)carboxamido-3',6'-dioxaoctanyl]carbamoyl-[omega]-methyl-poly(ethylene glycol), PEG-DMB (3,4-ditetradecoxylbenzyl-[omega]-methyl-poly(ethylene glycol)ether), 1,2-dimyristoyl-sn-glycero-3-phosphoethanolamine-N-[methoxy(polyethylene glycol)-2000] (PEG2k-DMG), 1,2-distearoyl-sn-glycero-3-phosphoethanolamine-N-[methoxy(polyethylene glycol)-2000] (PEG2k-DSPE), 1,2-distearoyl-sn-glycerol, methoxypoly ethylene glycol (PEG2k-DSG), poly(ethylene glycol)-2000-dimethacrylate (PEG2k-DMA), and 1,2-distearyloxypropyl-3-amine-N-[methoxy(polyethylene glycol)-2000] (PEG2k-DSA). In one particular example, the stealth lipid may be PEG2k-DMG.

The LNPs can comprise different respective molar ratios of the component lipids in the formulation. The mol-% of the CCD lipid may be, for example, from about 30 mol-% to about 60 mol-%, from about 35 mol-% to about 55 mol-%, from about 40 mol-% to about 50 mol-%, from about 42 mol-% to about 47 mol-%, or about 45%. The mol-% of the helper lipid may be, for example, from about 30 mol-% to about 60 mol-%, from about 35 mol-% to about 55 mol-%, from about 40 mol-% to about 50 mol-%, from about 41 mol-% to about 46 mol-%, or about 44 mol-%. The mol-% of the neutral lipid may be, for example, from about 1 mol-% to about 20 mol-%, from about 5 mol-% to about 15 mol-%, from about 7 mol-% to about 12 mol-%, or about 9 mol-%. The mol-% of the stealth lipid may be, for example, from about 1 mol-% to about 10 mol-%, from about 1 mol-% to about 5 mol-%, from about 1 mol-% to about 3 mol-%, about 2 mol-%, or about 1 mol-%.

The LNPs can have different ratios between the positively charged amine groups of the biodegradable lipid (N) and the negatively charged phosphate groups (P) of the nucleic acid to be encapsulated. This may be mathematically represented by the equation N/P. For example, the N/P ratio may be from about 0.5 to about 100, from about 1 to about 50, from about 1 to about 25, from about 1 to about 10, from about 1 to about 7, from about 3 to about 5, from about 4 to about 5, about 4, about 4.5, or about 5. The N/P ratio can also be from about 4 to about 7 or from about 4.5 to about 6. In specific examples, the N/P ratio can be 4.5 or can be 6.

In some LNPs, the cargo can comprise Cas mRNA and gRNA. The Cas mRNA and gRNAs can be in different ratios. For example, the LNP formulation can include a ratio of Cas mRNA to gRNA nucleic acid ranging from about 25:1 to about 1:25, ranging from about 10:1 to about 1:10, ranging from about 5:1 to about 1:5, or about 1:1. Alternatively, the LNP formulation can include a ratio of Cas mRNA to gRNA nucleic acid from about 1:1 to about 1:5, or about 10:1. Alternatively, the LNP formulation can include a ratio of Cas mRNA to gRNA nucleic acid of about 1:10, 25:1, 10:1, 5:1, 3:1, 1:1, 1:3, 1:5, 1:10, or 1:25. Alternatively, the LNP formulation can include a ratio of Cas mRNA to gRNA nucleic acid of from about 1:1 to about 1:2. In specific examples, the ratio of Cas mRNA to gRNA can be about 1:1 or about 1:2.

In some LNPs, the cargo can comprise exogenous donor nucleic acid and gRNA. The exogenous donor nucleic acid and gRNAs can be in different ratios. For example, the LNP formulation can include a ratio of exogenous donor nucleic acid to gRNA nucleic acid ranging from about 25:1 to about 1:25, ranging from about 10:1 to about 1:10, ranging from about 5:1 to about 1:5, or about 1:1. Alternatively, the LNP formulation can include a ratio of exogenous donor nucleic acid to gRNA nucleic acid from about 1:1 to about 1:5, about 5:1 to about 1:1, about 10:1, or about 1:10. Alternatively, the LNP formulation can include a ratio of exogenous donor nucleic acid to gRNA nucleic acid of about 1:10, 25:1, 10:1, 5:1, 3:1, 1:1, 1:3, 1:5, 1:10, or 1:25.

A specific example of a suitable LNP has a nitrogen-to-phosphate (N/P) ratio of 4.5 and contains biodegradable cationic lipid, cholesterol, DSPC, and PEG2k-DMG in a 45:44:9:2 molar ratio. The biodegradable cationic lipid can be (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl) oxy)-2-((((3-(diethylamino)propoxy)carbonyl)oxy)methyl) propyl (9Z,12Z)-octadeca-9,12-dienoate. See, e.g., Finn et al. (2018) *Cell Reports* 22:1-9, herein incorporated by reference in its entirety for all purposes. The Cas9 mRNA can be in a 1:1 ratio by weight to the guide RNA. Another specific example of a suitable LNP contains Dlin-MC3-DMA (MC3), cholesterol, DSPC, and PEG-DMG in a 50:38.5:10:1.5 molar ratio.

Another specific example of a suitable LNP has a nitrogen-to-phosphate (N/P) ratio of 6 and contains biodegradable cationic lipid, cholesterol, DSPC, and PEG2k-DMG in a 50:38:9:3 molar ratio. The biodegradable cationic lipid can be (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl) oxy)-2-((((3-(diethylamino)propoxy)carbonyl)oxy)methyl) propyl (9Z,12Z)-octadeca-9,12-dienoate. The Cas9 mRNA can be in a 1:2 ratio by weight to the guide RNA.

The mode of delivery can be selected to decrease immunogenicity. For example, a Cas protein and a gRNA may be delivered by different modes (e.g., bi-modal delivery). These different modes may confer different pharmacodynamics or pharmacokinetic properties on the subject delivered molecule (e.g., Cas or nucleic acid encoding, gRNA or nucleic acid encoding, or exogenous donor nucleic acid/repair template). For example, the different modes can result in different tissue distribution, different half-life, or different temporal distribution. Some modes of delivery (e.g., delivery of a nucleic acid vector that persists in a cell by autonomous replication or genomic integration) result in more persistent expression and presence of the molecule, whereas other modes of delivery are transient and less persistent (e.g., delivery of an RNA or a protein). Delivery of Cas proteins in a more transient manner, for example as mRNA or protein, can ensure that the Cas/gRNA complex is only present and active for a short period of time and can reduce immunogenicity caused by peptides from the bacterially-derived Cas enzyme being displayed on the surface of the cell by WIC molecules. Such transient delivery can also reduce the possibility of off-target modifications.

Administration in vivo can be by any suitable route including, for example, parenteral, intravenous, oral, subcutaneous, intra-arterial, intracranial, intrathecal, intraperitoneal, topical, intranasal, or intramuscular. Systemic modes of administration include, for example, oral and parenteral routes. Examples of parenteral routes include intravenous, intraarterial, intraosseous, intramuscular, intradermal, subcutaneous, intranasal, and intraperitoneal routes. A specific example is intravenous infusion. Nasal instillation and intravitreal injection are other specific examples. Local modes of administration include, for example, intrathecal, intracerebroventricular, intraparenchymal (e.g., localized intraparenchymal delivery to the striatum (e.g., into the caudate or into the putamen), cerebral cortex, precentral gyms, hippocampus (e.g., into the dentate gyrus or CA3 region), temporal cortex, amygdala, frontal cortex, thalamus, cerebellum, medulla, hypothalamus, tectum, tegmentum, or substantia nigra), intraocular, intraorbital, subconjuctival, intravitreal, subretinal, and transscleral routes. Significantly smaller amounts of the components (compared with systemic approaches) may exert an effect when administered locally (for example, intraparenchymal or intravitreal) compared to when administered systemically (for example, intravenously). Local modes of administration may also reduce or eliminate the incidence of potentially toxic side effects that may occur when therapeutically effective amounts of a component are administered systemically.

Administration in vivo can be by any suitable route including, for example, parenteral, intravenous, oral, subcutaneous, intra-arterial, intracranial, intrathecal, intraperitoneal, topical, intranasal, or intramuscular. A specific example is intravenous infusion. Compositions comprising the guide RNAs and/or Cas proteins (or nucleic acids encoding the guide RNAs and/or Cas proteins) can be formulated using one or more physiologically and pharmaceutically acceptable carriers, diluents, excipients or auxiliaries. The formulation can depend on the route of administration chosen. The term "pharmaceutically acceptable" means that the carrier, diluent, excipient, or auxiliary is compatible with the other ingredients of the formulation and not substantially deleterious to the recipient thereof.

The frequency of administration and the number of dosages can depend on the half-life of the exogenous donor nucleic acids, guide RNAs, or Cas proteins (or nucleic acids encoding the guide RNAs or Cas proteins) and the route of administration among other factors. The introduction of nucleic acids or proteins into the cell or non-human animal can be performed one time or multiple times over a period of time. For example, the introduction can be performed at least two times over a period of time, at least three times over a period of time, at least four times over a period of time, at least five times over a period of time, at least six times over a period of time, at least seven times over a period of time, at least eight times over a period of time, at least nine times over a period of times, at least ten times over a period of time, at least eleven times, at least twelve times over a period of time, at least thirteen times over a period of time, at least fourteen times over a period of time, at least fifteen times over a period of time, at least sixteen times over a period of time, at least seventeen times over a period of time, at least eighteen times over a period of time, at least nineteen times over a period of time, or at least twenty times over a period of time.

E. Measuring Delivery, Activity, or Efficacy of Human-TTR-Targeting Reagents In Vivo or Ex Vivo The methods disclosed herein can further comprise detecting or measuring activity of human-TTR-targeting reagents. For example, if the human-TTR-targeting reagent is a genome editing reagent (e.g., CRISPR/Cas designed to target the human TTR locus), the measuring can comprise assessing the humanized TTR locus comprising the beta-slip mutation for modifications.

Various methods can be used to identify cells having a targeted genetic modification. The screening can comprise a quantitative assay for assessing modification of allele (MOA) of a parental chromosome. See, e.g., US 2004/0018626; US 2014/0178879; US 2016/0145646; WO 2016/081923; and Frendewey et al. (2010) *Methods Enzymol.* 476:295-307, each of which is herein incorporated by reference in its entirety for all purposes. For example, the quantitative assay can be carried out via a quantitative PCR, such as a real-time PCR (qPCR). The real-time PCR can utilize a first primer set that recognizes the target locus and a second primer set that recognizes a non-targeted reference locus. The primer set can comprise a fluorescent probe that recognizes the amplified sequence. Other examples of suitable quantitative assays include fluorescence-mediated in situ hybridization (FISH), comparative genomic hybridization, isothermal DNA amplification, quantitative hybridization to an immobilized probe(s), INVADER® Probes, TAQMAN® Molecular Beacon probes, or ECLIPSE™ probe technology (see, e.g., US 2005/0144655, herein incorporated by reference in its entirety for all purposes).

Next-generation sequencing (NGS) can also be used for screening. Next-generation sequencing can also be referred to as "NGS" or "massively parallel sequencing" or "high throughput sequencing." NGS can be used as a screening tool in addition to the MOA assays to define the exact nature of the targeted genetic modification and whether it is consistent across cell types or tissue types or organ types.

Assessing modification of the humanized TTR locus comprising the beta-slip mutation in a non-human animal can be in any cell type from any tissue or organ. For example, the assessment can be in multiple cell types from the same tissue or organ or in cells from multiple locations within the tissue or organ. This can provide information about which cell types within a target tissue or organ are being targeted or which sections of a tissue or organ are being reached by the human-TTR-targeting reagent. As another example, the assessment can be in multiple types of tissue or in multiple organs. In methods in which a particular tissue, organ, or cell type is being targeted, this can provide information about how effectively that tissue or organ is being targeted and whether there are off-target effects in other tissues or organs.

One example of an assay that can be used are the RNASCOPE™ and BASESCOPE™ RNA in situ hybridization (ISH) assays, which are methods that can quantify cell-specific edited transcripts, including single nucleotide changes, in the context of intact fixed tissue. The BASESCOPE™ RNA ISH assay can complement NGS and qPCR in characterization of gene editing. Whereas NGS/qPCR can provide quantitative average values of wild type and edited sequences, they provide no information on heterogeneity or percentage of edited cells within a tissue. The BASESCOPE™ ISH assay can provide a landscape view of an entire tissue and quantification of wild type versus edited transcripts with single-cell resolution, where the actual number of cells within the target tissue containing the edited mRNA transcript can be quantified. The BASESCOPE™ assay achieves single-molecule RNA detection using paired oligo ("ZZ") probes to amplify signal without non-specific background. However, the BASESCOPE™ probe design and signal amplification system enables single-molecule RNA detection with a ZZ probe, and it can differentially detect single nucleotide edits and mutations in intact fixed tissue.

If the reagent is designed to inactivate the humanized TTR locus comprising the beta-slip mutation, affect expression of the humanized TTR locus, prevent translation of the humanized TTR mRNA, or clear the humanized TTR protein, the measuring can comprise assessing humanized TTR mRNA or protein expression. This measuring can be within the liver or particular cell types or regions within the liver, or it can involve measuring serum levels of secreted humanized TTR protein.

Production and secretion of the humanized TTR protein comprising the beta-slip mutation can be assessed by any known means. For example, expression can be assessed by measuring levels of the encoded mRNA in the liver of the non-human animal or levels of the encoded protein in the liver of the non-human animal using known assays. Secretion of the humanized TTR protein can be assessed by measuring or plasma levels or serum levels of the encoded humanized TTR protein in the non-human animal using known assays. For example, the measuring can be to determine if the human-TTR-targeting reagent reduces TTR levels in the non-human animal.

The measuring can also comprise assessing aggregation of the humanized TTR protein. For example, native PAGE and western blots can be used to assess the presence of aggregated humanized TTR protein (e.g., higher molecular weight forms of humanized TTR protein) and whether the human-TTR-targeting reagent prevents aggregation, reduces aggregation, disrupts aggregation, or increases clearance of aggregated forms of humanized TTR protein.

The measuring can also comprise assessing amyloid deposition or the presence of amyloid deposits (amyloidosis). For example, the measuring can be to determine whether the human-TTR-targeting reagent prevents, reduces, disrupts, or clears amyloid deposits. As on example, Congo Red is a widely used stain to detect amyloidosis.

Tissues can be imaged under white light which reveals overall tissue architecture and a characteristic red stain. When Congo Red stained tissue is illuminated using linear polarized light, only the dye which is bound to amyloids will refract the polarized light (e.g., amyloid bound CongoRed dye will become birefringent), which is viewed as a light green/white color. The presence of these greenish-white deposits is indicative of amyloid deposition. Such assays can be used to assess whether the human-TTR-targeting reagent prevents or reduces or disrupts or clears amyloid deposits. The assessment can be in any tissue or organ in which TTR amyloid deposition occurs. As one non-limiting example, the assessment can be in the sciatic nerve.

The measuring can also comprise assessing activity or hyperactivity levels in the non-human animal. For example, the measuring can be to determine if the human-TTR-targeting reagent prevents or reduces hyperactivity in the non-human animal. Hyperactivity can be assessed by measuring one or more or all of total distance, total activity, and total rearings in an open field test. The open field test gives an overall measure of mouse locomotion and hyperactivity. Three of the readouts from the open field test are the total distance traveled, the total activity, and the total number of rearings. The open field is a behavioral test used to measure the general motor health and activity of mice during a 60-minute period. The mouse is tracked for the total distance it travels inside an enclosed, square apparatus during a 60-minute time period. Total activity is measured by the number of times a mouse in the apparatus interrupts the path of infrared breams in the X and Y planes. Rearings are a measure of how many times a mouse will stand on its hindlimbs to explore the walls of the apparatus. A greater rearings value is indicative of less anxious and hyperactive mice. Rearings are measured by infrared beam breaks in the Z-plane (beams placed at a height above that of a quadrupedal mouse).

The assessment can also comprise assessing the presence of dystonia or dystonic phenotypes. For example, the assessment can comprise assessing whether the non-human animal displays hindlimb dystonia or a hindlimb dystonic phenotype (e.g., dystonic hindlimb retraction) as described in the working examples. For example, the measuring can be to determine whether a human-TTR-targeting reagent ameliorates or prevents such phenotypes.

The assessment of any of these phenotypes can be at any age of non-human animal, such as at least about 1, 2, 3, 4, 5, 6, 7, 8, 9, 10, 11, or 12 months of age. In a specific example, the non-human animal can be at least about 2 months of age.

The assessment of any of these phenotypes can be done in comparison to a control non-human animal. One example of a control non-human animal is a corresponding wild type animal (e.g., of the same species). For example, the control non-human animal can be a wild type littermate. Another example of a control non-human animal is a corresponding non-human animal comprising a humanized TTR locus without the beta-slip mutation (e.g., the humanized TTR locus is identical except for the absence of the beta-slip mutation). The control non-human animals can be, for example, the same age as the test non-human animal and/or the same sex as the test non-human animal. The assessment of any of these phenotypes can also be done in comparison to a control non-human animal that is identical to the test non-human animal except not treated with the human-TTR-targeting reagent.

The assessment of any of these phenotypes can be in a single non-human animal and assessing changes in that non-human animal. Alternatively, the assessment can be in a population of non-human animals and comparing, for example, the percentage of non-human animals having a particular phenotype. As one example, the assessment can comprise assessing the percentage of non-human animals having amyloid deposits or having a dystonic phenotype in a test population (treated with the human-TTR-targeting reagent) compared to a control population (not treated with the human-TTR-targeting reagent).

IV. Methods of Making Non-Human Animals Comprising a Humanized TTR Locus Comprising a Beta-Slip Mutation Various methods are provided for making a non-human animal comprising a humanized TTR locus comprising a beta-slip mutation as disclosed elsewhere herein. Any convenient method or protocol for producing a genetically modified organism is suitable for producing such a genetically modified non-human animal. See, e.g., Cho et al. (2009) *Current Protocols in Cell Biology* 42:19.11:19.11.1-19.11.22 and Gama Sosa et al. (2010) *Brain Struct. Funct.* 214(2-3):91-109, each of which is herein incorporated by reference in its entirety for all purposes. Such genetically modified non-human animals can be generated, for example, through gene knock-in at a targeted Ttr locus.

For example, the method of producing a non-human animal comprising a humanized TTR locus comprising a beta-slip mutation can comprise: (1) modifying the genome of a pluripotent cell to comprise the humanized TTR locus comprising the beta-slip mutation; (2) identifying or selecting the genetically modified pluripotent cell comprising the humanized TTR locus comprising the beta-slip mutation; (3) introducing the genetically modified pluripotent cell into a non-human animal host embryo; and (4) implanting and gestating the host embryo in a surrogate mother. Alternatively, the method of producing a non-human animal comprising a humanized TTR locus comprising a beta-slip mutation can comprise: (1) modifying the genome of a pluripotent cell to comprise the humanized TTR locus comprising the beta-slip mutation; (2) identifying or selecting the genetically modified pluripotent cell comprising the humanized TTR locus comprising the beta-slip mutation; (3) introducing the genetically modified pluripotent cell into a non-human animal host embryo; and (4) gestating the host embryo in a surrogate mother. Optionally, the host embryo comprising modified pluripotent cell (e.g., a non-human ES cell) can be incubated until the blastocyst stage before being implanted into and gestated in the surrogate mother to produce an F0 non-human animal. The surrogate mother can then produce an F0 generation non-human animal comprising the humanized TTR locus comprising the beta-slip mutation.

The methods can further comprise identifying a cell or animal having a modified target genomic locus (i.e., a humanized TTR locus comprising the beta-slip mutation). Various methods can be used to identify cells and animals having a targeted genetic modification.

The screening step can comprise, for example, a quantitative assay for assessing modification of allele (MOA) of a parental chromosome. For example, the quantitative assay can be carried out via a quantitative PCR, such as a real-time PCR (qPCR). The real-time PCR can utilize a first primer set that recognizes the target locus and a second primer set that recognizes a non-targeted reference locus. The primer set can comprise a fluorescent probe that recognizes the amplified sequence.

Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology (see, e.g., US 2005/0144655, incorporated herein by reference in its entirety for all purposes).

An example of a suitable pluripotent cell is an embryonic stem (ES) cell (e.g., a mouse ES cell or a rat ES cell). The modified pluripotent cell can be generated, for example, through recombination by (a) introducing into the cell one or more targeting vectors comprising an insert nucleic acid flanked by 5' and 3' homology arms corresponding to 5' and 3' target sites, wherein the insert nucleic acid comprises a humanized TTR locus comprising the beta-slip mutation; and (b) identifying at least one cell comprising in its genome the insert nucleic acid integrated at the endogenous Ttr locus. Alternatively, the modified pluripotent cell can be generated by (a) introducing into the cell: (i) a nuclease agent, wherein the nuclease agent induces a nick or double-strand break at a target sequence within the endogenous Ttr locus; and (ii) one or more targeting vectors comprising an insert nucleic acid flanked by 5' and 3' homology arms corresponding to 5' and 3' target sites located in sufficient proximity to the nuclease target sequence, wherein the insert nucleic acid comprises the humanized TTR locus comprising the beta-slip mutation; and (c) identifying at least one cell comprising a modification (e.g., integration of the insert nucleic acid) at the endogenous Ttr locus. Any nuclease agent that induces a nick or double-strand break into a desired target sequence can be used. Examples of suitable nucleases include a Transcription Activator-Like Effector Nuclease (TALEN), a zinc-finger nuclease (ZFN), a meganuclease, and Clustered Regularly Interspersed Short Palindromic Repeats (CRISPR)/CRISPR-associated (Cas) systems or components of such systems (e.g., CRISPR/Cas9). See, e.g., US 2013/0309670 and US 2015/0159175, each of which is herein incorporated by reference in its entirety for all purposes.

The donor cell can be introduced into a host embryo at any stage, such as the blastocyst stage or the pre-morula stage (i.e., the 4 cell stage or the 8 cell stage). Progeny that are capable of transmitting the genetic modification though the germline are generated. See, e.g., U.S. Pat. No. 7,294,754, herein incorporated by reference in its entirety for all purposes.

Alternatively, the method of producing the non-human animals described elsewhere herein can comprise: (1) modifying the genome of a one-cell stage embryo to comprise the humanized TTR locus comprising the beta-slip mutation using the methods described above for modifying pluripotent cells; (2) selecting the genetically modified embryo; and (3) implanting and gestating the genetically modified embryo into a surrogate mother. Alternatively, the method of producing the non-human animals described elsewhere herein can comprise: (1) modifying the genome of a one-cell stage embryo to comprise the humanized TTR locus comprising the beta-slip mutation using the methods described above for modifying pluripotent cells; (2) selecting the genetically modified embryo; and (3) gestating the genetically modified embryo into a surrogate mother. Progeny that are capable of transmitting the genetic modification though the germline are generated.

Nuclear transfer techniques can also be used to generate the non-human mammalian animals. Briefly, methods for nuclear transfer can include the steps of: (1) enucleating an oocyte or providing an enucleated oocyte; (2) isolating or providing a donor cell or nucleus to be combined with the enucleated oocyte; (3) inserting the cell or nucleus into the enucleated oocyte to form a reconstituted cell; (4) implanting the reconstituted cell into the womb of an animal to form an embryo; and (5) allowing the embryo to develop. In such methods, oocytes are generally retrieved from deceased animals, although they may be isolated also from either oviducts and/or ovaries of live animals. Oocytes can be matured in a variety of well-known media prior to enucleation. Enucleation of the oocyte can be performed in a number of well-known manners. Insertion of the donor cell or nucleus into the enucleated oocyte to form a reconstituted cell can be by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell can be activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, can be cultured in well-known media and then transferred to the womb of an animal. See, e.g., US 2008/0092249, WO 1999/005266, US 2004/0177390, WO 2008/017234, and U.S. Pat. No. 7,612,250, each of which is herein incorporated by reference in its entirety for all purposes.

The various methods provided herein allow for the generation of a genetically modified non-human F0 animal wherein the cells of the genetically modified F0 animal comprise the humanized TTR locus comprising the beta-slip mutation. Depending on the method used to generate the F0 animal, the number of cells within the F0 animal that have the humanized TTR locus comprising the beta-slip mutation will vary. The introduction of the donor ES cells into a pre-morula stage embryo from a corresponding organism (e.g., an 8-cell stage mouse embryo) via for example, the VELOCIMOUSE® method allows for a greater percentage of the cell population of the F0 animal to comprise cells having the nucleotide sequence of interest comprising the targeted genetic modification. For example, at least 50%, 60%, 65%, 70%, 75%, 85%, 86%, 87%, 87%, 88%, 89%, 90%, 91%, 92%, 93%, 94%, 95%, 96%, 97%, 98%, 99% or 100% of the cellular contribution of the non-human F0 animal can comprise a cell population having the targeted modification.

The cells of the genetically modified F0 animal can be heterozygous for the humanized TTR locus comprising the beta-slip mutation or can be homozygous for the humanized TTR locus comprising the beta-slip mutation.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

BRIEF DESCRIPTION OF THE SEQUENCES

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. When a nucleotide sequence encoding an amino acid sequence is provided, it is understood that codon degenerate variants thereof that encode the same amino acid sequence are also provided. The amino acid sequences follow the standard convention of beginning at the amino terminus of the sequence and proceeding forward (i.e., from left to right in each line) to the carboxy terminus.

TABLE 2

Description of Sequences.

| SEQ ID NO | Type | Description |
|---|---|---|
| 1 | Protein | Human TTR Protein NP_000362.1 and P02766.1 |
| 2 | DNA | Human TTR mRNA NM_000371.3 |
| 3 | DNA | Human TTR Gene NG_009490.1 |
| 4 | DNA | Human TTR CDS |
| 5 | Protein | Mouse TTR protein P07309.1 and NP_038725.1 |
| 6 | DNA | Mouse Ttr mRNA NM_013697.5 |
| 7 | DNA | Mouse Ttr gene NC_000084.6 |
| 8 | DNA | Mouse TTR CDS |
| 9 | DNA | Human TTR Beta-Slip Protein |
| 10 | DNA | Human TTR Beta-Slip CDS |
| 11 | DNA | Mouse Ttr Locus - Start Codon to Stop Codon |
| 12 | DNA | Expected Beta-Slip TTR Humanization - F0, with SDC Puro cassette |
| 13 | DNA | Expected Beta-Slip TTR Humanization - F1, Cassette-Deleted |
| 14 | DNA | Human TTR Sequence Inserted in Humanized Beta-Slip TTR |
| 15 | DNA | Expected WT TTR Humanization - F0, with SDC Neo cassette |
| 16 | DNA | Expected WT TTR Humanization - F1, Cassette-Deleted |
| 17 | DNA | Human TTR Sequence Inserted in Humanized WT TTR |
| 18 | DNA | 9090retU3 - F Primer |
| 19 | DNA | 9090retU2 - F Primer |
| 20 | DNA | 9090retU - F Primer |
| 21 | DNA | 9090mTGU - F Primer |
| 22 | DNA | 7576mTU - F Primer |
| 23 | DNA | 9090mTM - F Primer |
| 24 | DNA | 7576mTD - F Primer |
| 25 | DNA | 9090mTGD - F Primer |
| 26 | DNA | 9090retD - F Primer |
| 27 | DNA | 9090retD2 - F Primer |
| 28 | DNA | 9090retD3 - F Primer |
| 29 | DNA | 7576hTU - F Primer |
| 30 | DNA | 7576hTD - F Primer |
| 31 | DNA | Puro - F Primer |
| 32 | DNA | 7655hTU - F Primer |
| 33 | DNA | 9212mTU - F Primer |
| 34 | DNA | 9212mTGD - F Primer |
| 35 | DNA | 7655mTU - F Primer |
| 36 | DNA | 7655mTD - F Primer |

TABLE 2-continued

Description of Sequences.

| SEQ ID NO | Type | Description |
|---|---|---|
| 37 | DNA | 9204mretD - F Primer |
| 38 | DNA | 9204mretU - F Primer |
| 39 | DNA | 4552mTU - F Primer |
| 40 | DNA | 9090retU3 - R Primer |
| 41 | DNA | 9090retU2 - R Primer |
| 42 | DNA | 9090retU - R Primer |
| 43 | DNA | 9090mTGU - R Primer |
| 44 | DNA | 7576mTU - R Primer |
| 45 | DNA | 9090mTM - R Primer |
| 46 | DNA | 7576mTD - R Primer |
| 47 | DNA | 9090mTGD - R Primer |
| 48 | DNA | 9090retD - R Primer |
| 49 | DNA | 9090retD2 - R Primer |
| 50 | DNA | 9090retD3 - R Primer |
| 51 | DNA | 7576hTU - R Primer |
| 52 | DNA | 7576hTD - R Primer |
| 53 | DNA | Puro - R Primer |
| 54 | DNA | 7655hTU - R Primer |
| 55 | DNA | 9212mTU - R Primer |
| 56 | DNA | 9212mTGD - R Primer |
| 57 | DNA | 7655mTU - R Primer |
| 58 | DNA | 7655mTD - R Primer |
| 59 | DNA | 9204mretD - R Primer |
| 60 | DNA | 9204mretU - R Primer |
| 61 | DNA | 4552mTU - R Primer |
| 62 | DNA | 9090retU3 - Probe |
| 63 | DNA | 9090retU2 - Probe |
| 64 | DNA | 9090retU - Probe |
| 65 | DNA | 9090mTGU - Probe |
| 66 | DNA | 7576mTU - Probe |
| 67 | DNA | 9090mTM - Probe |
| 68 | DNA | 7576mTD - Probe |
| 69 | DNA | 9090mTGD - Probe |
| 70 | DNA | 9090retD - Probe |
| 71 | DNA | 9090retD2 - Probe |
| 72 | DNA | 9090retD3 - Probe |
| 73 | DNA | 7576hTU - Probe |
| 74 | DNA | 7576hTD - Probe |
| 75 | DNA | Puro - Probe |
| 76 | DNA | 7655hTU - Probe |
| 77 | DNA | 9212mTU - Probe |
| 78 | DNA | 9212mTGD - Probe |
| 79 | DNA | 7655mTU - Probe |
| 80 | DNA | 7655mTD - Probe |
| 81 | DNA | 9204mretD - Probe |
| 82 | DNA | 9204mretU - Probe |
| 83 | DNA | 4552mTU - Probe |
| 84 | RNA | crRNA tail |
| 85 | RNA | tracrRNA |
| 86 | RNA | Generic Guide RNA Scaffold v1 |
| 87 | RNA | Generic Guide RNA Scaffold v2 |
| 88 | RNA | Generic Guide RNA Scaffold v3 |
| 89 | RNA | Generic Guide RNA Scaffold v4 |
| 90 | DNA | Generic Guide RNA Recognition Sequence plus PAM v1 |
| 91 | DNA | Generic Guide RNA Recognition Sequence plus PAM v2 |
| 92 | DNA | Generic Guide RNA Recognition Sequence plus PAM v3 |

EXAMPLES

Example 1. Generation of Mice Comprising a Humanized TTR Beta-Slip Locus

A humanized Ttr allele made was a complete deletion of the mouse transthyretin coding sequence and its replacement with the orthologous part of the human TTR gene. The orthologous part of the human TTR gene encoded three point mutations (G53S, E54D, and L55S, referred to collectively as TTR beta-slip) that shift the position of a beta-sheet involved in intermolecular interactions of the TTR complex and renders the TTR particularly aggregate-prone. The altered interactions the TTR complex that is formed by the beta-slip mutations results in the formation of protofibrils and amyloids (see, e.g., Eneqvist et al. (2000) *Mol. Cell* 6(5):1207-1218, herein incorporated by reference in its entirety for all purposes), which have been reported to be toxic to the IMR-32 cell line (see, e.g., Andersson et al. (2013) *PLoS One* 8(2):e55766, herein incorporated by reference in its entirety for all purposes). These mutations, however, have never been modeled in vivo.

Figure 3:
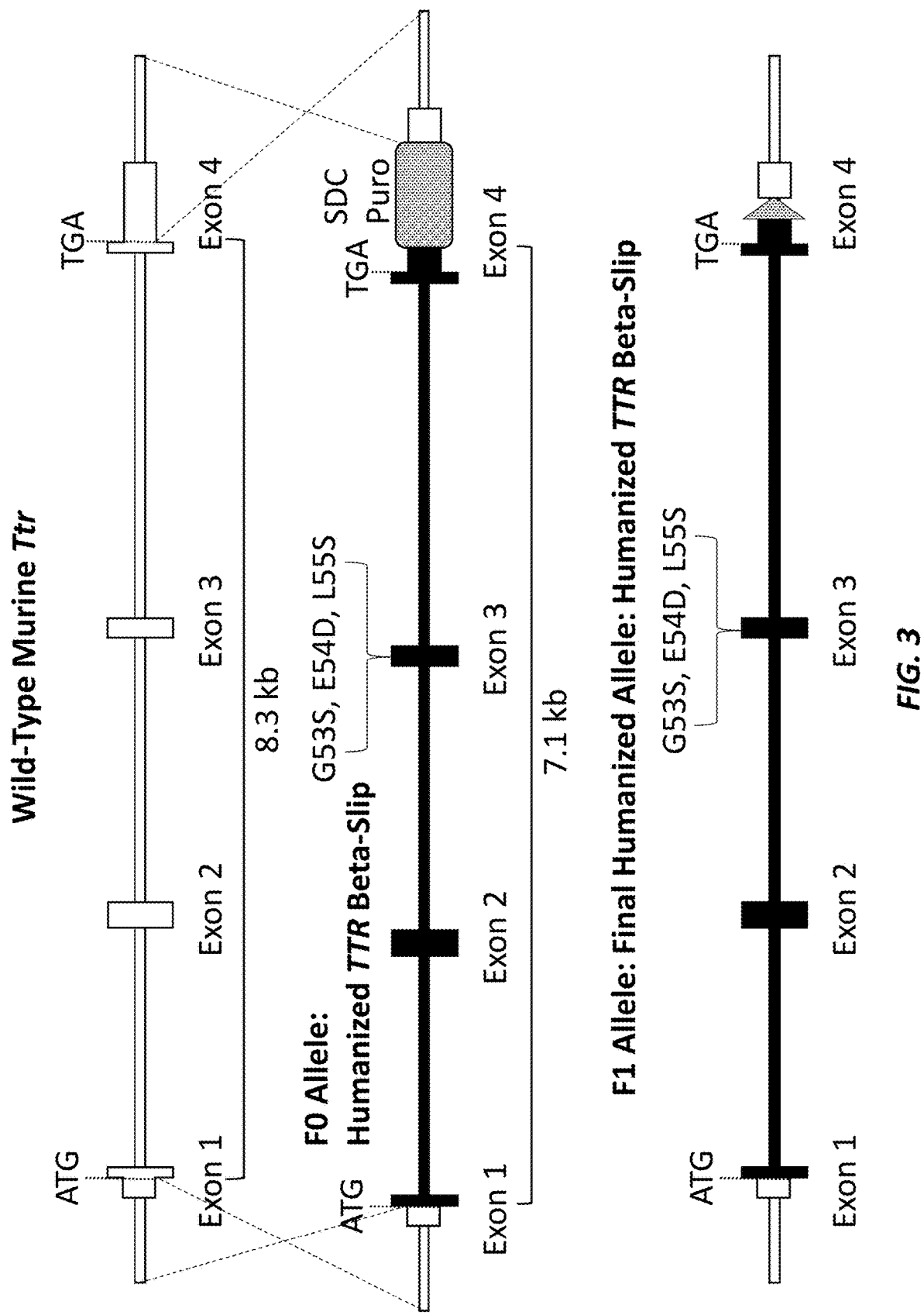
FIG. 3 shows a schematic (not drawn to scale) of the targeting to create the mutant (beta-slip) humanized mouse Ttr locus. The wild type mouse Ttr locus, the F0 allele of the mutant humanized mouse Ttr locus with the self-deleting neomycin (SDC-Puro) selection cassette (MAID 8530), and the F1 allele of the mutant humanized mouse Ttr locus with the loxP scar from removal of the SDC-Puro selection cassette (MAID 8531) are shown. White boxes indicate murine sequence; black boxes indicate human sequence.
Figure 4:
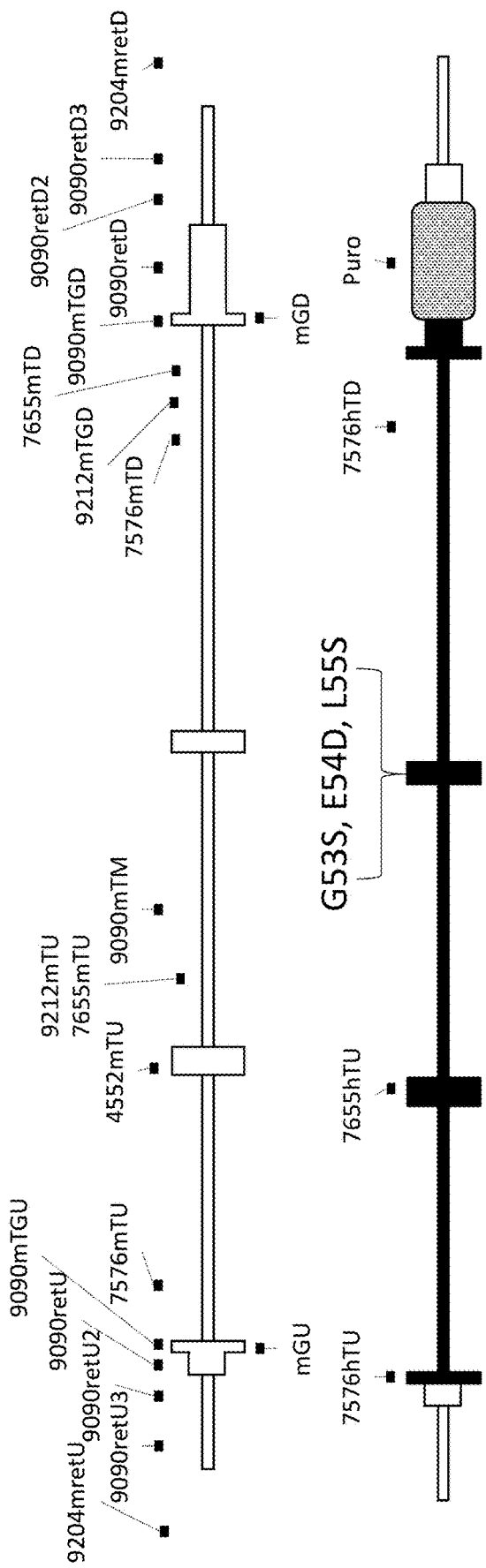
FIG. 4 shows a schematic (not drawn to scale) of the strategy for screening of the targeted mouse Ttr locus, including loss-of-allele assays (7576mTU, 4552mTU, 9212mTU, 7655mTU, 9090mTM, 7576mTD, 9212mTD, and 7655mTD), gain of allele assays (7576hTU, 7655hTU, 7576hTD, Puro), retention assays (9204mretU, 9090retU, 9090retU2, 9090retU3, 9090retD, 9090retD2, 9090retD3, 9204mretD), and CRISPR assays designed to cover the region that is disrupted by the CRISPR guides (9090mTGU, mGU, 9090mTGD, and mGD). White boxes indicate murine sequence; black boxes indicate human sequence.

A large targeting vector comprising a 5' homology arm including 33.7 kb of sequence upstream from the mouse Ttr start codon and 34.5 kb of the sequence downstream of the mouse Ttr stop codon was generated to replace the approximately 8.3 kb region from the mouse Ttr start codon to the mouse Ttr stop codon with the approximately 7.1 kb orthologous human TTR sequence from the human TTR start codon to the end of the last human TTR exon (exon 4, including the human 3' UTR) and a self-deleting puromycin selection cassette (SDC Puro) flanked by loxP sites. See FIG. 3. The SDC Puro cassette includes the following components from 5' to 3': loxP site, mouse protamine (Prm1) promoter, Crei (Cre coding sequence optimized to include intron), polyA, human ubiquitin promoter, puromycin-N-acetyltransferase (puro$_r$) coding sequence, polyA, loxP. To generate the humanized allele, CRISPR/Cas9 components were introduced into F1H4 mouse embryonic stem cells together with the large targeting vector. Loss-of-allele assays, gain-of-allele assays, retention assays, and CRISPR assays using primers and probes set forth in FIG. 4 and in Table 3 were performed to confirm the humanization of the mouse Ttr allele. Loss-of-allele, gain-of-allele assays, and retention assays are described, for example, in US 2014/0178879; US 2016/0145646; WO 2016/081923; and Frendewey et al. (2010) *Methods Enzymol.* 476:295-307, each of which is herein incorporated by reference in its entirety for all purposes. CRISPR assays are TAQMAN® assays designed to cover the region that is disrupted by the CRISPR gRNAs. When a CRISPR gRNA cuts and creates an indel (insertion or deletion), the TAQMAN® assay will fail to amplify and thus reports CRISPR cleavage. Versions with the SDC Puro cassette and after excision of the SDC Puro cassette are shown in FIG. 3. F0 mice were then generated using the VELOCIMOUSE® method. See, e.g., U.S. Pat. Nos. 7,576, 259; 7,659,442; 7,294,754; US 2008/007800; and Poueymirou et al. (2007) *Nature Biotech.* 25(1):91-99, each of which is herein incorporated by reference in its entirety for all purposes.

F0 generation mice (50% C57BL/6NTac and 50% 12956/SvEvTac) were generated from multiple humanized ES cell clones. The sequence for the expected humanized TTR beta-slip locus in the F0 generation mice is set forth in SEQ ID NO: 12 and includes the SDC Puro cassette (referred to as MAID8530). F1 and F2 generation mice (75% C57BL/6NTac and 25% 129S6/SvEvTac) were then generated by breeding. The sequence for the expected humanized TTR beta-slip locus in the F1 and F2 generation mice is set forth in SEQ ID NO: 13 and does not include the SDC Puro cassette (referred to as MAID8531). All humanized TTR beta-slip mice that were characterized in the experiments below were TTR$^{8531/8531}$ (cassette removed in both humanized TTR beta-slip alleles).

Corresponding humanized TTR wild type mice were made in the same manner except with a SDC Neo cassette. The sequence for the expected humanized mouse Ttr wild type locus in the F0 generation mice is set forth in SEQ ID NO: 15 and includes the SDC Neo cassette (referred to as 7576). F1 and F2 generation mice (75% C57BL/6NTac and 25% 12956/SvEvTac) were then generated by breeding. The sequence for the expected humanized mouse Ttr wild type locus in the F1 and F2 generation mice is set forth in SEQ ID NO: 16 and does not include the SDC Neo cassette (referred to as MAID7577). All humanized TTR wild type mice that were characterized in the experiments below were TTR$^{7577/7577}$ (cassette removed in both humanized TTR wild type alleles).

Figure 2:
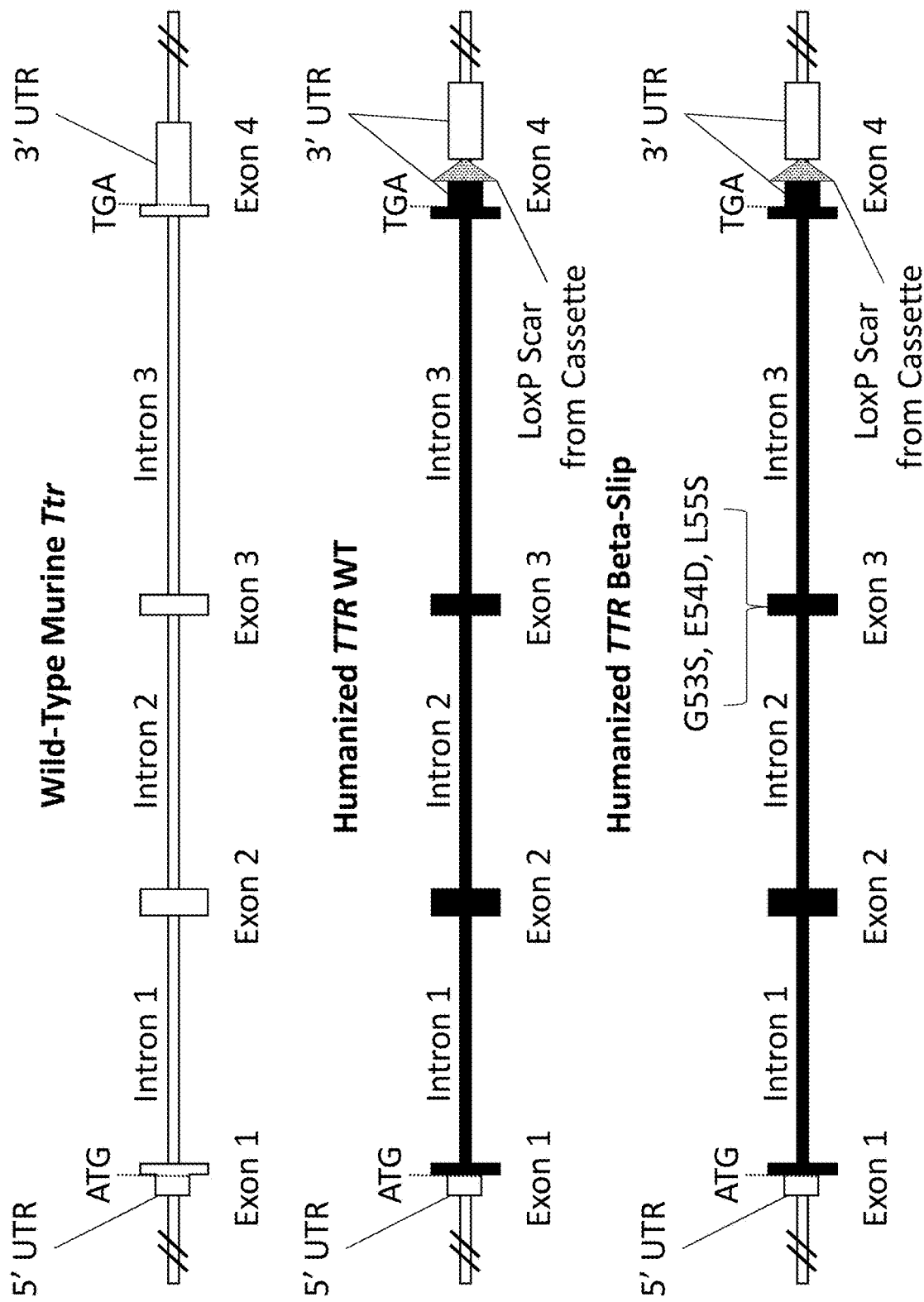
FIG. 2 shows schematics (not drawn to scale) of the wild-type murine Ttr locus, a wild type humanized mouse Ttr locus (wild type human TTR), and a mutant humanized mouse Ttr locus (beta-slip human TTR). Exons, introns, 5' untranslated regions (UTRs), 3' UTRs, start codons (ATG), stop codons (TGA), and loxP scars from selection cassettes are denoted. White boxes indicate murine sequence; black boxes indicate human sequence.

A comparison of the mouse transthyretin precursor protein, human wild type transthyretin precursor protein, and human beta-slip transthyretin precursor protein sequences is shown in FIG. 1A. A comparison of the mouse transthyretin, human wild type transthyretin, and human beta-slip transthyretin coding sequences is shown in FIG. 1B. A schematic showing the wild type mouse Ttr locus, the final wild type humanized mouse Ttr locus (with the SDC Neo cassette deleted) and the final beta-slip humanized mouse Ttr locus (with the SDC Puro cassette deleted) is shown in FIG. 2. The endogenous mouse Ttr locus sequence from the start codon to the stop codon is provided in SEQ ID NO: 11. The coding sequence for the endogenous mouse Ttr locus is provided in SEQ ID NO: 8. The transthyretin precursor protein encoded by the endogenous mouse Ttr locus is provided in SEQ ID NO: 5. Sequences for the expected wild type humanized mouse Ttr locus with the SDC Neo cassette and without the SDC Neo cassette are set forth in SEQ ID NOS: 15 and 16, respectively. The expected coding sequence (CDS) of the wild type humanized mouse Ttr locus is set forth in SEQ ID NO: 4. The expected transthyretin precursor protein encoded by the wild type humanized mouse Ttr locus is set forth in SEQ ID NO: 1. Sequences for the expected beta-slip humanized mouse Ttr locus with the SDC Puro cassette and without the SDC Puro cassette are set forth in SEQ ID NOS: 12 and 13, respectively. The expected coding sequence (CDS) of the beta-slip humanized mouse Ttr locus is set forth in SEQ ID NO: 10. The expected transthyretin precursor protein encoded by the beta slip humanized mouse Ttr locus is set forth in SEQ ID NO: 9. These alleles provides a true human target of human TTR therapeutics, thereby enabling testing of the efficacy and mode of action of therapeutics in live animals as well as pharmacokinetic and pharmacodynamics studies in a setting where the mutated human protein is the only version of TTR present.

TABLE 3

Primers and Probes for Loss-of-Allele Assays, Gain-of-Allele Assays, and Retention Assays.

| Assay | Forward Primer | Reverse Primer | Probe |
|---|---|---|---|
| 9090retU3 | CACAGACAATCAGACGTACCAGTA (SEQ ID NO: 18) | GGGACATCTCGGTTTCCTGACTT (SEQ ID NO: 40) | TCATGTAATCTGGCTTCAGAGTGGGA (SEQ ID NO: 62) |
| 9090retU2 | CCAGCTTTGCCAGTTTACGA (SEQ ID NO: 19) | TCCACACTACTGAACTCCACAA (SEQ ID NO: 41) | TGGGAGGCAATTCTTAGTTTCAATGGA (SEQ ID NO: 63) |

TABLE 3-continued

Primers and Probes for Loss-of-Allele Assays, Gain-of-Allele Assays, and Retention Assays.

| Assay | Forward Primer | Reverse Primer | Probe |
|---|---|---|---|
| 9090retU | TTGGACGGTTGCCCTCTT (SEQ ID NO: 20) | CGGAACACTCGCTCTACGAAA (SEQ ID NO: 42) | TCCCAAAGGTGTCTGTCTGCACA (SEQ ID NO: 64) |
| 9090mTGU | GATGGCTTCCCTTCGACTCTTC (SEQ ID NO: 21) | GGGCCAGCTTCAGACACA (SEQ ID NO: 43) | CTCCTTTGCCTCGCTGGACTGG (SEQ ID NO: 65) |
| 7576mTU | CACTGACATTTCTCTTGTCTCCTCT (SEQ ID NO: 22) | CCCAGGGTGCTGGAGAATCCAA (SEQ ID NO: 44) | CGGACAGCATCCAGGACTT (SEQ ID NO: 66) |
| 9090mTM | GGGCTCACCACAGATGAGAAG (SEQ ID NO: 23) | GCCAAGTGTCTTCCAGTACGAT (SEQ ID NO: 45) | AGAAGGAGTGTACAGAGTAGAACTGGACA (SEQ ID NO: 67) |
| 7576mTD | CACTGTTCGCCACAGGTCTT (SEQ ID NO: 24) | GTTCCCTTTCTTGGGTTCAGA (SEQ ID NO: 46) | TGTTTGTGGGTGTCAGTGTTTCTACTC (SEQ ID NO: 68) |
| 9090mTGD | GCTCAGCCCATACTCCTACA (SEQ ID NO: 25) | GATGCTACTGCTTTGGCAAGATC (SEQ ID NO: 47) | CACCACGGCTGTCGTCAGCAA (SEQ ID NO: 69) |
| 9090retD | GCCCAGGAGGACCAGGAT (SEQ ID NO: 26) | CCTGAGCTGCTAACACGGTT (SEQ ID NO: 48) | CTTGCCAAAGCAGTAGCATCCCA (SEQ ID NO: 70) |
| 9090retD2 | GGCAACTTGCTTGAGGAAGA (SEQ ID NO: 27) | AGCTACAGACCATGCTTAGTGTA (SEQ ID NO: 49) | AGGTCAGAAAGCAGAGTGGACCA (SEQ ID NO: 71) |
| 9090retD3 | GCAGCAACCCAGCTTCACTT (SEQ ID NO: 28) | TGCCAGTTTAGGAGGAATATGTTC (SEQ ID NO: 50) | CCCAGGCAATTCCTACCTTCCCA (SEQ ID NO: 72) |
| 7576hTU | ACTGAGCTGGGACTTGAAC (SEQ ID NO: 29) | CTGAGGAAACAGAGGTACCAGATAT (SEQ ID NO: 51) | TCTGAGCATTCTACCTCATTGCTTTGGT (SEQ ID NO: 73) |
| 7576hTD | TGCCTCACTCTGAGAACCA (SEQ ID NO: 30) | AGTCACACAGTTCTGTCAAATCAG (SEQ ID NO: 52) | AGGCTGTCCCAGCACCTGAGTCG (SEQ ID NO: 74) |
| Puro | CGCAACCTCCCCTTCTACG (SEQ ID NO: 31) | GTCCTTCGGGCACCTCG (SEQ ID NO: 53) | CGGCTCGGCTTCACCGTCACC (SEQ ID NO: 75) |
| 7655hTU | GGCCGTGCATGTGTTCAG (SEQ ID NO: 32) | TCCTGTGGGAGGGTTCTTTG (SEQ ID NO: 54) | AAGGCTGCTGATGACACCTGGGA (SEQ ID NO: 76) |
| 9212mTU | GGTTCCCATTTGCTCTTATTCGT (SEQ ID NO: 33) | CCCTCTCTCTGAGCCCTCTA (SEQ ID NO: 55) | AGATTCAGACACACACAACTTACCAGC (SEQ ID NO: 77) |
| 9212mTGD | CCCACACTGCAGAAGGAAACTTG (SEQ ID NO: 34) | GCTGCCTAAGTCTTTGGAGCT (SEQ ID NO: 56) | AGACCTGCAATTCTCTAAGAGCTCCACA (SEQ ID NO: 78) |
| 7655mTU | GGTTCCCATTTGCTCTTATTCGT (SEQ ID NO: 35) | CCCTCTCTCTGAGCCCTCTA (SEQ ID NO: 57) | AGATTCAGACACACACAACTTACCAGC (SEQ ID NO: 79) |
| 7655mTD | CCAGCTTAGCATCCTGTGAACA (SEQ ID NO: 36) | GAGAGGAGAGACAGCTAGTTCTAAC (SEQ ID NO: 58) | TTGTCTGCAGCTCCTACCTCTGGG (SEQ ID NO: 80) |
| 9204mretD | GGCAACTTGCTTGAGGAAGA (SEQ ID NO: 37) | AGCTACAGACCATGCTTAGTGTA (SEQ ID NO: 59) | AGGTCAGAAAGCAGAGTGGACCA (SEQ ID NO: 81) |

TABLE 3-continued

Primers and Probes for Loss-of-Allele Assays, Gain-of-Allele Assays, and Retention Assays.

| Assay | Forward Primer | Reverse Primer | Probe |
|---|---|---|---|
| 9204mretU | TGTGGAGTTCAGTAGTGTGGAG (SEQ ID NO: 38) | GCCCTCTTCATACAGGAATCAC (SEQ ID NO: 60) | TTGACATGTGTGGGTGAGAGATTTTACTG (SEQ ID NO: 82) |
| 4552mTU | CACTGACATTTCTCTTGTCTCCTCT (SEQ ID NO: 39) | CGGACAGCATCCAGGACTT (SEQ ID NO: 61) | CCCAGGGTGCTGGAGAATCCAA (SEQ ID NO: 83) |

Example 2. Characterization of Mice Comprising a Humanized TTR Beta-Slip Locus

Figure 5B:
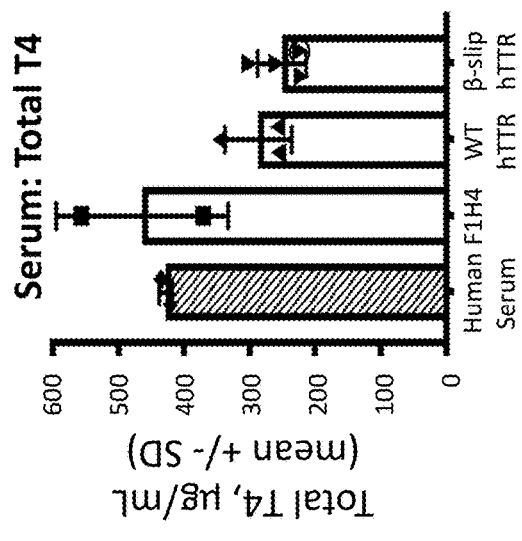
FIGS. 5A-5D show plasma hTTR levels (FIG. 5A), serum total T4 levels (FIG. 5B), serum free T4 levels (FIG. 5C), and body temperature (FIG. 5D) in two-month-old humanized TTR wild type mice, humanized TTR beta-slip mice, and F1H4 control mice. Dystonic mice are marked by the encircled red triangles. TTR and T4 levels were measured by ELISA.
Figure 5D:
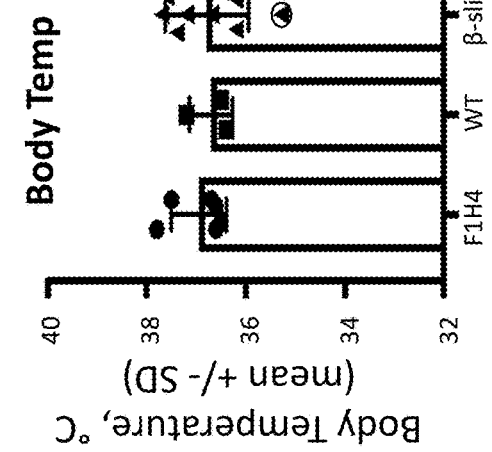
Figure 5A:
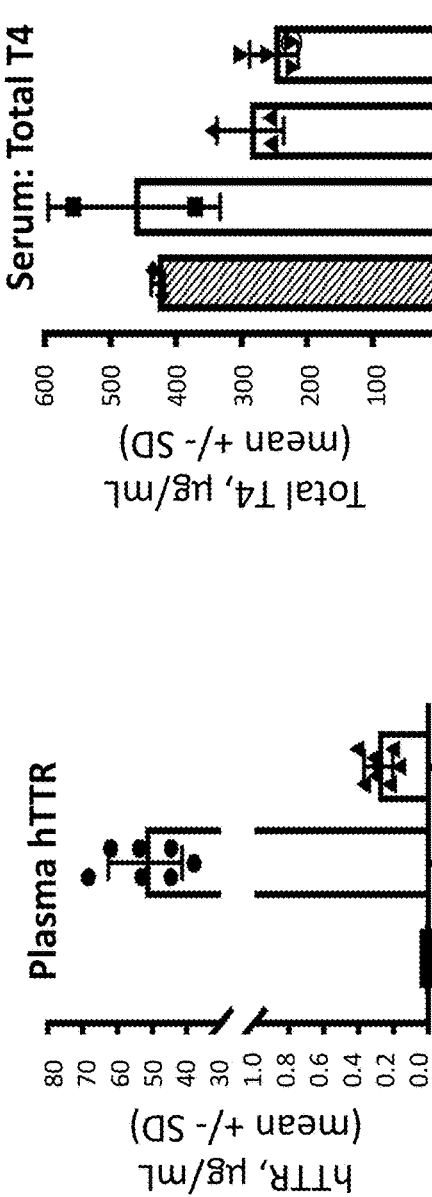

A humanized TTR beta-slip mouse colony was established, and F2 cohorts were characterized at two months of age. Human TTR was measured in serum and detected at 0.3 µg/mL, which is substantially lower than the levels typically detected in the serum of the control wild type mice (approximately 1000 µg/mL of mouse TTR) or that circulating in humans (approximately 200 µg/mL). It is also lower than the levels seen in the humanized TTR wild type mice. See FIG. 5A and Table 4.

Scientific MotorMonitor software, Kinder Scientific, Poway, CA) for the total distance they traveled inside an enclosed, square apparatus during a 60-minute time period. Total activity was measured by the number of times a mouse in the apparatus interrupts the path of infrared breams in the X and Y planes (i.e., "beam breaks"). Rearings were a measure of how many times a mouse stood on its hindlimbs (i.e., "rear") to explore the walls of the apparatus. A greater rearings value is indicative of less anxious and more active mice. Rearings were measured by infrared beam breaks in the Z-plane (beams placed at a height above that of a quadrupedal mouse).

TABLE 4

Plasma TTR levels in, Serum T4 Levels in, and Body Temperature of Humanized TTR Beta-Slip Mice, Humanized TTR Wild Type Mice, and Control F1H4 Mice.

| Strain | hTTR, µg/mL (SD) | mTTR, µg/mL (SD) | Total T4, ng/mL (SD) | Free T4, ng/mL (SD) | Body Temp, °C. (SD) |
|---|---|---|---|---|---|
| F1H4 | N.D. | ~800 | 158.6 (20.85) | 423.1 (6.93) | 36.95 (0.55) |
| WT hTTR$^{7577/7577}$ | 52.07 (10.67) | N.D. | 66.88 (18) | 286.8 (51.19) | 36.7 (0.44) |
| β-slip hTTR$^{8531/8531}$ | 0.291 (0.083) | N.D. | 51.19 (34.09) | 250.9 (36.76) | 36.79 (0.84) |
| Human Serum | 234.5 (n.a.) | N.D. | 64.71 (n.a.) | 423.1 (n.a.) | N.D. |

Figures 6A, 6B:
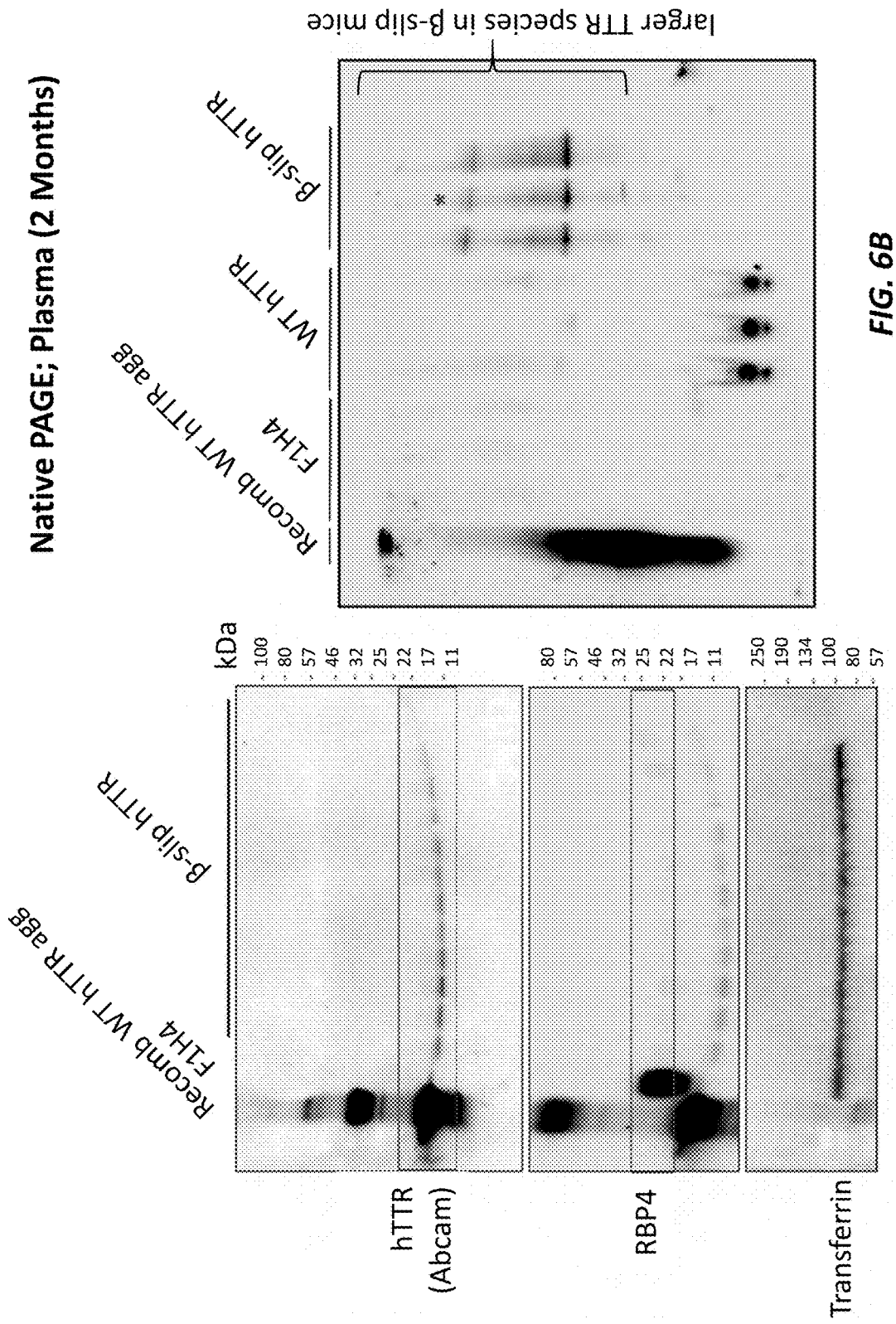
FIG. 6A shows a western blot following denaturing PAGE of plasma samples from two-month old humanized TTR beta-slip mice. F1H4 samples were used as a negative control, and recombinant WT human TTR was used as a positive control. Transferrin was used as a loading control.
FIG. 6B shows a western blot following native PAGE of plasma samples from two-month old humanized TTR beta-slip mice and samples from two-month old humanized TTR wild type mice. F1H4 samples were used as a negative control, and recombinant WT human TTR was used as a positive control.

When the blood of humanized TTR beta-slip mice was analyzed on native PAGE, followed by western blot with an anti-human-specific antibody, TTR was observed as expected. See FIG. 6A. Human mature WT TTR (pI: 5.31; MW: 13.76 kDa) and human mature beta-slip TTR (pI: 5.30/MW: 13.75 kDa) have nearly identical molecular weights. When the blood of humanized TTR beta-slip mice was analyzed on native PAGE, followed by western blot with an anti-human-specific antibody, high molecular weight TTR species were observed in the serum of the humanized TTR beta-slip mice but not the corresponding humanized TTR wild type mice. See FIG. 6B.

Despite having low levels of circulating TTR, the humanized TTR beta-slip mice had phenotypic differences when tested in behavioral assays. See FIGS. 8A-8C. One assay is the open field test, which gives an overall measure of mouse locomotion and hyperactivity. Three of the readouts from the open field test are the total distance traveled, the total activity, and the total number of rearings, measures which were each significantly increased in the humanized TTR beta-slip mice when compared to humanized TTR WT mice or littermate (F1H4) controls. See FIGS. 8A, 8B, and 8C, respectively. See also Tables 5, 6, and 7, respectively. The open field is a behavioral test used to measure the general motor health and activity of mice during a 60-minute period. The mice were tracked using computer software (Kinder

TABLE 5

Total Distance in Open Field Test of Humanized TTR Beta-Slip Mice, Humanized TTR Wild Type Mice, and Control F1H4 Mice.

| | F1H4, cm (SD) | WT hTTR$^{7577/7577}$ cm (SD) | β-slip hTTR$^{8531/8531}$ cm (SD) |
|---|---|---|---|
| Total distance | 10240 (3399) | 9863 (4134) | 16052 (2146)** |

**= p < 0.01 vs. F1H4 and vs. WT hTTR$^{7577/7577}$ (ANOVA, Tukey)

TABLE 6

Total Activity of Humanized TTR Beta-Slip Mice, Humanized TTR Wild Type Mice, and Control F1H4 Mice.

| | F1H4 n (SD) | WT hTTR$^{7577/7577}$ n (SD) | β-slip hTTR$^{8531/8531}$ n (SD) |
|---|---|---|---|
| Total Activity (Beam Breaks) | 4217 (1306) | 3470 (1856) | 6717 (872.2) |

TABLE 7

Total Rearings of Humanized TTR Beta-Slip Mice, Humanized TTR Wild Type Mice, and Control F1H4 Mice.

|  | F1H4 n (SD) | WT hTTR$^{7577/7577}$ n (SD) | β-slip hTTR$^{8531/8531}$ n (SD) |
|---|---|---|---|
| Rearings | 174.2 (77.7) | 153.3 (121.2) | 497.8 (125.2)*** |

***= $p < 0.001$ vs. F1H4 and vs. WT hTTR$^{7577/7577}$ (ANOVA, Tukey)

Figure 5C:
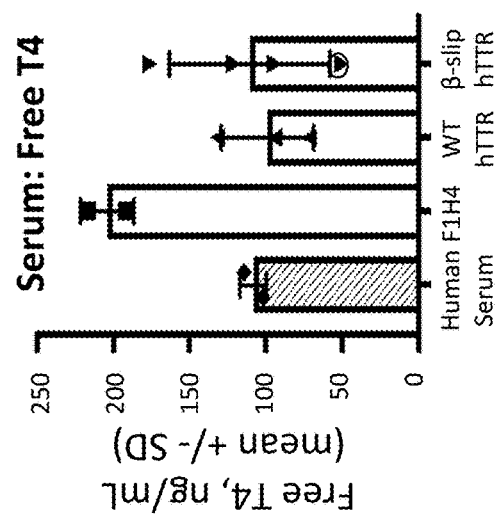

Increased hyperactivity has been reported in TTR-null mice (see, e.g., Sousa et al. (2004) *J Neurochem.* 88(5): 1052-1058, herein incorporated by reference in its entirety for all purposes), suggesting TTR beta-slip may act as a loss-of-function mutant, despite being detectable in serum. Additional correlates of the expressed TTR beta-slip protein being non-functional is the decrease in serum total T4 and free T4, which were associated with a decreased body temperature, which suggests TTR beta-slip mice may be hypothyroid due to the loss of function of TTR. See FIGS. 5B, 5C, and 5D, respectively.

At least two possible explanations may account for the low level of circulating human TTR in the humanized TTR beta-slip mice. One possible explanation is poor or inefficient secretion of beta-slip TTR from liver hepatocytes. A second possible explanation is that the circulating human beta-slip TTR may be rapidly deposited onto peripheral organs/tissues.

The possibility of tissue deposition of human beta-slip TTR is supported by our observation that some mice had weak muscle tone in their hindlimbs, muscles which are highly innervated by the sciatic nerve. See FIGS. 7A-7B. This observation of humanized TTR beta-slip mice having altered muscle tone in hindlimbs (i.e., "dystonic") is an observation not previously reported in the literature for TTR null mice or transgenic mice expressing human forms of TTR. This phenotype was evaluated by scruffing the mouse and assessing the angle of its hindlimbs relative to the axis of the body. Normally, mice have a wide angle between the body axis and the hindlimb angle (see F1H4 and TTR WT humanization pictures in FIG. 7A). In contrast, the beta-slip mice did not have their hindlimbs extended from their body (see TTR β-slip humanization pictures in FIG. 7A). The significance of this is that it could be a proxy measure for sciatic nerve dysfunction because the sciatic nerve controls hindlimb function. The sciatic nerve is one of the major sites of amyloid deposition in human TTR diseases (e.g., FAP). Thus, the dystonic phenotype could be an indicator for abnormal sciatic nerve function.

Figure 9B:
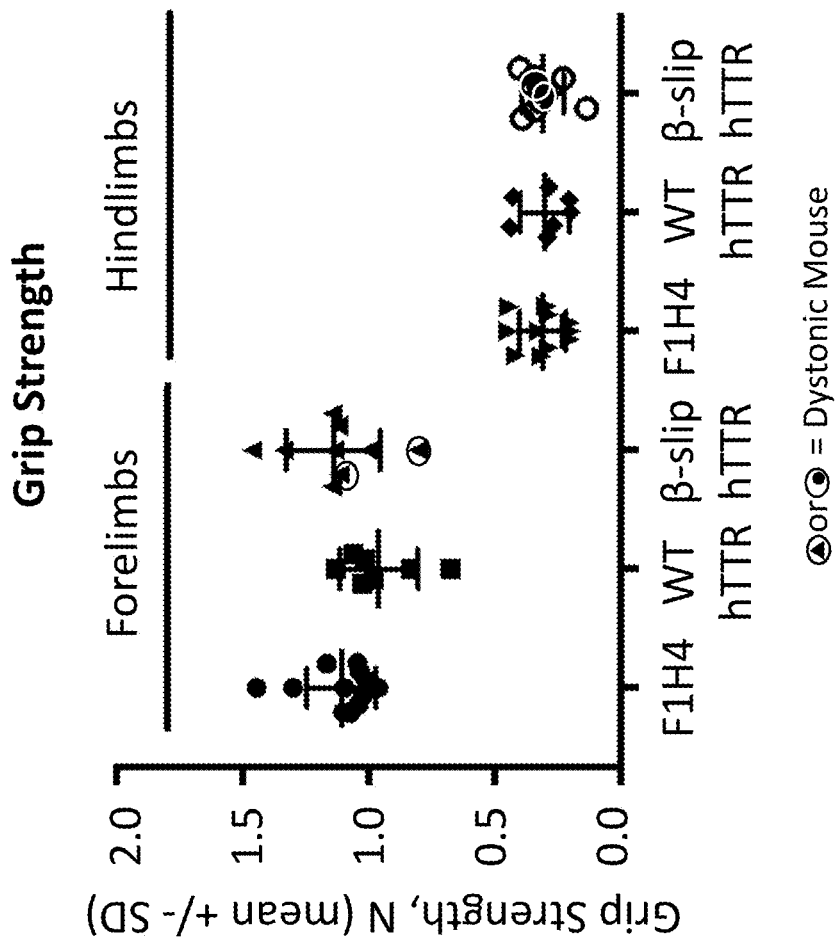
FIGS. 9A-9B show body weight (FIG. 9A) and grip strength (FIG. 9B) in two-month old humanized TTR beta-slip mice, humanized TTR wild type mice, and control F1H4 mice. Dystonic mice are marked by the encircled red triangles and dots.
Figure 9A:
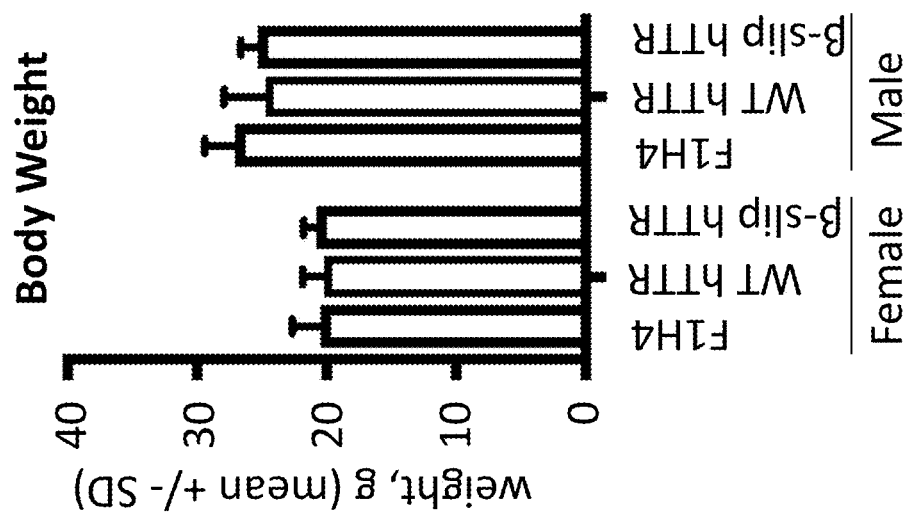

Grip strength was then measured. Grip strength was measured by allowing the mouse to grab a bar connected to a grip strength meter, then manually pulling the mouse away from bar at a constant rate. The apparatus measures the maximal force at which the mouse pulls the bar before losing grip and releasing it. The forelimbs and hindlimbs were tested separately and graphed as the average units of force from three attempts per mouse. Grip strength did not correlate with the dystonic phenotype and was similar in humanized TTR beta-slip mice, humanized TTR wild type mice, and control (F1H4) mice. See FIG. 9B and Table 8. Likewise, body weight was similar in humanized TTR beta-slip mice, humanized TTR wild type mice, and control (F1H4) mice. See FIG. 9A and Table 9.

TABLE 8

Grip Strength of Humanized TTR Beta-Slip Mice, Humanized TTR Wild Type Mice, and Control F1H4 Mice.

|  | Forelimb, N (SD) | Hindlimb, N (SD) |
|---|---|---|
| F1H4 | 1.109 (0.137) | 0.3115 (0.092) |
| WT hTTR$^{7577/7577}$ | 0.961 (0.155) | 0.3029 (0.096) |
| β-slip hTTR$^{8531/8531}$ | 1.141 (0.185) | 0.3107 (0.083) |

TABLE 9

Body Weight of Humanized TTR Beta-Slip Mice, Humanized TTR Wild Type Mice, and Control F1H4 Mice.

|  | Males, g (SD) | Females, g (SD) |
|---|---|---|
| F1H4 | 27.12 (2.31) | 20.51 (2.12) |
| WT hTTR$^{7577/7577}$ | 24.77 (3.16) | 20.22 (1.67) |
| β-slip hTTR$^{8531/8531}$ | 25.38 (1.26) | 20.69 (0.99) |

Figure 10A:
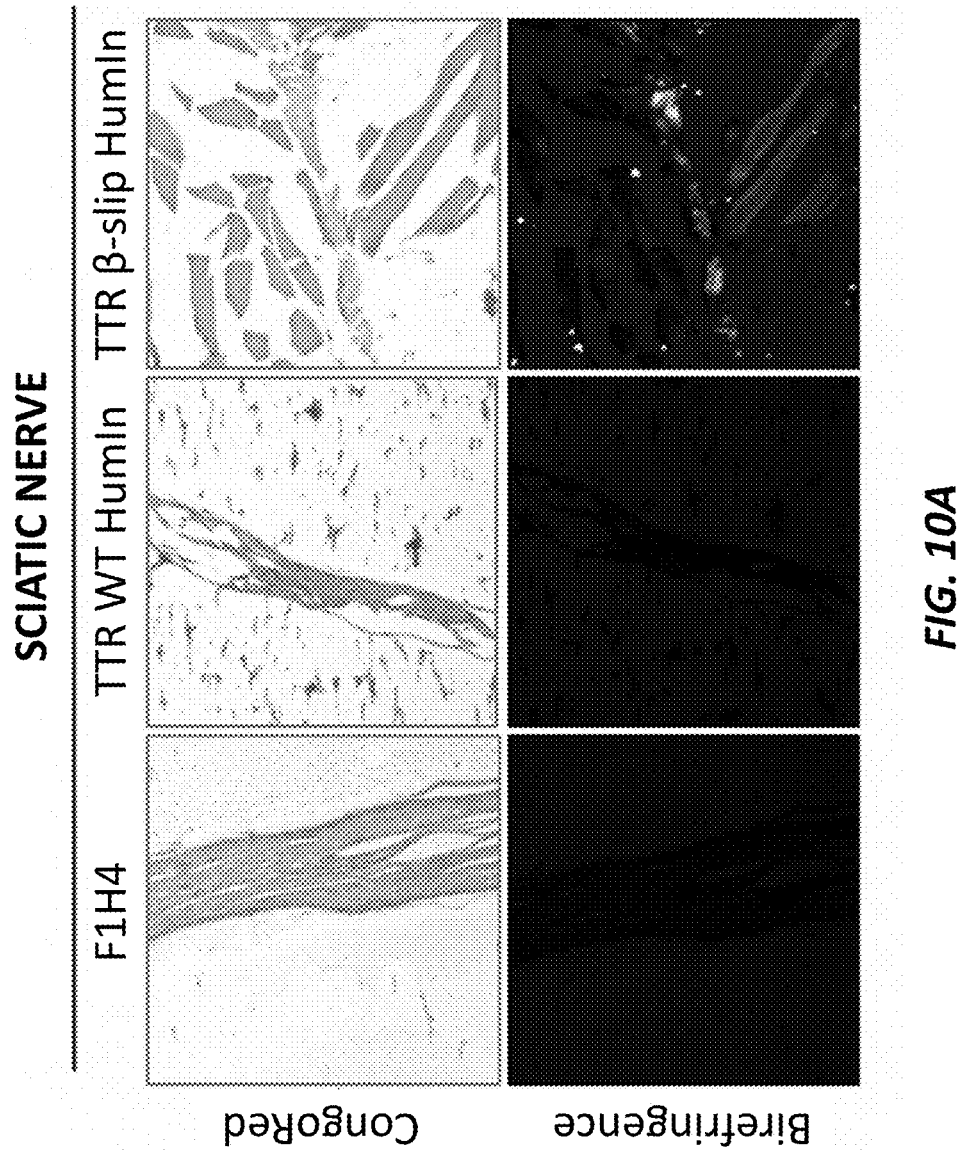
FIGS. 10A-10B show Congo Red staining in sciatic nerve samples (FIG. 10A) and liver samples (FIG. 10B) isolated from two-month old humanized TTR beta-slip mice, humanized TTR wild type mice, and control F1H4 mice. The top portions of each show the stained tissue imaged under white light. The bottom portions of each show the stained tissue illuminated using linear polarized light.
Figure 10B:
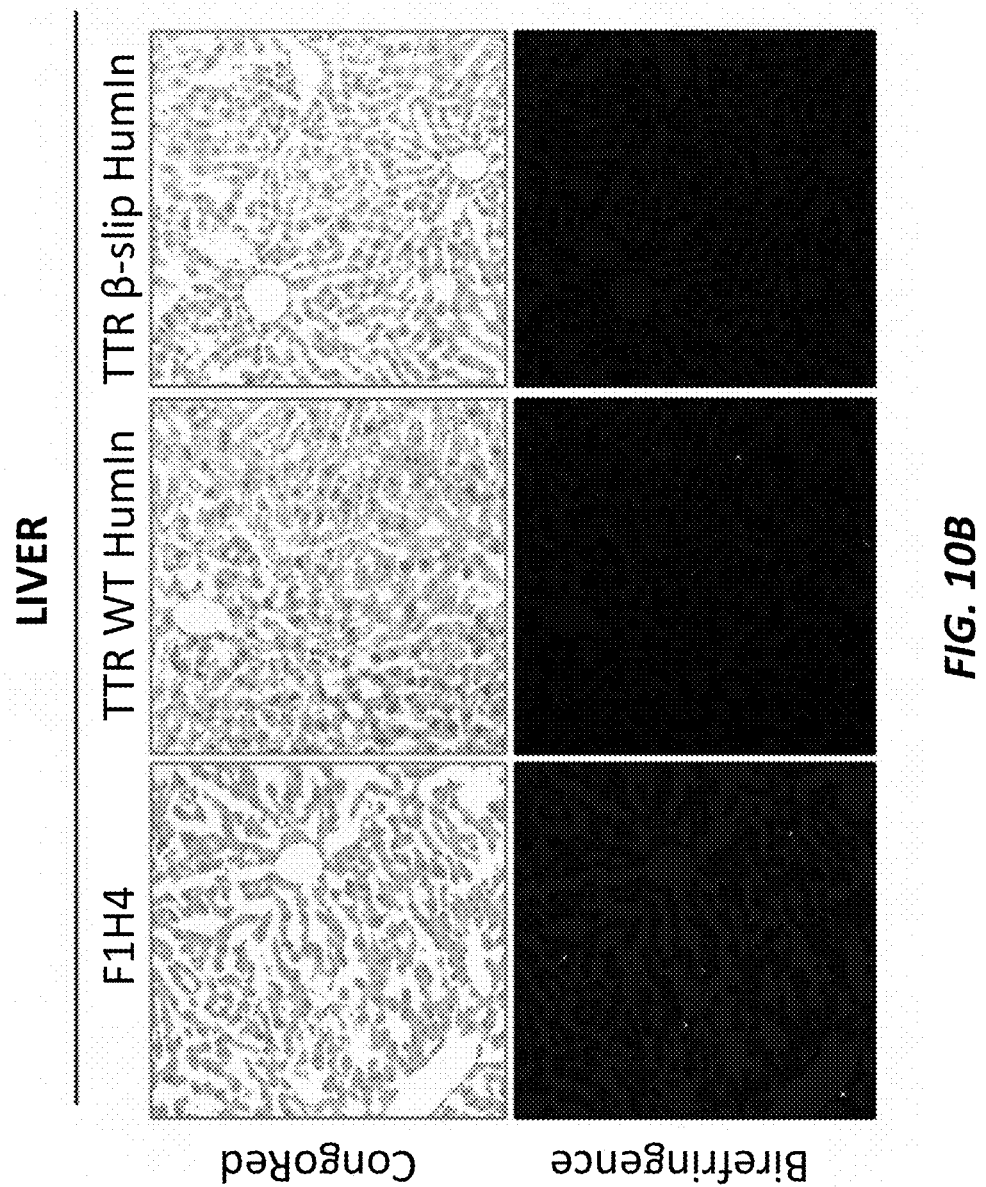

Post-mortem histopathological analysis with an amyloid-specific dye, Congo Red, showed birefringent-positive amyloid deposits on the sciatic nerve of humanized TTR beta-slip mice and not on the sciatic nerves of F1H4 (littermate controls) or humanized TTR wild type mice. See FIGS. 10A and 10B, respectively. Two-month old beta-slip mice were euthanized using $CO_2$ and transcardially perfused with phosphate buffer (20 mL) followed by perfusion with 20 mL of 4% paraformaldehyde (PFA). The liver and sciatic nerve were removed and post-fixed in 4% PFA for 2 days at 4° C., followed by a cryopreservation step by soaking the tissue in 30% (w/v) sucrose in phosphate buffer overnight. The next day, tissues were immersed and frozen in OCT ("optimal cutting temperature"). Sections were cut on a cryostat at 10 micron and mounted onto frosted microscope slides. The slides were stained with Congo Red solution according to the manufacturer's protocol (Sigma, cat no: HT60-1KT). Congo Red is a widely used stain to detect amyloidosis. Slides were imaged under white light which revealed overall tissue architecture and a characteristic red stain. See top panels in FIGS. 10A and 10B. When the Congo Red stained tissue was illuminated using linear polarized light, only the dye which was bound to amyloids refracted the polarized light (e.g., amyloid bound CongoRed dye will become birefringent), which was viewed as a light green/white color. See bottom panels in FIGS. 10A and 10B. The presence of these greenish-white deposits was indicative of amyloid deposition. We observed birefringence (i.e., the presence of amyloid deposits) in the sciatic nerve, which could explain the dystonic phenotype of mice. See bottom right panel (TTR β-slip humanization) in FIG. 10A. As expected, we did not observe amyloids in the liver. See bottom right panel (TTR β-slip humanization) in FIG. 10B.

This is the first reported in vivo model to develop amyloidosis so rapidly, with amyloid deposits observed in two-month-old beta-slip mice. Experiments are then done to co-stain with an anti-TTR antibody to co-label the birefringent deposits and confirm that they are caused by TTR deposition. Additional experiments are done to analyze whether there are deposits in other organs and tissues.

We claim:

1. A non human animal mouse comprising in its genome a genetically modified endogenous Ttr locus, wherein a region of the endogenous Ttr locus comprising both Ttr coding sequence and non-coding sequence has been deleted and replaced with a corresponding human TTR sequence comprising both TTR coding sequence and non-coding sequence, and wherein the genetically modified endogenous Ttr locus comprises a mutation that causes a shift in beta-strand D of the encoded transthyretin protein,
   wherein the mutation is a triple mutation corresponding to G53S/E54D/L55S in the human transthyretin protein when the encoded transthyretin protein is optimally aligned with the human transthyretin protein.

2. The mouse of claim 1, wherein the genetically modified endogenous Ttr locus comprises the endogenous Ttr promoter, wherein the human TTR sequence is operably linked to the endogenous Ttr promoter.

3. The mouse of claim 1, wherein at least one intron and at least one exon of the endogenous Ttr locus have been deleted and replaced with the corresponding human TTR sequence.

4. The mouse of claim 1, wherein the entire Ttr coding sequence of the endogenous Ttr locus has been deleted and replaced with the corresponding human TTR sequence.

5. The mouse of claim 4, wherein the region of the endogenous Ttr locus from the Ttr start codon to the Ttr stop codon has been deleted and replaced with the corresponding human TTR sequence.

6. The mouse of claim 1, wherein the genetically modified endogenous Ttr locus comprises a human TTR 3' untranslated region.

7. The mouse of claim 1, wherein the endogenous Ttr 5' untranslated region has not been deleted and replaced with the corresponding human TTR sequence.

8. The mouse of claim 1, wherein the region of the endogenous Ttr locus from the Ttr start codon to the Ttr stop codon has been deleted and replaced with a human TTR sequence comprising the corresponding human TTR sequence and a human TTR 3' untranslated region, and
   wherein the endogenous Ttr 5' untranslated region has not been deleted and replaced with the corresponding human TTR sequence, and
   wherein the endogenous Ttr promoter has not been deleted and replaced with the corresponding human TTR sequence.

9. The mouse of claim 8, wherein:
   (i) the human TTR sequence at the genetically modified endogenous Ttr locus comprises a sequence at least 90%, at least 95%, at least 96%, at least 97%, at least 98%, at least 99%, or 100% identical to the sequence set forth in SEQ ID NO: 14;
   (ii) the genetically modified endogenous Ttr locus encodes a protein comprising a sequence at least 90%, at least 95%, at least 96%, at least 97%, at least 98%, at least 99%, or 100% identical to the sequence set forth in SEQ ID NO: 9;
   (iii) the genetically modified endogenous Ttr locus comprises a coding sequence comprising a sequence at least 90%, at least 95%, at least 96%, at least 97%, at least 98%, at least 99%, or 100% identical to the sequence set forth in SEQ ID NO: 10; or
   (iv) the genetically modified endogenous Ttr locus comprises a sequence at least 90%, at least 95%, at least 96%, at least 97%, at least 98%, at least 99%, or 100% identical to the sequence set forth in SEQ ID NO: 12 or 13.

10. The mouse of claim 1, wherein the genetically modified endogenous Ttr locus encodes a transthyretin precursor protein comprising a signal peptide, and the region of the endogenous Ttr locus encoding the signal peptide has not been deleted and replaced with the corresponding human TTR sequence.

11. The mouse of claim 10, wherein the first exon of the endogenous Ttr locus has not been deleted and replaced with the corresponding human TTR sequence.

12. The mouse of claim 11, wherein the first exon and first intron of the endogenous Ttr locus have not been deleted and replaced with the corresponding human TTR sequence.

13. The mouse of claim 10, wherein the region of the endogenous Ttr locus from the start of the second Ttr exon to the Ttr stop codon has been deleted and replaced with the corresponding human TTR sequence.

14. The mouse of claim 10, wherein the genetically modified endogenous Ttr locus comprises a human TTR 3' untranslated region.

15. The mouse of claim 10, wherein the region of the endogenous Ttr locus from the second Ttr exon to the Ttr stop codon has been deleted and replaced with a human TTR sequence comprising the corresponding human TTR sequence and a human TTR 3' untranslated region, and
   wherein the endogenous Ttr 5' untranslated region has not been deleted and replaced with the corresponding human TTR sequence, and
   wherein the endogenous Ttr promoter has not been deleted and replaced with the corresponding human TTR sequence.

16. The mouse of claim 1, wherein the genetically modified endogenous Ttr locus does not comprise a selection cassette or a reporter gene.

17. The mouse of claim 1, wherein the mouse is homozygous for the genetically modified endogenous Ttr locus.

18. The mouse of claim 1, wherein the mouse comprises the genetically modified endogenous Ttr locus in its germline.

19. The mouse of claim 1, wherein the mouse is hyperactive relative to a control wild type mouse or a mouse comprising the genetically modified endogenous Ttr locus without the mutation.

20. The mouse of claim 19, wherein the hyperactivity is as measured by one or more or all of total distance, total activity, or total rearings in an open field test.

21. The mouse of claim 1, wherein the mouse displays hindlimb dystonia.

22. The mouse of claim 1, wherein the mouse comprises amyloid deposits.

23. The mouse of claim 22, wherein the mouse comprises amyloid deposits in the sciatic nerve.

24. The mouse of claim 22, wherein the mouse develops amyloidosis by about two months of age.

25. A mouse cell comprising in its genome a genetically modified endogenous Ttr locus, wherein a region of the endogenous Ttr locus comprising both Ttr coding sequence and non-coding sequence has been deleted and replaced with a corresponding human TTR sequence comprising both TTR coding sequence and non-coding sequence, and wherein the genetically modified endogenous Ttr locus comprises a mutation that causes a shift in beta-strand D of the encoded transthyretin protein,
wherein the mutation is a triple mutation corresponding to G53S/E54D/L55S in the human transthyretin protein when the encoded transthyretin protein is optimally aligned with the human transthyretin protein.

26. A method of assessing the activity of a human-TTR-targeting reagent in vivo, comprising:
(a) administering the human-TTR-targeting reagent to the mouse of claim 1; and
(b) assessing the activity of the human-TTR-targeting reagent in the mouse.

27. A method of optimizing the activity of a human-TTR-targeting reagent in vivo, comprising:
(I) performing the method of claim 26 a first time in a first mouse comprising in its genome the genetically modified endogenous Ttr locus;
(II) changing a variable and performing the method of step (I) a second time with the changed variable in a second mouse comprising in its genome the genetically modified endogenous Ttr locus; and
(III) comparing the activity of the human-TTR-targeting reagent in step (I) with the activity of the human-TTR-targeting reagent in step (II), and selecting the method resulting in the higher efficacy, higher precision, higher consistency, or higher specificity.

28. A method of making the mouse of claim 1, comprising:
(I) (a) modifying the genome of a pluripotent mouse cell to comprise the genetically modified endogenous Ttr locus;
(b) identifying or selecting the genetically modified pluripotent mouse cell comprising the genetically modified endogenous Ttr locus;
(c) introducing the genetically modified pluripotent mouse cell into a mouse host embryo; and
(d) gestating the mouse host embryo in a surrogate mother; or
(II) (a) modifying the genome of a mouse one-cell stage embryo to comprise the genetically modified endogenous Ttr locus;
(b) selecting the genetically modified mouse one-cell stage embryo comprising the genetically modified endogenous Ttr locus; and
(c) gestating the genetically modified mouse one-cell stage embryo in a surrogate mother.

* * * * *

SEQUENCE LISTING

<160> NUMBER OF SEQ ID NOS: 92

<210> SEQ ID NO 1
<211> LENGTH: 147
<212> TYPE: PRT
<213> ORGANISM: Homo sapiens

<400> SEQUENCE: 1

Met Ala Ser His Arg Leu Leu Leu Cys Leu Ala Gly Leu Val Phe
1               5                   10                  15

Val Ser Glu Ala Gly Pro Thr Gly Thr Gly Glu Ser Lys Cys Pro Leu
            20                  25                  30

Met Val Lys Val Leu Asp Ala Val Arg Gly Ser Pro Ala Ile Asn Val
        35                  40                  45

Ala Val His Val Phe Arg Lys Ala Ala Asp Asp Thr Trp Glu Pro Phe
    50                  55                  60

Ala Ser Gly Lys Thr Ser Glu Ser Gly Glu Leu His Gly Leu Thr Thr
65                  70                  75                  80

Glu Glu Glu Phe Val Glu Gly Ile Tyr Lys Val Glu Ile Asp Thr Lys
                85                  90                  95

Ser Tyr Trp Lys Ala Leu Gly Ile Ser Pro Phe His Glu His Ala Glu
                100                 105                 110

Val Val Phe Thr Ala Asn Asp Ser Gly Pro Arg Arg Tyr Thr Ile Ala
            115                 120                 125

Ala Leu Leu Ser Pro Tyr Ser Tyr Ser Thr Thr Ala Val Val Thr Asn
    130                 135                 140

Pro Lys Glu
145

<210> SEQ ID NO 2
<211> LENGTH: 938
<212> TYPE: DNA
<213> ORGANISM: Homo sapiens

<400> SEQUENCE: 2
gttgactaag tcaataatca gaatcagcag gtttgcagtc agattggcag ggataagcag    60
cctagctcag gagaagtgag tataaaagcc ccaggctggg agcagccatc acagaagtcc   120
actcattctt ggcaggatgg cttctcatcg tctgctcctc ctctgccttg ctggactggt   180
atttgtgtct gaggctggcc ctacgggcac cggtgaatcc aagtgtcctc tgatggtcaa   240
agttctagat gctgtccgag gcagtcctgc catcaatgtg gccgtgcatg tgttcagaaa   300
ggctgctgat gacacctggg agccatttgc ctctgggaaa accagtgagt ctggagagct   360
gcatgggctc acaactgagg aggaatttgt agaagggata tacaaagtgg aaatagacac   420
caaatcttac tggaaggcac ttggcatctc cccattccat gagcatgcag aggtggtatt   480
cacagccaac gactccggcc cccgccgcta caccattgcc gccctgctga gcccctactc   540
ctattccacc acggctgtcg tcaccaatcc caaggaatga gggacttctc ctccagtgga   600
cctgaaggac gagggatggg atttcatgta accaagagta ttccattttt actaaagcag   660
tgttttcacc tcatatgcta tgttagaagt ccaggcagag acaataaaac attcctgtga   720
aaggcacttt tcattccact ttaacttgat tttttaaatt cccttattgt cccttccaaa   780
aaaaagagaa tcaaaatttt acaaagaatc aaggaattc tagaaagtat ctgggcagaa   840
cgctaggaga gatccaaatt tccattgtct tgcaagcaaa gcacgtatta aatatgatct   900
gcagccatta aaaagacaca ttctgtaaaa aaaaaaaa                            938

<210> SEQ ID NO 3
<211> LENGTH: 7258
<212> TYPE: DNA
<213> ORGANISM: Homo sapiens

<400> SEQUENCE: 3

| | | | | | |
|---|---|---|---|---|---|
| gttgactaag | tcaataatca | gaatcagcag | gtttgcagtc | agattggcag | ggataagcag | 60 |
| cctagctcag | gagaagtgag | tataaaagcc | ccaggctggg | agcagccatc | acagaagtcc | 120 |
| actcattctt | ggcaggatgg | cttctcatcg | tctgctcctc | ctctgccttg | ctggactggt | 180 |
| atttgtgtct | gaggctggcc | ctacggtgag | tgtttctgtg | acatcccatt | cctacattta | 240 |
| agattcacgc | taaatgaagt | agaagtgact | ccttccagct | ttgccaacca | gcttttatta | 300 |
| ctagggcaag | ggtacccagc | atctattttt | aatataatta | attcaaactt | caaaagaat | 360 |
| gaagttccac | tgagcttact | gagctgggac | ttgaactctg | agcattctac | ctcattgctt | 420 |
| tggtgcatta | ggtttgtaat | atctggtacc | tctgtttcct | cagatagatg | atagaaataa | 480 |
| agatatgata | ttaaggaagc | tgttaatact | gaattttcag | aaaagtatcc | ctccataaaa | 540 |
| tgtatttggg | ggacaaactg | caggagatta | tattctggcc | ctatagttat | tcaaaacgta | 600 |
| tttattgatt | aatcttaaa | aggcttagtg | aacaatattc | tagtcagata | tctaattctt | 660 |
| aaatcctcta | gaagaattaa | ctaatactat | aaaatgggtc | tggatgtagt | tctgacatta | 720 |
| ttttataaca | actggtaaga | gggagtgact | atagcaacaa | ctaaaatgat | ctcaggaaaa | 780 |
| cctgtttggc | cctatgtatg | gtacattaca | tcttttcagt | aattccactc | aaatggagac | 840 |
| ttttaacaaa | gcaactgttc | tcaggggacc | tattttctcc | cttaaaattc | attatacaca | 900 |
| tccctggttg | atagcagtgt | gtctggaggc | agaaaccatt | cttgctttgg | aaacaattac | 960 |
| gtctgtgtta | tactgagtag | ggaagctcat | taattgtcga | cacttacgtt | cctgataatg | 1020 |
| ggatcagtgt | gtaattcttg | tttcgctcca | gatttctaat | accacaaaga | ataaatcctt | 1080 |
| tcactctgat | caattttgtt | aacttctcac | gtgtcttctc | tacacccagg | gcaccggtga | 1140 |
| atccaagtgt | cctctgatgg | tcaaagttct | agatgctgtc | cgaggcagtc | ctgccatcaa | 1200 |
| tgtggccgtg | catgtgttca | gaaaggctgc | tgatgacacc | tgggagccat | tgcctctgg | 1260 |
| gtaagttgcc | aaagaaccct | cccacaggac | ttggttttat | cttcccgttt | gcccctcact | 1320 |
| tggtagagag | aggctcacat | catctgctaa | agaatttaca | agtagattga | aaaacgtagg | 1380 |
| cagaggtcaa | gtatgccctc | tgaaggatgc | cctcttttg | ttttgcttag | ctaggaagtg | 1440 |
| accaggaacc | tgagcatcat | ttaggggcag | acagtagaga | aaagaaggaa | tcagaactcc | 1500 |
| tctcctctag | ctgtggtttg | caaccctttt | gggtcacaga | acactttatg | taggtgatga | 1560 |
| aaagtaaaca | ttctatgccc | agaaaaaatg | cacagataca | cacacataca | aaatcatata | 1620 |
| tgtgatttta | ggagtttcac | agattccctg | gtgtccctgg | gtaacaccaa | agctaagtgt | 1680 |
| ccttgtctta | gaatttttagg | aaaaggtata | atgtgtatta | acccattaac | aaaaggaaag | 1740 |
| gaattcagaa | atattattaa | ccaggcatct | gtctgtagtt | aatatggatc | acccaaaacc | 1800 |
| caaggctttt | gcctaatgaa | cactttgggg | cacctactgt | gtgcaaggct | ggggctgtc | 1860 |
| aagctcagtt | aaaaaaaaaa | agatagaaga | gatggatcca | tgaggcaaag | tacagcccca | 1920 |
| ggctaatccc | acgatcaccc | gacttcatgt | ccaagagtgg | cttctcacct | tcattagcca | 1980 |
| gttcacaatt | ttcatggagt | ttttctacct | gcactagcaa | aaacttcaag | gaaaatacat | 2040 |
| attaataaat | ctaagcaaag | tgaccagaag | acagagcaat | caggagaccc | tttgcatcca | 2100 |

```
gcagaagagg aactgctaag tatttacatc tccacagaga agaatttctg ttgggtttta    2160
attgaacccc aagaaccaca tgattcttca accattattg ggaagatcat tttcttaggt    2220
ctggttttaa ctggcttttt atttgggaat tcatttatgt ttatataaaa tgccaagcat    2280
aacatgaaaa gtggttacag gactattcta agggagagac agaatggaca ccaaaaatat    2340
tccaatgttc ttgtgaatct tttccttgca ccaggacaaa aaaaaaaaga agtgaaaaga    2400
agaaaggagg aggggcataa tcagagtcag taaagacaac tgctattttt atctatcgta    2460
gctgttgcag tcaaatggga agcaatttcc aacattcaac tatggagctg gtacttacat    2520
ggaaatagaa gttgcctagt gtttgttgct ggcaaagagt tatcagagag gttaaatata    2580
taaaagggaa aagagtcaga tacaggttct tcttcctact ttaggttttc cactgtgtgt    2640
gcaaatgata ctccctggtg gtgtgcagat gcctcaaagc tatcctcaca ccacaaggga    2700
gaggagcgag atcctgctgt cctggagaag tgcagagtta gaacagctgt ggccacttgc    2760
atccaatcat caatcttgaa tcacaggggac tctttcttaa gtaaacatta tacctggccg    2820
ggcacggtgg ctcacgcctg taatcccagc actttgggat gccaaagtgg gcatatcatc    2880
tgaggtcagg agttcaagac cagcctggcc aacatggcaa aactccgtct ttatgaaaaa    2940
tacaaaaatt agccaggcat ggtggcaggc gcctgtaatc ccagctaatt gggaggctga    3000
ggctggagaa tcccttgaat ctaggaggca gaggttgcag tgagctgaga tcgtgccatt    3060
gcactccagc ctgggtgaca agagtaaaac tctgtctcaa aaaaaaaaa ttatacctac    3120 attctcttct tatcagagaa aaaaatctac agtgagcttt tcaaaaagtt tttacaaact    3180
ttttgccatt taatttcagt taggagtttt ccctacttct gacttagttg aggggaaatg    3240
ttcataacat gtttataaca tgtttatgtg tgttagttgg tgggggtgta ttactttgcc    3300
atgccatttg tttcctccat gcgtaactta atccagactt tcacacctta taggaaaacc    3360
agtgagtctg gagagctgca tgggctcaca actgaggagg aatttgtaga agggatatac    3420
aaagtggaaa tagacaccaa atcttactgg aaggcacttg gcatctcccc attccatgag    3480
catgcagagg tgagtataca gaccttcgag ggttgttttg gttttggttt ttgcttttgg    3540
cattccagga aatgcacagt tttactcagt gtaccacaga aatgtcctaa ggaaggtgat    3600
gaatgaccaa aggttccctt tcctattata caagaaaaaa ttcacaacac tctgagaagc    3660
aaatttcttt ttgactttga tgaaaatcca cttagtaaca tgacttgaac ttacatgaaa    3720
ctactcatag tctattcatt ccactttata tgaatattga tgtatctgct gttgaaataa    3780
tagtttatga ggcagccctc cagacccac gtagagtgta tgtaacaaga gatgcaccat    3840
tttatttctc gaaacccgt aacattcttc attccaaaac acatctggct tctcggaggt    3900
ctggacaagt gattcttggc aacacatacc tatagagaca ataaaatcaa agtaataatg    3960
gcaacacaat agataacatt taccaagcat acaccatgtg gcagacacaa ttataagtgt    4020
tttccatatt taacctactt aatcctcagg aataagccac tgaggtcagt cctattatta    4080
tccccatctt atagatgaag aaaatgaggc accaggaagt caaataactt gtcaaaggtc    4140
acaagactag gaaatacaca agtagaaatg tttacaatta aggcccaggc tgggtttgcc    4200
ctcagttctg ctatgcctcg cattatgccc caggaaactt tttcccttgt gaaagccaag    4260
cttaaaaaaa gaaaagccac atttgtaacg tgctctgttc ccctgcctat ggtgaggatc    4320
ttcaaacagt tatacatgga cccagtcccc ctgccttctc cttaatttct taagtcattt    4380
gaaacagatg gctgtcatgg aaatagaatc cagacatgtt ggtcagagtt aaagatcaac    4440
taattccatc aaaaatagct cggcatgaaa gggaactatt ctctggctta gtcatggatg    4500
```

```
agactttcaa ttgctataaa gtggttcctt tattagacaa tgttaccagg gaaacaacag    4560
gggtttgttt gacttctggg gcccacaagt caacaagaga gccccatcta ccaaggagca    4620
tgtccctgac tacccctcag ccagcagcaa gacatggacc ccagtcaggg caggagcagg    4680
gtttcggcgg cgcccagcac aagacattgc ccctagagtc tcagccccta ccctcgagta    4740
atagatctgc ctacctgaga ctgttgtttg cccaagagct gggtctcagc ctgatgggaa    4800
ccatataaaa aggttcactg acatactgcc cacatgttgt tctctttcat tagatcttag    4860
cttccttgtc tgctcttcat tcttgcagta ttcattcaac aaacattaaa aaaaaaaaa    4920 agcattctat gtgtgaaaca ctctgctaga tgctgtggat ttagaaatga aaatacatcc    4980
cgacccttgg aatggaaggg aaaggactga agtaagacag attaagcagg accgtcagcc    5040
cagcttgaag cccagataaa tacggagaac aagagagagc gagtagtgag agatgagtcc    5100
caatgcctca ctttggtgac gggtgcgtgg tgggcttcat gcagcttctt ctgataaatg    5160
cctccttcag aactggtcaa ctctaccttg gccagtgacc caggtggtca tagtagattt    5220
accaagggaa aatggaaact tttattagga gctcttaggc ctcttcactt catggatttt    5280
tttttccttt tttttttgaga tggagttttg ccctgtcacc caggctggaa tgcagtggtg    5340
caatctcagc tcactgcaac ctccgcctcc caggttcaag caattctcct gcctcagcct    5400
cccgagtagc tgggactaca ggtgtgcgcc accacaccag gctaatttt gtatttttg    5460 taaagacagg ttttcaccac gttggccagg ctggtctgaa ctccagacct caggtgattc    5520
acctgtctca gcctcccaaa gtgctgggat tacaggtgtg agccaccgtg cccggctact    5580
tcatggattt ttgattacag attatgcctc ttacaatttt taagaagaat caagtgggct    5640
gaaggtcaat gtcaccataa gacaaaagac atttttatta gttgattcta gggaattggc    5700
cttaagggga gcccttctt cctaagagat tcttaggtga ttctcacttc ctcttgcccc    5760
agtattattt ttgttttgg tatggctcac tcagatcctt ttttcctcct atccctaagt    5820
aatccgggtt tctttttccc atatttagaa caaaatgtat ttatgcagag tgtgtccaaa    5880
cctcaaccca aggcctgtat acaaaataaa tcaaattaaa cacatcttta ctgtcttcta    5940
cctctttcct gacctcaata tatcccaact tgcctcactc tgagaaccaa ggctgtccca    6000
gcacctgagt cgcagatatt ctactgattt gacagaactg tgtgactatc tggaacagca    6060
ttttgatcca caatttgccc agttacaaag cttaaatgag ctctagtgca tgcatatata    6120
tttcaaaatt ccaccatgat cttccacact ctgtattgta aatagagccc tgtaatgctt    6180
ttacttcgta tttcattgct tgttatacat aaaaatatac ttttcttctt catgttagaa    6240
aatgcaaaga ataggagggt gggggaatct ctgggcttgg agacaggaga cttgccttcc    6300
tactatggtt ccatcagaat gtagactggg acaatacaat aattcaagtc tggtttgctc    6360
atctgtaaat tgggaagaat gtttccagct ccagaatgct aaatctctaa gtctgtggtt    6420
ggcagccact attgcagcag ctcttcaatg actcaatgca gttttgcatt ctccctacct    6480
tttttttcta aaaccaataa aatagataca gcctttaggc tttctgggat ttcccttagt    6540
caagctaggg tcatcctgac tttcggcgtg aatttgcaaa acaagacctg actctgtact    6600
cctgctctaa ggactgtgca tggttccaaa ggcttagctt gccagcatat ttgagcttt   6660 tccttctgtt caaactgttc caaaatataa aagaataaaa ttaattaagt tggcactgga    6720
cttccggtgg tcagtcatgt gtgtcatctg tcacgttttt cgggctctgg tggaaatgga    6780
tctgtctgtc ttctctcata ggtggtattc acagccaacg actccggccc ccgccgctac    6840
```

```
accattgccg ccctgctgag cccctactcc tattccacca cggctgtcgt caccaatccc    6900
aaggaatgag ggacttctcc tccagtggac ctgaaggacg agggatggga tttcatgtaa    6960
ccaagagtat tccattttta ctaaagcagt gttttcacct catatgctat gttagaagtc    7020
caggcagaga caataaaaca ttcctgtgaa aggcactttt cattccactt taacttgatt    7080
ttttaaattc ccttattgtc ccttccaaaa aaaagagaat caaaatttta caaagaatca    7140
aaggaattct agaaagtatc tgggcagaac gctaggagag atccaaattt ccattgtctt    7200
gcaagcaaag cacgtattaa atatgatctg cagccattaa aaagacacat tctgtaaa     7258
```

<210> SEQ ID NO 4
<211> LENGTH: 444
<212> TYPE: DNA
<213> ORGANISM: Artificial Sequence
<220> FEATURE:
<223> OTHER INFORMATION: Synthetic

<400> SEQUENCE: 4

```
atggcttctc atcgtctgct cctcctctgc cttgctggac tggtatttgt gtctgaggct     60
ggccctacgg gcaccggtga atccaagtgt cctctgatgg tcaaagttct agatgctgtc    120
cgaggcagtc ctgccatcaa tgtggccgtg catgtgttca aaaaggctgc tgatgacacc    180
tgggagccat tgcctctgg gaaaaccagt gagtctggag agctgcatgg gctcacaact    240
gaggaggaat ttgtagaagg gatatacaaa gtggaaatag acaccaaatc ttactggaag    300
gcacttggca tctccccatt ccatgagcat gcagaggtgg tattcacagc caacgactcc    360
ggcccccgcc gctacaccat tgccgccctg ctgagcccct actcctattc caccacggct    420
gtcgtcacca atcccaagga atga                                           444
```

<210> SEQ ID NO 5
<211> LENGTH: 147
<212> TYPE: PRT
<213> ORGANISM: Mus musculus

<400> SEQUENCE: 5

```
Met Ala Ser Leu Arg Leu Phe Leu Leu Cys Leu Ala Gly Leu Val Phe
1               5                   10                  15

Val Ser Glu Ala Gly Pro Ala Gly Ala Gly Glu Ser Lys Cys Pro Leu
            20                  25                  30

Met Val Lys Val Leu Asp Ala Val Arg Gly Ser Pro Ala Val Asp Val
        35                  40                  45

Ala Val Lys Val Phe Lys Lys Thr Ser Glu Gly Ser Trp Glu Pro Phe
    50                  55                  60

Ala Ser Gly Lys Thr Ala Glu Ser Gly Glu Leu His Gly Leu Thr Thr
65                  70                  75                  80

Asp Glu Lys Phe Val Glu Gly Val Tyr Arg Val Glu Leu Asp Thr Lys
                85                  90                  95

Ser Tyr Trp Lys Thr Leu Gly Ile Ser Pro Phe His Glu Phe Ala Asp
            100                 105                 110

Val Val Phe Thr Ala Asn Asp Ser Gly His Arg His Tyr Thr Ile Ala
        115                 120                 125

Ala Leu Leu Ser Pro Tyr Ser Tyr Ser Thr Thr Ala Val Val Ser Asn
    130                 135                 140

Pro Gln Asn
145
```

```
<210> SEQ ID NO 6
<211> LENGTH: 1237
<212> TYPE: DNA
<213> ORGANISM: Mus musculus

<400> SEQUENCE: 6
ctaatctccc taggcaaggt tcatatttgt gtaggttact tattctcctt ttgttgacta      60
agtcaataat cagaatcagc aggtttggag tcagcttggc agggatcagc agcctgggtt     120
ggaaggaggg ggtataaaag ccccttcacc aggagaagcc gtcacacaga tccacaagct     180
cctgacagga tggcttccct tcgactcttc ctcctttgcc tcgctggact ggtatttgtg     240
tctgaagctg gccccgcggg tgctggagaa tccaaatgtc ctctgatggt caaagtcctg     300
gatgctgtcc gaggcagccc tgctgtagac gtggctgtaa aagtgttcaa aaagacctct     360
gagggatcct gggagccctt tgcctctggg aagaccgcgg agtctggaga gctgcacggg     420
ctcaccacag atgagaagtt tgtagaagga gtgtacagag tagaactgga caccaaatcg     480
tactggaaga cacttggcat ttccccgttc catgaattcg cggatgtggt tttcacagcc     540
aacgactctg ccatcgcca ctacaccatc gcagccctgc tcagcccata ctcctacagc      600
accacggctg tcgtcagcaa cccccagaat tgagagactc agcccaggag gaccaggatc     660
ttgccaaagc agtagcatcc catttgtacc aaaacagtgt tcttgctcta taaccgtgt      720 tagcagctca ggaagatgcc gtgaagcatt cttattaaac cacctgctat ttcattcaaa     780
ctgtgtttct tttttatttc ctcatttttc tcccctgctc ctaaaaccca aaatcttcta     840
aagaattcta gaaggtatgc gatcaaactt tttaaagaaa gaaatactt tttgactcat     900 ggtttaaagg catcctttcc atcttgggga ggtcatgggt gctcctggca acttgcttga     960
ggaagatagg tcagaaagca gagtggacca accgttcaat gttttacaag caaaacatac    1020
actaagcatg gtctgtagct attaaaagca cacaatctga agggctgtag atgcacagta    1080
gtgttttccc agagcatgtt caaaagcccct gggttcaatc acaatactga aaagtaggcc    1140
aaaaaacatt ctgaaaatga aatatttggg ttttttttta taacctttag tgactaaata    1200
aagacaaatc taagagacta aaaaaaaaaa aaaaaaa                             1237

<210> SEQ ID NO 7
<211> LENGTH: 9077
<212> TYPE: DNA
<213> ORGANISM: Mus musculus

<400> SEQUENCE: 7
ctaatctccc taggcaaggt tcatatttgt gtaggttact tattctcctt ttgttgacta      60
agtcaataat cagaatcagc aggtttggag tcagcttggc agggatcagc agcctgggtt     120
ggaaggaggg ggtataaaag ccccttcacc aggagaagcc gtcacacaga tccacaagct     180
cctgacagga tggcttccct tcgactcttc ctcctttgcc tcgctggact ggtatttgtg     240
tctgaagctg gccccgcggt gagtgatcct gtgagcgatc cagacatggc agttagacct     300
tagataaaga agaagtgcct tcttccagat gtgagaacta gagtactcag actctatatt     360
taccattaga ctccaaagag aagagctgga gtgcctctgg ctcttccttc tattgcttta     420
gcgcattggg tctgtagtgc tcagtctctg gtgtccttag ataataaaga tatgagatta     480
acatagaaat aaagatataa aagggctgga tgtatagttt agtggtccag tgtatgccta     540
gtatgtgaaa agccttctgt tcaacctcta gcaatagaaa aacaagatat attctcggtg     600
gggctgttaa tattgaattc tcataaaatc tttaatatat ttagtatgcc tattatgttg     660
```

```
ttatatttta gttctttagc taatcaaaat gcattattga tctttctttg tcttttttg     720 gccaacactc tattccagtc tttgaaaaag tcctttaaaa gagttaatca gtataattaa     780
atgagtcagg aagtatgtga gggttatttt acaaccagag ggaattacta tagcaacagc     840
tgattagaat gatctcaaga aaaagcccat tctgtctttt tgcaccatgc acctttcagt     900
ggctccattc agatggagag gcaaacagag caatggctct cagagggcct attttccctt     960
tgaacattca ttatccatat ccctggtgca cagcagtgca tctgggggca gaaactgttc    1020
ttgctttgga aacaatgctg tctatgtcat actggataaa gaagctcatt aattgtcaac    1080
acttatgtta tcataatggg atcagcatgt acttttggtt ttgttccaga gtctatcacc    1140
ggaaagaaca agccggttta ctctgaccca tttcactgac atttctcttg tctcctctgt    1200
gcccagggtg ctggagaatc caaatgtcct ctgatggtca agtcctgga tgctgtccga     1260 ggcagccctg ctgtagacgt ggctgtaaaa gtgttcaaaa agacctctga gggatcctgg    1320
gagccctttg cctctgggta agcttgtaga aagcccacca tgggaccggt tccaggttcc    1380
catttgctct tattcgtgtt agattcagac acacacaact taccagctag agggctcaga    1440
gagagggctc aggggcgaag gcacgtatt gctcttgtaa gagacacagg tttaattcct     1500
agcaccagaa tggcagctca taaccatctg aaactcacag tcttaggaga tctgggtatc    1560
tgacattctc ttctacccac catgtgtgtg gtgcacaaat tcacatgcag gcatcaaatc    1620
ttataaacaa caacaaaaaa ccaacaaacc tggtagcaaa agaagattag aaggttaaac    1680
atatgagccg agagcttttg ttttgttttg ttttgttttg ttttgtttac atttcaaatg    1740
ttatccccct tctcggtccc cctccccaaa ccctctaccc cattctctcc tcccttctt     1800 ctatgagggt gttccccacc aacccactcc caccttcctg ctctcgaatt ccctatact     1860 gggacatcaa gccttcacag aatcaagggc ctctcctccc attgatgccc gacaatgtca    1920
tcctctgcta cctatgtggc tggagccatg ggtcccttca tgtatcctcc ttggttggtg    1980
gtttagtctc tgggaggtct gggggatctg gttgattgat attattgttc ttcctatgag    2040
attgcaaacc ccttcagctc cttcggtcct ttaactcctc cactggggac cccgagctca    2100
gtccaatggt tggctgtgag catccaccag cagaggcctt ttttttttt tttaacaaag     2160 ctgctttatt atgttgctta gagcatgacc aggaaccaga gcacagtcca agactgaagg    2220
gaggaaaagg gggggagtca ataacccccac tgtttcatag tggtttgcaa cccttttata   2280
tcacagccca ctttaggcaa ataatgaaaa ttatagtctc cagggacaga aagatggtg     2340 caggaagtga agtgcctgct cagaaaatgg gggcttgaat gtgagttccc agactctgtg    2400
taagatgccc agcatcgaag tgcatgctta taacaccagc ctggaggtag aagcttagaa    2460 acagggtac cctgaagttg cttgttcacc agtgtccctg aatgggtagg tgcatgtttg     2520
gtgagagacc ctgtctcaaa aatcaaggtg taggataatt gaaaatacct agctttgagc    2580
ttagatcatg caaatgtgta cacacactca cacacaccac acacacaaaa aaatgcagag    2640
acagagagat acagagagac agagagatac agagacagag acagagagaa aaggagaaag    2700
taaaaaacaa ataatttaaa gacccatggc cacaaagagg ctcaaagaca agcacgtata    2760
aaaccataca catgtaattt taggagtttt cagattccct ggtacccgtg ggtgatgcac    2820
aagctttgaa tcccagtctt aaaatcttac gaagaacgtg ttcgtgtgtg ctaatttatt    2880
gatgagagga aaggaattga caaagtgccc ttccggagct tcctgcatta cccagactca    2940
gggttttttt aaatgtacac tcagaacaga gtagctctgt gcaagggtag caaccacgaa    3000
gcttaataag aaacatatcg tgagagatct gcaaggcaaa tctagggct gaccaatctc     3060
```

```
acagtcaccc actagcatgt caacacaact tcccacctgt gctagccact tagcaatttt    3120
gtgttgttct gttttgtttt tgttttaac aaagcaattt caaagagatt tctaattcat     3180
ctaaacaaac aaaccaaaag gaaaacagca aagacgccct gagcacttag cagagcagct    3240
atgcagttat gactcctggg tggagacttt atatcaggct tcaactgaat acctagaacc    3300
tactagtgct cttcatcaat ccttgggaag gtcattttct tttggtgctg ttttgagttt    3360
ctatttgtta atgtcttcat aattatacac gtgttgagca cagcatgcaa agtgattagg    3420
ggaatctagt tggagtggaa tggatacccca aatattcaga cttcttgtg actcttcttt    3480 cttgtaccca catcaaaaaa aaaaaaaatg gagatgagca atggtcagag tcactaaaac    3540
cagctgctac ttttaattac gtggggagca gtttctaaca ttgccattat tgaactgatg    3600
ctgcctgggt ggaaatggaa atcacttagt atttcttgtt ggcaaagaat tactgaatgg    3660
attaaatttc caagggaga agtcagttac aagtcttttc tttgtttatt aggctttctg     3720
ctatgataaa ttacactact tccagaagtt acccttaggc catgggacac tggactatca    3780
ctctgctgtc acaagagatt acagagttag tcaaggcagc ttgtgacacc ttcagggact    3840
gtcataaact tccagcaagt cattaatcct gaatgcaata ctgtgtgtgt gtgtctatgt    3900
gtgtttgtat gtctgtgtgt gtcttatgtc tgtgtctctg tgtgtgtgtg tgtttgtgtg    3960
tgtgtgtgta tgtatgcctg tgtgtgtctt atgtctgtgt ttgtgtgtct gtgtgtgtct    4020
tatgtctgtg tttgtatgtc tgtgtgtgtc tgtgtgtgtc ttatgtctgt gtctctgtgt    4080
gtgtgtgtgt gtatgtatgt atgtatgtat gtatgtgtat gtgtttgcat ctctctgtgt    4140
gtctgcgctt atatatttgt gtatgtgttt atgtgttcgc ctttgtgcgt tgttggggat    4200
tgaatccagg ggaatacaaa tgttaagaaa gaacgttacc actaagcttc acctgtaggc    4260
cttaaagctt ttctttcttt taaaaattgt aattaattca ttttcagtca ggatctccac    4320
acctcgtccc tgctgctcta gaactcacta tttaaacaca atcgccctca aacctgcagc    4380
aaccctcccg cctctaccct gcgagcacta gaataataac aggtgacccc acacgcctag    4440
attaagacct ttaaggtaaa cattttacta tattttagtc tcataagaca agatgctaca    4500
ataaagctgt acataaagtt ccctcgaatt tcttgctatt ttaactcaaa cataaggatt    4560
tcctcctttt tgattcaggt aacagaaaaa atacacaggt acatacatgt acacacatga    4620
acacacacgc atcacaacca catatgcgca cgcttgtgtg atctatcatt taccatgcca    4680
ctgaactctt cttctcccat aaattcctct ggacttgtgt gccctccagg aagaccgcgg    4740
agtctggaga gctgcacggg ctcaccacag atgagaagtt tgtagaagga gtgtacagag    4800
tagaactgga caccaaatcg tactggaaga cacttggcat ttccccgttc catgaattcg    4860
cggatgtaag tggacacacc aagttgtttg gattttgttt ttagtctcag gaaattccct    4920
tcgctcttgc tgtacgatgg gcatgagtgg aaagtagatt ccacagccag aatccacagt    4980
gctgggaaag caagccttct gaattttct aaaactcatt tagcaacatg gcctgaacct     5040
gttcacactg cttatggtca gctaactata tttatgtaaa tattcatttc tctgttgagg    5100
aaatgttagt atttgctttt gaggcaacct ccagatacca tggagggcat gtcatagtca    5160
aagagagggc tccctatggt atttctctaa attctgcat ttcctttatt ccaaagcaca     5220
tctagtgtcc ccagaagttt gggtagacaa ttcttggcaa cacagagaat tacaacatgt    5280
tcaaaaccca acagcttaat atctaaatca tcaagcaaac atcacatggc aaagggattt    5340
ctgaatcaaa actgtttcat ccttatgatc aacctatgga ggtctagcct cgacttacac    5400
```

```
ccatttta cc aataagctaa gagaagctaa gttcctcatc aaggacacaa ggctagcatg    5460
tgtgagcaag tgacagagtt gccctctatg ttggttagtg tgccttagcc agtgtctcag    5520
taagaaatgg agctaaatca aacccaagg ccaacagcca aaggcacatg agtaaccttt     5580
gcttggcact gggctcagtt tccctggctc ctctcagtcc tcagttcaca gaggcagctg    5640
tcatgcaaat agaatccaag cttgttggtc agacctggag ataacaaatt ccatcaaaaa    5700
tagctcctca tgtgacctag tttgctgtct gttgctatga tacacaccat gaccgaaaag    5760
caaccctggg gagagaaggg tttatttcat cttacagctt acagttcacc atggaggaaa    5820
gccaggtggg aacctggaag tggaaattga agcagagacc agaaaggaat gctgtttact    5880
ggctggctta gctccttttc ttatacagct taggtctatg tgcccagggg atggtactgc    5940
cgagcatagg ctgagcccgc ctacatcaac cattagtcaa aaaaaggtcc atagacttgc    6000
ctacaggcca atctcatgga ggcaataccc cagtggaggg tccctcttcg caggttactc    6060
tagtttgtgt caagttgaca aaacctaacc acaaagcaca aacagggtct gcccttgtgg    6120
cttagccatg gatgacactc tcagatgatg gtgttaccag acaaaccaga ggggctcacc    6180
aagagtctgc cacctaccaa ggtagtactc tactcctcac tgggcaccaa cacccatatt    6240
agctgggcca gtacaggacc cttgctgttt cctgcatgaa ttgtccatag accctgggtc    6300
tcagcctgcc gggagtacct gtaagtagtc gcctcaaaca cattattcct gttggaagac    6360
ttgtctgatt ctcttttaga actcaatcaa caaacgtttt tattttgttt tggcttttttg    6420 gagacaagat ctctcatagg ccagcctgac ttgaatgtag ctgaggatga cctgtgctgc    6480
taatcttctc gcctcttcct cccaagtggt aggataatag gcataagaca ccacagcagt    6540
tttactccat accagggctc tgaacccaga ctttaaacac tctatcaact gattcacatt    6600
cccaccccat cattcaacaa acatttgaaa aataaaaccc ttctgccttg agcactctgc    6660
taaatacagc ctttgagtgc ggagtatttc ctcacaacca gggtccaaga tgaccccatc    6720
atacatacca cggaaaatta ggagatgttt ttaggtctct ttgcttgggg taattttat    6780 gtgtgtgtgt acacagccct gtgcgtgtgt gtgtgtgtgt gtgtgtgtgt gtacaggcac    6840
acacgtgtat gcatgtagag gctacataaa aaccttaggt gtcattctca ggcactctgt    6900
tcaccccttc acacagcccg aacacacaaa atttgaggca ttagcctgga gctcaccagt    6960
taggctagac tgacttgcca gcagacccca ggctgtctcc atctccccag ctctgggatt    7020
acaaactcta tcataccaga cattttttata catattctga gcataaaatt catgtcttca    7080
ggctaacaag tcaagagctt aaatgactga gctctcttac gtggtggatt tttttaaaa    7140 ctacataata tctttttttt tttttcact tctggggaag aaacaaatga gcctgagtga    7200
caatgcgaca gaaagaaat tttgaggagt gtgtgtgtct gtgtgtgtgg tggcacatgc    7260
ctctcatcta atgctagagg ctacagtaga atgctcctga attagtggcc agccaaggcc    7320
aagggctagg gttgtaactc agtggcagag ggcttgccta gcattcgcag gatttgatcc    7380
atagcgctat aaataataat aaataaatac aacagtctaa gatgattctc cctttcattt    7440
atctggatgt tattttttgtg ttagtttttac tctgtcatcc aatcattgtt tgccctatat    7500
ttggacattt aaaaaaaatc tttattccaa gtgtgttcaa agctgtatcc aaaacctgtc    7560
caccaaatga gtccaatgac atacatcttc tatattacca tctgttccag atttggctga    7620
ctcccggcac ctgggctgtt gctgcaccca tgtctcagat agtctagtga tttgagaagt    7680
gactagtaat tgcaaaatcc agactttgtc cagaaacttc tatgagctcc aaaactttca    7740
tttacatttc tgccagccac aaaccgcttg tgttgtggag agaaccctgt gatgtcttcc    7800
```

```
cacagcatct cagccttgtt tcttccctta aaatattcat cttttcacat tagaacatgc    7860
aaagggacag tgggagcgaa accctggac tgggacgcac gaagccttcc tttctggtca    7920
ggctctcact gtagaaactt aggccggttt cagcatgcag tctgctggag aatggctcct    7980
gccaacattc caggtctgga agtttgtagt ggagttgttg ataaccactg ttcgccacag    8040
gtcttttgtt tgtgggtgtc agtgtttcta ctctcctgac ttttatctga acccaagaaa    8100
gggaacaata gccttcaagc tctctgtgac tctgatctga ccagggccac ccacactgca    8160
gaaggaaact tgcaaagaga gacctgcaat tctctaagag ctccacacag ctccaaagac    8220
ttaggcagca tattttaatc taattattcg tcccccaacc ccaccccaga ggacagttag    8280
acaataaaag gaagattacc agcttagcat cctgtgaaca ctttgtctgc agctcctacc    8340
tctgggctct gttagaacta gctgtctctc ctctctccta ggtggttttc acagccaacg    8400
actctggcca tcgccactac accatcgcag ccctgctcag cccatactcc tacagcacca    8460
cggctgtcgt cagcaaccc cagaattgag agactcagcc caggaggacc aggatcttgc    8520
caaagcagta gcatcccatt tgtaccaaaa cagtgttctt gctctataaa ccgtgttagc    8580
agctcaggaa gatgccgtga agcattctta ttaaaccacc tgctatttca ttcaaactgt    8640
gtttcttttt tatttcctca tttttctccc ctgctcctaa acccaaaat cttctaaaga    8700 attctagaag gtatgcgatc aaacttttta aagaaagaaa atacttttg actcatggtt    8760 taaaggcatc ctttccatct tggggaggtc atgggtgctc ctggcaactt gcttgaggaa    8820
gataggtcag aaagcagagt ggaccaaccg ttcaatgttt tacaagcaaa acatacacta    8880
agcatggtct gtagctatta aaagcacaca atctgaaggg ctgtagatgc acagtagtgt    8940
tttcccagag catgttcaaa agccctgggt tcaatcacaa tactgaaaag taggccaaaa    9000
aacattctga aaatgaaata tttgggtttt tttttataac ctttagtgac taaataaaga    9060
caaatctaag agactaa                                                   9077

<210> SEQ ID NO 8
<211> LENGTH: 444
<212> TYPE: DNA
<213> ORGANISM: Artificial Sequence
<220> FEATURE:
<223> OTHER INFORMATION: Synthetic

<400> SEQUENCE: 8
atggcttccc ttcgactctt cctcctttgc ctcgctggac tggtatttgt gtctgaagct     60
ggccccgcgg gtgctggaga atccaaatgt cctctgatgg tcaaagtcct ggatgctgtc    120
cgaggcagcc ctgctgtaga cgtggctgta aaagtgttca aaagacctc tgagggatcc    180 tgggagccct ttgcctctgg aagaccgcg gagtctggaa agctgcacgg gctcaccaca    240
gatgagaagt ttgtagaagg agtgtacaga gtagaactgg acaccaaatc gtactggaag    300
acacttggca tttccccgtt ccatgaattc gcggatgtgg ttttcacagc caacgactct    360
ggccatcgcc actacaccat cgcagccctg ctcagcccat actcctacag caccacggct    420
gtcgtcagca accccagaa ttga                                            444

<210> SEQ ID NO 9
<211> LENGTH: 147
<212> TYPE: PRT
<213> ORGANISM: Artificial Sequence
<220> FEATURE:
<223> OTHER INFORMATION: Synthetic
```

<400> SEQUENCE: 9

Met Ala Ser His Arg Leu Leu Leu Cys Leu Ala Gly Leu Val Phe
1               5                   10                  15

Val Ser Glu Ala Gly Pro Thr Gly Thr Gly Glu Ser Lys Cys Pro Leu
            20                  25                  30

Met Val Lys Val Leu Asp Ala Val Arg Gly Ser Pro Ala Ile Asn Val
        35                  40                  45

Ala Val His Val Phe Arg Lys Ala Ala Asp Thr Trp Glu Pro Phe
    50                  55                  60

Ala Ser Gly Lys Thr Ser Glu Ser Ser Asp Ser His Gly Leu Thr Thr
65              70                  75                  80

Glu Glu Glu Phe Val Glu Gly Ile Tyr Lys Val Glu Ile Asp Thr Lys
                85                  90                  95

Ser Tyr Trp Lys Ala Leu Gly Ile Ser Pro Phe His Glu His Ala Glu
                100                 105                 110

Val Val Phe Thr Ala Asn Asp Ser Gly Pro Arg Arg Tyr Thr Ile Ala
            115                 120                 125

Ala Leu Leu Ser Pro Tyr Ser Tyr Ser Thr Thr Ala Val Val Thr Asn
130                 135                 140

Pro Lys Glu
145

<210> SEQ ID NO 10
<211> LENGTH: 444
<212> TYPE: DNA
<213> ORGANISM: Artificial Sequence
<220> FEATURE:
<223> OTHER INFORMATION: Synthetic

<400> SEQUENCE: 10

```
atggcttctc atcgtctgct cctcctctgc cttgctggac tggtatttgt gtctgaggct    60
ggccctacgg gcaccggtga atccaagtgt cctctgatgg tcaaagttct agatgctgtc   120
cgaggcagtc ctgccatcaa tgtggccgtg catgtgttca gaaaggctgc tgatgacacc   180
tgggagccat ttgcctctgg aaaaccagt gagtctagcg attcgcatgg gctcacaact   240
gaggaggaat ttgtagaagg gatatacaaa gtggaaatag acaccaaatc ttactggaag   300
gcacttggca tctccccatt ccatgagcat gcagaggtgg tattcacagc caacgactcc   360
ggccccgcc gctacaccat tgccgccctg ctgagcccct actcctattc caccacggct   420
gtcgtcacca atcccaagga atga                                         444
```

<210> SEQ ID NO 11
<211> LENGTH: 8300
<212> TYPE: DNA
<213> ORGANISM: Mus musculus

<400> SEQUENCE: 11

```
atggcttccc ttcgactctt cctcctttgc ctcgctggac tggtatttgt gtctgaagct    60
ggccccgcgg tgagtgatcc tgtgagcgat ccagacatgg cagttagacc ttagataaag   120
aagaagtgcc tcttccaga tgtgagaact agagtactca gactctatat ttaccattag   180
actccaaaga gaagagctgg agtgcctctg gctcttcctt ctattgcttt agcgcattgg   240
gtctgtagtg ctcagtctct ggtgtcctta gataataaag atatgagatt aacatagaaa   300
taaagatata aagggctgg atgtatagtt tagtggtcca gtgtatgcct agtatgtgaa   360
aagccttctg ttcaacctct agcaatagaa aaacaagata tattctcggt ggggctgtta   420
```

```
atattgaatt ctcataaaat ctttaatata tttagtatgc ctattatgtt gttatatttt      480
agttctttag ctaatcaaaa tgcattattg atctttcttt gtcttttttt ggccaacact      540
ctattccagt ctttgaaaaa gtcctttaaa agagttaatc agtataatta aatgagtcag      600
gaagtatgtg agggttattt tacaaccaga gggaattact atagcaacag ctgattagaa      660
tgatctcaag aaaaagccca ttctgtcttt ttgcaccatg cacctttcag tggctccatt      720
cagatggaga ggcaaacaga gcaatggctc tcagagggcc tattttccct ttgaacattc      780
attatccata tccctggtgc acagcagtgc atctggggc agaaactgtt cttgctttgg       840
aaacaatgct gtctatgtca tactggataa agaagctcat taattgtcaa cacttatgtt      900
atcataatgg gatcagcatg tacttttggt tttgttccag agtctatcac cggaaagaac      960
aagccggttt actctgaccc atttcactga catttctctt gtctcctctg tgcccagggt     1020
gctggagaat ccaaatgtcc tctgatggtc aaagtcctgg atgctgtccg aggcagccct     1080
gctgtagacg tggctgtaaa agtgttcaaa aagacctctg agggatcctg ggagcccttt     1140
gcctctgggt aagcttgtag aaagcccacc atgggaccgg ttccaggttc ccatttgctc     1200
ttattcgtgt tagattcaga cacacacaac ttaccagcta gagggctcag agagagggct     1260
caggggcgaa gggcacgtat tgctcttgta agagacacag gtttaattcc tagcaccaga     1320
atggcagctc ataaccatct gaaactcaca gtcttaggag atctgggtat ctgacattct     1380
cttctaccca ccatgtgtgt ggtgcacaaa ttcacatgca ggcatcaaat cttataaaca     1440
acaacaaaaa accaacaaac ctggtagcaa aagaagatta aaggttaaa catatgagcc      1500 gagagctttt gttttgtttt gttttgtttt gttttgttta catttcaaat gttatcccct     1560
ttctcggtcc ccctccccaa accctctacc ccattctctc ctccccttct tctatgaggg     1620
tgttccccac caacccactc ccaccttcct gctctcgaat tccctatac tgggacatca      1680 agccttcaca gaatcaaggg cctctcctcc cattgatgcc cgacaatgtc atcctctgct     1740
acctatgtgg ctggagccat gggtcccttc atgtatcctc cttggttggt ggtttagtct     1800 ctggaggtc tggggatct ggttgattga tattattgtt cttcctatga gattgcaaac        1860
cccttcagct ccttcggtcc tttaactcct ccactgggga ccccgagctc agtccaatgg     1920
ttggctgtga gcatccacca gcagaggcct ttttttttt ttttaacaaa gctgctttat      1980
tatgttgctt agagcatgac caggaaccag agcacagtcc aagactgaag ggaggaaaag     2040 gggggagtc aataacccca ctgtttcata gtggtttgca accctttat atcacagccc       2100 actttaggca aataatgaaa attatagtct ccagggacag agaagatggt gcaggaagtg     2160
aagtgcctgc tcagaaaatg ggggcttgaa tgtgagttcc cagactctgt gtaagatgcc     2220
cagcatcgaa gtgcatgctt ataacaccag cctggaggta gaagcttaga aacagggta      2280 ccctgaagtt gcttgttcac cagtgtccct gaatgggtag gtgcatgttt ggtgagagac     2340
cctgtctcaa aaatcaaggt gtaggataat tgaaaatacc tagctttgag cttagatcat     2400
gcaaatgtgt acacacactc acacacacca cacacacaaa aaaatgcaga gacagagaga     2460
tacagagaga cagagagata cagagacaga gacagagaga aaaggagaaa gtaaaaaaca     2520
aataatttaa agaccatgg ccacaaagag gctcaaagac aagcacgtat aaaaccatac      2580
acatgtaatt ttaggagttt tcagattccc tggtacccgt gggtgatgca caagctttga     2640
atcccagtct taaaatctta cgaagaacgt gttcgtgtgt gctaatttat tgatgagagg     2700
aaaggaattg acaaagtgcc cttccggagc ttcctgcatt acccagactc agggtttttt     2760
```

```
taaatgtaca ctcagaacag agtagctctg tgcaagggta gcaaccacga agcttaataa    2820
gaaacatatc gtgagagatc tgcaaggcaa atctaggggc tgaccaatct cacagtcacc    2880
cactagcatg tcaacacaac ttcccacctg tgctagccac ttagcaattt tgtgttgttc    2940
tgttttgttt ttgtttttaa caaagcaatt tcaaagagat ttctaattca tctaaacaaa    3000
caaaccaaaa ggaaaacagc aaagacgccc tgagcactta gcagagcagc tatgcagtta    3060
tgactcctgg gtggagactt tatatcaggc ttcaactgaa tacctagaac ctactagtgc    3120
tcttcatcaa tccttgggaa ggtcattttc ttttggtgct gttttgagtt tctatttgtt    3180
aatgtcttca taattataca cgtgttgagc acagcatgca aagtgattag ggaatctag    3240 ttggagtgga atggataccc aaatattcag actttcttgt gactcttctt tcttgtaccc    3300
acatcaaaaa aaaaaaaaat ggagatgaga catggtcaga gtcactaaaa ccagctgcta    3360
cttttaatta cgtggggagc agtttctaac attgccatta ttgaactgat gctgcctggg    3420
tggaaatgga aatcacttag tatttcttgt tggcaaagaa ttactgaatg gattaaattt    3480
ccaaagggag aagtcagtta caagtctttt ctttgtttat taggctttct gctatgataa    3540
attacactac ttccagaagt tacccttagg ccatgggaca ctggactatc actctgctgt    3600
cacaagagat tacagagtta gtcaaggcag cttgtgacac cttcagggac tgtcataaac    3660
ttccagcaag tcattaatcc tgaatgcaat actgtgtgtg tgtgtctatg tgtgtttgta    3720
tgtctgtgtg tgtcttatgt ctgtgtctct gtgtgtgtgt gtgtttgtgt gtgtgtgtgt    3780
atgtatgcct gtgtgtgtct tatgtctgtg tttgtgtgtc tgtgtgtgtc ttatgtctgt    3840
gtttgtatgt ctgtgtgtgt ctgtgtgtgt cttatgtctg tgtctctgtg tgtgtgtgtg    3900
tgtatgtatg tatgtatgta tgtatgtgta tgtgtttgca tctctctgtg tgtctgcgct    3960
tatatatttg tgtatgtgtt tatgtgttcg cctttgtgcg ttgttgggga ttgaatccag    4020
gggaatacaa atgttaagaa agaacgttac cactaagctt cacctgtagg ccttaaagct    4080
tttctttctt ttaaaaattg taattaattc attttcagtc aggatctcca cacctcgtcc    4140
ctgctgctct agaactcact atttaaacac aatcgccctc aaacctgcag caaccctccc    4200
gcctctaccc tgcgagcact agaataataa caggtgaccc cacacgccta gattaagacc    4260
tttaaggtaa acattttact atattttagt ctcataagac aagatgctac aataaagctg    4320
tacataaagt tccctcgaat ttcttgctat tttaactcaa acataaggat ttcctccttt    4380
ttgattcagg taacagaaaa aatacacagg tacatacatg tacacacatg aacacacacg    4440
catcacaacc acatatgcgc acgcttgtgt gatctatcat ttaccatgcc actgaactct    4500 tcttcccca taaattcctc tggacttgtg tgccctccag gaagaccgcg gagtctggag    4560
agctgcacgg gctcaccaca gatgagaagt ttgtagaagg agtgtacaga gtagaactgg    4620
acaccaaatc gtactggaag acacttggca tttccccgtt ccatgaattc gcggatgtaa    4680
gtggacacac caagttgttt ggattttgtt tttagtctca ggaaattccc ttcgctcttg    4740
ctgtacgatg ggcatgagtg gaaagtagat tccacagcca gaatccacag tgctgggaaa    4800
gcaagccttc tgaatttttc taaaactcat ttagcaacat ggcctgaacc tgttcacact    4860
gcttatggtc agctaactat atttatgtaa atattcattt ctctgttgag gaatgttag    4920 tatttgcttt tgaggcaacc tccagatacc atggagggca tgtcatagtc aaagagaggg    4980
ctccctatgg tatttctcta aattctggca tttcctttat tccaaagcac atctagtgtc    5040
cccagaagtt tgggtagaca attccttgca acacagagaa ttacaacatg ttcaaaaccc    5100
aacagcttaa tatctaaatc atcaagcaaa catcacatgg caaagggatt tctgaatcaa    5160
```

```
aactgtttca tccttatgat caacctatgg aggtctagcc tcgacttaca cccatttttac    5220 caataagcta agagaagcta agttcctcat caaggacaca aggctagcat gtgtgagcaa    5280
gtgacagagt tgccctctat gttggttagt gtgccttagc cagtgtctca gtaagaaatg    5340
gagctaaatc aaaacccaag gccaacagcc aaaggcacat gagtaacctt tgcttggcac    5400
tgggctcagt ttccctggct cctctcagtc ctcagttcac agaggcagct gtcatgcaaa    5460
tagaatccaa gcttgttggt cagacctgga gataacaaat tccatcaaaa atagctcctc    5520
atgtgaccta gtttgctgtc tgttgctatg atacacacca tgaccgaaaa gcaaccctgg    5580
ggagagaagg gtttatttca tcttacagct tacagttcac catggaggaa agccaggtgg    5640
gaacctggaa gtggaaattg aagcagagac cagaaaggaa tgctgtttac tggctggctt    5700
agctcctttt cttatacagc ttaggtctat gtgcccaggg gatggtactg ccgagcatag    5760
gctgagcccg cctacatcaa ccattagtca aaaaaggtc catagacttg cctacaggcc    5820
aatctcatgg aggcaatacc ccagtggagg gtccctcttc gcaggttact ctagtttgtg    5880
tcaagttgac aaaacctaac cacaaagcac aaacagggtc tgcccttgtg gcttagccat    5940
ggatgacact ctcagatgat ggtgttacca gacaaaccag aggggctcac caagagtctg    6000
ccacctacca aggtagtact ctactcctca ctgggcacca cacccatat agctgggcc     6060 agtacaggac cctgctgtt tcctgcatga attgtccata gaccctgggt ctcagcctgc    6120
cgggagtacc tgtaagtagt cgcctcaaac acattattcc tgttggaaga cttgtctgat    6180
tctcttttag aactcaatca acaaacgttt ttatttttgtt ttggctttt ggagacaaga    6240 tctctcatag gccagcctga cttgaatgta gctgaggatg acctgtgctg ctaatcttct    6300
cgcctcttcc tcccaagtgg taggataata ggcataagac accacagcag ttttactcca    6360
taccagggct ctgaacccag actttaaaca ctctatcaac tgattcacat tcccacccca    6420
tcattcaaca acatttgaa aaataaaacc cttctgcctt gagcactctg ctaaatacag    6480
cctttgagtg cggagtattt cctcacaacc agggtccaag atgaccccat catacatacc    6540
acggaaaatt aggagatgtt tttaggtctc tttgcttggg gtaattttta tgtgtgtgtg    6600
tacacagccc tgtgcgtgtg tgtgtgtgtg tgtgtgtgtg tgtacaggca cacacgtgta    6660
tgcatgtaga ggctacataa aaaccttagg tgtcattctc aggcactctg ttcccccctt    6720
cacacagccc gaacacacaa aatttgaggc attagcctgg agctcaccag ttaggctaga    6780
ctgacttgcc agcagacccc aggctgtctc catctcccca gctctgggat tacaaactct    6840
atcataccag acattttat acatattctg agcataaaat tcatgtcttc aggctaacaa    6900
gtcaagagct taaatgactg agctctctta cgtggtggat ttttttttaaa actacataat    6960 atcttttttt tttttttcac ttctggggaa gaaacaaatg agcctgagtg acaatgcgac    7020
agaaaagaaa ttttgaggag tgtgtgtgtc tgtgtgtgtg gtggcacatg cctctcatct    7080
aatgctagag gctacagtag aatgctcctg aattagtggc cagccaaggc caagggctag    7140
ggttgtaact cagtggcaga gggcttgcct agcattcgca ggatttgatc catagcgcta    7200
taaataataa taaataaata caacagtcta agatgattct cccttttcatt tatctggatg    7260 ttatttttgt gttagtttta ctctgtcatc caatcattgt ttgccctata tttggacatt    7320
taaaaaaaat cttattccaa agtgtgttca aagctgtatc caaaacctgt ccaccaaatg    7380
agtccaatga catacatctt ctatattacc atctgttcca gatttggctg actcccggca    7440
cctgggctgt tgctgcaccc atgtctcaga tagtctagtg atttgagaag tgactagtaa    7500
```

| | |
|---|---|
| ttgcaaaatc cagactttgt ccagaaactt ctatgagctc caaaactttc atttacattt | 7560 |
| ctgccagcca caaccgcttg tgttgtgga gagaaccctg tgatgtcttc ccacagcatc | 7620 |
| tcagccttgt ttcttcsctt aaaatattca tcttttcaca ttagaacatg caaagggaca | 7680 |
| gtgggagcga aaccsctgga ctgggacgca cgaagccttc ctttctggtc aggctctcac | 7740 |
| tgtagaaact taggccggtt tcagcatgca gtctgctgga gaatggctcc tgccaacatt | 7800 |
| ccaggtctgg aagtttgtag tggagttgtt gataaccact gttcgccaca ggtcttttgt | 7860 |
| ttgtgggtgt cagtgtttct actctcctga cttttatctg aacccaagaa agggaacaat | 7920 |
| agccttcaag ctctctgtga ctctgatctg accagggcca cccacactgc agaaggaaac | 7980 |
| ttgcaaagag agacctgcaa ttctctaaga gctccacaca gctccaaaga cttaggcagc | 8040 |
| atattttaat ctaattattc gtcccccaac cccacccag aggacagtta gacaataaaa | 8100 |
| ggaagattac cagcttagca tcctgtgaac actttgtctg cagctcctac ctctgggctc | 8160 |
| tgttagaact agctgtctct cctctctcct aggtggtttt cacagccaac gactctggcc | 8220 |
| atcgccacta caccatcgca gccctgctca gcccatactc ctacagcacc acggctgtcg | 8280 |
| tcagcaaccc ccagaattga | 8300 |

<210> SEQ ID NO 12
<211> LENGTH: 11817
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(97)
<223> OTHER INFORMATION: Mouse Sequence
<220> FEATURE:
<221> NAME/KEY: misc_feature
<222> LOCATION: (98)..(7298)
<223> OTHER INFORMATION: Human Sequence
<220> FEATURE:
<221> NAME/KEY: misc_feature
<222> LOCATION: (7299)..(11717)
<223> OTHER INFORMATION: Cassette Sequence
<220> FEATURE:
<221> NAME/KEY: misc_feature
<222> LOCATION: (11718)..(11817)
<223> OTHER INFORMATION: Mouse Sequence

<400> SEQUENCE: 12

| | |
|---|---|
| agcttggcag ggatcagcag cctgggttgg aaggaggggg tataaaagcc ccttcaccag | 60 |
| gagaagccgt cacacagatc cacaagctcc tgacaggatg gcttctcatc gtctgctcct | 120 |
| cctctgcctt gctggactgg tatttgtgtc tgaggctggc cctacggtga gtgtttctgt | 180 |
| gacatcccat tcctacattt aagattcacg ctaaatgaag tagaagtgac tccttccagc | 240 |
| tttgccaacc agcttttatt actagggcaa gggtacccag catctatttt taatataatt | 300 |
| aattcaaact tcaaaagaa tgaagttcca ctgagcttac tgagctggga cttgaactct | 360 |
| gagcattcta cctcattgct ttggtgcatt aggtttgtaa tatctggtac ctctgtttcc | 420 |
| tcagatagat gatagaaata aagatatgat attaaggaag ctgttaatac tgaattttca | 480 |
| gaaaagtatc cctccataaa atgtatttgg gggacaaact gcaggagatt atattctggc | 540 |
| cctatagtta ttcaaaacgt atttattgat taatctttaa aaggcttagt gaacaatatt | 600 |
| ctagtcagat atctaattct taaatcctct agaagaatta actatacta taaaatgggt | 660 |
| ctggatgtag ttctgacatt attttataac aactggtaag agggagtgac tatagcaaca | 720 |
| actaaaatga tctcaggaaa acctgtttgg ccctatgtat ggtacattac atcttttcag | 780 |

```
taattccact caaatggaga cttttaacaa agcaactgtt ctcagggac ctatttctc      840 ccttaaaatt cattatacac atccctggtt gatagcagtg tgtctggagg cagaaaccat    900
tcttgctttg gaaacaatta cgtctgtgtt atactgagta gggaagctca ttaattgtcg    960
acacttacgt tcctgataat gggatcagtg tgtaattctt gtttcgctcc agatttctaa    1020
taccacaaag aataaatcct ttcactctga tcaattttgt taacttctca cgtgtcttct    1080
ctacacccag ggcaccggtg aatccaagtg tcctctgatg gtcaaagttc tagatgctgt    1140
ccgaggcagt cctgccatca atgtggccgt gcatgtgttc agaaaggctg ctgatgacac    1200
ctgggagcca tttgcctctg gtaagttgc caaagaaccc tcccacagga cttggtttta    1260
tcttcccgtt tgcccctcac ttggtagaga gaggctcaca tcatctgcta agaatttac    1320 aagtagattg aaaaacgtag gcagaggtca agtatgccct ctgaaggatg ccctcttttt    1380
gttttgctta gctaggaagt gaccaggaac ctgagcatca tttaggggca gacagtagag    1440
aaaagaagga atcagaactc ctctcctcta gctgtggttt gcaacccttt tgggtcacag    1500
aacactttat gtaggtgatg aaaagtaaac attctatgcc cagaaaaaat gcacagatac    1560
acacacatac aaaatcatat atgtgatttt aggagtttca cagattccct ggtgtccctg    1620
ggtaacacca agctaagtg tccttgtctt agaatttag gaaaaggtat aatgtgtatt       1680
aacccattaa caaaggaaa ggaattcaga aatattatta accaggcatc tgtctgtagt      1740
taatatggat cacccaaaac ccaaggcttt tgcctaatga acactttggg gcacctactg    1800
tgtgcaaggc tgggggctgt caagctcagt taaaaaaaaa aagatagaag agatggatcc    1860
atgaggcaaa gtacagcccc aggctaatcc cacgatcacc cgacttcatg tccaagagtg    1920
gcttctcacc ttcattagcc agttcacaat tttcatggag ttttctacc tgcactagca     1980 aaaacttcaa ggaaaataca tattaataaa tctaagcaaa gtgaccagaa acagagcaa     2040 tcaggagacc ctttgcatcc agcagaagag gaactgctaa gtatttacat ctccacagag    2100
aagaatttct gttgggtttt aattgaaccc caagaaccac atgattcttc aaccattatt    2160
gggaagatca ttttcttagg tctggtttta actggctttt tatttgggaa ttcatttatg    2220
tttatataaa atgccaagca taacatgaaa agtggttaca ggactattct aagggagaga    2280
cagaatggac accaaaaata ttccaatgtt cttgtgaatc ttttccttgc accaggacaa    2340
aaaaaaaaag aagtgaaaag aagaaggag gagggcata atcagagtca gtaaagacaa      2400
ctgctatttt tatctatcgt agctgttgca gtcaaatggg aagcaatttc caacattcaa    2460
ctatggagct ggtacttaca tggaaataga agttgcctag tgtttgttgc tggcaaagag    2520
ttatcagaga ggttaaatat ataaaggga aagagtcag atacaggttc ttcttcctac      2580
tttaggtttt ccactgtgtg tgcaaatgat actccctggt ggtgtgcaga tgcctcaaag    2640
ctatcctcac accacaaggg agaggagcga atcctgctg tcctggagaa gtgcagagtt     2700
agaacagctg tggccacttg catccaatca tcaatcttga atcacaggga ctcttttctta   2760 agtaaacatt atacctggcc gggcacggtg gctcacgcct gtaatcccag cactttggga    2820
tgccaaagtg ggcatatcat ctgaggtcag gagttcaaga ccagcctggc caacatggca    2880
aaactccgtc tttatgaaaa atacaaaaat tagccaggca tggtggcagg cgcctgtaat    2940
cccagctaat tgggaggctg aggctggaga atcccttgaa tctaggaggc agaggttgca    3000
gtgagctgag atcgtgccat tgcactccag cctgggtgac aagagtaaaa ctctgtctca    3060
aaaaaaaaaa attataccta cattctcttc ttatcagaga aaaaaatcta cagtgagctt    3120
```

```
ttcaaaaagt ttttacaaac tttttgccat ttaatttcag ttaggagttt tccctacttc    3180
tgacttagtt gagggaaat gttcataaca tgtttataac atgtttatgt gtgttagttg      3240 gtggggtgt attactttgc catgccattt gtttcctcca tgcgtaactt aatccagact      3300
ttcacacctt ataggaaaac cagtgagtct agcgattcgc atgggctcac aactgaggag     3360
gaatttgtag aagggatata caaagtggaa atagacacca atcttactg gaaggcactt      3420 ggcatctccc cattccatga gcatgcgag gtgagtatac agaccttcga gggttgtttt      3480
ggttttggtt tttgcttttg gcattccagg aaatgcacag ttttactcag tgtaccacag    3540
aaatgtccta aggaaggtga tgaatgacca aaggttccct ttcctattat acaagaaaaa     3600
attcacaaca ctctgagaag caaatttctt tttgactttg atgaaaatcc acttagtaac    3660
atgacttgaa cttacatgaa actactcata gtctattcat tccactttat atgaatattg    3720
atgtatctgc tgttgaaata atagtttatg aggcagccct ccagaccca cgtagagtgt     3780 atgtaacaag agatgcacca ttttatttct cgaaacccg taacattctt cattccaaaa     3840
cacatctggc ttctcggagg tctggacaag tgattcttgg caacacatac ctatagagac    3900
aataaaatca aagtaataat ggcaacacaa tagataacat ttaccaagca tacaccatgt    3960
ggcagacaca attataagtg ttttccatat ttaacctact taatcctcag gaataagcca    4020
ctgaggtcag tcctattatt atccccatct tatagatgaa gaaatgagg caccaggaag     4080 tcaaataact tgtcaaaggt cacaagacta ggaaatacac aagtagaaat gtttacaatt    4140
aaggcccagg ctgggtttgc cctcagttct gctatgcctc gcattatgcc ccaggaaact    4200
ttttcccttg tgaaagccaa gcttaaaaaa agaaaagcca catttgtaac gtgctctgtt    4260
cccctgccta tggtgaggat cttcaaacag ttatacatgg acccagtccc cctgccttct    4320
ccttaatttc ttaagtcatt tgaaacagat ggctgtcatg gaaatagaat ccagacatgt    4380
tggtcagagt taaagatcaa ctaattccat caaaaatagc tcggcatgaa agggaactat    4440
tctctggctt agtcatggat gagactttca attgctataa agtggttcct ttattagaca    4500
atgttaccag ggaaacaaca ggggtttgtt tgacttctgg ggcccacaag tcaacaagag    4560
agccccatct accaaggagc atgtccctga ctacccctca gccagcagca agacatggac    4620
cccagtcagg gcaggagcag ggtttcggcg gcgcccagca caagacattg ccctagagt     4680 ctcagcccct accctcgagt aatagatctg cctacctgag actgttgttt gcccaagagc    4740
tgggtctcag cctgatggga accatataaa aaggttcact gacatactgc ccacatgttg    4800
ttctctttca ttagatctta gcttccttgt ctgctcttca ttcttgcagt attcattcaa    4860
caaacattaa aaaaaaaaa aagcattcta tgtgtggaac actctgctag atgctgtgga    4920
tttagaaatg aaaatacatc ccgacccttg gaatggaagg gaaaggactg aagtaagaca    4980
gattaagcag gaccgtcagc ccagcttgaa gcccagataa atacggagaa caagagagag    5040
cgagtagtga gagatgagtc ccaatgcctc actttggtga cgggtgcgtg gtgggcttca    5100
tgcagcttct tctgataaat gcctccttca gaactggtca actctacctt ggccagtgac    5160
ccaggtggtc atagtagatt taccaaggga aaatggaaac ttttattagg agctcttagg    5220
cctcttcact tcatggattt tttttccctt tttttttgag atggagtttt gcctgtcac     5280 ccaggctgga atgcagtggt gcaatctcag ctcactgcaa cctccgcctc ccaggttcaa    5340
gcaattctcc tgcctcagcc tcccgagtag ctgggactac aggtgtgcgc caccacacca    5400
ggctaatttt tgtattttt gtaaagacag ttttcacca cgttggccag gctggtctga     5460
actccagacc tcaggtgatt cacctgtctc agcctcccaa agtgctggga ttacaggtgt    5520
```

```
gagccaccgt gcccggctac ttcatggatt tttgattaca gattatgcct cttacaattt    5580
ttaagaagaa tcaagtgggc tgaaggtcaa tgtcaccata agacaaaaga catttttatt    5640
agttgattct agggaattgg ccttaagggg agcccttcct tcctaagaga ttcttaggtg    5700
attctcactt cctcttgccc cagtattatt tttgttttg gtatggctca ctcagatcct    5760
tttttcctcc tatccctaag taatccgggt ttcttttcc catatttaga acaaaatgta     5820
tttatgcaga gtgtgtccaa acctcaaccc aaggcctgta tacaaaataa atcaaattaa    5880
acacatcttt actgtcttct acctcttcc tgacctcaat atatcccaac ttgcctcact     5940
ctgagaacca aggctgtccc agcacctgag tcgcagatat tctactgatt tgacagaact    6000
gtgtgactat ctggaacagc attttgatcc acaatttgcc cagttacaaa gcttaaatga    6060
gctctagtgc atgcatatat atttcaaaat tccaccatga tcttccacac tctgtattgt    6120
aaatagagcc ctgtaatgct tttacttcgt atttcattgc ttgttataca taaaaatata    6180
cttttcttct tcatgttaga aaatgcaaag aataggaggg tggggaatc tctgggcttg     6240 gagacaggag acttgccttc ctactatggt tccatcagaa tgtagactgg gacaatacaa    6300
taattcaagt ctggtttgct catctgtaaa ttgggaagaa tgtttccagc tccagaatgc    6360
taaatctcta agtctgtggt tggcagccac tattgcagca gctcttcaat gactcaatgc    6420
agttttgcat tctccctacc tttttttct aaaaccaata aaatagatac agcctttagg     6480 cttctctggga tttcccttag tcaagctagg gtcatcctga ctttcggcgt gaatttgcaa    6540
aacaagacct gactctgtac tcctgctcta aggactgtgc atggttccaa aggcttagct    6600
tgccagcata tttgagcttt ttccttctgt tcaaactgtt ccaaaatata aagaataaa     6660 attaattaag ttggcactgg acttccggtg gtcagtcatg tgtgtcatct gtcacgtttt    6720
tcgggctctg gtggaaatgg atctgtctgt cttctctcat aggtggtatt cacagccaac    6780
gactccggcc cccgccgcta caccattgcc gccctgctga gccccctactc ctattccacc   6840 acggctgtcg tcaccaatcc caaggaatga gggacttctc ctccagtgga cctgaaggac    6900
gagggatggg atttcatgta accaagagta ttccattttt actaaagcag tgttttcacc    6960
tcatatgcta tgttagaagt ccaggcagag acaataaaac attcctgtga aaggcacttt    7020
tcattccact ttaacttgat tttttaaatt cccttattgt cccttccaaa aaaagagaa    7080 tcaaatttt acaagaatc aaaggaattc tagaaagtat ctgggcagaa cgctaggaga     7140
gatccaaatt tccattgtct tgcaagcaaa gcacgtatta aatatgatct gcagccatta    7200
aaaagacaca ttctgtaaat gagagagcct tattttcctg taaccttcag caaatagcaa    7260
aagacacatt ccaagggccc acttcttac tgtgggcaat gtatgctata cgaagttata    7320
tgcatgccag tagcagcacc cacgtccacc ttctgtctag taatgtccaa cacctccctc    7380
agtccaaaca ctgctctgca tccatgtggc tcccatttat acctgaagca cttgatgggg    7440
cctcaatgtt ttactagagc ccaccccct gcaactctga acccctctgg atttgtctgt     7500
cagtgcctca ctggggcgtt ggataatttc ttaaaaggtc aagttccctc agcagcattc    7560
tctgagcagt ctgaagatgt gtgcttttca cagttcaaat ccatgtggct gtttcaccca    7620
cctgcctggc cttgggttat ctatcaggac ctagcctaga agcaggtgtg tggcacttaa    7680
cacctaagct gagtgactaa ctgaacactc aagtggatgc catctttgtc acttcttgac    7740
tgtgacacaa gcaactcctg atgccaaagc cctgcccacc cctctcatgc ccatatttgg    7800
acatggtaca ggtcctcact ggccatggtc tgtgaggtcc tggtcctctt tgacttcata    7860
```

```
attcctaggg gccactagta tctataagag gaagagggtg ctggctccca ggccacagcc      7920
cacaaaattc cacctgctca caggttggct ggctcgaccc aggtggtgtc ccctgctctg      7980
agccagctcc cggccaagcc agcaccatgg gaaccccaa gaagaagagg aaggtgcgta       8040
ccgatttaaa ttccaattta ctgaccgtac accaaaattt gcctgcatta ccggtcgatg      8100
caacgagtga tgaggttcgc aagaacctga tggacatgtt cagggatcgc caggcgtttt     8160
ctgagcatac ctggaaaatg cttctgtccg tttgccggtc gtgggcggca tggtgcaagt      8220
tgaataaccg gaaatggttt cccgcagaac ctgaagatgt tcgcgattat cttctatatc     8280
ttcaggcgcg cggtctggca gtaaaaacta tccagcaaca tttgggccag ctaaacatgc    8340
ttcatcgtcg gtccgggctg ccacgaccaa gtgacagcaa tgctgtttca ctggttatgc     8400
ggcggatccg aaaagaaaac gttgatgccg gtgaacgtgc aaaacaggta aatataaaat     8460
ttttaagtgt ataatgatgt taaactactg attctaattg tttgtgtatt ttaggctcta    8520
gcgttcgaac gcactgattt cgaccaggtt cgttcactca tggaaaatag cgatcgctgc    8580
caggatatac gtaatctggc atttctgggg attgcttata caccctgtt acgtatagcc      8640
gaaattgcca ggatcagggt taaagatatc tcacgtactg acggtgggag aatgttaatc     8700
catattggca gaacgaaaac gctggttagc accgcaggtg tagagaaggc acttagcctg    8760
ggggtaacta aactggtcga gcgatggatt tccgtctctg gtgtagctga tgatccgaat     8820
aactacctgt tttgccgggt cagaaaaaat ggtgttgccg cgccatctgc caccagccag    8880
ctatcaactc gcgccctgga agggattttt gaagcaactc atcgattgat ttacggcgct    8940
aaggatgact ctggtcagag ataccctggcc tggtctggac acagtgcccg tgtcggagcc   9000
gcgcgagata tggcccgcgc tggagtttca taccggaga tcatgcaagc tggtggctgg    9060
accaatgtaa atattgtcat gaactatatc cgtaacctgg atagtgaaac aggggcaatg    9120
gtgcgcctgc tggaagatgg cgattaggcg gccggccgct aatcagccat accacatttg    9180
tagaggtttt acttgcttta aaaaaccctcc cacacctccc cctgaacctg aaacataaaa    9240
tgaatgcaat tgttgttgtt aacttgttta ttgcagctta taatggttac aaataaagca    9300
atagcatcac aaatttcaca aataaagcat ttttttcact gcattctagt tgtggtttgt    9360
ccaaactcat caatgtatct tatcatgtct ggatccccg gctagagttt aaacactaga     9420
actagtggat cccccgggat catggcctcc gcgccgggtt ttggcgcctc ccgcgggcgc    9480
cccctcctc acggcgagcg ctgccacgtc agacgaaggg cgcagcgagc gtcctgatcc    9540
ttccgcccgg acgctcagga cagcggcccg ctgctcataa gactcggcct tagaaccccca  9600
gtatcagcag aaggacattt taggacggga cttgggtgac tctagggcac tggttttctt    9660
tccagagagc ggaacaggcg aggaaaagta gtcccttctc ggcgattctg cggagggatc    9720
tccgtggggc ggtgaacgcc gatgattata taaggacgcg ccgggtgtgg cacagctagt    9780
tccgtcgcag ccgggatttg ggtcgcggtt cttgtttgtg gatcgctgtg atcgtcactt     9840
ggtgagtagc gggctgctgg gctggccggg gctttcgtgg ccgccgggcc gctcggtggg     9900
acggaagcgt gtggagagac cgccaagggc tgtagtctgg gtccgcgagc aaggttgccc     9960
tgaactgggg gttgggggga gcgcagcaaa atggcggctg ttcccgagtc ttgaatggaa    10020
gacgcttgtg aggcgggctg tgaggtcgtt gaaacaaggt gggggcatg gtgggcggca     10080
agaacccaag gtcttgaggc cttcgctaat gcgggaaagc tcttattcgg gtgagatggg    10140
ctggggcacc atctggggac cctgacgtga agtttgtcac tgactggaga actcggtttg    10200
tcgtctgttg cggggcggc agttatggcg gtgccgttgg gcagtgcacc cgtacctttg     10260
```

-continued

```
ggagcgcgcg ccctcgtcgt gtcgtgacgt cacccgttct gttggcttat aatgcagggt    10320
ggggccacct gccggtaggt gtgcggtagg cttttctccg tcgcaggacg cagggttcgg    10380
gcctagggta ggctctcctg aatcgacagg cgccggacct ctggtgaggg gagggataag    10440
tgaggcgtca gtttctttgg tcggttttat gtacctatct tcttaagtag ctgaagctcc    10500
ggttttgaac tatgcgctcg ggttggcga gtgtgttttg tgaagttttt taggcaccttc    10560 ttgaaatgta atcatttggg tcaatatgta attttcagtg ttagactagt aaattgtccg    10620
ctaaattctg gccgtttttg gcttttttgt tagacgtgtt gacaattaat catcggcata    10680
gtatatcggc atagtataat acgacaaggt gaggaactaa accatgaccg agtacaagcc    10740
cacggtgcgc ctcgccaccc gcgacgacgt ccccagggcc gtacgcaccc tcgccgccgc    10800
gttcgccgac tacccgcca cgcgccacac cgtcgatccg gaccgccaca tcgagcgggt    10860
caccgagctg caagaactct tcctcacgcg cgtcgggctc gacatcggca aggtgtgggt    10920
cgcggacgac ggcgccgcgg tggcggtctg gaccacgccg gagagcgtcg aagcgggggc    10980
ggtgttcgcc gagatcggcc cgcgcatggc cgagttgagc ggttcccggc tggccgcgca    11040
gcaacagatg gaaggcctcc tggcgccgca ccggcccaag gagcccgcgt ggttcctggc    11100
caccgtcggc gtctcgcccg accaccaggg caagggtctg ggcagcgccg tcgtgctccc    11160
cggagtggag gcggccgagc gcgccggggt gcccgccttc ctggagacct ccgcgccccg    11220
caacctcccc ttctacgagc ggctcggctt caccgtcacc gccgacgtcg aggtgcccga    11280
aggaccgcgc acctggtgca tgacccgcaa gcccggtgcc tgacgccgc cccacgaccc    11340 gcagcgcccg accgaaagga gcgcacgacc ccatgcatcg atgatctaga gctcgctgat    11400
cagcctcgac tgtgccttct agttgccagc catctgttgt ttgcccctcc cccgtgcctt    11460
ccttgaccct ggaaggtgcc actcccactg tcctttccta ataaaatgag gaaattgcat    11520
cgcattgtct gagtaggtgt cattctattc tggggggtgg ggtggggcag gacagcaagg    11580
gggaggattg ggaagacaat agcaggcatg ctggggatgc ggtgggctct atggcttctg    11640
aggcggccta gataacttcg tataatgtat gctatacgaa gttatgctag gtaactataa    11700
cggtcctaag gtagcgagag actcagccca ggaggaccag gatcttgcca aagcagtagc    11760
atcccatttg taccaaaaca gtgttcttgc tctataaacc gtgttagcag ctcagga       11817
```

<210> SEQ ID NO 13
<211> LENGTH: 7476
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(97)
<223> OTHER INFORMATION: Mouse Sequence
<220> FEATURE:
<221> NAME/KEY: misc_feature
<222> LOCATION: (98)..(7298)
<223> OTHER INFORMATION: Human Sequence
<220> FEATURE:
<221> NAME/KEY: misc_feature
<222> LOCATION: (7299)..(7376)
<223> OTHER INFORMATION: Cassette LoxP Scar
<220> FEATURE:
<221> NAME/KEY: misc_feature
<222> LOCATION: (7377)..(7476)
<223> OTHER INFORMATION: Mouse Sequence

<400> SEQUENCE: 13

```
agcttggcag ggatcagcag cctgggttgg aaggaggggg tataaaagcc ccttcaccag      60
gagaagccgt cacacagatc cacaagctcc tgacaggatg gcttctcatc gtctgctcct     120
cctctgcctt gctggactgg tatttgtgtc tgaggctggc cctacggtga gtgtttctgt     180
gacatcccat tcctacattt aagattcacg ctaaatgaag tagaagtgac tccttccagc     240
tttgccaacc agcttttatt actagggcaa gggtacccag catctatttt taatataatt     300
aattcaaact tcaaaaagaa tgaagttcca ctgagcttac tgagctggga cttgaactct     360
gagcattcta cctcattgct ttggtgcatt aggtttgtaa tatctggtac ctctgtttcc     420
tcagatagat gatagaaata aagatatgat attaaggaag ctgttaatac tgaattttca     480
gaaaagtatc cctccataaa atgtatttgg gggacaaact gcaggagatt atattctggc     540
cctatagtta ttcaaaacgt atttattgat taatctttaa aaggcttagt gaacaatatt     600
ctagtcagat atctaattct taaatcctct agaagaatta actaatacta taaaatgggt     660
ctggatgtag ttctgacatt attttataac aactggtaag agggagtgac tatagcaaca     720
actaaaatga tctcaggaaa acctgtttgg ccctatgtat ggtacattac atcttttcag     780
taattccact caaatggaga cttttaacaa agcaactgtt ctcagggac ctattttctc     840 ccttaaaatt cattatacac atccctggtt gatagcagtg tgtctggagg cagaaaccat     900
tcttgctttg gaaacaatta cgtctgtgtt atactgagta gggaagctca ttaattgtcg     960
acacttacgt tcctgataat gggatcagtg tgtaattctt gtttcgctcc agatttctaa    1020
taccacaaag aataaatcct ttcactctga tcaattttgt taacttctca cgtgtcttct    1080
ctacacccag ggcaccggtg aatccaagtg tcctctgatg gtcaaagttc tagatgctgt    1140
ccgaggcagt cctgccatca atgtggccgt gcatgtgttc agaaaggctg ctgatgacac    1200
ctgggagcca tttgcctctg gtaagttgc caaagaaccc tcccacagga cttggtttta    1260
tcttcccgtt tgcccctcac ttggtagaga gaggctcaca tcatctgcta aagaatttac    1320
aagtagattg aaaaacgtag gcagaggtca agtatgccct ctgaaggatg ccctcttttt    1380
gttttgctta gctaggaagt gaccaggaac ctgagcatca tttaggggca gacagtagag    1440
aaaagaagga atcagaactc ctctcctcta gctgtggttt gcaacccttt tgggtcacag    1500
aacactttat gtaggtgatg aaaagtaaac attctatgcc cagaaaaaat gcacagatac    1560
acacacatac aaaatcatat atgtgatttt aggagtttca cagattccct ggtgtccctg    1620
ggtaacacca agctaagtg tccttgtctt agaatttag gaaaaggtat aatgtgtatt    1680
aacccattaa caaaggaaa ggaattcaga aatattatta accaggcatc tgtctgtagt    1740
taatatggat cacccaaaac ccaaggcttt tgcctaatga acactttggg gcacctactg    1800
tgtgcaaggc tggggctgt caagctcagt taaaaaaaaa aagatagaag agatggatcc    1860
atgaggcaaa gtacagcccc aggctaatcc cacgatcacc cgacttcatg tccaagagtg    1920
gcttctcacc ttcattagcc agttcacaat tttcatggag ttttctacc tgcactagca    1980 aaaacttcaa ggaaaataca tattaataaa tctaagcaaa gtgaccagaa gacagagcaa    2040
tcaggagacc ctttgcatcc agcagaagag gaactgctaa gtatttacat ctccacagag    2100
aagaatttct gttgggtttt aattgaaccc caagaaccac atgattcttc aaccattatt    2160
gggaagatca ttttcttagg tctggttta actggctttt tatttgggaa ttcatttatg    2220
tttatataaa atgccaagca taacatgaaa agtggttaca ggactattct aagggagaga    2280
cagaatggac accaaaaata ttccaatgtt cttgtgaatc ttttccttgc accaggacaa    2340
aaaaaaaaag aagtgaaaag aagaaaggag gagggggcata atcagagtca gtaaagacaa    2400
```

-continued

```
ctgctatttt tatctatcgt agctgttgca gtcaaatggg aagcaatttc caacattcaa    2460
ctatggagct ggtacttaca tggaaataga agttgcctag tgtttgttgc tggcaaagag    2520
ttatcagaga ggttaaatat ataaaaggga aagagtcag atacaggttc ttcttcctac     2580
tttaggtttt ccactgtgtg tgcaaatgat actccctggt ggtgtgcaga tgcctcaaag    2640
ctatcctcac accacaaggg agaggagcga gatcctgctg tcctggagaa gtgcagagtt    2700
agaacagctg tggccacttg catccaatca tcaatcttga atcacaggga ctctttctta    2760
agtaaacatt atacctggcc gggcacggtg gctcacgcct gtaatcccag cactttggga    2820
tgccaaagtg ggcatatcat ctgaggtcag gagttcaaga ccagcctggc caacatggca    2880
aaactccgtc tttatgaaaa atacaaaaat tagccaggca tggtggcagg cgcctgtaat    2940
cccagctaat gggaggctg aggctggaga tcccttgaa tctaggaggc agaggttgca     3000
gtgagctgag atcgtgccat tgcactccag cctgggtgac aagagtaaaa ctctgtctca    3060
aaaaaaaaaa attataccta cattctcttc ttatcagaga aaaaaatcta cagtgagctt    3120
ttcaaaaagt ttttacaaac ttttttgccat ttaatttcag ttaggagttt tccctacttc    3180
tgacttagtt gagggaaat gttcataaca tgtttataac atgtttatgt gtgttagttg     3240 gtggggtgt attactttgc catgccattt gtttcctcca tgcgtaactt aatccagact     3300
ttcacacctt ataggaaaac cagtgagtct agcgattcgc atgggctcac aactgaggag    3360
gaatttgtag aagggatata caaagtggaa atagacacca aatcttactg gaaggcactt    3420
ggcatctccc cattccatga gcatgcagag gtgagtatac agaccttcga gggttgtttt    3480
ggttttggtt tttgcttttg gcattccagg aaatgcacag ttttactcag tgtaccacag    3540
aaatgtccta aggaaggtga tgaatgacca aaggttccct ttcctattat acaagaaaaa    3600
attcacaaca ctctgagaag caaatttctt tttgactttg atgaaaatcc acttagtaac    3660
atgacttgaa cttacatgaa actactcata gtctattcat tccactttat atgaatattg    3720
atgtatctgc tgttgaaata atagtttatg aggcagccct ccagaccca cgtagagtgt     3780 atgtaacaag agatgcacca tttattctt cgaaaacccg taacattctt cattccaaaa     3840
cacatctggc ttctcggagg tctggacaag tgattcttgg caacacatac ctatagagac    3900
aataaaatca agtaataat ggcaacacaa tagataacat ttaccaagca tacaccatgt     3960
ggcagacaca attataagtg ttttccatat ttaacctact taatcctcag gaataagcca    4020
ctgaggtcag tcctattatt atccccatct tatagatgaa gaaatgagg caccaggaag     4080 tcaaataact tgtcaaaggt cacaagacta ggaaatacac aagtagaaat gtttacaatt    4140
aaggcccagg ctgggtttgc cctcagttct gctatgcctc gcattatgcc ccaggaaact    4200
ttttcccttg tgaaagccaa gcttaaaaaa agaaaagcca catttgtaac gtgctctgtt    4260
cccctgccta tggtgaggat cttcaaacag ttatacatgg acccagtccc cctgccttct    4320
ccttaatttc ttaagtcatt tgaaacagat ggctgtcatg gaaatagaat ccagacatgt    4380
tggtcagagt taaagatcaa ctaattccat caaaaatagc tcggcatgaa agggaactat    4440
tctctggctt agtcatggat gagactttca attgctataa agtggttcct ttattagaca    4500
atgttaccag ggaaacaaca gggtttgtt tgacttctgg ggcccacaag tcaacaagag     4560
agccccatct accaaggagc atgtccctga ctacccctca gccagcagca agacatggac    4620
cccagtcagg gcaggagcag ggtttcggcg gcgcccagca caagacattg ccctagagt     4680 ctcagcccct accctcgagt aatagatctg cctacctgag actgttgttt gcccaagagc    4740
```

-continued

```
tgggtctcag cctgatggga accatataaa aaggttcact gacatactgc ccacatgttg    4800
ttctctttca ttagatctta gcttccttgt ctgctcttca ttcttgcagt attcattcaa    4860
caaacattaa aaaaaaaaaa aagcattcta tgtgtggaac actctgctag atgctgtgga    4920
tttagaaatg aaaatacatc ccgacccttg gaatggaagg gaaaggactg aagtaagaca    4980
gattaagcag gaccgtcagc ccagcttgaa gcccagataa atacggagaa caagagagag    5040
cgagtagtga gagatgagtc ccaatgcctc actttggtga cgggtgcgtg gtgggcttca    5100
tgcagcttct tctgataaat gcctccttca gaactggtca actctacctt ggccagtgac    5160
ccaggtggtc atagtagatt taccaaggga aaatggaaac ttttattagg agctcttagg    5220
cctcttcact tcatggattt ttttttcctt tttttttgag atggagtttt gccctgtcac    5280
ccaggctgga atgcagtggt gcaatctcag ctcactgcaa cctccgcctc ccaggttcaa    5340
gcaattctcc tgcctcagcc tcccgagtag ctgggactac aggtgtgcgc caccacacca    5400
ggctaatttt tgtattttt gtaaagacag gttttcacca cgttggccag gctggtctga    5460
actccagacc tcaggtgatt cacctgtctc agcctcccaa agtgctggga ttacaggtgt    5520
gagccaccgt gcccggctac ttcatggatt tttgattaca gattatgcct cttacaattt    5580
ttaagaagaa tcagtgggc tgaaggtcaa tgtcaccata agacaaaaga catttttatt    5640
agttgattct agggaattgg ccttaagggg agcccttct tcctaagaga ttcttaggtg    5700
attctcactt cctcttgccc cagtattatt tttgttttg gtatggctca ctcagatcct    5760
tttttcctcc tatccctaag taatccgggt ttcttttcc catatttaga acaaaatgta    5820
tttatgcaga gtgtgtccaa acctcaaccc aaggcctgta tacaaaataa atcaaattaa    5880
acacatcttt actgtcttct acctcttcc tgacctcaat atatcccaac ttgcctcact    5940
ctgagaacca aggctgtccc agcacctgag tcgcagatat tctactgatt tgacagaact    6000
gtgtgactat ctggaacagc attttgatcc acaatttgcc cagttacaaa gcttaaatga    6060
gctctagtgc atgcatatat atttcaaaat tccaccatga tcttccacac tctgtattgt    6120
aaatagagcc ctgtaatgct tttacttcgt atttcattgc ttgttataca taaaaatata    6180
cttttcttct tcatgttaga aaatgcaaag aataggaggg tggggaatc tctgggcttg    6240 gagacaggag acttgccttc ctactatggt tccatcagaa tgtagactgg gacaatacaa    6300
taattcaagt ctggtttgct catctgtaaa ttgggaagaa tgtttccagc tccagaatgc    6360
taaatctcta agtctgtggt tggcagccac tattgcagca gctcttcaat gactcaatgc    6420
agttttgcat tctccctacc ttttttttct aaaaccaata aaatagatac agcctttagg    6480 cttttctggga tttcccttag tcaagctagg gtcatcctga ctttcggcgt gaatttgcaa    6540
aacaagacct gactctgtac tcctgctcta aggactgtgc atggttccaa aggcttagct    6600
tgccagcata tttgagcttt ttccttctgt tcaaactgtt ccaaaatata aagaataaa    6660 attaattaag ttggcactgg acttccggtg gtcagtcatg tgtgtcatct gtcacgtttt    6720
tcgggctctg gtggaaatgg atctgtctgt cttctctcat aggtggtatt cacagccaac    6780
gactccggcc ccgccgcta caccattgcc gccctgctga gccctactc ctattccacc    6840 acggctgtcg tcaccaatcc caaggaatga gggacttctc ctccagtgga cctgaaggac    6900
gagggatggg atttcatgta accaagagta ttccattttt actaaagcag tgttttcacc    6960
tcatatgcta tgttagaaagt ccaggcagag acaataaaac attcctgtga aaggcacttt    7020
tcattccact ttaacttgat tttttaaatt cccttattgt cccttccaaa aaaagagaa    7080 tcaaaatttt acaaagaatc aaaggaattc tagaaagtat ctgggcagaa cgctaggaga    7140
```

-continued

| | |
|---|---|
| gatccaaatt tccattgtct tgcaagcaaa gcacgtatta aatatgatct gcagccatta | 7200 |
| aaaagacaca ttctgtaaat gagagagcct tattttcctg taaccttcag caaatagcaa | 7260 |
| aagacacatt ccaagggccc acttctttac tgtgggcact cgagataact tcgtataatg | 7320 |
| tatgctatac gaagttatgc taggtaacta taacggtcct aaggtagcga gctagcgaga | 7380 |
| ctcagcccag gaggaccagg atcttgccaa agcagtagca tcccatttgt accaaaacag | 7440 |
| tgttcttgct ctataaaccg tgttagcagc tcagga | 7476 |

<210> SEQ ID NO 14
<211> LENGTH: 7201
<212> TYPE: DNA
<213> ORGANISM: Artificial Sequence
<220> FEATURE:
<223> OTHER INFORMATION: Synthetic

<400> SEQUENCE: 14

| | |
|---|---|
| atggcttctc atcgtctgct cctcctctgc cttgctggac tggtatttgt gtctgaggct | 60 |
| ggccctacgg tgagtgtttc tgtgacatcc cattcctaca tttaagattc acgctaaatg | 120 |
| aagtagaagt gactccttcc agctttgcca accagctttt attactaggg caagggtacc | 180 |
| cagcatctat ttttaatata attaattcaa acttcaaaaa gaatgaagtt ccactgagct | 240 |
| tactgagctg ggacttgaac tctgagcatt ctacctcatt gctttggtgc attaggtttg | 300 |
| taatatctgg tacctctgtt tcctcagata gatgatagaa ataagatat gatattaagg | 360 |
| aagctgttaa tactgaattt tcagaaaagt atccctccat aaaatgtatt tgggggacaa | 420 |
| actgcaggag attatattct ggccctatag ttattcaaaa cgtatttatt gattaatctt | 480 |
| taaaaggctt agtgaacaat attcagtca gatatctaat tcttaaatcc tctagaagaa | 540 |
| ttaactaata ctataaaatg ggtctggatg tagttctgac attatttat aacaactggt | 600 |
| aagagggagt gactatagca acaactaaaa tgatctcagg aaaacctgtt tggccctatg | 660 |
| tatggtacat tacatctttt cagtaattcc actcaaatgg agacttttaa caaagcaact | 720 |
| gttctcaggg gacctatttt ctcccttaaa attcattata cacatccctg gttgatagca | 780 |
| gtgtgtctgg aggcagaaac cattcttgct ttggaaacaa ttacgtctgt gttatactga | 840 |
| gtagggaagc tcattaattg tcgacactta cgttcctgat aatgggatca gtgtgtaatt | 900 |
| cttgtttcgc tccagatttc taataccaca agaataaat cctttcactc tgatcaattt | 960 |
| tgttaacttc tcacgtgtct tctctacacc cagggcaccg tgaatccaa gtgtcctctg | 1020 |
| atggtcaaag ttctagatgc tgtccgaggc agtcctgcca tcaatgtggc cgtgcatgtg | 1080 |
| ttcagaaagg ctgctgatga cacctgggag ccatttgcct ctgggtaagt tgccaaagaa | 1140 |
| ccctcccaca ggacttggtt ttatcttccc gtttgccct cacttggtag agagaggctc | 1200 |
| acatcatctg ctaaagaatt tacaagtaga ttgaaaaacg taggcagagg tcaagtatgc | 1260 |
| cctctgaagg atgccctctt tttgttttgc ttagctagga agtgaccagg aacctgagca | 1320 |
| tcatttaggg gcagacagta gagaaaagaa ggaatcagaa ctcctctcct ctagctgtgg | 1380 |
| tttgcaaccc ttttgggtca cagaacactt tatgtaggtg atgaaaagta aacattctat | 1440 |
| gcccagaaaa aatgcacaga tacacacaca tacaaaatca tatatgtgat ttaggagtt | 1500 |
| tcacagattc cctggtgtcc ctgggtaaca ccaaagctaa gtgtccttgt cttagaattt | 1560 |
| taggaaaagt tataatgtgt attaacccat taacaaaagg aaaggaattc agaaatatta | 1620 |
| ttaaccaggc atctgtctgt agttaatatg gatcacccaa aacccaaggc ttttgcctaa | 1680 |

```
tgaacacttt ggggcaccta ctgtgtgcaa ggctggggc tgtcaagctc agttaaaaaa    1740
aaaaagatag aagagatgga tccatgaggc aaagtacagc cccaggctaa tcccacgatc    1800
acccgacttc atgtccaaga gtggcttctc accttcatta gccagttcac aattttcatg    1860
gagtttttct acctgcacta gcaaaaactt caaggaaaat acatattaat aaatctaagc    1920
aaagtgacca gaagacagag caatcaggag acccttgca tccagcagaa gaggaactgc    1980
taagtattta catctccaca gagaagaatt tctgttgggt tttaattgaa ccccaagaac    2040
cacatgattc ttcaaccatt attgggaaga tcattttctt aggtctggtt ttaactggct    2100
ttttatttgg gaattcattt atgtttatat aaaatgccaa gcataacatg aaaagtggtt    2160
acaggactat tctaagggag agacagaatg gacaccaaaa atattccaat gttcttgtga    2220
atcttttcct tgcaccagga caaaaaaaaa aagaagtgaa aagaagaaag gaggaggggc    2280
ataatcagag tcagtaaaga caactgctat ttttatctat cgtagctgtt gcagtcaaat    2340
gggaagcaat ttccaacatt caactatgga gctggtactt acatggaaat agaagttgcc    2400
tagtgtttgt tgctggcaaa gagttatcag agaggttaaa tatataaaag ggaaagagt    2460 cagatacagg ttcttcttcc tactttaggt tttccactgt gtgtgcaaat gatactccct    2520
ggtggtgtgc agatgcctca aagctatcct cacaccacaa gggagaggag cgagatcctg    2580
ctgtcctgga gaagtgcaga gttagaacag ctgtggccac ttgcatccaa tcatcaatct    2640
tgaatcacag ggactctttc ttaagtaaac attatacctg gccgggcacg gtggctcacg    2700
cctgtaatcc cagcactttg ggatgccaaa gtgggcatat catctgaggt caggagttca    2760
agaccagcct ggccaacatg gcaaaactcc gtctttatga aaaatacaaa aattagccag    2820
gcatggtggc aggcgcctgt aatcccagct aattgggagg ctgaggctgg agaatccctt    2880
gaatctagga ggcagaggtt gcagtgagct gagatcgtgc cattgcactc cagcctgggt    2940
gacaagagta aaactctgtc tcaaaaaaaa aaaattatac ctacattctc ttcttatcag    3000
agaaaaaaat ctacagtgag cttttcaaaa agttttttaca aacttttgc catttaattt    3060 cagttaggag ttttccctac ttctgactta gttgagggga aatgttcata acatgtttat    3120
aacatgttta tgtgtgttag ttggtgggg tgtattactt gccatgcca tttgtttcct    3180 ccatgcgtaa cttaatccag acttcacac cttataggaa aaccagtgag tctagcgatt    3240
cgcatgggct cacaactgag gaggaatttg tagaagggat atacaaagtg gaaatagaca    3300
ccaaatctta ctggaaggca cttggcatct ccccattcca tgagcatgca gaggtgagta    3360
tacagacctt cgagggttgt tttggttttg gtttttgctt ttggcattcc aggaaatgca    3420 cagtttttact cagtgtacca cagaaatgtc ctaaggaagg tgatgaatga ccaaaggttc    3480
cctttcctat tatacaagaa aaaattcaca cactctgag aagcaaattt ctttttgact    3540
ttgatgaaaa tccacttagt aacatgactt gaacttacat gaaactactc atagtctatt    3600
cattccactt tatatgaata ttgatgtatc tgctgttgaa ataatagttt atgaggcagc    3660
cctccagacc ccacgtagag tgtatgtaac aagagatgca ccattttatt tctcgaaaac    3720
ccgtaacatt cttcattcca aaacacatct ggcttctcgg aggtctggac aagtgattct    3780
tggcaacaca tacctataga gacaataaaa tcaaagtaat aatggcaaca caatagataa    3840
catttaccaa gcatacacca tgtggcagac acaattataa gtgttttcca tatttaacct    3900
acttaatcct caggaataag ccactgaggt cagtcctatt attatcccca tcttatagat    3960
gaagaaaatg aggcaccagg aagtcaaata acttgtcaaa ggtcacaaga ctaggaaata    4020
cacaagtaga aatgtttaca attaaggccc aggctgggtt tgccctcagt tctgctatgc    4080
```

```
ctcgcattat gccccaggaa acttttccc ttgtgaaagc caagcttaaa aaaagaaaag    4140
ccacatttgt aacgtgctct gttccctgc ctatggtgag gatcttcaaa cagttataca    4200
tggacccagt cccctgcct tctccttaat ttcttaagtc atttgaaaca gatggctgtc    4260
atggaaatag aatccagaca tgttggtcag agttaaagat caactaattc catcaaaaat    4320
agctcggcat gaaagggaac tattctctgg cttagtcatg gatgagactt tcaattgcta    4380
taaagtggtt cctttattag acaatgttac cagggaaaca acaggggttt gtttgacttc    4440
tggggcccac aagtcaacaa gagagcccca tctaccaagg agcatgtccc tgactacccc    4500
tcagccagca gcaagacatg gaccccagtc agggcaggag cagggtttcg gcggcgccca    4560
gcacaagaca ttgcccctag agtctcagcc cctaccctcg agtaatagat ctgcctacct    4620
gagactgttg tttgcccaag agctgggtct cagcctgatg ggaaccatat aaaaaggttc    4680
actgacatac tgcccacatg ttgttctctt tcattagatc ttagcttcct tgtctgctct    4740
tcattcttgc agtattcatt caacaaacat taaaaaaaaa aaaaagcatt ctatgtgtgg    4800
aacactctgc tagatgctgt ggatttagaa atgaaaatac atcccgaccc ttggaatgga    4860
agggaaagga ctgaagtaag acagattaag caggaccgtc agcccagctt gaagcccaga    4920
taaatacgga gaacaagaga gagcgagtag tgagagatga gtcccaatgc ctcactttgg    4980
tgacgggtgc gtggtgggct tcatgcagct tcttctgata aatgcctcct tcagaactgg    5040
tcaactctac cttggccagt gacccaggtg gtcatagtag atttaccaag ggaaaatgga    5100 aactttatt aggagctctt aggcctcttc acttcatgga tttttttttc cttttttttt    5160
gagatggagt tttgccctgt cacccaggct ggaatgcagt ggtgcaatct cagctcactg    5220
caacctccgc ctcccaggtt caagcaattc tcctgcctca gcctcccgag tagctgggac    5280
tacaggtgtg cgccaccaca ccaggctaat ttttgtattt tttgtaaaga caggttttca    5340
ccacgttggc caggctggtc tgaactccag acctcaggtg attcacctgt ctcagcctcc    5400
caaagtgctg ggattacagg tgtgagccac cgtgcccggc tacttcatgg attttttgatt    5460 acagattatg cctcttacaa tttttaagaa gaatcaagtg ggctgaaggt caatgtcacc    5520
ataagacaaa agacattttt attagttgat tctagggaat tggccttaag gggagcectt    5580 tcttcctaag agattcttag gtgattctca cttcctcttg ccccagtatt attttgttt    5640 ttggtatggc tcactcagat cctttttcc tcctatccct aagtaatccg ggtttctttt    5700
tcccatattt agaacaaaat gtatttatgc agagtgtgtc caaacctcaa cccaaggcct    5760
gtatacaaaa taaatcaaat taaacacatc tttactgtct tctacctctt tcctgacctc    5820
aatatatccc aacttgcctc actctgagaa ccaaggctgt cccagcacct gagtcgcaga    5880
tattctactg atttgacaga actgtgtgac tatctggaac agcattttga tccacaattt    5940
gcccagttac aaagcttaaa tgagctctag tgcatgcata tatttcaa aattccacca    6000 tgatcttcca cactctgtat tgtaaataga gccctgtaat gcttttactt cgtatttcat    6060
tgcttgttat acataaaaat atacttttct tcttcatgtt agaaaatgca aagaatagga    6120
gggtggggga atctctgggc ttggagacag gagacttgcc ttcctactat ggttccatca    6180
gaatgtagac tgggacaata caataattca agtctggttt gctcatcgtg aaattgggaa    6240
gaatgtttcc agctccagaa tgctaaatct ctaagtctgt ggttggcagc cactattgca    6300
gcagctcttc aatgactcaa tgcagtttg cattctccct accttttttt tctaaaacca    6360
ataaaataga tacagccttt aggctttctg ggatttccct tagtcaagct agggtcatcc    6420
```

```
tgactttcgg cgtgaatttg caaaacaaga cctgactctg tactcctgct ctaaggactg    6480
tgcatggttc caaaggctta gcttgccagc atatttgagc ttttccttc tgttcaaact     6540 gttccaaaat ataaagaat aaaattaatt aagttggcac tggacttccg gtggtcagtc     6600
atgtgtgtca tctgtcacgt ttttcgggct ctggtggaaa tggatctgtc tgtcttctct    6660
cataggtggt attcacagcc aacgactccg gccccgccg ctacaccatt gccgccctgc      6720
tgagccccta ctcctattcc accacggctg tcgtcaccaa tcccaaggaa tgagggactt    6780
ctcctccagt ggacctgaag gacgagggat gggatttcat gtaaccaaga gtattccatt    6840
tttactaaag cagtgttttc acctcatatg ctatgttaga agtccaggca gagacaataa    6900
aacattcctg tgaaaggcac ttttcattcc actttaactt gatttttttaa attcccttat   6960 tgtcccttcc aaaaaaaaga gaatcaaaat tttacaaaga atcaaaggaa ttctagaaag    7020
tatctgggca gaacgctagg agagatccaa atttccattg tcttgcaagc aaagcacgta    7080
ttaaatatga tctgcagcca ttaaaaagac acattctgta aatgagagag ccttattttc    7140
ctgtaacctt cagcaaatag caaaagacac attccaaggg cccacttctt tactgtgggc    7200
a                                                                    7201
```

<210> SEQ ID NO 15
<211> LENGTH: 12208
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(97)
<223> OTHER INFORMATION: Mouse Sequence
<220> FEATURE:
<221> NAME/KEY: misc_feature
<222> LOCATION: (98)..(7298)
<223> OTHER INFORMATION: Human Sequence
<220> FEATURE:
<221> NAME/KEY: misc_feature
<222> LOCATION: (7299)..(12108)
<223> OTHER INFORMATION: Cassette Sequence
<220> FEATURE:
<221> NAME/KEY: misc_feature
<222> LOCATION: (12109)..(12208)
<223> OTHER INFORMATION: Mouse Sequence

<400> SEQUENCE: 15

```
agcttggcag ggatcagcag cctgggttgg aaggaggggg tataaaagcc ccttcaccag      60
gagaagccgt cacacagatc cacaagctcc tgacaggatg gcttctcatc gtctgctcct    120
cctctgcctt gctggactgg tatttgtgtc tgaggctggc cctacggtga gtgtttctgt    180
gacatcccat tcctacattt aagattcacg ctaaatgaag tagaagtgac tccttccagc    240
tttgccaacc agcttttatt actagggcaa gggtacccag catctatttt taatataatt    300
aattcaaact tcaaaagaa tgaagttcca ctgagcttac tgagctggga cttgaactct      360
gagcattcta cctcattgct ttggtgcatt aggtttgtaa tatctggtac ctctgtttcc    420
tcagatagat gatagaaata aagatatgat attaaggaag ctgttaatac tgaattttca    480
gaaaagtatc cctccataaa atgtatttgg gggacaaact gcaggagatt atattctggc    540
cctatagtta ttcaaaacgt atttattgat taatctttaa aaggcttagt gaacaatatt    600
ctagtcagat atctaattct taaatcctct agaagaatta actatactaa taaaatgggt   660
ctggatgtag ttctgacatt attttataac aactggtaag agggagtgac tatagcaaca    720
actaaaatga tctcaggaaa acctgtttgg ccctatgtat ggtacattac atctttttcag  780
```

-continued

```
taattccact caaatggaga cttttaacaa agcaactgtt ctcagggac ctatttctc      840 ccttaaaatt cattatacac atccctggtt gatagcagtg tgtctggagg cagaaaccat    900
tcttgctttg gaaacaatta cgtctgtgtt atactgagta gggaagctca ttaattgtcg    960
acacttacgt tcctgataat gggatcagtg tgtaattctt gtttcgctcc agatttctaa   1020
taccacaaag aataaatcct ttcactctga tcaattttgt taacttctca cgtgtcttct   1080
ctacacccag ggcaccggtg aatccaagtg tcctctgatg gtcaaagttc tagatgctgt   1140
ccgaggcagt cctgccatca atgtggccgt gcatgtgttc agaaaggctg ctgatgacac   1200
ctgggagcca tttgcctctg gtaagttgc caaagaaccc tcccacagga cttggtttta    1260
tcttcccgtt tgcccctcac ttggtagaga gaggctcaca tcatctgcta aagaatttac   1320
aagtagattg aaaaacgtag gcagaggtca agtatgccct ctgaaggatg ccctcttttt   1380
gttttgctta gctaggaagt gaccaggaac ctgagcatca tttaggggca gacagtagag   1440
aaaagaagga atcagaactc ctctcctcta gctgtggttt gcaaccctt tgggtcacag    1500 aacactttat gtaggtgatg aaagtaaac attctatgcc cagaaaaaat gcacagatac    1560
acacacatac aaaatcatat atgtgatttt aggagtttca cagattccct ggtgtccctg   1620
ggtaacacca agctaagtg tccttgtctt agaatttag gaaaaggtat aatgtgtatt    1680
aacccattaa caaaggaaa ggaattcaga aatattatta accaggcatc tgtctgtagt    1740
taatatggat cacccaaaac ccaaggcttt tgcctaatga acactttggg gcacctactg   1800
tgtgcaaggc tgggggctgt caagctcagt taaaaaaaaa aagatagaag agatggatcc   1860
atgaggcaaa gtacagcccc aggctaatcc cacgatcacc cgacttcatg tccaagagtg   1920
gcttctcacc ttcattagcc agttcacaat ttcatggag ttttctacc tgcactagca    1980 aaaacttcaa ggaaaataca tattaataaa tctaagcaaa gtgaccagaa gacagagcaa   2040
tcaggagacc ctttgcatcc agcagaagag gaactgctaa gtatttacat ctccacagag   2100
aagaatttct gttgggtttt aattgaaccc caagaaccac atgattcttc aaccattatt   2160
gggaagatca ttttcttagg tctggtttta actggctttt tatttgggaa ttcatttatg   2220
tttatataaa atgccaagca taacatgaaa agtggttaca ggactattct aagggagaga   2280
cagaatggac accaaaaata ttccaatgtt cttgtgaatc ttttccttgc accaggacaa   2340
aaaaaaaaag aagtgaaaag aagaaggag gagggcata atcagagtca gtaaagacaa    2400
ctgctatttt tatctatcgt agctgttgca gtcaaatggg aagcaatttc caacattcaa   2460
ctatggagct ggtacttaca tggaaataga agttgcctag tgtttgttgc tggcaaagag   2520
ttatcagaga ggttaaatat ataaaggga aagagtcag atacaggttc ttcttcctac    2580
tttaggtttt ccactgtgtg tgcaaatgat actccctggt ggtgtgcaga tgcctcaaag   2640
ctatcctcac accacaaggg agaggagcga atcctgctg tcctggagaa gtgcagagtt    2700
agaacagctg tggccacttg catccaatca tcaatcttga atcacaggga ctcttttctta  2760 agtaaacatt atacctggcc gggcacggtg gctcacgcct gtaatcccag cactttggga   2820
tgccaaagtg ggcatatcat ctgaggtcag gagttcaaga ccagcctggc caacatggca   2880
aaactccgtc tttatgaaaa atacaaaaat tagccaggca tggtggcagg cgcctgtaat   2940
cccagctaat tgggaggctg aggctggaga atcccttgaa tctaggaggc agaggttgca   3000
gtgagctgag atcgtgccat tgcactccag cctgggtgac aagagtaaaa ctctgtctca   3060
aaaaaaaaaa attataccta cattctcttc ttatcagaga aaaaaatcta cagtgagctt   3120
```

```
ttcaaaaagt ttttacaaac tttttgccat ttaatttcag ttaggagttt tccctacttc    3180
tgacttagtt gagggaaat gttcataaca tgtttataac atgtttatgt gtgttagttg     3240 gtggggtgt attactttgc catgccattt gtttcctcca tgcgtaactt aatccagact     3300
ttcacacctt ataggaaaac cagtgagtct ggagagctgc atgggctcac aactgaggag    3360
gaatttgtag aagggatata caaagtggaa atagacacca atcttactg gaaggcactt     3420 ggcatctccc cattccatga gcatgcagag gtgagtatac agaccttcga gggttgtttt    3480
ggttttggtt tttgcttttg gcattccagg aaatgcacag ttttactcag tgtaccacag    3540
aaatgtccta aggaaggtga tgaatgacca aaggttccct ttcctattat acaagaaaaa    3600
attcacaaca ctctgagaag caaatttctt tttgactttg atgaaaatcc acttagtaac    3660
atgacttgaa cttacatgaa actactcata gtctattcat tccactttat atgaatattg    3720
atgtatctgc tgttgaaata atagtttatg aggcagccct ccagacccca cgtagagtgt    3780
atgtaacaag agatgcacca ttttatttct cgaaacccg taacattctt cattccaaaa     3840
cacatctggc ttctcggagg tctggacaag tgattcttgg caacacatac ctatagagac    3900
aataaaatca aagtaataat ggcaacacaa tagataacat ttaccaagca tacaccatgt    3960
ggcagacaca attataagtg ttttccatat ttaacctact taatcctcag gaataagcca    4020
ctgaggtcag tcctattatt atccccatct tatagatgaa gaaatgagg caccaggaag     4080 tcaaataact tgtcaaaggt cacaagacta ggaaatacac aagtagaaat gtttacaatt    4140
aaggcccagg ctgggtttgc cctcagttct gctatgcctc gcattatgcc ccaggaaact    4200
ttttcccttg tgaaagccaa gcttaaaaaa agaaaagcca catttgtaac gtgctctgtt    4260
cccctgccta tggtgaggat cttcaaacag ttatacatgg acccagtccc cctgccttct    4320
ccttaatttc ttaagtcatt tgaaacagat ggctgtcatg gaaatagaat ccagacatgt    4380
tggtcagagt taaagatcaa ctaattccat caaaaatagc tcggcatgaa agggaactat    4440
tctctggctt agtcatggat gagactttca attgctataa agtggttcct ttattagaca    4500
atgttaccag ggaaacaaca ggggtttgtt tgacttctgg ggcccacaag tcaacaagag    4560
agccccatct accaaggagc atgtccctga ctacccctca gccagcagca agacatggac    4620
cccagtcagg gcaggagcag ggtttcggcg gcgcccagca caagacattg cccctagagt    4680
ctcagcccct accctcgagt aatagatctg cctacctgag actgttgttt gcccaagagc    4740
tgggtctcag cctgatggga accatataaa aaggttcact gacatactgc ccacatgttg    4800 ttctcttca ttagatctta gcttccttgt ctgctcttca ttcttgcagt attcattcaa     4860
caaacattaa aaaaaaaaa aagcattcta tgtgtggaac actctgctag atgctgtgga    4920
tttagaaatg aaaatacatc ccgacccttg gaatggaagg gaaggactg aagtaagaca     4980 gattaagcag gaccgtcagc ccagcttgaa gcccagataa atacggagaa caagagagag    5040
cgagtagtga gagatgagtc ccaatgcctc actttggtga cgggtgcgtg gtgggcttca    5100
tgcagcttct tctgataaat gcctccttca gaactggtca actctacctt ggccagtgac    5160
ccaggtggtc atagtagatt taccaaggga aaatggaaac ttttattagg agctcttagg    5220
cctcttcact tcatggattt tttttccttt ttttttgag atggagtttt gcctgtcac      5280 ccaggctgga atgcagtggt gcaatctcag ctcactgcaa cctccgcctc ccaggttcaa    5340
gcaattctcc tgcctcagcc tcccgagtag ctgggactac aggtgtgcgc caccacacca    5400
ggctaatttt tgtattttt gtaaagacag gttttcacca cgttggccag gctggtctga    5460
actccagacc tcaggtgatt cacctgtctc agcctcccaa agtgctggga ttacaggtgt    5520
```

```
gagccaccgt gcccggctac ttcatggatt tttgattaca gattatgcct cttacaattt    5580
ttaagaagaa tcaagtgggc tgaaggtcaa tgtcaccata agacaaaaga catttttatt    5640
agttgattct agggaattgg ccttaagggg agccctttct tcctaagaga ttcttaggtg    5700
attctcactt cctcttgccc cagtattatt tttgtttttg gtatggctca ctcagatcct    5760
tttttcctcc tatccctaag taatccgggt ttcttttttcc catatttaga acaaaatgta    5820
tttatgcaga gtgtgtccaa acctcaaccc aaggcctgta tacaaaataa atcaaattaa    5880
acacatcttt actgtcttct acctcttttcc tgacctcaat atatcccaac ttgcctcact    5940
ctgagaacca aggctgtccc agcacctgag tcgcagatat tctactgatt tgacagaact    6000
gtgtgactat ctggaacagc attttgatcc acaatttgcc cagttacaaa gcttaaatga    6060
gctctagtgc atgcatatat atttcaaaat tccaccatga tcttccacac tctgtattgt    6120
aaatagagcc ctgtaatgct tttacttcgt atttcattgc ttgttataca taaaaatata    6180
cttttcttct tcatgttaga aaatgcaaag aataggaggg tggggaatc tctgggcttg     6240 gagacaggag acttgccttc ctactatggt tccatcagaa tgtagactgg gacaatacaa    6300
taattcaagt ctggtttgct catctgtaaa ttgggaagaa tgtttccagc tccagaatgc    6360
taaatctcta agtctgtggt tggcagccac tattgcagca gctcttcaat gactcaatgc    6420
agttttgcat tctccctacc tttttttttct aaaaccaata aaatagatac agcctttagg    6480
ctttctggga tttcccttag tcaagctagg gtcatcctga ctttcggcgt gaatttgcaa    6540
aacaagacct gactctgtac tcctgctcta aggactgtgc atggttccaa aggcttagct    6600
tgccagcata tttgagcttt ttccttctgt tcaaactgtt ccaaaatata aagaataaa    6660 attaattaag ttggcactgg acttccggtg gtcagtcatg tgtgtcatct gtcacgtttt    6720
tcgggctctg gtggaaatgg atctgtctgt cttctctcat aggtggtatt cacagccaac    6780
gactccggcc cccgccgcta caccattgcc gccctgctga gccctactc ctattccacc     6840 acggctgtcg tcaccaatcc caaggaatga gggacttctc ctccagtgga cctgaaggac    6900
gagggatggg atttcatgta accaagagta ttccattttt actaaagcag tgttttcacc    6960
tcatatgcta tgttagaagt ccaggcagag acaataaaac attcctgtga aaggcacttt    7020
tcattccact ttaacttgat ttttttaaatt ccctttattgt cccttccaaa aaaaagagaa    7080
tcaaaatttt acaagaatc aaaggaattc tagaaagtat ctgggcagaa cgctaggaga     7140
gatccaaatt tccattgtct tgcaagcaaa gcacgtatta aatatgatct gcagccatta    7200
aaaagacaca ttctgtaaat gagagagcct tattttcctg taaccttcag caaatagcaa    7260
aagacacatt ccaagggccc acttctttac tgtgggcact cgagataact tcgtataatg    7320
tatgctatac gaagttatat gcatgccagt agcagcaccc acgtccacct tctgtctagt    7380
aatgtccaac acctccctca gtccaaacac tgctctgcat ccatgtggct cccatttata    7440
cctgaagcac ttgatgggc ctcaatgttt tactagagcc cacccccctg caactctgag     7500
accctctgga tttgtctgtc agtgcctcac tggggcgttg gataatttct taaaaggtca    7560
agttccctca gcagcattct ctgagcagtc tgaagatgtg tgcttttcac agttcaaatc    7620
catgtggctg tttcacccac ctgcctggcc ttggttatc tatcaggacc tagcctagaa     7680
gcaggtgtgt ggcacttaac acctaagctg agtgactaac tgaacactca agtggatgcc    7740
atctttgtca cttcttgact gtgacacaag caactcctga tgccaaagcc ctgcccaccc    7800
ctctcatgcc catatttgga catggtacag gtcctcactg gccatggtct gtgaggtcct    7860
```

-continued

| | |
|---|---|
| ggtcctcttt gacttcataa ttcctagggg ccactagtat ctataagagg aagagggtgc | 7920 |
| tggctcccag gccacagccc acaaaattcc acctgctcac aggttggctg gctcgaccca | 7980 |
| ggtggtgtcc cctgctctga gccagctccc ggccaagcca gcaccatggg aaccccaag | 8040 |
| aagaagagga aggtgcgtac cgatttaaat tccaatttac tgaccgtaca ccaaaatttg | 8100 |
| cctgcattac cggtcgatgc aacgagtgat gaggttcgca agaacctgat ggacatgttc | 8160 |
| agggatcgcc aggcgttttc tgagcatacc tggaaaatgc ttctgtccgt ttgccggtcg | 8220 |
| tgggcggcat ggtgcaagtt gaataaccgg aaatggtttc ccgcagaacc tgaagatgtt | 8280 |
| cgcgattatc ttctatatct tcaggcgcgc ggtctggcag taaaaactat ccagcaacat | 8340 |
| ttgggccagc taaacatgct tcatcgtcgg tccgggctgc cacgaccaag tgacagcaat | 8400 |
| gctgttttcac tggttatgcg gcggatccga aaagaaaacg ttgatgccgg tgaacgtgca | 8460 |
| aaacaggtaa atataaaatt tttaagtgta taatgatgtt aaactactga ttctaattgt | 8520 |
| ttgtgtattt taggctctag cgttcgaacg cactgatttc gaccaggttc gttcactcat | 8580 |
| ggaaaatagc gatcgctgcc aggatatacg taatctggca tttctgggga ttgcttataa | 8640 |
| caccctgtta cgtatagccg aaattgccag gatcagggtt aaagatatct cacgtactga | 8700 |
| cggtgggaga atgttaatcc atattggcag aacgaaaacg ctggttagca ccgcaggtgt | 8760 |
| agagaaggca cttagcctgg gggtaactaa actggtcgag cgatggattt ccgtctctgg | 8820 |
| tgtagctgat gatccgaata actacctgtt ttgccgggtc agaaaaaatg tgttgccgc | 8880 |
| gccatctgcc accagccagc tatcaactcg cgccctggaa gggattttg aagcaactca | 8940 |
| tcgattgatt tacggcgcta aggatgactc tggtcagaga tacctggcct ggtctggaca | 9000 |
| cagtgcccgt gtcggagccg cgcgagatat ggcccgcgct ggagtttcaa taccggagat | 9060 |
| catgcaagct ggtggctgga ccaatgtaaa tattgtcatg aactatatcc gtaacctgga | 9120 |
| tagtgaaaca ggggcaatgg tgcgcctgct ggaagatggc gattaggcgg ccggccgcta | 9180 |
| atcagccata ccacatttgt agaggtttta cttgctttaa aaaacctccc acacctcccc | 9240 |
| ctgaacctga acataaaat gaatgcaatt gttgttgtta acttgtttat tgcagcttat | 9300 |
| aatggttaca aataaagcaa tagcatcaca aatttcacaa ataaagcatt tttttcactg | 9360 |
| cattctagtt gtggtttgtc caaactcatc aatgtatctt atcatgtctg atccccgg | 9420 |
| ctagagttta aacactagaa ctagtggatc ccccgggatc atggcctccg cgccgggttt | 9480 |
| tggcgcctcc cgcgggcgcc cccctcctca cggcgagcgc tgccacgtca gacgaagggc | 9540 |
| gcagcgagcg tcctgatcct tccgcccgga cgctcaggac agcggcccgc tgctcataag | 9600 |
| actcggcctt agaaccccag tatcagcaga aggacatttt aggacgggac ttgggtgact | 9660 |
| ctagggcact ggttttcttt ccagagagcg aacaggcga ggaaaagtag tcccttctcg | 9720 |
| gcgattctgc ggagggatct ccgtggggcg gtgaacgccg atgattatat aaggacgcgc | 9780 |
| cgggtgtggc acagctagtt ccgtcgcagc cgggatttgg gtcgcggttc ttgtttgtgg | 9840 |
| atcgctgtga tcgtcacttg gtgagtagcg ggctgctggg ctggcgggg ctttcgtggc | 9900 |
| cgccgggccg ctcggtggga cggaagcgtg tggagagacc gccaagggct gtagtctggg | 9960 |
| tccgcgagca aggttgccct gaactggggg ttggggggag cgcagcaaaa tggcggctgt | 10020 |
| tcccgagtct tgaatggaag acgcttgtga ggcgggctgt gaggtcgttg aaacaaggtg | 10080 |
| gggggcatgg tgggcggcaa gaacccaagg tcttgaggcc ttcgctaatg cgggaaagct | 10140 |
| cttattcggg tgagatgggc tggggcacca tctgggacc ctgacgtgaa gtttgtcact | 10200 |
| gactggagaa ctcggtttgt cgtctgttgc gggggcggca gttatggcgg tgccgttggg | 10260 |

```
cagtgcaccc gtacctttgg gagcgcgcgc cctcgtcgtg tcgtgacgtc acccgttctg    10320
ttggcttata atgcagggtg gggccacctg ccggtaggtg tgcggtaggc ttttctccgt    10380
cgcaggacgc agggttcggg cctagggtag gctctcctga atcgacaggc gccggacctc    10440
tggtgagggg agggataagt gaggcgtcag tttctttggt cggttttatg tacctatctt    10500
cttaagtagc tgaagctccg gttttgaact atgcgctcgg ggttggcgag tgtgttttgt    10560 gaagttttt aggcaccttt tgaaatgtaa tcatttgggt caatatgtaa ttttcagtgt    10620
tagactagta aattgtccgc taaattctgg ccgttttggg cttttttgtt agacgtgttg    10680
acaattaatc atcggcatag tatatcggca tagtataata cgacaaggtg aggaactaaa    10740
ccatgggatc ggccattgaa caagatggat tgcacgcagg ttctccggcc gcttgggtgg    10800
agaggctatt cggctatgac tgggcacaac agacaatcgg ctgctctgat gccgccgtgt    10860
tccggctgtc agcgcagggg cgcccggttc ttttttgtcaa gaccgacctg tccggtgccc    10920
tgaatgaact gcaggacgag gcagcgcggc tatcgtggct ggccacgacg ggcgttcctt    10980
gcgcagctgt gctcgacgtt gtcactgaag cgggaaggga ctggctgcta ttgggcgaag    11040
tgccggggca ggatctcctg tcatctcacc ttgctcctgc cgagaaagta tccatcatgg    11100
ctgatgcaat gcggcggctg catacgcttg atccggctac ctgcccattc gaccaccaag    11160
cgaaacatcg catcgagcga gcacgtactc ggatggaagc cggtcttgtc gatcaggatg    11220
atctggacga agagcatcag gggctcgcgc cagccgaact gttcgccagg ctcaaggcgc    11280
gcatgcccga cggcgatgat ctcgtcgtga cccatggcga tgcctgcttg ccgaatatca    11340
tggtggaaaa tggccgcttt tctggattca tcgactgtgg ccggctgggt gtggcggacc    11400
gctatcagga catagcgttg gctacccgtg atattgctga agagcttggc ggcgaatggg    11460
ctgaccgctt cctcgtgctt tacggtatcg ccgctcccga ttcgcagcgc atcgccttct    11520
atcgccttct tgacgagttc ttctgagggg atccgctgta agtctgcaga aattgatgat    11580
ctattaaaca ataaagatgt ccactaaaat ggaagttttt cctgtcatac tttgttaaga    11640
agggtgagaa cagagtacct acattttgaa tggaaggatt ggagctacgg gggtgggggt    11700
ggggtgggat tagataaatg cctgctcttt actgaaggct ctttactatt gctttatgat    11760
aatgtttcat agttggatat cataatttaa acaagcaaaa ccaaattaag ggccagctca    11820
ttcctcccac tcatgatcta tagatctata gatctctcgt gggatcattg ttttttctctt    11880 gattcccact ttgtggttct aagtactgtg gtttccaaat gtgtcagttt catagcctga    11940
agaacgagat cagcagcctc tgttccacat acacttcatt ctcagtattg ttttgccaag    12000
ttctaattcc atcagacctc gacctgcagc ccctagataa cttcgtataa tgtatgctat    12060
acgaagttat gctaggtaac tataacggtc taaggtagc gagctagcga gactcagccc    12120
aggaggacca ggatcttgcc aaagcagtag catcccattt gtaccaaaac agtgttcttg    12180
ctctataaac cgtgttagca gctcagga                                      12208
```

<210> SEQ ID NO 16
<211> LENGTH: 7476
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(97)
<223> OTHER INFORMATION: Mouse Sequence
<220> FEATURE:

```
<221> NAME/KEY: misc_feature
<222> LOCATION: (98)..(7298)
<223> OTHER INFORMATION: Human Sequence
<220> FEATURE:
<221> NAME/KEY: misc_feature
<222> LOCATION: (7299)..(7376)
<223> OTHER INFORMATION: Cassette LoxP Scar
<220> FEATURE:
<221> NAME/KEY: misc_feature
<222> LOCATION: (7377)..(7476)
<223> OTHER INFORMATION: Mouse Sequence

<400> SEQUENCE: 16
```

| | | | | | |
|---|---|---|---|---|---|
| agcttggcag | ggatcagcag | cctgggttgg | aaggagggg | tataaaagcc | ccttcaccag | 60 |
| gagaagccgt | cacacagatc | cacaagctcc | tgacaggatg | gcttctcatc | gtctgctcct | 120 |
| cctctgcctt | gctggactgg | tatttgtgtc | tgaggctggc | cctacggtga | gtgtttctgt | 180 |
| gacatcccat | tcctacattt | aagattcacg | ctaaatgaag | tagaagtgac | tccttccagc | 240 |
| tttgccaacc | agcttttatt | actagggcaa | gggtacccag | catctatttt | taatataatt | 300 |
| aattcaaact | tcaaaagaa | tgaagttcca | ctgagcttac | tgagctggga | cttgaactct | 360 |
| gagcattcta | cctcattgct | ttggtgcatt | aggtttgtaa | tatctggtac | ctctgtttcc | 420 |
| tcagatagat | gatagaaata | aagatatgat | attaaggaag | ctgttaatac | tgaattttca | 480 |
| gaaaagtatc | cctccataaa | atgtatttgg | gggacaaact | gcaggagatt | atattctggc | 540 |
| cctatagtta | ttcaaaacgt | atttattgat | taatctttaa | aaggcttagt | gaacaatatt | 600 |
| ctagtcagat | atctaattct | taaatcctct | agaagaatta | actaatacta | taaaatgggt | 660 |
| ctggatgtag | ttctgacatt | attttataac | aactggtaag | agggagtgac | tatagcaaca | 720 |
| actaaaatga | tctcaggaaa | acctgtttgg | ccctatgtat | ggtacattac | atcttttcag | 780 |
| taattccact | caaatggaga | cttttaacaa | agcaactgtt | ctcaggggac | ctattttctc | 840 |
| ccttaaaatt | cattatacac | atccctggtt | gatagcagtg | tgtctggagg | cagaaaccat | 900 |
| tcttgctttg | gaaacaatta | cgtctgtgtt | atactgagta | gggaagctca | ttaattgtcg | 960 |
| acacttacgt | tcctgataat | gggatcagtg | tgtaattctt | gtttcgctcc | agatttctaa | 1020 |
| taccacaaag | aataaatcct | ttcactctga | tcaattttgt | taacttctca | cgtgtcttct | 1080 |
| ctacacccag | ggcaccggtg | aatccaagtg | tcctctgatg | gtcaaagttc | tagatgctgt | 1140 |
| ccgaggcagt | cctgccatca | atgtggccgt | gcatgtgttc | agaaaggctg | ctgatgacac | 1200 |
| ctgggagcca | tttgcctctg | ggtaagttgc | caaagaaccc | tcccacagga | cttggtttta | 1260 |
| tcttcccgtt | tgcccctcac | ttggtagaga | gaggctcaca | tcatctgcta | aagaatttac | 1320 |
| aagtagattg | aaaaacgtag | gcagaggtca | agtatgccct | ctgaaggatg | ccctcttttt | 1380 |
| gttttgctta | gctaggaagt | gaccaggaac | ctgagcatca | tttagggca | gacagtagag | 1440 |
| aaaagaagga | atcagaactc | ctctcctcta | gctgtggttt | gcaacccttt | tgggtcacag | 1500 |
| aacactttat | gtaggtgatg | aaaagtaaac | attctatgcc | cagaaaaaat | gcacagatac | 1560 |
| acacacatac | aaaatcatat | atgtgatttt | aggagtttca | cagattccct | ggtgtccctg | 1620 |
| ggtaacacca | agctaagtg | tccttgtctt | agaattttag | gaaaaggtat | aatgtgtatt | 1680 |
| aacccattaa | caaaggaaa | ggaattcaga | aatattatta | accaggcatc | tgtctgtagt | 1740 |
| taatatggat | cacccaaaac | ccaaggcttt | tgcctaatga | acactttggg | gcacctactg | 1800 |
| tgtgcaaggc | tgggggctgt | caagctcagt | taaaaaaaa | aagatagaag | agatggatcc | 1860 |
| atgaggcaaa | gtcagccccc | aggctaatcc | cacgatcacc | cgacttcatg | tccaagagtg | 1920 |
| gcttctcacc | ttcattagcc | agttcacaat | tttcatggag | tttttctacc | tgcactagca | 1980 |

```
aaaacttcaa ggaaaataca tattaataaa tctaagcaaa gtgaccagaa gacagagcaa    2040
tcaggagacc ctttgcatcc agcagaagag gaactgctaa gtatttacat ctccacagag    2100
aagaatttct gttgggtttt aattgaaccc caagaaccac atgattcttc aaccattatt    2160
gggaagatca ttttcttagg tctggtttta actggctttt tatttgggaa ttcatttatg    2220
tttatataaa atgccaagca taacatgaaa agtggttaca ggactattct aagggagaga    2280
cagaatggac accaaaaata ttccaatgtt cttgtgaatc ttttccttgc accaggacaa    2340
aaaaaaaaag aagtgaaaag aagaaggag gaggggcata atcagagtca gtaaagacaa    2400
ctgctatttt tatctatcgt agctgttgca gtcaaatggg aagcaatttc caacattcaa    2460
ctatggagct ggtacttaca tggaaataga agttgcctag tgtttgttgc tggcaaagag    2520
ttatcagaga ggttaaatat ataaaaggga aaagagtcag atacaggttc ttcttcctac    2580
tttaggtttt ccactgtgtg tgcaaatgat actccctggt ggtgtgcaga tgcctcaaag    2640
ctatcctcac accacaaggg agaggagcga atcctgctg tcctggagaa gtgcagagtt    2700
agaacagctg tggccacttg catccaatca tcaatcttga atcacaggga ctctttctta    2760
agtaaacatt atacctggcc gggcacggtg gctcacgcct gtaatcccag cactttggga    2820
tgccaaagtg ggcatatcat ctgaggtcag gagttcaaga ccagcctggc caacatggca    2880
aaactccgtc tttatgaaaa atacaaaaat tagccaggca tggtggcagg cgcctgtaat    2940
cccagctaat tgggaggctg aggctggaga atcccttgaa tctaggaggc agaggttgca    3000
gtgagctgag atcgtgccat tgcactccag cctgggtgac aagagtaaaa ctctgtctca    3060 aaaaaaaaa attataccta cattctcttc ttatcagaga aaaaaatcta cagtgagctt    3120
ttcaaaaagt ttttacaaac tttttgccat ttaatttcag ttaggagttt tccctacttc    3180
tgacttagtt gaggggaaat gttcataaca tgtttataac atgtttatgt gtgttagttg    3240 gtggggtgt attactttgc catgccattt gtttcctcca tgcgtaactt aatccagact    3300
ttcacacctt ataggaaaac cagtgagtct ggagagctgc atgggctcac aactgaggag    3360
gaatttgtag aagggatata caaagtggaa atagacacca atcttactg gaaggcactt    3420 ggcatctccc cattccatga gcatgcagag gtgagtatac agaccttcga gggttgtttt    3480
ggttttggtt tttgcttttg gcattccagg aaatgcacag ttttactcag tgtaccacag    3540
aaatgtccta aggaaggtga tgaatgacca aaggttccct ttcctattat acaagaaaaa    3600
attcacaaca ctctgagaag caaatttctt tttgactttg atgaaaatcc acttagtaac    3660
atgacttgaa cttacatgaa actactcata gtctattcat tccactttat atgaatattg    3720
atgtatctgc tgttgaaata atagtttatg aggcagccct ccagacccca cgtagagtgt    3780
atgtaacaag agatgcacca ttttatttct cgaaacccg taacattctt cattccaaaa    3840
cacatctggc ttctcggagg tctggacaag tgattcttgg caacacatac ctatagagac    3900
aataaaatca agtaataat ggcaacacaa tagataacat ttaccaagca tacaccatgt    3960
ggcagacaca attataagtg ttttccatat ttaacctact taatcctcag gaataagcca    4020
ctgaggtcag tcctattatt atccccatct tatagatgaa gaaaatgagg caccaggaag    4080
tcaaataact tgtcaaggt cacaagacta ggaaatacac aagtagaaat gtttacaatt    4140
aaggcccagg ctgggtttgc cctcagttct gctatgcctc gcattatgcc ccaggaaact    4200
ttttcccttg tgaaagccaa gcttaaaaaa agaaaagcca catttgtaac gtgctctgtt    4260
cccctgccta tggtgaggat cttcaaacag ttatacatgg acccagtccc cctgccttct    4320
```

```
ccttaatttc ttaagtcatt tgaaacagat ggctgtcatg gaaatagaat ccagacatgt    4380
tggtcagagt taaagatcaa ctaattccat caaaaatagc tcggcatgaa agggaactat    4440
tctctggctt agtcatggat gagactttca attgctataa agtggttcct ttattagaca    4500
atgttaccag ggaaacaaca ggggtttgtt tgacttctgg ggcccacaag tcaacaagag    4560
agccccatct accaaggagc atgtccctga ctaccoctca gccagcagca agacatggac    4620
cccagtcagg gcaggagcag ggtttcggcg gcgcccagca caagacattg cccctagagt    4680
ctcagcccct accctcgagt aatagatctg cctacctgag actgttgttt gcccaagagc    4740
tgggtctcag cctgatggga accatataaa aaggttcact gacatactgc ccacatgttg    4800
ttctctttca ttagatctta gcttccttgt ctgctcttca ttcttgcagt attcattcaa    4860
caaacattaa aaaaaaaaaa aagcattcta tgtgtggaac actctgctag atgctgtgga    4920
tttagaaatg aaaatacatc ccgacccttg gaatggaagg gaaaggactg aagtaagaca    4980
gattaagcag gaccgtcagc ccagcttgaa gcccagataa atacggagaa caagagagag    5040
cgagtagtga gagatgagtc ccaatgcctc actttggtga cgggtgcgtg gtgggcttca    5100
tgcagcttct tctgataaat gcctccttca gaactggtca actctacctt ggccagtgac    5160
ccaggtggtc atagtagatt taccaaggga aaatggaaac ttttattagg agctcttagg    5220
cctcttcact tcatggattt ttttttcctt tttttttgag atggagtttt gccctgtcac    5280
ccaggctgga atgcagtggt gcaatctcag ctcactgcaa cctccgcctc ccaggttcaa    5340
gcaattctcc tgcctcagcc tcccgagtag ctgggactac aggtgtgcgc caccacacca    5400
ggctaatttt tgtatttttt gtaaagacag gttttcacca cgttggccag gctggtctga    5460
actccagacc tcaggtgatt cacctgtctc agcctcccaa agtgctggga ttacaggtgt    5520
gagccaccgt gcccggctac ttcatggatt tttgattaca gattatgcct cttacaattt    5580
ttaagaagaa tcaagtgggc tgaaggtcaa tgtcaccata agacaaaaga cattttatt    5640 agttgattct agggaattgg ccttaagggg agccctttct tcctaagaga ttcttaggtg    5700
attctcactt cctcttgccc cagtattatt tttgttttg gtatggctca ctcagatcct    5760
tttttcctcc tatccctaag taatccgggt ttcttttttcc catatttaga acaaaatgta    5820
tttatgcaga gtgtgtccaa acctcaaccc aaggcctgta tacaaaataa atcaaattaa    5880
acacatcttt actgtcttct acctctttcc tgacctcaat atatcccaac ttgcctcact    5940
ctgagaacca aggctgtccc agcacctgag tcgcagatat tctactgatt tgacagaact    6000
gtgtgactat ctggaacagc attttgatcc acaatttgcc cagttacaaa gcttaaatga    6060
gctctagtgc atgcatatat atttcaaaat tccaccatga tcttccacac tctgtattgt    6120
aaatagagcc ctgtaatgct tttacttcgt atttcattgc ttgttataca taaaatata    6180 cttttcttct tcatgttaga aaatgcaaag aataggaggg tgggggaatc tctgggcttg    6240
gagacaggag acttgccttc ctactatggt tccatcagaa tgtagactgg gacaatacaa    6300
taattcaagt ctggtttgct catctgtaaa ttggaagaa tgtttccagc tccagaatgc    6360
taaatctcta agtctgtggt tggcagccac tattgcagca gctcttcaat gactcaatgc    6420
agttttgcat tctccctacc ttttttttct aaaaccaata aaatagatac agcctttagg    6480 cttttctggga tttcccttag tcaagctagg gtcatcctga ctttcggcgt gaatttgcaa    6540
aacaagacct gactctgtac tcctgctcta aggactgtgc atggttccaa aggcttagct    6600
tgccagcata tttgagcttt ttccttctgt tcaaactgtt ccaaaatata aagaataaa    6660 attaattaag ttggcactgg acttccggtg gtcagtcatg tgtgtcatct gtcacgtttt    6720
```

-continued

| | | |
|---|---|---|
| tcgggctctg gtggaaatgg atctgtctgt cttctctcat aggtggtatt cacagccaac | 6780 |
| gactccggcc cccgccgcta caccattgcc gccctgctga gccctactc ctattccacc | 6840 |
| acggctgtcg tcaccaatcc caaggaatga gggacttctc ctccagtgga cctgaaggac | 6900 |
| gagggatggg atttcatgta accaagagta ttccattttt actaaagcag tgttttcacc | 6960 |
| tcatatgcta tgttagaagt ccaggcagag acaataaaac attcctgtga aaggcacttt | 7020 |
| tcattccact ttaacttgat tttttaaatt cccttattgt cccttccaaa aaaagagaa | 7080 |
| tcaaaatttt acaaagaatc aaggaattc tagaaagtat ctgggcagaa cgctaggaga | 7140 |
| gatccaaatt tccattgtct tgcaagcaaa gcacgtatta aatatgatct gcagccatta | 7200 |
| aaaagacaca ttctgtaaat gagagagcct tattttcctg taaccttcag caaatagcaa | 7260 |
| aagcacacatt ccaagggccc acttctttac tgtgggcact cgagataact tcgtataatg | 7320 |
| tatgctatac gaagttatgc taggtaacta taacggtcct aaggtagcga gctagcgaga | 7380 |
| ctcagcccag gaggaccagg atcttgccaa agcagtagca tcccatttgt accaaaacag | 7440 |
| tgttcttgct ctataaaccg tgttagcagc tcagga | 7476 |

<210> SEQ ID NO 17
<211> LENGTH: 7201
<212> TYPE: DNA
<213> ORGANISM: Homo sapiens

<400> SEQUENCE: 17

| | | |
|---|---|---|
| atggcttctc atcgtctgct cctcctctgc cttgctggac tggtatttgt gtctgaggct | 60 |
| ggccctacgg tgagtgtttc tgtgacatcc cattcctaca tttaagattc acgctaaatg | 120 |
| aagtagaagt gactccttcc agctttgcca accagctttt attactaggg caagggtacc | 180 |
| cagcatctat ttttaatata attaattcaa acttcaaaaa gaatgaagtt ccactgagct | 240 |
| tactgagctg ggacttgaac tctgagcatt ctacctcatt gctttggtgc attaggtttg | 300 |
| taatatctgg tacctctgtt tcctcagata gatgatagaa ataaagatat gatattaagg | 360 |
| aagctgttaa tactgaattt tcagaaaagt atccctccat aaaatgtatt tgggggacaa | 420 |
| actgcaggag attatattct ggccctatag ttattcaaaa cgtatttatt gattaatctt | 480 |
| taaaaggctt agtgaacaat attctagtca gatatctaat tcttaaatcc tctagaagaa | 540 |
| ttaactaata ctataaaatg ggtctggatg tagttctgac attattttat aacaactggt | 600 |
| aagagggagt gactatagca acaactaaaa tgatctcagg aaaacctgtt tggccctatg | 660 |
| tatggtacat tacatctttt cagtaattcc actcaaatgg agacttttaa caaagcaact | 720 |
| gttctcaggg gacctatttt ctcccttaaa attcattata cacatccctg gttgatagca | 780 |
| gtgtgtctgg aggcagaaac cattcttgct ttggaaacaa ttacgtctgt gttatactga | 840 |
| gtagggaagc tcattaattg tcgacactta cgttcctgat aatgggatca gtgtgtaatt | 900 |
| cttgtttcgc tccagatttc taataccaca agaataaat cctttcactc tgatcaattt | 960 |
| tgttaacttc tcacgtgtct tctctacacc cagggcaccg tgaatccaa gtgtcctctg | 1020 |
| atggtcaaag ttctagatgc tgtccgaggc agtcctgcca tcaatgtggc cgtgcatgtg | 1080 |
| ttcagaaagg ctgctgatga cacctgggag ccatttgcct ctgggtaagt tgccaaagaa | 1140 |
| ccctccaca ggacttggtt ttatcttccc gtttgccct cacttggtag agagaggctc | 1200 |
| acatcatctg ctaaagaatt tacaagtaga ttgaaaaacg taggcagagg tcaagtatgc | 1260 |
| cctctgaagg atgccctctt tttgttttgc ttagctagga agtgaccagg aacctgagca | 1320 |

```
tcatttaggg gcagacagta gagaaaagaa ggaatcagaa ctcctctcct ctagctgtgg    1380
tttgcaaccc ttttgggtca cagaacactt tatgtaggtg atgaaaagta aacattctat    1440
gcccagaaaa aatgcacaga tacacacaca tacaaaatca tatatgtgat tttaggagtt    1500
tcacagattc cctggtgtcc ctgggtaaca ccaaagctaa gtgtccttgt cttagaattt    1560
taggaaaagg tataatgtgt attaacccat taacaaaagg aaaggaattc agaaatatta    1620
ttaaccaggc atctgtctgt agttaatatg gatcacccaa aacccaaggc ttttgcctaa    1680
tgaacacttt ggggcaccta ctgtgtgcaa ggctggggc tgtcaagctc agttaaaaaa    1740
aaaaagatag aagagatgga tccatgaggc aaagtacagc cccaggctaa tcccacgatc    1800
acccgacttc atgtccaaga gtggcttctc accttcatta gccagttcac aattttcatg    1860
gagtttttct acctgcacta gcaaaaactt caaggaaaat acatattaat aaatctaagc    1920
aaagtgacca gaagacagag caatcaggag acccctttgca tccagcagaa gaggaactgc    1980
taagtattta catctccaca gagaagaatt tctgttgggt tttaattgaa ccccaagaac    2040
cacatgattc ttcaaccatt attgggaaga tcattttctt aggtctggtt ttaactggct    2100
ttttatttgg gaattcattt atgtttatat aaaatgccaa gcataacatg aaaagtggtt    2160
acaggactat tctaagggag agacagaatg gacaccaaaa atattccaat gttcttgtga    2220
atcttttcct tgcaccagga caaaaaaaaa aagaagtgaa aagaagaaag gaggaggggc    2280
ataatcagag tcagtaaaga caactgctat ttttatctat cgtagctgtt gcagtcaaat    2340
gggaagcaat ttccaacatt caactatgga gctggtactt acatggaaat agaagttgcc    2400
tagtgtttgt tgctggcaaa gagttatcag agaggttaaa tatataaaag ggaaaagagt    2460
cagatacagg ttcttcttcc tactttaggt tttccactgt gtgtgcaaat gatactccct    2520
ggtggtgtgc agatgcctca aagctatcct cacaccacaa gggagaggag cgagatcctg    2580
ctgtcctgga gaagtgcaga gttagaacag ctgtggccac ttgcatccaa tcatcaatct    2640
tgaatcacag ggactctttc ttaagtaaac attatacctg gccgggcacg gtggctcacg    2700
cctgtaatcc cagcactttg ggatgccaaa gtgggcatat catctgaggt caggagttca    2760
agaccagcct ggccaacatg gcaaaactcc gtctttatga aaaatacaaa aattagccag    2820
gcatggtggc aggcgcctgt aatcccagct aattgggagg ctgaggctgg agaatccctt    2880
gaatctagga ggcagaggtt gcagtgagct gagatcgtgc cattgcactc cagcctgggt    2940
gacaagagta aaactctgtc tcaaaaaaaa aaaattatac ctacattctc ttcttatcag    3000
agaaaaaaat ctacagtgag cttttcaaaa agttttttaca aacttttttgc catttaattt    3060 cagttaggag ttttccctac ttctgactta gttgagggga aatgttcata acatgtttat    3120
aacatgttta tgtgtgttag ttggtggggg tgtattactt tgccatgcca tttgtttcct    3180
ccatgcgtaa cttaatccag actttcacac cttataggaa aaccagtgag tctggagagc    3240
tgcatgggct cacaactgag gaggaatttg tagaagggat atacaaagtg aaatagaca    3300 ccaaatctta ctggaaggca cttggcatct ccccattcca tgagcatgca gaggtgagta    3360
tacagacctt cgagggttgt tttggttttg gttttgtgctt ttggcattcc aggaaatgca    3420
cagttttact cagtgtacca cagaaatgtc ctaaggaagg tgatgaatga ccaaaggttc    3480
cctttcctat tatacaagaa aaaattcaca acactctgag aagcaaattt cttttttgact    3540 ttgatgaaaa tccacttagt aacatgactt gaacttacat gaaactactc atagtctatt    3600
cattccactt tatatgaata ttgatgtatc tgctgttgaa ataatagttt atgaggcagc    3660
cctccagacc ccacgtagag tgtatgtaac aagagatgca ccattttatt tctcgaaaac    3720
```

```
ccgtaacatt cttcattcca aaacacatct ggcttctcgg aggtctggac aagtgattct    3780
tggcaacaca tacctataga gacaataaaa tcaaagtaat aatggcaaca caatagataa    3840
catttaccaa gcatacacca tgtggcagac acaattataa gtgttttcca tatttaacct    3900
acttaatcct caggaataag ccactgaggt cagtcctatt attatcccca tcttatagat    3960
gaagaaaatg aggcaccagg aagtcaaata acttgtcaaa ggtcacaaga ctaggaaata    4020
cacaagtaga aatgtttaca attaaggccc aggctgggtt tgccctcagt tctgctatgc    4080
ctcgcattat gccccaggaa acttttccc ttgtgaaagc caagcttaaa aaagaaaag     4140
ccacatttgt aacgtgctct gttccctgc ctatggtgag gatcttcaaa cagttataca    4200
tggacccagt ccccctgcct tctccttaat ttcttaagtc atttgaaaca gatggctgtc    4260
atggaaatag aatccagaca tgttggtcag agttaaagat caactaattc catcaaaaat    4320
agctcggcat gaaagggaac tattctctgg cttagtcatg gatgagactt tcaattgcta    4380
taaagtggtt cctttattag acaatgttac caggaaaaca acaggggttt gtttgacttc    4440
tggggcccac aagtcaacaa gagagcccca tctaccaagg agcatgtccc tgactacccc    4500
tcagccagca gcaagacatg gaccccagtc agggcaggag cagggtttcg gcggcgccca    4560
gcacaagaca ttgcccctag agtctcagcc cctaccctcg agtaatagat ctgcctacct    4620
gagactgttg tttgcccaag agctgggtct cagcctgatg ggaaccatat aaaaaggttc    4680
actgacatac tgcccacatg ttgttctctt tcattagatc ttagcttcct tgtctgctct    4740
tcattcttgc agtattcatt caacaaacat taaaaaaaaa aaaaagcatt ctatgtgtgg    4800
aacactctgc tagatgctgt ggatttagaa atgaaaatac atcccgaccc ttggaatgga    4860
agggaaagga ctgaagtaag acagattaag caggaccgtc agcccagctt gaagcccaga    4920
taaatacgga gaacaagaga gagcgagtag tgagagatga gtcccaatgc ctcactttgg    4980
tgacgggtgc gtggtgggct tcatgcagct tcttctgata aatgcctcct tcagaactgg    5040
tcaactctac cttggccagt gacccaggtg gtcatagtag atttaccaag ggaaaatgga    5100
aactttatt aggagctctt aggcctcttc acttcatgga tttttttttc cttttttttt     5160
gagatggagt tttgccctgt cacccaggct ggaatgcagt ggtgcaatct cagctcactg    5220
caacctccgc ctcccaggtt caagcaattc tcctgcctca gcctcccgag tagctgggac    5280
tacaggtgtg cgccaccaca ccaggctaat ttttgtattt tttgtaaaga caggttttca    5340
ccacgttggc caggctggtc tgaactccag acctcaggtg attcacctgt ctcagcctcc    5400
caaagtgctg ggattacagg tgtgagccac cgtgcccggc tacttcatgg attttttgatt   5460
acagattatg cctcttacaa ttttttaagaa gaatcaagtg ggctgaaggt caatgtcacc    5520
ataagacaaa agacatttt attagttgat tctagggaat tggccttaag gggagccctt    5580
tcttcctaag agattcttag gtgattctca cttcctcttg ccccagtatt attttttgttt    5640
ttggtatggc tcactcagat ccttttttcc tcctatccct aagtaatccg ggtttctttt    5700
tcccatattt agaacaaaat gtatttatgc agagtgtgtc caaacctcaa cccaaggcct    5760
gtatacaaaa taaatcaaat taaacacatc tttactgtct tctacctctt tcctgacctc    5820
aatatatccc aacttgcctc actctgagaa ccaaggctgt cccagcacct gagtcgcaga    5880
tattctactg atttgacaga actgtgtgac tatctggaac agcattttga tccacaattt    5940
gcccagttac aaagcttaaa tgagctctag tgcatgcata tatatttcaa aattccacca    6000
tgatcttcca cactctgtat tgtaaataga gccctgtaat gctttttactt cgtatttcat    6060
```

```
tgcttgttat acataaaaat atactttct tcttcatgtt agaaaatgca aagaatagga    6120
gggtggggga atctctgggc ttggagacag gagacttgcc ttcctactat ggttccatca    6180
gaatgtagac tgggacaata caataattca agtctggttt gctcatctgt aaattgggaa    6240
gaatgtttcc agctccagaa tgctaaatct ctaagtctgt ggttggcagc cactattgca    6300
gcagctcttc aatgactcaa tgcagttttg cattctccct accttttttt tctaaaacca    6360
ataaaataga tacagccttt aggctttctg ggatttccct tagtcaagct agggtcatcc    6420
tgactttcgg cgtgaatttg caaaacaaga cctgactctg tactcctgct ctaaggactg    6480
tgcatggttc caaaggctta gcttgccagc atatttgagc ttttccttc tgttcaaact     6540 gttccaaaat ataaagaat aaaattaatt aagttggcac tggacttccg gtggtcagtc     6600
atgtgtgtca tctgtcacgt ttttcgggct ctggtggaaa tggatctgtc tgtcttctct    6660
cataggtggt attcacagcc aacgactccg gcccccgccg ctacaccatt gccgccctgc    6720
tgagccccta ctcctattcc accacggctc tcgtcaccaa tcccaaggaa tgagggactt    6780
ctcctccagt ggacctgaag gacgagggat gggatttcat gtaaccaaga gtattccatt    6840
tttactaaag cagtgttttc acctcatatg ctatgttaga agtccaggca gagacaataa    6900
aacattcctg tgaaaggcac ttttcattcc actttaactt gatttttaa attcccttat     6960 tgtcccttcc aaaaaaaga gaatcaaaat tttacaaaga atcaaggaa ttctagaaag       7020 tatctgggca gaacgctagg agagatccaa atttccattg tcttgcaagc aaagcacgta    7080
ttaaatatga tctgcagcca ttaaaaagac acattctgta aatgagagag ccttattttc    7140
ctgtaacctt cagcaaatag caaaagacac attccaaggg cccacttctt tactgtgggc    7200
a                                                                    7201

<210> SEQ ID NO 18
<211> LENGTH: 24
<212> TYPE: DNA
<213> ORGANISM: Artificial Sequence
<220> FEATURE:
<223> OTHER INFORMATION: Synthetic

<400> SEQUENCE: 18
cacagacaat cagacgtacc agta                                             24

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
ccagctttgc cagtttacga                                                  20

<210> SEQ ID NO 20
<211> LENGTH: 18
<212> TYPE: DNA
<213> ORGANISM: Artificial Sequence
<220> FEATURE:
<223> OTHER INFORMATION: Synthetic

<400> SEQUENCE: 20
ttggacggtt gccctctt                                                    18

<210> SEQ ID NO 21
<211> LENGTH: 22
```

```
<212> TYPE: DNA
<213> ORGANISM: Artificial Sequence
<220> FEATURE:
<223> OTHER INFORMATION: Synthetic

<400> SEQUENCE: 21
gatggcttcc cttcgactct tc                                            22

<210> SEQ ID NO 22
<211> LENGTH: 25
<212> TYPE: DNA
<213> ORGANISM: Artificial Sequence
<220> FEATURE:
<223> OTHER INFORMATION: Synthetic

<400> SEQUENCE: 22
cactgacatt tctcttgtct cctct                                         25

<210> SEQ ID NO 23
<211> LENGTH: 21
<212> TYPE: DNA
<213> ORGANISM: Artificial Sequence
<220> FEATURE:
<223> OTHER INFORMATION: Synthetic

<400> SEQUENCE: 23
gggctcacca cagatgagaa g                                             21

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
cactgttcgc cacaggtctt                                               20

<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
gctcagccca tactcctaca                                               20

<210> SEQ ID NO 26
<211> LENGTH: 18
<212> TYPE: DNA
<213> ORGANISM: Artificial Sequence
<220> FEATURE:
<223> OTHER INFORMATION: Synthetic

<400> SEQUENCE: 26
gcccaggagg accaggat                                                 18

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
```
ggcaacttgc ttgaggaaga                                              20

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
gcagcaaccc agcttcactt                                              20

<210> SEQ ID NO 29
<211> LENGTH: 19
<212> TYPE: DNA
<213> ORGANISM: Artificial Sequence
<220> FEATURE:
<223> OTHER INFORMATION: Synthetic

<400> SEQUENCE: 29
actgagctgg gacttgaac                                               19

<210> SEQ ID NO 30
<211> LENGTH: 19
<212> TYPE: DNA
<213> ORGANISM: Artificial Sequence
<220> FEATURE:
<223> OTHER INFORMATION: Synthetic

<400> SEQUENCE: 30
tgcctcactc tgagaacca                                               19

<210> SEQ ID NO 31
<211> LENGTH: 19
<212> TYPE: DNA
<213> ORGANISM: Artificial Sequence
<220> FEATURE:
<223> OTHER INFORMATION: Synthetic

<400> SEQUENCE: 31
cgcaacctcc ccttctacg                                               19

<210> SEQ ID NO 32
<211> LENGTH: 18
<212> TYPE: DNA
<213> ORGANISM: Artificial Sequence
<220> FEATURE:
<223> OTHER INFORMATION: Synthetic

<400> SEQUENCE: 32
ggccgtgcat gtgttcag                                                18

<210> SEQ ID NO 33
<211> LENGTH: 23
<212> TYPE: DNA
<213> ORGANISM: Artificial Sequence
<220> FEATURE:
<223> OTHER INFORMATION: Synthetic

<400> SEQUENCE: 33
ggttcccatt tgctcttatt cgt                                          23

<210> SEQ ID NO 34
<211> LENGTH: 23
<212> TYPE: DNA
<213> ORGANISM: Artificial Sequence

```
<220> FEATURE:
<223> OTHER INFORMATION: Synthetic

<400> SEQUENCE: 34
cccacactgc agaaggaaac ttg                                              23

<210> SEQ ID NO 35
<211> LENGTH: 23
<212> TYPE: DNA
<213> ORGANISM: Artificial Sequence
<220> FEATURE:
<223> OTHER INFORMATION: Synthetic

<400> SEQUENCE: 35
ggttcccatt tgctcttatt cgt                                              23

<210> SEQ ID NO 36
<211> LENGTH: 22
<212> TYPE: DNA
<213> ORGANISM: Artificial Sequence
<220> FEATURE:
<223> OTHER INFORMATION: Synthetic

<400> SEQUENCE: 36
ccagcttagc atcctgtgaa ca                                               22

<210> SEQ ID NO 37
<211> LENGTH: 20
<212> TYPE: DNA
<213> ORGANISM: Artificial Sequence
<220> FEATURE:
<223> OTHER INFORMATION: Synthetic

<400> SEQUENCE: 37
ggcaacttgc ttgaggaaga                                                  20

<210> SEQ ID NO 38
<211> LENGTH: 22
<212> TYPE: DNA
<213> ORGANISM: Artificial Sequence
<220> FEATURE:
<223> OTHER INFORMATION: Synthetic

<400> SEQUENCE: 38
tgtggagttc agtagtgtgg ag                                               22

<210> SEQ ID NO 39
<211> LENGTH: 25
<212> TYPE: DNA
<213> ORGANISM: Artificial Sequence
<220> FEATURE:
<223> OTHER INFORMATION: Synthetic

<400> SEQUENCE: 39
cactgacatt tctcttgtct cctct                                            25

<210> SEQ ID NO 40
<211> LENGTH: 23
<212> TYPE: DNA
<213> ORGANISM: Artificial Sequence
<220> FEATURE:
<223> OTHER INFORMATION: Synthetic

<400> SEQUENCE: 40
gggacatctc ggtttcctga ctt                                              23
```

```
<210> SEQ ID NO 41
<211> LENGTH: 22
<212> TYPE: DNA
<213> ORGANISM: Artificial Sequence
<220> FEATURE:
<223> OTHER INFORMATION: Synthetic

<400> SEQUENCE: 41
tccacactac tgaactccac aa                                              22

<210> SEQ ID NO 42
<211> LENGTH: 21
<212> TYPE: DNA
<213> ORGANISM: Artificial Sequence
<220> FEATURE:
<223> OTHER INFORMATION: Synthetic

<400> SEQUENCE: 42
cggaacactc gctctacgaa a                                               21

<210> SEQ ID NO 43
<211> LENGTH: 18
<212> TYPE: DNA
<213> ORGANISM: Artificial Sequence
<220> FEATURE:
<223> OTHER INFORMATION: Synthetic

<400> SEQUENCE: 43
gggccagctt cagacaca                                                   18

<210> SEQ ID NO 44
<211> LENGTH: 22
<212> TYPE: DNA
<213> ORGANISM: Artificial Sequence
<220> FEATURE:
<223> OTHER INFORMATION: Synthetic

<400> SEQUENCE: 44
cccagggtgc tggagaatcc aa                                              22

<210> SEQ ID NO 45
<211> LENGTH: 22
<212> TYPE: DNA
<213> ORGANISM: Artificial Sequence
<220> FEATURE:
<223> OTHER INFORMATION: Synthetic

<400> SEQUENCE: 45
gccaagtgtc ttccagtacg at                                              22

<210> SEQ ID NO 46
<211> LENGTH: 21
<212> TYPE: DNA
<213> ORGANISM: Artificial Sequence
<220> FEATURE:
<223> OTHER INFORMATION: Synthetic

<400> SEQUENCE: 46
gttccctttc ttgggttcag a                                               21

<210> SEQ ID NO 47
<211> LENGTH: 23
<212> TYPE: DNA
<213> ORGANISM: Artificial Sequence
<220> FEATURE:
<223> OTHER INFORMATION: Synthetic
```

```
<400> SEQUENCE: 47
gatgctactg ctttggcaag atc                                          23

<210> SEQ ID NO 48
<211> LENGTH: 20
<212> TYPE: DNA
<213> ORGANISM: Artificial Sequence
<220> FEATURE:
<223> OTHER INFORMATION: Synthetic

<400> SEQUENCE: 48
cctgagctgc taacacggtt                                              20

<210> SEQ ID NO 49
<211> LENGTH: 23
<212> TYPE: DNA
<213> ORGANISM: Artificial Sequence
<220> FEATURE:
<223> OTHER INFORMATION: Synthetic

<400> SEQUENCE: 49
agctacagac catgcttagt gta                                          23

<210> SEQ ID NO 50
<211> LENGTH: 24
<212> TYPE: DNA
<213> ORGANISM: Artificial Sequence
<220> FEATURE:
<223> OTHER INFORMATION: Synthetic

<400> SEQUENCE: 50
tgccagttta ggaggaatat gttc                                         24

<210> SEQ ID NO 51
<211> LENGTH: 25
<212> TYPE: DNA
<213> ORGANISM: Artificial Sequence
<220> FEATURE:
<223> OTHER INFORMATION: Synthetic

<400> SEQUENCE: 51
ctgaggaaac agaggtacca gatat                                        25

<210> SEQ ID NO 52
<211> LENGTH: 24
<212> TYPE: DNA
<213> ORGANISM: Artificial Sequence
<220> FEATURE:
<223> OTHER INFORMATION: Synthetic

<400> SEQUENCE: 52
agtcacacag ttctgtcaaa tcag                                         24

<210> SEQ ID NO 53
<211> LENGTH: 17
<212> TYPE: DNA
<213> ORGANISM: Artificial Sequence
<220> FEATURE:
<223> OTHER INFORMATION: Synthetic

<400> SEQUENCE: 53
gtccttcggg cacctcg                                                 17

<210> SEQ ID NO 54
```

<211> LENGTH: 20
<212> TYPE: DNA
<213> ORGANISM: Artificial Sequence
<220> FEATURE:
<223> OTHER INFORMATION: Synthetic

<400> SEQUENCE: 54
tcctgtggga gggttctttg						20

<210> SEQ ID NO 55
<211> LENGTH: 20
<212> TYPE: DNA
<213> ORGANISM: Artificial Sequence
<220> FEATURE:
<223> OTHER INFORMATION: Synthetic

<400> SEQUENCE: 55
ccctctctct gagccctcta						20

<210> SEQ ID NO 56
<211> LENGTH: 21
<212> TYPE: DNA
<213> ORGANISM: Artificial Sequence
<220> FEATURE:
<223> OTHER INFORMATION: Synthetic

<400> SEQUENCE: 56
gctgcctaag tctttggagc t						21

<210> SEQ ID NO 57
<211> LENGTH: 20
<212> TYPE: DNA
<213> ORGANISM: Artificial Sequence
<220> FEATURE:
<223> OTHER INFORMATION: Synthetic

<400> SEQUENCE: 57
ccctctctct gagccctcta						20

<210> SEQ ID NO 58
<211> LENGTH: 25
<212> TYPE: DNA
<213> ORGANISM: Artificial Sequence
<220> FEATURE:
<223> OTHER INFORMATION: Synthetic

<400> SEQUENCE: 58
gagaggagag acagctagtt ctaac					25

<210> SEQ ID NO 59
<211> LENGTH: 23
<212> TYPE: DNA
<213> ORGANISM: Artificial Sequence
<220> FEATURE:
<223> OTHER INFORMATION: Synthetic

<400> SEQUENCE: 59
agctacagac catgcttagt gta					23

<210> SEQ ID NO 60
<211> LENGTH: 22
<212> TYPE: DNA
<213> ORGANISM: Artificial Sequence
<220> FEATURE:
<223> OTHER INFORMATION: Synthetic

<400> SEQUENCE: 60
gccctcttca tacaggaatc ac                                               22

<210> SEQ ID NO 61
<211> LENGTH: 19
<212> TYPE: DNA
<213> ORGANISM: Artificial Sequence
<220> FEATURE:
<223> OTHER INFORMATION: Synthetic

<400> SEQUENCE: 61
cggacagcat ccaggactt                                                   19

<210> SEQ ID NO 62
<211> LENGTH: 26
<212> TYPE: DNA
<213> ORGANISM: Artificial Sequence
<220> FEATURE:
<223> OTHER INFORMATION: Synthetic

<400> SEQUENCE: 62
tcatgtaatc tggcttcaga gtggga                                           26

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
tgggaggcaa ttcttagttt caatgga                                          27

<210> SEQ ID NO 64
<211> LENGTH: 23
<212> TYPE: DNA
<213> ORGANISM: Artificial Sequence
<220> FEATURE:
<223> OTHER INFORMATION: Synthetic

<400> SEQUENCE: 64
tcccaaaggt gtctgtctgc aca                                              23

<210> SEQ ID NO 65
<211> LENGTH: 22
<212> TYPE: DNA
<213> ORGANISM: Artificial Sequence
<220> FEATURE:
<223> OTHER INFORMATION: Synthetic

<400> SEQUENCE: 65
ctcctttgcc tcgctggact gg                                               22

<210> SEQ ID NO 66
<211> LENGTH: 19
<212> TYPE: DNA
<213> ORGANISM: Artificial Sequence
<220> FEATURE:
<223> OTHER INFORMATION: Synthetic

<400> SEQUENCE: 66
cggacagcat ccaggactt                                                   19

<210> SEQ ID NO 67
<211> LENGTH: 29
<212> TYPE: DNA

```
<213> ORGANISM: Artificial Sequence
<220> FEATURE:
<223> OTHER INFORMATION: Synthetic

<400> SEQUENCE: 67
agaaggagtg tacagagtag aactggaca                                              29

<210> SEQ ID NO 68
<211> LENGTH: 27
<212> TYPE: DNA
<213> ORGANISM: Artificial Sequence
<220> FEATURE:
<223> OTHER INFORMATION: Synthetic

<400> SEQUENCE: 68
tgtttgtggg tgtcagtgtt tctactc                                                27

<210> SEQ ID NO 69
<211> LENGTH: 21
<212> TYPE: DNA
<213> ORGANISM: Artificial Sequence
<220> FEATURE:
<223> OTHER INFORMATION: Synthetic

<400> SEQUENCE: 69
caccacggct gtcgtcagca a                                                      21

<210> SEQ ID NO 70
<211> LENGTH: 23
<212> TYPE: DNA
<213> ORGANISM: Artificial Sequence
<220> FEATURE:
<223> OTHER INFORMATION: Synthetic

<400> SEQUENCE: 70
cttgccaaag cagtagcatc cca                                                    23

<210> SEQ ID NO 71
<211> LENGTH: 23
<212> TYPE: DNA
<213> ORGANISM: Artificial Sequence
<220> FEATURE:
<223> OTHER INFORMATION: Synthetic

<400> SEQUENCE: 71
aggtcagaaa gcagagtgga cca                                                    23

<210> SEQ ID NO 72
<211> LENGTH: 23
<212> TYPE: DNA
<213> ORGANISM: Artificial Sequence
<220> FEATURE:
<223> OTHER INFORMATION: Synthetic

<400> SEQUENCE: 72
cccaggcaat tcctaccttc cca                                                    23

<210> SEQ ID NO 73
<211> LENGTH: 28
<212> TYPE: DNA
<213> ORGANISM: Artificial Sequence
<220> FEATURE:
<223> OTHER INFORMATION: Synthetic

<400> SEQUENCE: 73
tctgagcatt ctacctcatt gctttggt                                               28
```

<210> SEQ ID NO 74
<211> LENGTH: 23
<212> TYPE: DNA
<213> ORGANISM: Artificial Sequence
<220> FEATURE:
<223> OTHER INFORMATION: Synthetic

<400> SEQUENCE: 74
aggctgtccc agcacctgag tcg                                              23

<210> SEQ ID NO 75
<211> LENGTH: 21
<212> TYPE: DNA
<213> ORGANISM: Artificial Sequence
<220> FEATURE:
<223> OTHER INFORMATION: Synthetic

<400> SEQUENCE: 75
cggctcggct tcaccgtcac c                                                21

<210> SEQ ID NO 76
<211> LENGTH: 23
<212> TYPE: DNA
<213> ORGANISM: Artificial Sequence
<220> FEATURE:
<223> OTHER INFORMATION: Synthetic

<400> SEQUENCE: 76
aaggctgctg atgacacctg gga                                              23

<210> SEQ ID NO 77
<211> LENGTH: 27
<212> TYPE: DNA
<213> ORGANISM: Artificial Sequence
<220> FEATURE:
<223> OTHER INFORMATION: Synthetic

<400> SEQUENCE: 77
agattcagac acacacaact taccagc                                          27

<210> SEQ ID NO 78
<211> LENGTH: 28
<212> TYPE: DNA
<213> ORGANISM: Artificial Sequence
<220> FEATURE:
<223> OTHER INFORMATION: Synthetic

<400> SEQUENCE: 78
agacctgcaa ttctctaaga gctccaca                                         28

<210> SEQ ID NO 79
<211> LENGTH: 27
<212> TYPE: DNA
<213> ORGANISM: Artificial Sequence
<220> FEATURE:
<223> OTHER INFORMATION: Synthetic

<400> SEQUENCE: 79
agattcagac acacacaact taccagc                                          27

<210> SEQ ID NO 80
<211> LENGTH: 24
<212> TYPE: DNA
<213> ORGANISM: Artificial Sequence
<220> FEATURE:

```
<223> OTHER INFORMATION: Synthetic

<400> SEQUENCE: 80
ttgtctgcag ctcctacctc tggg                                        24

<210> SEQ ID NO 81
<211> LENGTH: 23
<212> TYPE: DNA
<213> ORGANISM: Artificial Sequence
<220> FEATURE:
<223> OTHER INFORMATION: Synthetic

<400> SEQUENCE: 81
aggtcagaaa gcagagtgga cca                                         23

<210> SEQ ID NO 82
<211> LENGTH: 29
<212> TYPE: DNA
<213> ORGANISM: Artificial Sequence
<220> FEATURE:
<223> OTHER INFORMATION: Synthetic

<400> SEQUENCE: 82
ttgacatgtg tgggtgagag attttactg                                   29

<210> SEQ ID NO 83
<211> LENGTH: 22
<212> TYPE: DNA
<213> ORGANISM: Artificial Sequence
<220> FEATURE:
<223> OTHER INFORMATION: Synthetic

<400> SEQUENCE: 83
cccagggtgc tggagaatcc aa                                          22

<210> SEQ ID NO 84
<211> LENGTH: 16
<212> TYPE: RNA
<213> ORGANISM: Artificial Sequence
<220> FEATURE:
<223> OTHER INFORMATION: Synthetic

<400> SEQUENCE: 84
guuuuagagc uaugcu                                                 16

<210> SEQ ID NO 85
<211> LENGTH: 67
<212> TYPE: RNA
<213> ORGANISM: Artificial Sequence
<220> FEATURE:
<223> OTHER INFORMATION: Synthetic

<400> SEQUENCE: 85
agcauagcaa guuaaaauaa ggcuaguccg uuaucaacuu gaaaaagugg caccgagucg   60
gugcuuu                                                           67

<210> SEQ ID NO 86
<211> LENGTH: 77
<212> TYPE: RNA
<213> ORGANISM: Artificial Sequence
<220> FEATURE:
<223> OTHER INFORMATION: Synthetic

<400> SEQUENCE: 86
guuuuagagc uagaaauagc aaguuaaaau aaggcuaguc cguuaucaac uugaaaagu   60
```
ggcaccgagu cggugcu                                                          77

<210> SEQ ID NO 87
<211> LENGTH: 82
<212> TYPE: RNA
<213> ORGANISM: Artificial Sequence
<220> FEATURE:
<223> OTHER INFORMATION: Synthetic

<400> SEQUENCE: 87
guuggaacca uucaaaacag cauagcaagu uaaaauaagg cuaguccguu aucaacuuga           60
aaaaguggca ccgagucggu gc                                                    82

<210> SEQ ID NO 88
<211> LENGTH: 76
<212> TYPE: RNA
<213> ORGANISM: Artificial Sequence
<220> FEATURE:
<223> OTHER INFORMATION: Synthetic

<400> SEQUENCE: 88
guuuuagagc uagaaauagc aaguuaaaau aaggcuaguc cguuaucaac uugaaaaagu           60
ggcaccgagu cggugc                                                          76

<210> SEQ ID NO 89
<211> LENGTH: 86
<212> TYPE: RNA
<213> ORGANISM: Artificial Sequence
<220> FEATURE:
<223> OTHER INFORMATION: Synthetic

<400> SEQUENCE: 89
guuuaagagc uaugcuggaa acagcauagc aaguuuaaau aaggcuaguc cguuaucaac           60
uugaaaaagu ggcaccgagu cggugc                                               86

<210> SEQ ID NO 90
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: n = A, T, C, or G

<400> SEQUENCE: 90
gnnnnnnnnn nnnnnnnnnn ngg                                                   23

<210> SEQ ID NO 91
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(21)
<223> OTHER INFORMATION: n = A, T, C, or G

<400> SEQUENCE: 91
nnnnnnnnnn nnnnnnnnnn ngg                                                   23

<210> SEQ ID NO 92

```
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(23)
<223> OTHER INFORMATION: n = A, T, C, or G

<400> SEQUENCE: 92
ggnnnnnnnn nnnnnnnnnn nnngg                                    25
```